United States Patent
Schmidt et al.

(10) Patent No.: US 11,266,727 B2
(45) Date of Patent: Mar. 8, 2022

(54) ARENAVIRUS PARTICLES AS CANCER VACCINES

(71) Applicant: Hookipa Biotech GmbH, Vienna (AT)

(72) Inventors: Sarah Schmidt, Vienna (AT); Klaus Orlinger, Vienna (AT); Katherine Cohen, Vienna (AT)

(73) Assignee: Hookipa Biotech GmbH, Vienna (AT)

( * ) Notice: Subject to any disclaimer, the term of this patent is extended or adjusted under 35 U.S.C. 154(b) by 93 days.

(21) Appl. No.: 15/775,360

(22) PCT Filed: Nov. 4, 2016

(86) PCT No.: PCT/EP2016/076668
§ 371 (c)(1),
(2) Date: May 10, 2018

(87) PCT Pub. No.: WO2017/080920
PCT Pub. Date: May 18, 2017

(65) Prior Publication Data
US 2018/0344830 A1    Dec. 6, 2018

Related U.S. Application Data

(60) Provisional application No. 62/254,651, filed on Nov. 12, 2015, provisional application No. 62/254,654, filed on Nov. 12, 2015.

(51) Int. Cl.
| | | |
|---|---|---|
| *A61K 39/12* | (2006.01) | |
| *A61K 39/00* | (2006.01) | |
| *A61P 35/00* | (2006.01) | |
| *C12N 15/62* | (2006.01) | |

(52) U.S. Cl.
CPC ..... *A61K 39/0011* (2013.01); *A61K 39/00111* (2018.08); *A61K 39/00116* (2018.08); *A61K 39/00117* (2018.08); *A61K 39/00118* (2018.08); *A61K 39/00119* (2018.08); *A61K 39/001103* (2018.08); *A61K 39/001104* (2018.08); *A61K 39/001106* (2018.08); *A61K 39/001108* (2018.08); *A61K 39/001109* (2018.08); *A61K 39/001112* (2018.08); *A61K 39/001113* (2018.08); *A61K 39/001117* (2018.08); *A61K 39/001122* (2018.08); *A61K 39/001124* (2018.08); *A61K 39/001126* (2018.08); *A61K 39/001135* (2018.08); *A61K 39/001138* (2018.08); *A61K 39/001139* (2018.08); *A61K 39/001149* (2018.08); *A61K 39/001151* (2018.08); *A61K 39/001152* (2018.08); *A61K 39/001153* (2018.08); *A61K 39/001156* (2018.08); *A61K 39/001157* (2018.08); *A61K 39/001159* (2018.08); *A61K 39/001162* (2018.08); *A61K 39/001164* (2018.08); *A61K 39/001166* (2018.08); *A61K 39/001168* (2018.08); *A61K 39/001171* (2018.08); *A61K 39/001172* (2018.08); *A61K 39/001174* (2018.08); *A61K 39/001176* (2018.08); *A61K 39/001182* (2018.08); *A61K 39/001184* (2018.08); *A61K 39/001186* (2018.08); *A61K 39/001188* (2018.08); *A61K 39/001189* (2018.08); *A61K 39/001191* (2018.08); *A61K 39/001192* (2018.08); *A61K 39/001193* (2018.08); *A61K 39/001194* (2018.08); *A61K 39/001195* (2018.08); *A61K 39/001197* (2018.08); *A61K 39/12* (2013.01); *A61P 35/00* (2018.01); *C12N 15/62* (2013.01); *A61K 2039/5256* (2013.01)

(58) Field of Classification Search
None
See application file for complete search history.

(56) References Cited

U.S. PATENT DOCUMENTS

| | | |
|---|---|---|
| 5,057,540 A | 10/1991 | Kensil et al. |
| 8,592,205 B2 | 11/2013 | Pinschewer et al. |
| 9,309,289 B2 | 4/2016 | Pinschewer et al. |
| 9,809,801 B2 | 11/2017 | Belnoue et al. |
| 9,944,952 B2 | 4/2018 | Pinschewer et al. |
| 10,111,945 B2 | 10/2018 | Orlinger et al. |
| 10,669,315 B2 | 6/2020 | Orlinger et al. |
| 10,722,564 B2 | 7/2020 | Pinschewer et al. |

(Continued)

FOREIGN PATENT DOCUMENTS

| | | |
|---|---|---|
| JP | A-H10-084967 | 4/1998 |
| JP | A-2006-340714 | 12/2006 |

(Continued)

OTHER PUBLICATIONS

Webster, R., Nat. Reviews, Oct. 2014, vol. 13: pp. 883-884.*

(Continued)

*Primary Examiner* — Michael D Burkhart
(74) *Attorney, Agent, or Firm* — Jones Day

(57) ABSTRACT

The present application relates generally to genetically modified arenaviruses that are suitable vaccines against neoplastic diseases, such as cancer. The arenaviruses described herein may be suitable for vaccines and/or treatment of neoplastic diseases and/or for the use in immunotherapies. In particular, provided herein are methods and compositions for treating a neoplastic disease by administering a genetically modified arenavirus in combination with an immune checkpoint inhibitor, wherein the arenavirus has been engineered to include a nucleotide sequence encoding a tumor antigen, tumor associated antigen or antigenic fragment thereof.

Figure 1:
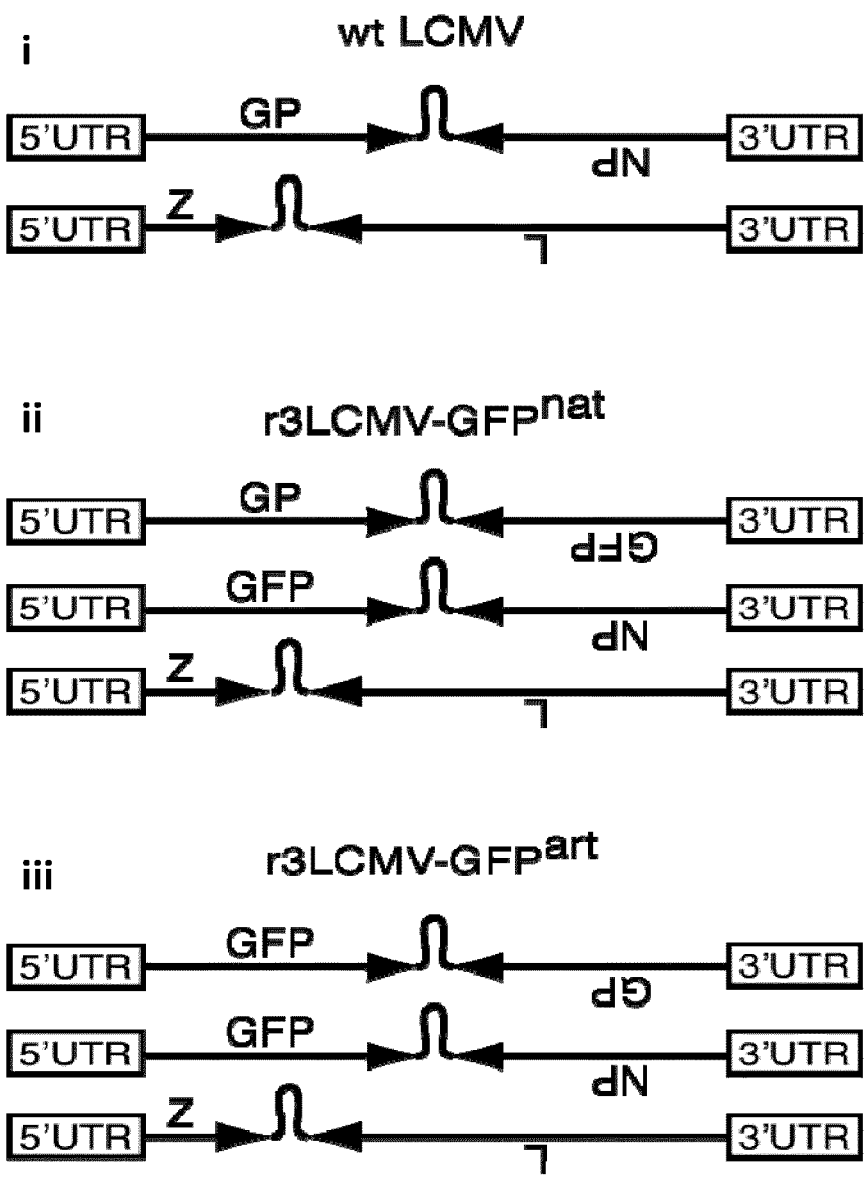
Figure 2:
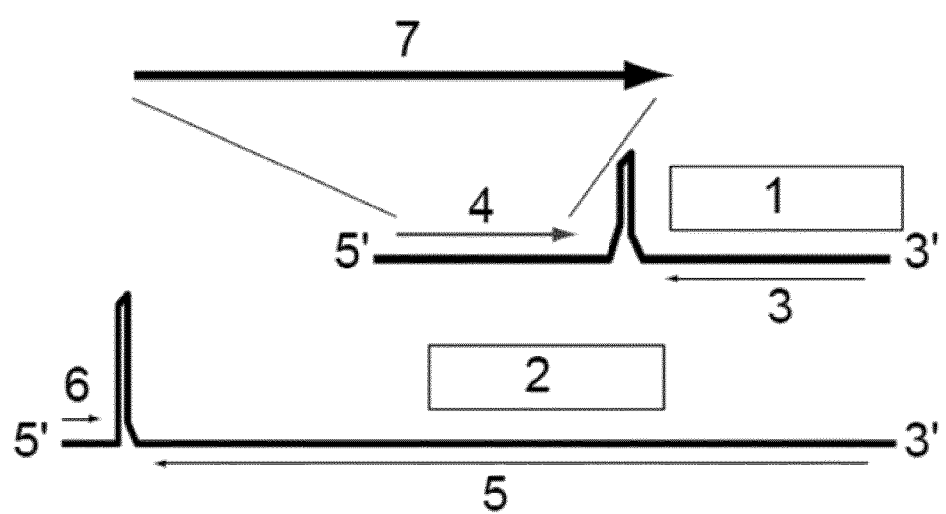

26 Claims, 12 Drawing Sheets
Specification includes a Sequence Listing.

(56) References Cited

U.S. PATENT DOCUMENTS

| | | |
|---|---|---|
| 2003/0129202 A1 | 7/2003 | Trepo et al. |
| 2010/0297172 A1 | 11/2010 | Pinschewer et al. |
| 2014/0050760 A1 | 2/2014 | Pinschewer et al. |
| 2016/0024476 A1 | 1/2016 | Belnoue et al. |
| 2016/0194663 A1 | 7/2016 | Pinschewer et al. |
| 2016/0206724 A1 | 7/2016 | De la Torre et al. |
| 2016/0296619 A1 | 10/2016 | Orlinger et al. |
| 2017/0319673 A1 | 11/2017 | Pinschewer et al. |
| 2018/0179257 A1 | 6/2018 | Orlinger et al. |
| 2018/0319845 A1 | 11/2018 | Monath et al. |
| 2019/0062784 A1 | 2/2019 | Pinschewer et al. |
| 2019/0135875 A1 | 5/2019 | Bonilla et al. |
| 2019/0247493 A1 | 8/2019 | Orlinger et al. |
| 2020/0113995 A1 | 4/2020 | Orlinger et al. |
| 2020/0206334 A1 | 7/2020 | Schmidt et al. |
| 2021/0024584 A1 | 1/2021 | Orlinger et al. |
| 2021/0071198 A1 | 3/2021 | Pinschewer et al. |
| 2021/0145950 A1 | 5/2021 | Pinschewer et al. |

FOREIGN PATENT DOCUMENTS

| | | |
|---|---|---|
| JP | A-2009-286795 | 12/2009 |
| JP | A-2014-065748 | 4/2014 |
| WO | WO 2006/125983 | 11/2006 |
| WO | WO 2007/109812 A2 | 9/2007 |
| WO | WO 2007/109813 A1 | 9/2007 |
| WO | WO 2009/083210 A1 | 7/2009 |
| WO | WO 2011/015656 | 2/2011 |
| WO | WO 2011/095760 | 8/2011 |
| WO | WO 2012/162428 A1 | 11/2012 |
| WO | WO 2013/112549 A1 | 8/2013 |
| WO | WO 2014/140301 A1 | 9/2014 |
| WO | WO 2014/155076 A1 | 10/2014 |
| WO | WO 2015/082570 A1 | 6/2015 |
| WO | WO 2015/103602 A1 | 7/2015 |
| WO | WO 2015/183895 A1 | 12/2015 |
| WO | WO 2016/048949 A1 | 3/2016 |
| WO | WO 2016/071683 A2 | 5/2016 |
| WO | WO 2016/075250 A1 | 5/2016 |
| WO | WO 2016/166285 A1 | 10/2016 |
| WO | WO 2016/198531 A2 | 12/2016 |
| WO | WO 2017/068190 A1 | 4/2017 |
| WO | WO 2017/076988 A1 | 5/2017 |
| WO | WO 2017/080920 A1 | 5/2017 |
| WO | WO 2017/190074 A1 | 11/2017 |
| WO | WO 2017/198726 A1 | 11/2017 |
| WO | WO 2018/083220 A2 | 5/2018 |
| WO | WO 2018/185307 A1 | 10/2018 |
| WO | WO 2021/089853 | 5/2021 |

OTHER PUBLICATIONS

Albarino et al., "Efficient rescue of recombinant Lassa virus reveals the influence of S segment noncoding regions on virus replication and virulence," *J. Virol.*, 85(8):4020-4024 (2011).

Altman et al., "Phenotypic analysis of antigen-specific T lymphocytes," *Science*, 274:94-96 (1996).

Barton, "Lymphocytic choriomeningitis virus: a neglected central nervous system pathogen," *Clin. Infect. Dis.*, 22(1):197 (1996).

Bonilla et al., "Interpretation of lymphocyte proliferation tests," *Ann. Allergy Asthma Immunol.*, 101:101-104 (2008).

Bonilla et al., "Practice parameter for the diagnosis and management of primary immunodeficiency," *Ann. Allergy Asthma Innumol.*, 94(5 Supp 1):S1-63 (2005).

Brennan et al., "The consequences of reconfiguring the ambisense S genome segment of Rift Valley fever virus on viral replication in mammalian and mosquito cells and for genome packaging," *PLoS Pathog.*, 10(2):e1003922 (2014).

Buchmeier et al., "Protein structure of lymphocytic choriomeningitis virus: evidence for a cell-associated precursor of the virion glycopeptides," *Virology*, 99(1):111-120 (1979).

Buchmeier et al., "Arenaviridae: The Viruses and Their Replication," *Fields Virol.*, 2:1635-1668 (2001).

Cao et al., "Identification of alpha-dystroglycan as a receptor for lymphocytic choriomeningitis virus and Lassa fever virus," *Science*, 282(5396):2079-2081 (1998).

Caruso et al., "Flow cytometric analysis of activation markers on stimulated T cells and their correlation with cell proliferation," *Cytometry*, 27:71-76 (1997).

Cheng et al., "Generation of recombinant arenavirus for vaccine development in FDA-approved Vero cells," *J. Vis. Exp.*, 78: 50662 (2013).

Cheng et al., "Arenavirus Genome Rearrangement for the Development of Live Attenuated Vaccines," J. Virol., 89(14):7373-7384 (2015).

Czerkinsky et al., "A solid-phase enzyme-linked immunospot (ELISPOT) assay for enumeration of specific antibody-secreting cells," *J. Immunol. Methods*, 65:109-121 (1983).

Dhanwani et al., "A Novel Live Pichinde Virus-Based Vaccine Vector Induces Enhanced Humoral and Cellular Immunity after a Booster Dose," J. Virol., 90(5):2551-2560 (2015).

Emonet et al., "Generation of recombinant lymphocytic choriomeningitis viruses with trisegmented genomes stably expressing two additional genes of interest," *Proc. Natl. Acad. Sci. U.S.A.*, 106(9):3473-3478 (2009).

Emonet et al., "Arenavirus reverse genetics: new approaches for the investigation of arenavirus biology and development of antiviral strategies," Virology, 411(2):416-425 (2011).

Emonet et al., "Rescue from Cloned cDNAs and In Vivo Characterization of Recombinant Pathogenic Romero and Live-Attenuated Candid #1 Strains of Junin Virus, the Causative Agent of Argentine Hemorrhagic Fever Disease," *J. Virol.*, 85(4):1473-1483 (2011).

Flatz et al., "Development of replication-defective lymphocytic choriomeningitis virus vectors for the induction of potent CD8+ T cell immunity," *Nat. Med.*, 16(3):339-345 (2010).

Flatz et al., "Gene-Based Vaccination with a Mismatched Envelope Protects against Simian Immunodeficiency Virus Infection in Nonhuman Primates," *J. Virol.*, 86(15):7760-7770.

Flatz et al., "Recovery of an arenavirus entirely from RNA polymerase I/II-driven cDNA," *Proc. Natl. Acad. Sci. U.S.A.*, 103(12):4663-4668 (2006).

Flick et al., "Transient Bicistronic vRNA Segments for Indirect Selection of Recombinant Influenza Viruses," *Virol.*, 262(1):93-103 (1999).

Garcia-Sastre et al., "Use of a mammalian internal ribosomal entry site element for expression of a foreign protein by a transfectant influenza virus," *J. Virol.*, 68(10):6254-6261 (1994).

Geisbert et al., "Exotic emerging viral diseases: progress and challenges," *Nat. Med.*, 10(12 Suppl): S110-S121 (2004).

Ghanekar et al., "Gamma interferon expression in CD8(+) T cells is a marker for circulating cytotoxic T lymphocytes that recognize an HLA A2-restricted epitope of human cytomegalovirus. phosphoprotein pp65," *Clin. Diagn. Lab Immunol.*, 8(3):628-631 (2001).

Hass et al., "Replicon system for Lassa virus," *J. Virol.*, 78(24):13793-13803 (2004).

Hicks et al., "Age-related changes in mitogen-induced lymphocyte function from birth to old age," *Am. J Clin. Pathol.*, 80(2):159-163 (1983).

Hutchings et al., "The detection and enumeration of cytokine-secreting cells in mice and man and the clinical application of these assays," *J. Immunol. Methods*, 120(1):1-8 (1989).

Iwasaki et al., "General Molecular Strategy for Development of Arenavirus Live-Attenuated Vaccines," J. Virol., 89(23):12166-12177 (2015).

Johnson et al., "Isolation of Machupo virus from wild rodent *Calomys callosus," Am. J. Trop. Med. Hyg.*, 15(1):103-106 (1966).

Kallert et al., "Replicating viral vector platform exploits alarmin signals for potent $CD8^+$ T cell-mediated tumour immunotherapy," *Nat. Comm.*, 8:15327 (2017).

Lechner et al., "Immunogenicity of murine solid tumor models as a defining feature of in vivo behavior and response to immunotherapy," *J. Immunother.*, 36(9):477-489 (2013).

Lee et al., "Identification of the lymphocytic choriomeningitis virus (LCMV) proteins required to rescue LCMV RNA analogs into LCMV-like particles," *J. Virol.*, 76(12):6393-6397 (2002).

(56) References Cited

OTHER PUBLICATIONS

Lee et al., "NP and L proteins of lymphocytic choriomeningitis virus (LCMV) are sufficient for efficient transcription and replication of LCMV genomic RNA analogs," *J. Virol.*, 74(8):3470-3477 (2000).
Lopez et al., "Transcription and RNA replication of tacaribe virus genome and antigenome analogs require N and L proteins: Z protein is an inhibitor of these processes," *J. Virol.*, 75(24):12241-12251 (2001).
Machado et al., "Expression of a foreign gene by stable recombinant influenza viruses harboring a dicistronic genomic segment with an internal promoter," *Virol.*, 313(1):235-249 (2003).
Mills et al., "Prevalence of infection with Junin virus in rodent populations in the epidemic area of Argentine hemorrhagic fever," *Am. J. trop. Med. Hyg.*, 51(5):554-562 (1994).
Murali-Krishna et al., "Counting antigen-specific CD8 T cells: a reevaluation of bystander activation during viral infection," *Immunity*, 8(2):177-187 (1998).
Nomura et al., "Optimization of whole blood antigen-specific cytokine assays for CD4(+) T cells," *Cytometry*, 40:60-68 (2000).
Oldstone, "Biology and pathogenesis of lymphocytic choriomeningitis virus infection," *Curr. Top. Microbiol. Immunol.*, 263:83-117 (2002).
Ortiz-Riano et al., "Arenavirus reverse genetics for vaccine development," *J. Gen. Virol.*, 94:1175-1188 (2013).
Percy et al., "Expression of a foreign protein by influenza A virus," *J. Virol.*, 68(7):4486-4492 (1994).
Perez et al., "Characterization of the genomic promoter of the prototypic arenavirus lymphocytic choriomeningitis virus," *J. Virol.*, 77(2):1184-1194 (2003).
Perfetto et al., "Seventeen-colour flow cytometry: unravelling the immune system," *Nat. Rev. Immunol.*, 4(8):648-655 (2004).
Pinschewer et al., "Dual role of the lymphocytic choriomeningitis virus intergenic region in transcription termination and virus propagation," *J. Virol.*, 79(7):4519-4526 (2005).
Pinschewer et al., "Role of the virus nucleoprotein in the regulation of lymphocytic choriomeningitis virus transcription and RNA replication," *J. Virol.*, 77(6):3882-3887 (2003).
Popkin et al., "Expanded Potential for Recombinant Trisegmented Lymphocytic Choriomeningitis Viruses: Protein Production, Antibody Production, and In Vivo Assessment of Biological Function of Genes of Interest," *J. Virol.*, 85(15):7928-7932 (2011).
Rivers et al., "Meningitis in Man Caused by a Filterable Virus," *Science*, 81(2015):439-440 (1935).
Salvato et al., "Virus-lymphocyte interactions. IV. Molecular characterization of LCMV Armstrong (CTL+) small genomic segment and that of its variant, Clone 13 (CTL-)," *Virology*, 164(2):517-522 (1988).
Sanchez et al., "Rescue of the prototypic Arenavirus LCMV entirely from plasmid," *Virology*, 350(2):370-380 (2006).
Schmidt et al., "Live-attenuated LCMV-based vector for active immunotherapy of HPV16+ cancer," poster presented at CIMT meeting, Sep. 2018.
Shanmugham et al., "Immunocapture Enzyme-Linked Immunosorbent Assay for Assessment of In Vitro Potency of Recombinant Hepatitis B Vaccines," *Clin. Vaccine Immunol.*, 17(8):1252-1260 (2010).
Shimojima et al., "Cell surface molecules involved in infection mediated by lymphocytic choriomeningitis virus glycoprotein," *J. Vet. Med. Sci.*, 74(1):1363-1366 (2012).
Shimojima et al., "Identification of cell surface molecules involved in dystroglycan-independent Lassa virus cell entry," *J. Virol.*, 86(4):2067-2078 (2012).
Stoute et al., "A preliminary evaluation of a recombinant circumsporozoite protein vaccine against plasmodium falciparum malaria," *N. Eng. J. Med.*, 336:86-91 (1997).
Suni et al., "Detection of antigen-specific T cell cytokine expression in whole blood by flow cytometry," *J. Immunol. Methods*, 212(1):89-98 (1998).
Tesh et al., "Field studies on the epidemiology of Venezuelan hemorrhagic fever: implication of the cotton rat *Sigmodon alstoni* as the probable rodent reservoir," *Am. J. Trop. Med. Hyg.*, 49(2):227-235 (1993).
Wright et al., "Congenital lymphocytic choriomeningitis virus syndrome: a disease that mimics congenital toxoplasmosis or Cytomegalovirus infection," *Pediatrics*, 100(1):E9 (1997).
Yadav et al., "Predicting immunogenic tumour mutations by combining mass spectrometry and exome sequencing," *Nature*, 515:572-576 (2014).
Zinkernagel, "Lymphocytic choriomeningitis virus and immunology," *Curr. Top. Microbiol. Immunol.*, 263:1-5 (2002).
U.S. Appl. No. 16/861,758, filed Apr. 29, 2020, Pinschewer et al.
U.S. Appl. No. 16/863,456, filed Apr. 30, 2020, Orlinger et al.
U.S. Appl. No. 16/922,489, filed Jul. 7, 2020, Pinschewer et al.
Horton et al., "The effects of MP virus infection in lymphoma," *Cancer Res.*, 31(8): 1066-1068 (1971).
Mettler et al., "Virus inoculation in mice bearing Ehrlich ascitic tumors: antigen production and tumor regression," *Infect. Immun.*, 37(1):23-27 (1982).
Molomut et al., "A Lymphocytopenic Filterable Agent Derived From Tissue Cell Cultures of Murine Carcinoma," *J. Natl. Cancer Inst.*, 34:403-413 (1965).
Molomut et al., "First Cautious Trial of MP Virus in Human Cancer Cases Reported," *Antibiotic News*, p. 5 (Jul.-Aug. 1968).
Molomut et al., "Immune recognition of tumor cells in mice infected with Pichinde virus," *Cancer Immunol. Immunother.*, 17(1):56-61 (1984).
Molomut et al., "Inhibition of a Transplantable Murine Leukaemia by a Lymphocytopenic Virus" *Nature*, 204:1003-1004 (1964).
Molomut et al., "Inhibition of transplantable and spontaneous murine tumours by the M-P virus," *Nature*, 208:948-950 (1965).
National Library of Medicine, "Unproven methods of cancer management: M-P virus," *CA: A Cancer Journal for Clinicians* 21.3:186-189 (1971).
Webb et al., "The treatment of 18 cases of malignant disease with an arenavirus," *Clin. Oncol.*, 1:157-169 (1975).
Webb, "Viruses in the treatment of cancer," *Lanet*, 1206-1208 (1970).
Bartkowiak et al., 2015, "Unique potential of 4-1BB agonist antibody to promote durable regression of HPV+ tumors when combined with an E6/E7 peptide vaccine", PNAS, E5290-E52999.
Hodi et al., 2010, "Improved Survival with Ipilimumab in Patients with Metastatic Melanoma", N Engl J Med, 363(8): 711-723.
Akbar et al., 2013, Heptatobiliary Pancreatic Dis. Int., 12(4): 363-369.
Beasley et al., "Overview on the Epidemiology of Hepatocellular Carcinoma," Viral Hepatitis and Liver Disease: Proceedings of the 1990 International Symposium on Viral Hepatitis and Liver Disease: Contemporary Issued and Future Prospects, Hollinger et al. eds., Williams & Wilkins, Baltimore MD, 532-535 (1991).
Boni et al., "Transient restoration of anti-viral T cell responses induced by lamivudine therapy in chronic hepatitis B," *J. Hepatol.*, 39:595-605 (2003).
Bourgine et al., "Optimization of immune responses induced by therapeutic vaccination with cross-reactive antigens in a humanized hepatitis B surface antigen transgenic mouse model," Virology, 430(1): 10-19 (2012).
Buchmeier et al., 1974, "Serological evidence of infection by Pichinde vims among laboratory workers," Infect Immun.,9(5):821-823.
Carter et al., "Characterization of Nucleic Acid of Pichinde Vims," J Viral., 11(1):61-68 (1973).
Chen et al., 2008, "Genomic and biological characterization of aggressive and docile strains of lymphocytic choriomeningitis virus rescued from a plasmidbased reverse-genetics system", J of Gen. Virology, vol. 89: 1421-1433.
Cines et al., "SARS-CoV-2 Vaccine-Induced Immune Thrombotic Thrombocytopenia," New England Journal of Medicine, doi: 10.1056/NEJMe2106315 (2021).
Couillin et al., "Specific vaccine therapy in chronic hepatitis B: induction of T cell proliferative responses specific for envelope antigens," J. Infect. Dis., 180:15-26 (1999).
De La Hoz et al., "Eight years of hepatitis B vaccination in Colombia with a recombinant vaccine: factors influencing hepatitis B virus infection and effectiveness," Int. J. Infet. Dis., 12:183-189 (2008).

(56) References Cited

OTHER PUBLICATIONS

Flick et al., 2001, "Reverse genetics system for Uukuniemi virus (Bunyaviridae): RNA polymerase I-catalyzed expression of chimeric viral RN As," J Viral., 75( 4): 1643-1655.
Goldstein et al., "A mathematical model to estimate global hepatitis B disease burden and vaccination impact," Int. J. Epidemiol., 34(6): 1329-1339 (2005).
Goldstein et al., "Incidence and risk factors for acute hepatitis B in the United States, 1982-1998: implications for vaccination programs," J. Infet. Dis., 185:713-719 (2002).
Grob et al., 1999, Role of the individual interferon systems and specific immunity in mice in controlling systemic dissemination of attenuated pseudorabies virus infection, J Viral., 73(6):4748-4754.
Guidotti et al., "High-level hepatitis B virus replication in transgenic mice," J. Virol., 69(10):6158-6169 (1995).
Hallam et al., "Review of Mammarenavirus Biology and Replication," Frontiers in Microbiology, 3(9):1751 (2018).
Hong et al., "Lentivector expressing HBsAg and immunoglobulin Fc fusion antigen induces potent immune responses and results in seroconversion in HBsAg transgenic mice," Vaccine, 29(22):3909-3916 (2011).
Horton et al., "The effects of MP vims infection in lymphoma," Cancer Res., 31(8): 1066-1068 (1971).
Huang et al., 2015, "In vitro and in vivo characterizations of pichinde viral nucleoprotein exoribonuclease functions", Journal of Virology, 89(13): 6595-6607.
Hyams, "Risks of chronicity following acute hepatitis B virus infection: a review," Clin. Infect. Dis., 20(4):992-1000 (1995).
Jenne et al., "Immune surveillance by the liver," Nat. Immunol., 14(10):996-1006 (2013).
Kalka Van et al., 2017, "Spatiotemporally restricted arenavirus replication induces immune surveillance and type I interferondeoendent tumour regression," Nat. Comm., 8: 14447.
Karwacz et al., "Nonintegrating Lentivector Vaccines Stimulate Prolonged T-Cell and Antibody Responses and Are Effective in Tumor Therapy," J. Virol., 83(7):3094-3103 (2009).
Kosinska et al., "Therapeutic vaccination in chronic hepatitis B: preclinical studies in the woodchuck," Hepat. Res. Treat., 2010:817580 (2010).
Lan et al., 2009, "Development of infectious clones for virulent and avirulent pichinde viruses: a model virus to study arenavirus-induced hemorrhagic fevers," J Viral., 83(13):6357-6362 (2009).
Liang et al., 2009, "Molecular determinants of Pichinde virus infection of guinea pigs—a small animal model system for arenaviral hemorrhagic fevers," Ann. N. Y. Acad. Sci., 11 71:E65-E7 4.
Liu et al., "New therapeutic vaccination strategies for the treatment of chronic hepatitis B," Virol. Sin., 29:10-16 (2014).
Margolis et al., "Prevention of hepatitis B virus transmission by immunization. An economic analysis of current recommendations," JAMA, 274(15):1201-1208 (1995).
Mayer et al., "Hepatitis B assays in scrum plasma and whole blood on filter paper," BMC Clin. Pathol., 12:8 (2012).
Mclay et al., 2014, "Comparative analysis of disease pathogenesis and molecular mechanisms of New World and Old World arenavirus infections," J Gen. Viral., 95:1-15.
Mendy et al., "Hepatitis B viral load and risk for liver cirrhosis and hepatocellular carcinoma in The Gambia, West Africa," J. Viral. Hepat., 17(2): 115-122 (2010).
Meyer et al., 1993, "Concurrent sequence analysis of 5' and 3' RNA termini by intramolecular circularization reveals 5' nontemplated bases and 3' terminal heterogeneity for lymphocytic choriomeningitis virus mRNAs", J Virol, 67(5): 2621-2627.
Michel et al., "Hepatitis B vaccines: protective efficacy and therapeutic potential," Pathol. Biol., 58:288-295 (2010).
Michel et al., "Therapeutic vaccines and immune-based therapies for the treatment of chronic hepatitis B: perspectives and challenges," J. Hepatol., 54:1286-1296 (2011).
Michel et al., "Therapeutic vaccines in treating chronic hepatitis B: the end of the beginning or the beginning of the end?," Med. Microbiol. Immunol., 204:121-129 (2015).
Moshkani et al., "A Highly Attenuated Vesicular Stomatitis Virus-Based Vaccine Platform Controls Hepatitis B Virus Replication in Mouse Models of Hepatitis B," J. Virol., 93(5): e01586 (2019).
Pai et al., "Vaccine-induced immune thrombotic thrombocytopenia (VITT) following adenovirus vector COVID-19 vaccination," Science Briefs of the Ontario COVID-19 Science Advisory Table 2(17) (2021).
Pinschewer et al., "Recombinant lymphocytic choriomeningitis virus expressing vesicular stomatitis virus glycoprotein," Proc. Natl. Acad. Sci. US.A., 100(13):7895-7900 (2003).
Pinschewer et al., "Recombinant lymphocytic choriomeningitis virus expressing vesicular stomatitis virus glycoprotein," Proc. Natl. Acad. Sci. US.A., 100(13):Supporting Figure 4 (2003).
Rapicetta et al., "New perspectives for hepatitis B vaccines and immunization," Vaccine, 27(25-26):3271-3275 (2009).
Remy-Ziller et al., "Immunological Characterization of a Modified Vaccinia Virus Ankara Vector Expressing the Human Papillomavirus 16 E1 Protein," Clinical and Vaccine Immunology, 21(2):147-155 (2014).
Ring et al., "Viral vector-mediated reprogramming of the fibroblastic tumor stroma sustains curative melanoma treatment," Nature Communications, 12:4734 (2012) (12 pages).
Sarute et al., "New World Arenavirus Biology," Annual Review of Virology, 4(1):141-158 (2017).
Schadler et al., 2014, "Immunosurveillance by antiangiogenesis: tumor growth arrest by T cell-derived thrombospondin-1", Cancer Research, 74(8): 2171-2181.
Stahl et al., 1989, Proc. Natl. Acad. Sci. USA, 86(16) 6283-6287.
Trapido et al., "Pichinde virus, a new virus of the Tacaribe group from Colombia," Am. J Trap. Med. Hy ., 20(4):631-641 (1971).
Van Helden et al., "Performance of hepatitis B assays on the Bayer ADVIA Centaur Immunoassay System," Clin. Lab., 50(1-2):63-73 (2004).
Villar et al., "Assessment of dried blood spot samples as a simple method for detection of hepatitis B virus markers," J. Med. Virol., 83(9):1522-1529 (2011).
WHO Informal Consultation: Development of Viral Vectored Vaccines for HIV, Malaria, Tuberculosis and other Indications Geneva, Oct. 1-2, 2013.
Wichgers et al., 2014, "Creation of Rift Valley fever viruses with four-segmented genomes reveals flexibility in bunyavirus genome packaging", J Virol., 88(1): 10883-10893.
Wingerath et al., "Recombinant LCMV Vectors Induce Protective Immunity following Homologous and Heterologous Vaccinations," Molecular Therapy, 25(ll):2533-2545 (2017).
Wong et al., "Prevention of the HBsAg carrier state in newborn infants of mothers who are chronic carriers of HBsAg and HBeAg by administration of hepatitis-B vaccine and hepatitis-B immunoglobulin. Double-blind randomised placebo-controlled study," Lancet, 1:921-926 (1984).
Xiong et al., 2009, "Genome Structures of Viruses", Chinese Journal of Disease Control & Prevention, 13(3): 362-366.
Opposition Brief filed on Apr. 16, 2021 in European Pat. App. No. 15794900.9 (26 pages).
International Search Report and Written Opinion dated Feb. 10, 2017 for PCT/EP2016/076668 (12 pages).
International Search Report dated Nov. 14, 2018 for PCT/EP2017/078149 (10 pages).

* cited by examiner

SEQUENCE LISTING

<160> NUMBER OF SEQ ID NOS: 22

<210> SEQ ID NO 1
<211> LENGTH: 7229
<212> TYPE: DNA
<213> ORGANISM: Artificial Sequence
<220> FEATURE:
<223> OTHER INFORMATION: Lymphocytic choriomeningitis virus (LCMV) clone
      13 segment L (GenBank: DQ361066.1)

<400> SEQUENCE: 1

```
gcgcaccggg gatcctaggc gtttagttgc gctgtttggt tgcacaactt tcttcgtgag      60
gctgtcagaa gtggacctgg ctgatagcga tgggtcaagg caagtccaga gaggagaaag     120
gcaccaatag tacaaacagg gccgaaatcc taccagatac cacctatctt ggccctttaa     180
gctgcaaatc ttgctggcag aaatttgaca gcttggtaag atgccatgac cactaccttt     240
gcaggcactg tttaaacctt ctgctgtcag tatccgacag gtgtcctctt tgtaaatatc     300
cattaccaac cagattgaag atatcaacag ccccaagctc tccacctccc tacgaagagt     360
aacaccgtcc ggccccggcc ccgacaaaca gcccagcaca agggaaccgc acgtcaccca     420
acgcacacag acacagcacc caacacagaa cacgcacaca cacacacaca cacacccaca     480
cgcacgcgcc cccaccaccg gggggcgccc ccccccgggg ggcggccccc cgggagcccg     540
ggcggagccc cacggagatg cccatcagtc gatgtcctcg gccaccgacc cgcccagcca     600
atcgtcgcag gacctcccct tgagtctaaa cctgcccccc actgtttcat acatcaaagt     660
gctcctagat ttgctaaaac aaagtctgca atccttaaag gcgaaccagt ctggcaaaag     720
cgacagtgga atcagcagaa tagatctgtc tatacatagt tcctggagga ttacacttat     780
ctctgaaccc aacaaatgtt caccagttct gaatcgatgc aggaagaggt tcccaaggac     840
atcactaatc ttttcatagc cctcaagtcc tgctagaaag actttcatgt ccttggtctc     900
cagcttcaca atgatatttt ggacaaggtt tcttccttca aaaagggcac ccatctttac     960
agtcagtggc acaggctccc actcaggtcc aactctctca aagtcaatag atctaatccc    1020
atccagtatt cttttggagc ccaacaactc aagctcaaga gaatcaccaa gtatcaaggg    1080
atcttccatg taatcctcaa actcttcaga tctgatatca aagacaccat cgttcacctt    1140
gaagacagag tctgtcctca gtaagtggag gcattcatcc aacattcttc tatctatctc    1200
acccttaaag aggtgagagc atgataaaag ttcagccaca cctggattct gtaattggca    1260
```

```
cctaaccaag aatatcaatg aaaatttcct taaacagtca gtattattct gattgtgcgt   1320
aaagtccact gaaattgaaa actccaatac ccctttgtg tagttgagca tgtagtccca   1380
cagatccttt aaggatttaa atgcctttgg gtttgtcagg ccctgcctaa tcaacatggc   1440
agcattacac acaacatctc ccattcggta agagaaccac ccaaaaccaa actgcaaatc   1500
attcctaaac ataggcctct ccacattttt gttcaccacc tttgagacaa atgattgaaa   1560
ggggcccagt gcctcagcac catcttcaga tggcatcatt tctttatgag gaaccatga    1620 aaaattgcct aatgtcctgg ttgttgcaac aaattctcga acaaatgatt caaaatacac   1680
ctgttttaag aagttcttgc agacatccct cgtgctaaca acaaattcat caaccagact   1740
ggagtcagat cgctgatgag aattggcaag gtcagaaaac agaacagtgt aatgttcatc   1800
ccttttccac ttaacaacat gagaaatgag tgacaaggat tctgagttaa tatcaattaa   1860
aacacagagg tcaaggaatt taattctggg actccacctc atgtttttg agctcatgtc    1920 agacataaat ggaagaagct gatcctcaaa gatcttggga tatagccgcc tcacagattg   1980
aatcacttgg ttcaaattca ctttgtcctc cagtagcctt gagctctcag gctttcttgc   2040
tacataatca catgggttta agtgcttaag agttaggttc tcactgttat tcttcccttt   2100
ggtcggttct gctaggaccc aaacacccaa ctcaaaagag ttgctcaatg aaatacaaat   2160
gtagtcccaa agaagaggcc ttaaaaggca tatatgatca cggtgggctt ctggatgaga   2220
ctgtttgtca caaatgtaca gcgttatacc atcccgattg caaactcttg tcacatgatc   2280
atctgtggtt agatcctcaa gcagcttttt gatatacaga ttttccctat ttttgtttct   2340
cacacacctg cttcctagag ttttgcaaag gcctataaag ccagatgaga tacaactctg   2400
gaaagctgac ttgttgattg cttctgacag cagcttctgt gcaccccttg tgaatttact   2460
acaaagtttg ttctggagtg tcttgatcaa tgatgggatt cttctcctctt ggaaagtcat  2520 cactgatgga taaaccacct tttgtcttaa aaccatcctt aatgggaaca tttcattcaa   2580
attcaaccag ttaacatctg ctaactgatt cagatcttct tcaagaccga ggaggtctcc   2640
caattgaaga atggcctcct ttttatctct gttaaatagg tctaagaaaa attcttcatt   2700 aaattccacca tttttgagct tatgatgcag tttccttaca agctttctta caaccttgt   2760 ttcattagga cacagttcct caatgagtct ttgtattctg taacctctag aaccatccag   2820
ccaatctttc acatcagtgt tggtattcag tagaaatgga tccaaaggga aattggcata   2880
ctttaggagg tccagtgttc tccttttggat actattaact agggagactg ggacgccatt   2940
tgcgatggct tgatctgcaa ttgtatctat tgtttcacaa agttgatgtg gctcttaca    3000 cttgacattg tgtagcgctg cagatacaaa cttttgtgaga agggactt cctcccccca    3060 tacatagaat ctagattaa attctgcagc gaacctccca gccacacttt tgggctgat     3120 aaatttgttt aacaagccgc tcagatgaga ttggaattcc aacaggacaa ggacttcctc   3180
cggatcactt acaaccaggt cactcagcct cctatcaaat aaagtgatct gatcatcact   3240
tgatgtgtaa gcctctggtc tttcgccaaa gataacacca atgcagtagt tgatgaacct   3300
ctcgctaagc aaaccataga agtcagaagc attatgcaag attccctgcc ccatatcaat   3360
aaggctggat atatgggatg gcactatccc cattcaaaa tattgtctga aaattctctc   3420
agtaacagtt gtttctgaac ccctgagaag ttttagcttc gacttgacat atgatttcat   3480
cattgcattc acaacaggaa aggggacctc gacaagctta tgcatgtgcc aagttaacaa   3540
agtgctaaca tgatctttcc cggaacgcac atactggtca tcacctagtt tgagattttg   3600
tagaaacatt aagaacaaaa atgggcacat cattggtccc catttgctgt gatccatact   3660
```

```
atagtttaag aacccttccc gcacattgat agtcattgac aagattgcat tttcaaattc    3720
cttatcattg tttaaacagg agcctgaaaa gaaacttgaa aaagactcaa aataatcttc    3780
tattaacctt gtgaacattt ttgtcctcaa atctccaata tagagttctc tatttccccc    3840
aacctgctct ttataagata gtgcaaattt cagccttcca gagtcaggac ctactgaggt    3900
gtatgatgtt ggtgattctt ctgagtagaa gcacagattt ttcaaagcag cactcataca    3960
ttgtgtcaac gacagagctt tactaaggga ctcagaatta cttcccctct cactgattct    4020
cacgtcttct tccagtttgt cccagtcaaa tttgaaattc aagccttgcc tttgcatatg    4080
cctgtatttc cctgagtacg catttgcatt catttgcaac agaatcatct tcatgcaaga    4140
aaaccaatca ttctcagaaa agaacttcct acaaggtttt tttgccatct catcgaggcc    4200
acactgatct ttaatgactg aggtgaaata caaaggtgac agctctgtgg aaccctcaac    4260
agcctcacag ataaatttca tgtcatcatt ggttagacat gatgggtcaa agtcttctac    4320
taaatggaaa gatatttctg acaagataac ttttcttaag tgagccatct tccctgttag    4380
aataagctgt aaatgatgta gtccttttgt atttgtaagt ttttctccat ctcctttgtc    4440
attggccctc ctacctcttc tgtaccgtgc tattgtggtg ttgacctttt cttcgagact    4500
tttgaagaag cttgtctctt cttctccatc aaaacatatt tctgccaggt tgtcttccga    4560
tctccctgtc tcttctccct tggaaccgat gaccaatcta gagactaact tggaaacttt    4620
atattcatag tctgagtggc tcaacttata cttttgtttt cttacgaaac tctccgtaat    4680
ttgactcaca gcactaacaa gcaatttgtt aaagtcatat tccagaagtc gttctccatt    4740
tagatgctta ttaaccacca cacttttgtt actagcaaga tctaatgctg tcgcacatcc    4800
agagttagtc atgggatcta ggctgtttag cttcttctct cctttgaaaa ttaaagtgcc    4860
gttgttaaat gaagacacca ttaggctaaa ggcttccaga ttaacacctg gagttgtatg    4920
ctgacagtca atttctttac tagtgaatct cttcatttgc tcatagaaca cacattcttc    4980
ctcaggagtg attgcttcct tggggttgac aaaaaaacca aattgacttt tgggctcaaa    5040
gaacttttca aaacattta tctgatctgt tagcctgtca ggggtctcct ttgtgatcaa    5100
atgacacagg tatgacacat tcaacataaa tttaaatttt gcactcaaca acaccttctc    5160
accagtacca aaaatagttt ttattaggaa tctaagcagc ttatacacca ccttctcagc    5220
aggtgtgatc agatcctccc tcaacttatc cattaatgat gtagatgaaa aatctgacac    5280
tattgccatc accaaatatc tgacactctg tacctgcttt tgatttctct ttgttgggtt    5340
ggtgagcatt agcaacaata gggtcctcag tgcaacctca atgtcggtga cagtctttt    5400 caaatcagga catgatctaa tccatgaaat catgatgtct atcatattgt ataagacctc    5460
atctgaaaaa attggtaaaa agaacctttt aggatctgca tagaaggaaa ttaaatgacc    5520
atccgggcct tgtatggagt agcaccttga agattctcca gtcttctggt ataataggtg    5580
gtattcttca gagtccagtt ttattacttg gcaaaacact tctttgcatt ctaccacttg    5640
atatctcaca gaccctattt gattttgcct tagtctagca actgagctag ttttcatact    5700
gtttgttaag gccagacaaa cagatgataa tcttctcagg ctctgtatgt tcttcagctg    5760
ctctgtgctg ggttggaaat tgtaatcttc aaacttcgta taatacatta tcgggtgagc    5820
tccaattttc ataaagttct caaattcagt gaatggtatg tggcattctt gctcaaggtg    5880
ttcagacagt ccgtaatgct cgaaactcag tcccaccact aacaggcatt tttgaatttt    5940
tgcaatgaac tcactaatag atgccctaaa caattcctca aaagacacct ttctaaacac    6000
```

```
ctttgacttt tttctattcc tcaaaagtct aatgaactcc tctttagtgc tgtgaaagct    6060
taccagccta tcattcacac tactatagca acaacccacc cagtgtttat cattttttaa    6120
cccctttgaat ttcgactgtt ttatcaatga ggaaagacac aaaacatcca gatttaacaa   6180
ctgtctcctt ctagtattca acagtttcaa actcttgact ttgtttaaca tagagaggag    6240
cctctcatat tcagtgctag tctcacttcc cctttcgtgc ccatgggtct ctgcagttat    6300
gaatctcatc aaaggacagg attcgactgc ctccctgctt aatgttaaga tatcatcact    6360
atcagcaagg ttttcataga gctcagagaa ttccttgatc aagccttcag ggtttacttt    6420
ctgaaagttt ctctttaatt tcccactttc taaatctctt ctaaacctgc tgaaaagaga    6480
gtttattcca aaaccacat catcacagct catgttgggg ttgatgcctt cgtggcacat     6540
cctcataatt tcatcattgt gagttgacct cgcatctttc agaattttca tagagtccat    6600
accggagcgc ttgtcgatag tagtcttcag ggactcacag agtctaaaat attcagactc    6660
ttcaaagact ttctcatttt ggttagaata ctccaaaagt ttgaataaaa ggtctctaaa    6720
tttgaagttt gcccactctg gcataaaact attatcataa tcacaacgac catctactat    6780
tggaactaat gtgacacccg caacagcaag gtcttccctg atgcatgcca atttgttagt    6840
gtcctctata aatttcttct caaaactggc tggagtgctc ctaacaaaac actcaagaag    6900
aatgagagaa ttgtctatca gcttgtaacc atcaggaatg ataagtggta gtcctgggca    6960
tacaattcca gactccacca aaattgtttc cacagactta tcgtcgtggt tgtgtgtgca    7020
gccactcttg tctgcactgt ctatttcaat gcagcgtgac agcaacttga gtccctcaat    7080
cagaaccatt ctgggttccc tttgtcccag aaagttgagt ttctgccttg acaacctctc    7140
atcctgttct atatagttta aacataactc tctcaattct gagatgattt catccattgc    7200
gcatcaaaaa gcctaggatc ctcggtgcg                                       7229
```

<210> SEQ ID NO 2
<211> LENGTH: 3376
<212> TYPE: DNA
<213> ORGANISM: Artificial Sequence
<220> FEATURE:
<223> OTHER INFORMATION: Lymphocytic choriomeningitis virus (LCMV)
      segment S

<400> SEQUENCE: 2

```
cgcaccgggg atcctaggct ttttggattg cgctttcctc tagatcaact gggtgtcagg     60
ccctatccta cagaaggatg ggtcagattg tgacaatgtt tgaggctctg cctcacatca    120
tcgatgaggt gatcaacatt gtcattattg tgcttatcgt gatcacgggt atcaaggctg    180
tctacaattt tgccacctgt gggatattcg cattgatcag tttcctactt ctggctggca    240
ggtcctgtgg catgtacggt cttaagggac ccgacattta caaggagtt taccaattta    300
agtcagtgga gtttgatatg tcacatctga acctgaccat gcccaacgca tgttcagcca    360
acaactccca ccattacatc agtatgggga cttctggact agaattgacc ttcaccaatg    420
attccatcat cagtcacaac ttttgcaatc tgacctctgc cttcaacaaa aagacctttg    480
accacacact catgagtata gtttcgagcc tacacctcag tatcagaggg aactccaact    540
ataaggcagt atcctgcgac ttcaacaatg gcataaccat ccaatacaac ttgacattct    600
cagatcgaca aagtgctcag agccagtgta gaaccttcag aggtagagtc ctagatatgt    660
ttagaactgc cttcggggg aaaatacatga ggagtggctg gggctggaca ggctcagatg    720
gcaagaccac ctggtgtagc cagacgagtt accaatacct gattatacaa aatagaacct    780
```

-continued

```
gggaaaaacca ctgcacatat gcaggtcctt ttgggatgtc caggattctc ctttcccaag      840
agaagactaa gttcttcact aggagactag cgggcacatt cacctggact ttgtcagact      900
cttcagggt ggagaatcca ggtggttatt gcctgaccaa atggatgatt cttgctgcag       960
agcttaagtg tttcgggaac acagcagttg cgaaatgcaa tgtaaatcat gatgccgaat     1020
tctgtgacat gctgcgacta attgactaca acaaggctgc tttgagtaag ttcaaagagg     1080
acgtagaatc tgccttgcac ttattcaaaa caacagtgaa ttctttgatt tcagatcaac     1140
tactgatgag gaaccacttg agagatctga tgggggtgcc atattgcaat tactcaaagt     1200
tttggtacct agaacatgca aagaccggcg aaactagtgt ccccaagtgc tggcttgtca     1260
ccaatggttc ttacttaaat gagacccact tcagtgatca aatcgaacag gaagccgata     1320
acatgattac agagatgttg aggaaggatt acataaagag gcaggggagt acccccctag     1380
cattgatgga ccttctgatg ttttccacat ctgcatatct agtcagcatc ttcctgcacc     1440
ttgtcaaaat accaacacac aggcacataa aaggtggctc atgtccaaag ccacaccgat     1500
taaccaacaa aggaatttgt agttgtggtg catttaaggt gcctggtgta aaaaccgtct     1560
ggaaaagacg ctgaagaaca gcgcctccct gactctccac ctcgaaagag gtggagagtc     1620
agggaggccc agagggtctt agagtgtcac aacatttggg cctctaaaaa ttaggtcatg     1680
tggcagaatg ttgtgaacag ttttcagatc tgggagcctt gctttggagg cgctttcaaa     1740
aatgatgcag tccatgagtg cacagtgcgg ggtgatctct ttcttctttt tgtcccttac     1800
tattccagta tgcatcttac acaaccagcc atatttgtcc cacactttgt cttcatactc     1860
cctcgaagct tccctggtca tttcaacatc gataagctta atgtccttcc tattctgtga     1920
gtccagaagc tttctgatgt catcggagcc ttgacagctt agaaccatcc cctgcggaag     1980
agcacctata actgacgagg tcaacccggg ttgcgcattg aagaggtcgg caagatccat     2040
gccgtgtgag tacttggaat cttgcttgaa ttgtttttga tcaacgggtt ccctgtaaaa     2100
gtgtatgaac tgcccgttct gtggttggaa aattgctatt tccactggat cattaaatct     2160
accctcaatg tcaatccatg taggagcgtt ggggtcaatt cctcccatga ggtctttaa      2220
aagcattgtc tggctgtagc ttaagcccac ctgaggtgga cctgctgctc caggcgctgg     2280
cctgggtgaa ttgactgcag gtttctcgct tgtgagatca attgttgtgt tttcccatgc     2340
tctccccaca atcgatgttc tacaagctat gtatggccat ccttcacctg aaaggcaaac     2400
tttatagagg atgttttcat aagggttcct gtccccaact tggtctgaaa caaacatgtt     2460
gagttttctc ttggccccga gaactgcctt caagaggtcc tcgctgttgc ttggcttgat     2520
caaaattgac tctaacatgt taccccccatc caacagggct gccccctgcct tcacggcagc     2580
accaagacta aagttatagc cagaaatgtt gatgctggac tgctgttcag tgatgacccc     2640
cagaactggg tgcttgtctt tcagcctttc aagatcatta agatttggat acttgactgt     2700
gtaaagcaag ccaaggtctg tgagcgcttg tacaacgtca ttgagcggag tctgtgactg     2760
tttggccata caagccatag ttagacttgg cattgtgcca aattgattgt tcaaaagtga     2820
tgagtctttc acatcccaaa ctcttaccac accacttgca ccctgctgag gctttctcat     2880
cccaactatc tgtaggatct gagatctttg gtctagttgc tgtgttgtta agttccccat     2940
atataccccct gaagcctggg gcctttcaga cctcatgatc ttggccttca gcttctcaag     3000
gtcagccgca agagacatca gttcttctgc actgagcctc cccactttca aaacattctt     3060
ctttgatgtt gactttaaat ccacaagaga atgtacagtc tggttgagac ttctgagtct     3120
ctgtaggtct ttgtcatctc tcttttcctt cctcatgatc ctctgaacat tgctgacctc     3180
```

```
agagaagtcc aacccattca gaaggttggt tgcatcctta atgacagcag ccttcacatc    3240
tgatgtgaag ctctgcaatt ctcttctcaa tgcttgcgtc cattggaagc tcttaacttc    3300
cttagacaag gacatcttgt tgctcaatgg tttctcaaga caaatgcgca atcaaatgcc    3360
taggatccac tgtgcg                                                    3376

<210> SEQ ID NO 3
<211> LENGTH: 3377
<212> TYPE: DNA
<213> ORGANISM: Artificial Sequence
<220> FEATURE:
<223> OTHER INFORMATION: Lymphocytic choriomeningitis virus (LCMV) clone
      13 segment S (GenBank: DQ361065.2)

<400> SEQUENCE: 3
gcgcaccggg gatcctaggc tttttggatt gcgctttcct ctagatcaac tgggtgtcag      60
gccctatcct acagaaggat gggtcagatt gtgacaatgt ttgaggctct gcctcacatc     120
atcgatgagg tgatcaacat tgtcattatt gtgcttatcg tgatcacggg tatcaaggct     180
gtctacaatt ttgccacctg tgggatattc gcattgatca gtttcctact tctggctggc     240
aggtcctgtg gcatgtacgg tcttaaggga cccgacattt acaaaggagt ttaccaattt     300
aagtcagtgg agtttgatat gtcacatctg aacctgacca tgcccaacgc atgttcagcc     360
aacaactccc accattacat cagtatgggg acttctggac tagaattgac cttcaccaat     420
gattccatca tcagtcacaa cttttgcaat ctgacctctg ccttcaacaa aaagaccttt     480
gaccacacac tcatgagtat agtttcgagc ctacacctca gtatcagagg gaactccaac     540
tataaggcag tatcctgcga cttcaacaat ggcataacca tccaatacaa cttgacattc     600
tcagatgcac aaagtgctca gagccagtgt agaaccttca gaggtagagt cctagatatg     660
tttagaactg ccttcggggg gaaatacatg aggagtggct ggggctggac aggctcagat     720
ggcaagacca cctggtgtag ccagacgagt taccaatacc tgattataca aaatagaacc     780
tgggaaaacc actgcacata tgcaggtcct ttgggatgt ccaggattct cctttcccaa     840
gagaagacta agttcctcac taggagacta gcgggcacat tcacctggac tttgtcagac     900
tcttcagggg tggagaatcc aggtggttat tgcctgacca atggatgat tcttgctgca     960 gagcttaagt gtttcgggaa cacagcagtt gcgaaatgca atgtaaatca tgatgaagaa    1020
ttctgtgaca tgctgcgact aattgactac aacaaggctg ctttgagtaa gttcaaagag    1080
gacgtagaat ctgccttgca cttattcaaa acaacagtga attctttgat ttcagatcaa    1140
ctactgatga ggaaccactt gagagatctg atgggggtgc atattgcaa ttactcaaag    1200 ttttggtacc tagaacatgc aaagaccggc gaaactagtg tccccaagtg ctggcttgtc    1260
accaatggtt cttacttaaa tgagacccac ttcagtgacc aaatcgaaca ggaagccgat    1320
aacatgatta cagagatgtt gaggaaggat tacataaaga gcagggggag tacccccta    1380 gcattgatgg accttctgat gttttccaca tctgcatatc tagtcagcat cttcctgcac    1440
cttgtcaaaa taccaacaca caggcacata aaaggtggct catgtccaaa gccacaccga    1500
ttaaccaaca aaggaattg tagttgtggt gcatttaagg tgcctggtgt aaaaaccgtc    1560
tggaaaagac gctgaagaac agcgcctccc tgactctcca cctcgaaaga ggtggagagt    1620
cagggaggcc cagagggtct tagagtgtca caacatttgg gcctctaaaa attaggtcat    1680
gtggcagaat gttgtgaaca gttttcagat ctggagcct tgcttggag cgctttcaa    1740 aaatgatgca gtccatgagt gcacagtgcg gggtgatctc tttcttcttt ttgtccctta    1800
```

```
ctattccagt atgcatctta cacaaccagc catatttgtc ccacactttg tcttcatact   1860
ccctcgaagc ttccctggtc atttcaacat cgataagctt aatgtccttc ctattctgtg   1920
agtccagaag ctttctgatg tcatcggagc cttgacagct tagaaccatc cctgcggaa    1980 gagcacctat aactgacgag gtcaacccgg gttgcgcatt gaagaggtcg gcaagatcca   2040
tgccgtgtga gtacttggaa tcttgcttga attgtttttg atcaacgggt tccctgtaaa   2100
agtgtatgaa ctgcccgttc tgtggttgga aaattgctat ttccactgga tcattaaatc   2160
taccctcaat gtcaatccat gtaggagcgt tggggtcaat tcctcccatg aggtctttta   2220
aaagcattgt ctggctgtag cttaagccca cctgaggtgg acctgctgct ccaggcgctg   2280
gcctgggtga attgactgca ggtttctcgc ttgtgagatc aattgttgtg ttttcccatg   2340
ctctccccac aatcgatgtt ctacaagcta tgtatggcca tccttcacct gaaaggcaaa   2400
ctttatagag gatgttttca taagggttcc tgtccccaac ttggtctgaa acaaacatgt   2460
tgagttttct cttggccccg agaactgcct tcaagaggtc ctcgctgttg cttggcttga   2520
tcaaaattga ctctaacatg ttacccccat ccaacagggc tgcccctgcc ttcacggcag   2580
caccaagact aaagttatag ccagaaatgt tgatgctgga ctgctgttca gtgatgaccc   2640
ccagaactgg gtgcttgtct ttcagccttt caagatcatt aagatttgga tacttgactg   2700
tgtaaagcaa gccaaggtct gtgagcgctt gtacaacgtc attgagcgga gtctgtgact   2760
gtttggccat acaagccata gttagacttg gcattgtgcc aaattgattg ttcaaaagtg   2820
atgagtcttt cacatcccaa actcttacca caccacttgc accctgctga ggctttctca   2880
tcccaactat ctgtaggatc tgagatcttt ggtctagttg ctgtgttgtt aagttcccca   2940
tatatacccc tgaagcctgg ggcctttcag acctcatgat cttggccttc agcttctcaa   3000
ggtcagccgc aagagacatc agttcttctg cactgagcct ccccactttc aaaacattct   3060
tctttgatgt tgactttaaa tccacaagag aatgtacagt ctggttgaga cttctgagtc   3120
tctgtaggtc tttgtcatct ctcttttcct tcctcatgat cctctgaaca ttgctgacct   3180
cagagaagtc caacccattc agaaggttgg ttgcatcctt aatgacagca gccttcacat   3240
ctgatgtgaa gctctgcaat tctcttctca atgcttgcgt ccattggaag ctcttaactt   3300
ccttagacaa ggacatcttg ttgctcaatg gtttctcaag acaaatgcgc aatcaaatgc   3360
ctaggatcca ctgtgcg                                                  3377
```

<210> SEQ ID NO 4
<211> LENGTH: 7205
<212> TYPE: DNA
<213> ORGANISM: Artificial Sequence
<220> FEATURE:
<223> OTHER INFORMATION: Lymphocytic choriomeningitis strain MP segment L

<400> SEQUENCE: 4

```
gcgcaccggg gatcctaggc atttttgttg cgcattttgt tgtgttattt gttgcacagc     60
ccttcatcgt gggaccttca caaacaaacc aaaccaccag ccatgggcca aggcaagtcc    120
aaagagggaa gggatgccag caatacgagc agagctgaaa ttctgccaga caccacctat    180
ctcggacctc tgaactgcaa gtcatgctgg cagagatttg acagtttagt cagatgccat    240
gaccactatc tctgcagaca ctgcctgaac ctcctgctgt cagtctccga caggtgccct    300
ctctgcaaac atccattgcc aaccaaactg aaaatatcca cggccccaag ctctccaccc    360
ccttacgagg agtgacgccc cgagccccaa caccgacaca aggaggccac caacacaacg    420
```

```
cccaacacgg aacacacaca cacacaccca cacacacatc cacacacacg cgcccccaca    480 acggggcgc ccccccgggg gtggcccccc gggtgctcgg gcggagcccc acggagaggc    540
caattagtcg atctcctcga ccaccgactt ggtcagccag tcatcacagg acttgccctt    600
aagtctgtac ttgcccacaa ctgtttcata catcaccgtg ttctttgact tactgaaaca    660
tagcctacag tctttgaaag tgaaccagtc aggcacaagt gacagcggta ccagtagaat    720
ggatctatct atacacaact cttggagaat tgtgctaatt tccgacccct gtagatgctc    780
accagttctg aatcgatgta gaagaaggct cccaaggacg tcatcaaaat ttccataacc    840
ctcgagctct gccaagaaaa ctctcatatc cttggtctcc agtttcacaa cgatgttctg    900
aacaaggctt cttccctcaa aaagagcacc cattctcaca gtcaagggca caggctccca    960
ttcaggccca atcctctcaa atcaaggga tctgatcccg tccagtattt tccttgagcc   1020
tatcagctca agctcaagag agtcaccgag tatcaggggg tcctccatat agtcctcaaa   1080
ctcttcagac ctaatgtcaa aaacaccatc gttcaccttg aagatagagt ctgatctcaa   1140
caggtggagg cattcgtcca agaaccttct gtccacctca cctttaaaga ggtgagagca   1200
tgataggaac tcagctacac ctggaccttg taactggcac ttcactaaaa agatcaatga   1260
aaacttcctc aaacaatcag tgttattctg gttgtgagtg aaatctactg taattgagaa   1320
ctctagcact ccctctgtat tatttatcat gtaatcccac aagtttctca agacttgaa   1380 tgcctttgga tttgtcaagc cttgtttgat tagcatggca gcattgcaca caatatctcc   1440
caatcggtaa gagaaccatc caaatccaaa ttgcaagtca ttcctaaaca tgggcctctc   1500 catattttg ttcactactt ttaagatgaa tgattggaaa ggccccaatg cttcagcgcc   1560
atcttcagat ggcatcatgt ctttatgagg gaaccatgaa aaacttccta gagttctgct   1620
tgttgctaca aattctcgta caaatgactc aaaatacact tgtttaaaa agtttttgca   1680 gacatccctt gtactaacga caaattcatc aacaaggctt gagtcagagc gctgatggga   1740
atttacaaga tcagaaaata gaacagtgta gtgttcgtcc ctcttccact taactacatg   1800
agaaatgagc gataaagatt ctgaattgat atcgatcaat acgcaaaggt caaggaattt   1860
gattctggga ctccatctca tgtttttga gctcatatca gacatgaagg gaagcagctg   1920
atcttcatag attttagggt acaatcgcct cacagattgg attacatggt ttaaacttat   1980
cttgtcctcc agtagccttg aactctcagg cttccttgct acataatcac atgggttcaa   2040
gtgcttgagg cttgagcttc cctcattctt cccctttcaca ggttcagcta agacccaaac   2100
acccaactca aaggaattac tcagtgagat gcaaatatag tcccaaagga ggggcctcaa   2160
gagactgatg tggtcgcagt gagcttctgg atgactttgc ctgtcacaaa tgtacaacat   2220
tatgccatca tgtctgtgga ttgctgtcac atgcgcatcc atagctagat cctcaagcac   2280
ttttctaatg tatagattgt ccctattttt atttctcaca catctacttc ccaaagtttt   2340
gcaaagacct ataagcctg atgagatgca actttgaaag gctgacttat tgattgcttc   2400
tgacagcaac ttctgtgcac ctcttgtgaa cttactgcag agcttgttct ggagtgtctt   2460
gattaatgat gggattcttt cctcttggaa agtcattact gatggataaa ccactttctg   2520
cctcaagacc attcttaatg ggaacaactc attcaaattc agccaattta tgtttgccaa   2580
ttgacttaga tcctcttcga ggccaaggat gtttcccaac tgaagaatgg cttccttttt   2640
atccctattg aagaggtcta agaagaattc ttcattgaac tcaccattct tgagcttatg   2700
atgtagtctc cttacaagcc ttctcatgac cttcgtttca ctaggacaca attcttcaat   2760
```

```
aagcctttgg attctgtaac ctctagagcc atccaaccaa tccttgacat cagtattagt   2820
gttaagcaaa aatgggtcca agggaaagtt ggcatatttt aagaggtcta atgttctctt   2880
ctggatgcag tttaccaatg aaactggaac accatttgca acagcttgat cggcaattgt   2940
atctattgtt tcacagagtt ggtgtggctc tttacactta acgttgtgta atgctgctga   3000
cacaaatttt gttaaaagtg ggacctcttc cccccacaca taaaatctgg atttaaattc   3060
tgcagcaaat cgccccacca cacttttcgg actgatgaac ttgttaagca agccactcaa   3120
atgagaatga aattccagca atacaaggac ttcctcaggg tcactatcaa ccagttcact   3180
caatctccta tcaaataagg tgatctgatc atcacttgat gtgtaagatt ctggtctctc   3240
accaaaaatg acaccgatac aataattaat gaatctctca ctgattaagc cgtaaaagtc   3300
agaggcatta tgtaagattc cctgtcccat gtcaatgaga ctgcttatat gggaaggcac   3360
tattcctaat tcaaatatt ctcgaaagat tctttcagtc acagttgtct ctgaaccccct   3420 aagaagtttc agctttgatt tgatatatga tttcatcatt gcattcacaa caggaaaagg   3480
gacctcaaca agtttgtgca tgtgccaagt taataaggtg ctgatatgat cctttccgga   3540
acgcacatac tggtcatcac ccagtttgag attttgaagg agcattaaaa acaaaaatgg   3600
gcacatcatt ggcccccatt tgctatgatc catactgtag ttcaacaacc cctctcgcac   3660
attgatggtc attgatagaa ttgcattttc aaattctttg tcattgttta agcatgaacc   3720
tgagaagaag ctagaaaaag actcaaaata atcctctatc aatcttgtaa acattttgt    3780 tctcaaatcc ccaatataaa gttctctgtt tcctccaacc tgctctttgt atgataacgc   3840
aaacttcaac cttccggaat caggaccaac tgaagtgtat gacgttggtg actcctctga   3900
gtaaaaacat aaattcttta agcagcact catgcatttt gtcaatgata gagccttact    3960
tagagactca gaattacttt ccctttcact aattctaaca tcttcttcta gtttgtccca   4020
gtcaaacttg aaattcagac cttgtctttg catgtgcctg tatttccctg agtatgcatt   4080
tgcattcatt tgcagtagaa tcattttcat acacgaaaac caatcaccct ctgaaaaaaa   4140
cttcctgcag aggttttttg ccatttcatc cagaccacat tgttctttga cagctgaagt   4200
gaaatacaat ggtgacagtt ctgtagaagt ttcaatagcc tcacagataa atttcatgtc   4260
atcattggtg agacaagatg ggtcaaaatc ttccacaaga tgaaaagaaa tttctgataa   4320
gatgaccttc cttaaatatg ccattttacc tgacaatata gtctgaaggt gatgcaatcc   4380 ttttgtatt tcaaccccca cctcatttt cccttcattg gtcttcttgc ttctttcata     4440
ccgctttatt gtggagttga ccttatcttc taaattcttg aagaaacttg tctcttcttc   4500
cccatcaaag catatgtctg ctgagtcacc ttctagtttc ccagcttctg tttctttaga   4560
gccgataacc aatctagaga ccaactttga aaccttgtac tcgtaatctg agtggttcaa   4620
tttgtacttc tgctttctca tgaagctctc tgtgatctga ctcacagcac taacaagcaa   4680
tttgttaaaa tcatactcta ggagccgttc cccatttaaa tgtttgttaa caaccacact   4740
tttgttgctg gcaaggtcta atgctgttgc acacccagag ttagtcatgg gatccaagct   4800
attgagcctc ttctcccctt tgaaaatcaa agtgccattg ttgaatgagg acaccatcat   4860
gctaaaggcc tccagattga cacctggggt tgtgcgctga cagtcaactt ctttcccagt   4920
gaacttcttc atttggtcat aaaaaacaca ctcttcctca ggggtgattg actctttagg   4980
gttaacaaag aagccaaact cacttttagg ctcaaagaat ttctcaaagc atttaatttg   5040
atctgtcagc ctatcagggg tttccttttgt gattaaatga cacaggtatg acacattcaa   5100
catgaacttg aactttgcgc tcaacagtac cttttcacca gtcccaaaaa cagttttgat   5160
```

-continued

```
caaaaatctg agcaatttgt acactacttt ctcagcaggt gtgatcaaat cctccttcaa    5220
cttgtccatc aatgatgtgg atgagaagtc tgagacaatg ccatcacta ataccctaat    5280 gttttgaacc tgttttgat cctctttgt tgggttggtg agcatgagta ataatagggt     5340
tctcaatgca atctcaacat catcaatgct gtccttcaag tcaggacatg atctgatcca    5400
tgagatcatg gtgtcaatca tgttgtgcaa cacttcatct gagaagattg gtaaaagaa    5460 cctttttggg tctgcataaa aagagattag atggccattg ggaccttgta tagaataaca    5520
ccttgaggat tctccagtct tttgatacag caggtgatat tcctcagagt ccaattttat    5580
cacttggcaa aatacctctt tacattccac cacttgatac cttacagagc caattggtt    5640 ttgtcttaat ctagcaactg aacttgtttt catactgttt gtcaaagcta gacagacaga    5700
tgacaatctt ttcaaactat gcatgttcct taattgttcc gtattaggct ggaaatcata    5760
atcttcaaac tttgtataat acattatagg atgagttccg gacctcatga aattctcaaa    5820
ctcaataaat ggtatgtggc actcatgctc aagatgttca gacagaccat agtgcccaaa    5880
actaagtccc accactgaca agcacctttg aacttttaaa atgaactcat ttatggatgt    5940
tctaaacaaa tcctcaagag ataccttct atacgccttt gactttctcc tgttccttag    6000
aagtctgatg aactcttcct tggtgctatg aaagctcacc aacctatcat tcacactccc    6060
atagcaacaa ccaacccagt gcttatcatt ttttgaccct ttgagtttag actgtttgat    6120
caacgaagag agacacaaga catccaaatt cagtaactgt ctccttctgg tgttcaataa    6180
ttttaaactt ttaactttgt tcaacataga gaggagcctc tcatactcag tgctagtctc    6240
acttcctctc tcataaccat gggtatctgc tgtgataaat ctcatcaaag acaggattc    6300 aactgcctcc ttgcttagtg ctgaaatgtc atcactgtca gcaagagtct cataaagctc    6360
agagaattcc ttaattaaat ttccggggtt gattttctga aaactcctct tgagcttccc    6420
agtttccaag tctcttctaa acctgctgta aagggagttt atgccaagaa ccacatcatc    6480
gcagttcatg tttgggttga caccatcatg gcacattttc ataatttcat cattgtgaaa    6540
tgatcttgca tctttcaaga ttttcataga gtctataccg gaacgcttat caacagtggt    6600
cttgagagat tcgcaaagtc tgaagtactc agattcctca aagactttct catcttggct    6660
agaatactct aaaagtttaa acagaaggtc tctgaacttg aaattcaccc actctggcat    6720
aaagctgtta tcataatcac accgaccatc cactattggg accaatgtga tacccgcaat    6780
ggcaaggtct tctttgatac aggctagttt attggtgtcc tctataaatt tcttctcaaa    6840
actagctggt gtgcttctaa cgaagcactc aagaagaatg agggaattgt caatcagttt    6900
ataaccatca ggaatgatca aaggcagtcc cgggcacaca atcccagact ctattagaat    6960
tgcctcaaca gatttatcat catggttgtg tatgcagccg ctcttgtcag cactgtctat    7020
ctctatacaa cgcgacaaaa gtttgagtcc ctctatcaat accattctgg gttctctttg    7080
ccctaaaaag ttgagcttct gccttgacaa cctctcatct tgttctatgt ggtttaagca    7140
caactctctc aactccgaaa tagcctcatc cattgcgcat caaaaagcct aggatcctcg    7200
gtgcg                                                               7205
```

<210> SEQ ID NO 5
<211> LENGTH: 3359
<212> TYPE: DNA
<213> ORGANISM: Artificial Sequence
<220> FEATURE:
<223> OTHER INFORMATION: Lymphocytic choriomeningitis strain MP segment S

<400> SEQUENCE: 5

```
cgcaccgggg atcctaggct ttttggattg cgctttcctc agctccgtct tgtgggagaa    60
tgggtcaaat tgtgacgatg tttgaggctc tgcctcacat cattgatgag gtcattaaca   120
ttgtcattat cgtgcttatt atcatcacga gcatcaaagc tgtgtacaat ttcgccacct   180
gcgggatact tgcattgatc agctttcttt ttctggctgg caggtcctgt ggaatgtatg   240
gtcttgatgg gcctgacatt tacaaagggg tttaccgatt caagtcagtg gagtttgaca   300
tgtcttacct taacctgacg atgcccaatg catgttcggc aaacaactcc catcattata   360
taagtatggg gacttctgga ttggagttaa ccttcacaaa tgactccatc atcacccaca   420
acttttgtaa tctgacttcc gccctcaaca agaggacttt tgaccacaca cttatgagta   480
tagtctcaag tctgcacctc agcattagag gggtccccag ctacaaagca gtgtcctgtg   540
attttaacaa tggcatcact attcaataca acctgtcatt ttctaatgca cagagcgctc   600
tgagtcaatg taagaccttc agggggagag tcctggatat gttcagaact gcttttggag   660
gaaagtacat gaggagtggc tggggctgga caggttcaga tggcaagact acttggtgca   720
gccagacaaa ctaccaatat ctgattatac aaaacaggac ttgggaaaac cactgcaggt   780
acgcaggccc tttcggaatg tctagaattc tcttcgctca agaaaagaca aggtttctaa   840
ctagaaggct tgcaggcaca ttcacttgga ctttatcaga ctcatcagga gtggagaatc   900
caggtggtta ctgcttgacc aagtggatga tcctcgctgc agagctcaag tgttttggga   960
acacagctgt tgcaaagtgc aatgtaaatc atgatgaaga gttctgtgat atgctacgac  1020
tgattgatta caacaaggct gctttgagta aattcaaaga agatgtagaa tccgctctac  1080
atctgttcaa gacaacagtg aattctttga tttctgatca gcttttgatg agaaatcacc  1140
taagagactt gatgggagtg ccatactgca attactcgaa attctggtat ctagagcatg  1200
caaagactgg tgagactagt gtccccaagt gctggcttgt cagcaatggt tcttatttga  1260
atgaaaccca tttcagcgac caaattgagc aggaagcaga taatatgatc acagaaatgc  1320
tgagaaagga ctacataaaa aggcaaggga gtacccctct agccttgatg gatctattga  1380
tgttttctac atcagcatat ttgatcagca tcttctgca tcttgtgagg ataccaacac  1440
acagacacat aaagggcggc tcatgcccaa aaccacatcg gttaaccagc aagggaatct  1500
gtagttgtgg tgcatttaaa gtaccaggtg tggaaaccac ctggaaaaga cgctgaacag  1560
cagcgcctcc ctgactcacc acctcgaaag aggtggtgag tcagggaggc ccagagggtc  1620
ttagagtgtt acgacatttg gacctctgaa gattaggtca tgtggtagga tattgtggac  1680
agttttcagg tcggggagcc ttgccttgga ggcgctttca aagatgatac agtccatgag  1740
tgcacagtgt ggggtgacct cttctttttt cttgtccctc actattccag tgtgcatctt  1800
gcatagccag ccatatttgt cccagacttt gtcctcatat tctcttgaag cttctttagt  1860
catctcaaca tcgatgagct taatgtctct tctgttttgt gaatctagga gtttcctgat  1920
gtcatcagat ccctgacaac ttaggaccat tccctgtgga agagcaccta ttactgaaga  1980
tgtcagccca ggttgtgcat tgaagaggtc agcaaggtcc atgccatgtg agtatttgga  2040
gtcctgcttg aattgttttt gatcagtggg ttctctatag aaatgtatgt actgcccatt  2100
ctgtggctga atattgcta tttctaccgg gtcattaaat ctgccctcaa tgtcaatcca  2160
tgtaggagcg ttagggtcaa tacctcccat gaggtccttc agcaacattg tttggctgta  2220
gcttaagccc acctgaggtg ggcccgctgc cccaggcgct ggtttgggtg agttggccat  2280
```

```
aggcctctca tttgtcagat caattgttgt gttctcccat gctctcccta caactgatgt    2340
tctacaagct atgtatggcc acccctcccc tgaaagacag actttgtaga ggatgttctc    2400
gtaaggattc ctgtctccaa cctgatcaga aacaaacatg ttgagtttct tcttggcccc    2460
aagaactgct ttcaggagat cctcactgtt gcttggctta attaagatgg attccaacat    2520
gttaccccca tctaacaagg ctgcccctgc tttcacagca gcaccgagac tgaaattgta    2580
gccagatatg ttgatgctag actgctgctc agtgatgact cccaagactg ggtgcttgtc    2640
tttcagcctt tcaaggtcac ttaggttcgg gtacttgact gtgtaaagca gcccaaggtc    2700
tgtgagtgct tgcacaacgt cattgagtga ggtttgtgat tgtttggcca tacaagccat    2760
tgttaagctt ggcattgtgc cgaattgatt gttcagaagt gatgagtcct tcacatccca    2820
gaccctcacc acaccatttg cactctgctg aggtctcctc attccaacca tttgcagaat    2880
ctgagatctt tggtcaagct gttgtgctgt taagttcccc atgtagactc cagaagttag    2940
aggcctttca gacctcatga ttttagcctt cagttttttca aggtcagctg caagggacat    3000
cagttcttct gcactaagcc tccctacttt tagaacattc ttttttgatg ttgactttag    3060
gtccacaagg gaatacacag tttggttgag gcttctgagt ctctgtaaat ctttgtcatc    3120
cctcttctct ttcctcatga tcctctgaac attgctcacc tcagagaagt ctaatccatt    3180
cagaaggctg gtggcatcct tgatcacagc agctttcaca tctgatgtga agccttgaag    3240
ctctctcctc aatgcctggg tccattgaaa gcttttaact tctttggaca gagacatttt    3300
gtcactcagt ggatttccaa gtcaaatgcg caatcaaaat gcctaggatc cactgtgcg     3359
```

<210> SEQ ID NO 6
<211> LENGTH: 558
<212> TYPE: PRT
<213> ORGANISM: Lymphocytic choriomeningitis virus
<220> FEATURE:
<223> OTHER INFORMATION: NP protein of the MP strain of LCMV

<400> SEQUENCE: 6

```
Met Ser Leu Ser Lys Glu Val Lys Ser Phe Gln Trp Thr Gln Ala Leu
1               5                   10                  15

Arg Arg Glu Leu Gln Gly Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val Tyr Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Leu Thr Ser Gly Val Tyr Met Gly Asn
        115                 120                 125

Leu Thr Ala Gln Gln Leu Asp Gln Arg Ser Gln Ile Leu Gln Met Val
    130                 135                 140

Gly Met Arg Arg Pro Gln Gln Ser Ala Asn Gly Val Val Arg Val Trp
145                 150                 155                 160

Asp Val Lys Asp Ser Ser Leu Leu Asn Asn Gln Phe Gly Thr Met Pro
                165                 170                 175
```

```
Ser Leu Thr Met Ala Cys Met Ala Lys Gln Ser Gln Thr Ser Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
    210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
            245                 250                 255

Gly Gly Asn Met Leu Glu Ser Ile Leu Ile Lys Pro Ser Asn Ser Glu
        260                 265                 270

Asp Leu Leu Lys Ala Val Leu Gly Ala Lys Lys Lys Leu Asn Met Phe
    275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
            325                 330                 335

Glu Arg Pro Met Ala Asn Ser Pro Lys Pro Ala Pro Gly Ala Ala Gly
        340                 345                 350

Pro Pro Gln Val Gly Leu Ser Tyr Ser Gln Thr Met Leu Leu Lys Asp
    355                 360                 365

Leu Met Gly Gly Ile Asp Pro Asn Ala Pro Thr Trp Ile Asp Ile Glu
370                 375                 380

Gly Arg Phe Asn Asp Pro Val Glu Ile Ala Ile Phe Gln Pro Gln Asn
385                 390                 395                 400

Gly Gln Tyr Ile His Phe Tyr Arg Glu Pro Thr Asp Gln Lys Gln Phe
            405                 410                 415

Lys Gln Asp Ser Lys Tyr Ser His Gly Met Asp Leu Ala Asp Leu Phe
        420                 425                 430

Asn Ala Gln Pro Gly Leu Thr Ser Ser Val Ile Gly Ala Leu Pro Gln
    435                 440                 445

Gly Met Val Leu Ser Cys Gln Gly Ser Asp Asp Ile Arg Lys Leu Leu
450                 455                 460

Asp Ser Gln Asn Arg Arg Asp Ile Lys Leu Ile Asp Val Glu Met Thr
465                 470                 475                 480

Lys Glu Ala Ser Arg Glu Tyr Glu Asp Lys Val Trp Asp Lys Tyr Gly
            485                 490                 495

Trp Leu Cys Lys Met His Thr Gly Ile Val Arg Asp Lys Lys Lys Lys
        500                 505                 510

Glu Val Thr Pro His Cys Ala Leu Met Asp Cys Ile Ile Phe Glu Ser
    515                 520                 525

Ala Ser Lys Ala Arg Leu Pro Asp Leu Lys Thr Val His Asn Ile Leu
530                 535                 540

Pro His Asp Leu Ile Phe Arg Gly Pro Asn Val Val Thr Leu
545                 550                 555

<210> SEQ ID NO 7
<211> LENGTH: 498
<212> TYPE: PRT
<213> ORGANISM: Lymphocytic choriomeningitis virus
<220> FEATURE:
<223> OTHER INFORMATION: GP protein of the MP strain of LCMV
```

```
<400> SEQUENCE: 7

Met Gly Gln Ile Val Thr Met Phe Glu Ala Leu Pro His Ile Ile Asp
1               5                   10                  15

Glu Val Ile Asn Ile Val Ile Val Leu Ile Ile Ile Thr Ser Ile
            20                  25                  30

Lys Ala Val Tyr Asn Phe Ala Thr Cys Gly Ile Leu Ala Leu Ile Ser
        35                  40                  45

Phe Leu Phe Leu Ala Gly Arg Ser Cys Gly Met Tyr Gly Leu Asp Gly
    50                  55                  60

Pro Asp Ile Tyr Lys Gly Val Tyr Arg Phe Lys Ser Val Glu Phe Asp
65                  70                  75                  80

Met Ser Tyr Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Thr His Asn Phe Cys Asn Leu Thr Ser Ala
            115                 120                 125

Leu Asn Lys Arg Thr Phe Asp His Thr Leu Met Ser Ile Val Ser Ser
130                 135                 140

Leu His Leu Ser Ile Arg Gly Val Pro Ser Tyr Lys Ala Val Ser Cys
145                 150                 155                 160

Asp Phe Asn Asn Gly Ile Thr Ile Gln Tyr Asn Leu Ser Phe Ser Asn
                165                 170                 175

Ala Gln Ser Ala Leu Ser Gln Cys Lys Thr Phe Arg Gly Arg Val Leu
            180                 185                 190

Asp Met Phe Arg Thr Ala Phe Gly Gly Lys Tyr Met Arg Ser Gly Trp
            195                 200                 205

Gly Trp Thr Gly Ser Asp Gly Lys Thr Thr Trp Cys Ser Gln Thr Asn
    210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Arg Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
            355                 360                 365

Tyr Cys Asn Tyr Ser Lys Phe Trp Tyr Leu Glu His Ala Lys Thr Gly
            370                 375                 380

Glu Thr Ser Val Pro Lys Cys Trp Leu Val Ser Asn Gly Ser Tyr Leu
385                 390                 395                 400

Asn Glu Thr His Phe Ser Asp Gln Ile Glu Gln Glu Ala Asp Asn Met
```

```
                        405                 410                 415
Ile Thr Glu Met Leu Arg Lys Asp Tyr Ile Lys Arg Gln Gly Ser Thr
                420                 425                 430

Pro Leu Ala Leu Met Asp Leu Leu Met Phe Ser Thr Ser Ala Tyr Leu
            435                 440                 445

Ile Ser Ile Phe Leu His Leu Val Arg Ile Pro Thr His Arg His Ile
        450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Glu Thr Thr Trp Lys
                485                 490                 495

Arg Arg

<210> SEQ ID NO 8
<211> LENGTH: 2209
<212> TYPE: PRT
<213> ORGANISM: Lymphocytic choriomeningitis virus
<220> FEATURE:
<223> OTHER INFORMATION: L protein of the MP strain of LCMV

<400> SEQUENCE: 8

Met Asp Glu Ala Ile Ser Glu Leu Arg Glu Leu Cys Leu Asn His Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Ile His Asn His
    50                  55                  60

Asp Asp Lys Ser Val Glu Ala Ile Leu Ile Glu Ser Gly Ile Val Cys
65                  70                  75                  80

Pro Gly Leu Pro Leu Ile Ile Pro Asp Gly Tyr Lys Leu Ile Asp Asn
                85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Ile Ala Gly Ile Thr Leu Val Pro Ile Val Asp Gly Arg
    130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
                165                 170                 175

Val Phe Glu Glu Ser Glu Tyr Phe Arg Leu Cys Glu Ser Leu Lys Thr
            180                 185                 190

Thr Val Asp Lys Arg Ser Gly Ile Asp Ser Met Lys Ile Leu Lys Asp
        195                 200                 205

Ala Arg Ser Phe His Asn Asp Glu Ile Met Lys Met Cys His Asp Gly
    210                 215                 220

Val Asn Pro Asn Met Asn Cys Asp Asp Val Val Leu Gly Ile Asn Ser
225                 230                 235                 240

Leu Tyr Ser Arg Phe Arg Arg Asp Leu Glu Thr Gly Lys Leu Lys Arg
                245                 250                 255

Ser Phe Gln Lys Ile Asn Pro Gly Asn Leu Ile Lys Glu Phe Ser Glu
            260                 265                 270
```

```
Leu Tyr Glu Thr Leu Ala Asp Ser Asp Asp Ile Ser Ala Leu Ser Lys
            275                 280                 285

Glu Ala Val Glu Ser Cys Pro Leu Met Arg Phe Ile Thr Ala Asp Thr
290                 295                 300

His Gly Tyr Glu Arg Gly Ser Glu Thr Ser Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
                340                 345                 350

Lys Gln Ser Lys Leu Lys Gly Ser Lys Asn Asp Lys His Trp Val Gly
                355                 360                 365

Cys Cys Tyr Gly Ser Val Asn Asp Arg Leu Val Ser Phe His Ser Thr
                370                 375                 380

Lys Glu Glu Phe Ile Arg Leu Leu Arg Asn Arg Arg Lys Ser Lys Ala
385                 390                 395                 400

Tyr Arg Lys Val Ser Leu Glu Asp Leu Phe Arg Thr Ser Ile Asn Glu
                405                 410                 415

Phe Ile Leu Lys Val Gln Arg Cys Leu Ser Val Val Gly Leu Ser Phe
                420                 425                 430

Gly His Tyr Gly Leu Ser Glu His Leu Glu His Glu Cys His Ile Pro
                435                 440                 445

Phe Ile Glu Phe Glu Asn Phe Met Arg Ser Gly Thr His Pro Ile Met
450                 455                 460

Tyr Tyr Thr Lys Phe Glu Asp Tyr Asp Phe Gln Pro Asn Thr Glu Gln
465                 470                 475                 480

Leu Arg Asn Met His Ser Leu Lys Arg Leu Ser Ser Val Cys Leu Ala
                485                 490                 495

Leu Thr Asn Ser Met Lys Thr Ser Ser Val Ala Arg Leu Arg Gln Asn
                500                 505                 510

Gln Leu Gly Ser Val Arg Tyr Gln Val Val Glu Cys Lys Glu Val Phe
                515                 520                 525

Cys Gln Val Ile Lys Leu Asp Ser Glu Glu Tyr His Leu Leu Tyr Gln
530                 535                 540

Lys Thr Gly Glu Ser Ser Arg Cys Tyr Ser Ile Gln Gly Pro Asn Gly
545                 550                 555                 560

His Leu Ile Ser Phe Tyr Ala Asp Pro Lys Arg Phe Phe Leu Pro Ile
                565                 570                 575

Phe Ser Asp Glu Val Leu His Asn Met Ile Asp Thr Met Ile Ser Trp
                580                 585                 590

Ile Arg Ser Cys Pro Asp Leu Lys Asp Ser Ile Asp Asp Val Glu Ile
                595                 600                 605

Ala Leu Arg Thr Leu Leu Leu Met Leu Thr Asn Pro Thr Lys Arg
610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
                645                 650                 655

Ile Thr Pro Ala Glu Lys Val Val Tyr Lys Leu Leu Arg Phe Leu Ile
                660                 665                 670

Lys Thr Val Phe Gly Thr Gly Glu Lys Val Leu Leu Ser Ala Lys Phe
                675                 680                 685
```

```
Lys Phe Met Leu Asn Val Ser Tyr Leu Cys His Leu Ile Thr Lys Glu
    690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Val Asn Pro Lys Glu Ser Ile
                725                 730                 735

Thr Pro Glu Glu Glu Cys Val Phe Tyr Asp Gln Met Lys Lys Phe Thr
            740                 745                 750

Gly Lys Glu Val Asp Cys Gln Arg Thr Thr Pro Gly Val Asn Leu Glu
                755                 760                 765

Ala Phe Ser Met Met Val Ser Ser Phe Asn Asn Gly Thr Leu Ile Phe
770                 775                 780

Lys Gly Glu Lys Arg Leu Asn Ser Leu Asp Pro Met Thr Asn Ser Gly
785                 790                 795                 800

Cys Ala Thr Ala Leu Asp Leu Ala Ser Asn Lys Ser Val Val Asn
                805                 810                 815

Lys His Leu Asn Gly Glu Arg Leu Leu Glu Tyr Asp Phe Asn Lys Leu
                820                 825                 830

Leu Val Ser Ala Val Ser Gln Ile Thr Glu Ser Phe Met Arg Lys Gln
                835                 840                 845

Lys Tyr Lys Leu Asn His Ser Asp Tyr Glu Tyr Lys Val Ser Lys Leu
850                 855                 860

Val Ser Arg Leu Val Ile Gly Ser Lys Glu Thr Glu Ala Gly Lys Leu
865                 870                 875                 880

Glu Gly Asp Ser Ala Asp Ile Cys Phe Asp Gly Glu Glu Thr Ser
                885                 890                 895

Phe Phe Lys Asn Leu Glu Asp Lys Val Asn Ser Thr Ile Lys Arg Tyr
                900                 905                 910

Glu Arg Ser Lys Lys Thr Asn Glu Gly Glu Asn Glu Val Gly Phe Glu
            915                 920                 925

Asn Thr Lys Gly Leu His His Leu Gln Thr Ile Leu Ser Gly Lys Met
    930                 935                 940

Ala Tyr Leu Arg Lys Val Ile Leu Ser Glu Ile Ser Phe His Leu Val
945                 950                 955                 960

Glu Asp Phe Asp Pro Ser Cys Leu Thr Asn Asp Met Lys Phe Ile
                965                 970                 975

Cys Glu Ala Ile Glu Thr Ser Thr Glu Leu Ser Pro Leu Tyr Phe Thr
                980                 985                 990

Ser Ala Val Lys Glu Gln Cys Gly Leu Asp Glu Met Ala Lys Asn Leu
            995                 1000                1005

Cys Arg Lys Phe Phe Ser Glu Gly Asp Trp Phe Ser Cys Met Lys
    1010                1015                1020

Met Ile Leu Leu Gln Met Asn Ala Asn Ala Tyr Ser Gly Lys Tyr
    1025                1030                1035

Arg His Met Gln Arg Gln Gly Leu Asn Phe Lys Phe Asp Trp Asp
    1040                1045                1050

Lys Leu Glu Glu Asp Val Arg Ile Ser Glu Arg Glu Ser Asn Ser
    1055                1060                1065

Glu Ser Leu Ser Lys Ala Leu Ser Leu Thr Lys Cys Met Ser Ala
    1070                1075                1080

Ala Leu Lys Asn Leu Cys Phe Tyr Ser Glu Glu Ser Pro Thr Ser
    1085                1090                1095

Tyr Thr Ser Val Gly Pro Asp Ser Gly Arg Leu Lys Phe Ala Leu
```

-continued

```
                1100                1105                1110
Ser Tyr Lys Glu Gln Val Gly Gly Asn Arg Glu Leu Tyr Ile Gly
                1115                1120                1125

Asp Leu Arg Thr Lys Met Phe Thr Arg Leu Ile Glu Asp Tyr Phe
                1130                1135                1140

Glu Ser Phe Ser Ser Phe Phe Ser Gly Ser Cys Leu Asn Asn Asp
                1145                1150                1155

Lys Glu Phe Glu Asn Ala Ile Leu Ser Met Thr Ile Asn Val Arg
                1160                1165                1170

Glu Gly Leu Leu Asn Tyr Ser Met Asp His Ser Lys Trp Gly Pro
                1175                1180                1185

Met Met Cys Pro Phe Leu Phe Leu Met Leu Leu Gln Asn Leu Lys
                1190                1195                1200

Leu Gly Asp Asp Gln Tyr Val Arg Ser Gly Lys Asp His Ile Ser
                1205                1210                1215

Thr Leu Leu Thr Trp His Met His Lys Leu Val Glu Val Pro Phe
                1220                1225                1230

Pro Val Val Asn Ala Met Met Lys Ser Tyr Ile Lys Ser Lys Leu
                1235                1240                1245

Lys Leu Leu Arg Gly Ser Glu Thr Thr Val Thr Glu Arg Ile Phe
                1250                1255                1260

Arg Glu Tyr Phe Glu Leu Gly Ile Val Pro Ser His Ile Ser Ser
                1265                1270                1275

Leu Ile Asp Met Gly Gln Gly Ile Leu His Asn Ala Ser Asp Phe
                1280                1285                1290

Tyr Gly Leu Ile Ser Glu Arg Phe Ile Asn Tyr Cys Ile Gly Val
                1295                1300                1305

Ile Phe Gly Glu Arg Pro Glu Ser Tyr Thr Ser Ser Asp Asp Gln
                1310                1315                1320

Ile Thr Leu Phe Asp Arg Arg Leu Ser Glu Leu Val Asp Ser Asp
                1325                1330                1335

Pro Glu Glu Val Leu Val Leu Leu Glu Phe His Ser His Leu Ser
                1340                1345                1350

Gly Leu Leu Asn Lys Phe Ile Ser Pro Lys Ser Val Val Gly Arg
                1355                1360                1365

Phe Ala Ala Glu Phe Lys Ser Arg Phe Tyr Val Trp Gly Glu Glu
                1370                1375                1380

Val Pro Leu Leu Thr Lys Phe Val Ser Ala Ala Leu His Asn Val
                1385                1390                1395

Lys Cys Lys Glu Pro His Gln Leu Cys Glu Thr Ile Asp Thr Ile
                1400                1405                1410

Ala Asp Gln Ala Val Ala Asn Gly Val Pro Val Ser Leu Val Asn
                1415                1420                1425

Cys Ile Gln Lys Arg Thr Leu Asp Leu Leu Lys Tyr Ala Asn Phe
                1430                1435                1440

Pro Leu Asp Pro Phe Leu Leu Asn Thr Asn Thr Asp Val Lys Asp
                1445                1450                1455

Trp Leu Asp Gly Ser Arg Gly Tyr Arg Ile Gln Arg Leu Ile Glu
                1460                1465                1470

Glu Leu Cys Pro Ser Glu Thr Lys Val Met Arg Arg Leu Val Arg
                1475                1480                1485

Arg Leu His His Lys Leu Lys Asn Gly Glu Phe Asn Glu Glu Phe
                1490                1495                1500
```

```
Phe Leu Asp Leu Phe Asn Arg Asp Lys Glu Ala Ile Leu Gln
    1505                1510            1515

Leu Gly Asn Ile Leu Gly Leu Glu Glu Asp Leu Ser Gln Leu Ala
    1520                1525            1530

Asn Ile Asn Trp Leu Asn Leu Asn Glu Leu Phe Pro Leu Arg Met
    1535                1540            1545

Val Leu Arg Gln Lys Val Val Tyr Pro Ser Val Met Thr Phe Gln
    1550                1555            1560

Glu Glu Arg Ile Pro Ser Leu Ile Lys Thr Leu Gln Asn Lys Leu
    1565                1570            1575

Cys Ser Lys Phe Thr Arg Gly Ala Gln Lys Leu Leu Ser Glu Ala
    1580                1585            1590

Ile Asn Lys Ser Ala Phe Gln Ser Cys Ile Ser Ser Gly Phe Ile
    1595                1600            1605

Gly Leu Cys Lys Thr Leu Gly Ser Arg Cys Val Arg Asn Lys Asn
    1610                1615            1620

Arg Asp Asn Leu Tyr Ile Arg Lys Val Leu Glu Asp Leu Ala Met
    1625                1630            1635

Asp Ala His Val Thr Ala Ile His Arg His Asp Gly Ile Met Leu
    1640                1645            1650

Tyr Ile Cys Asp Arg Gln Ser His Pro Glu Ala His Cys Asp His
    1655                1660            1665

Ile Ser Leu Leu Arg Pro Leu Leu Trp Asp Tyr Ile Cys Ile Ser
    1670                1675            1680

Leu Ser Asn Ser Phe Glu Leu Gly Val Trp Val Leu Ala Glu Pro
    1685                1690            1695

Val Lys Gly Lys Asn Glu Gly Ser Ser Ser Leu Lys His Leu Asn
    1700                1705            1710

Pro Cys Asp Tyr Val Ala Arg Lys Pro Glu Ser Ser Arg Leu Leu
    1715                1720            1725

Glu Asp Lys Ile Ser Leu Asn His Val Ile Gln Ser Val Arg Arg
    1730                1735            1740

Leu Tyr Pro Lys Ile Tyr Glu Asp Gln Leu Leu Pro Phe Met Ser
    1745                1750            1755

Asp Met Ser Ser Lys Asn Met Arg Trp Ser Pro Arg Ile Lys Phe
    1760                1765            1770

Leu Asp Leu Cys Val Leu Ile Asp Ile Asn Ser Glu Ser Leu Ser
    1775                1780            1785

Leu Ile Ser His Val Val Lys Trp Lys Arg Asp Glu His Tyr Thr
    1790                1795            1800

Val Leu Phe Ser Asp Leu Val Asn Ser His Gln Arg Ser Asp Ser
    1805                1810            1815

Ser Leu Val Asp Glu Phe Val Val Ser Thr Arg Asp Val Cys Lys
    1820                1825            1830

Asn Phe Leu Lys Gln Val Tyr Phe Glu Ser Phe Val Arg Glu Phe
    1835                1840            1845

Val Ala Thr Ser Arg Thr Leu Gly Ser Phe Ser Trp Phe Pro His
    1850                1855            1860

Lys Asp Met Met Pro Ser Glu Asp Gly Ala Glu Ala Leu Gly Pro
    1865                1870            1875

Phe Gln Ser Phe Ile Leu Lys Val Val Asn Lys Asn Met Glu Arg
    1880                1885            1890
```

```
Pro Met Phe Arg Asn Asp Leu Gln Phe Gly Phe Gly Trp Phe Ser
    1895                1900                1905
Tyr Arg Leu Gly Asp Ile Val Cys Asn Ala Ala Met Leu Ile Lys
    1910                1915                1920
Gln Gly Leu Thr Asn Pro Lys Ala Phe Lys Ser Leu Arg Asn Leu
    1925                1930                1935
Trp Asp Tyr Met Ile Asn Asn Thr Glu Gly Val Leu Glu Phe Ser
    1940                1945                1950
Ile Thr Val Asp Phe Thr His Asn Gln Asn Asn Thr Asp Cys Leu
    1955                1960                1965
Arg Lys Phe Ser Leu Ile Phe Leu Val Lys Cys Gln Leu Gln Gly
    1970                1975                1980
Pro Gly Val Ala Glu Phe Leu Ser Cys Ser His Leu Phe Lys Gly
    1985                1990                1995
Glu Val Asp Arg Arg Phe Leu Asp Glu Cys Leu His Leu Leu Arg
    2000                2005                2010
Ser Asp Ser Ile Phe Lys Val Asn Asp Gly Val Phe Asp Ile Arg
    2015                2020                2025
Ser Glu Glu Phe Glu Asp Tyr Met Glu Asp Pro Leu Ile Leu Gly
    2030                2035                2040
Asp Ser Leu Glu Leu Glu Leu Ile Gly Ser Arg Lys Ile Leu Asp
    2045                2050                2055
Gly Ile Arg Ser Leu Asp Phe Glu Arg Ile Gly Pro Glu Trp Glu
    2060                2065                2070
Pro Val Pro Leu Thr Val Arg Met Gly Ala Leu Phe Glu Gly Arg
    2075                2080                2085
Ser Leu Val Gln Asn Ile Val Val Lys Leu Glu Thr Lys Asp Met
    2090                2095                2100
Arg Val Phe Leu Ala Glu Leu Glu Gly Tyr Gly Asn Phe Asp Asp
    2105                2110                2115
Val Leu Gly Ser Leu Leu Leu His Arg Phe Arg Thr Gly Glu His
    2120                2125                2130
Leu Gln Gly Ser Glu Ile Ser Thr Ile Leu Gln Glu Leu Cys Ile
    2135                2140                2145
Asp Arg Ser Ile Leu Leu Val Pro Leu Ser Leu Val Pro Asp Trp
    2150                2155                2160
Phe Thr Phe Lys Asp Cys Arg Leu Cys Phe Ser Lys Ser Lys Asn
    2165                2170                2175
Thr Val Met Tyr Glu Thr Val Val Gly Lys Tyr Arg Leu Lys Gly
    2180                2185                2190
Lys Ser Cys Asp Asp Trp Leu Thr Lys Ser Val Val Glu Glu Ile
    2195                2200                2205
Asp
```

<210> SEQ ID NO 9
<211> LENGTH: 90
<212> TYPE: PRT
<213> ORGANISM: Lymphocytic choriomeningitis virus
<220> FEATURE:
<223> OTHER INFORMATION: Z protein of the MP strain of LCMV

<400> SEQUENCE: 9

```
Met Gly Gln Gly Lys Ser Lys Glu Gly Arg Asp Ala Ser Asn Thr Ser
1               5                   10                  15

Arg Ala Glu Ile Leu Pro Asp Thr Thr Tyr Leu Gly Pro Leu Asn Cys
```

```
                    20                  25                  30
Lys Ser Cys Trp Gln Arg Phe Asp Ser Leu Val Arg Cys His Asp His
                35                  40                  45

Tyr Leu Cys Arg His Cys Leu Asn Leu Leu Leu Ser Val Ser Asp Arg
            50                  55                  60

Cys Pro Leu Cys Lys His Pro Leu Pro Thr Lys Leu Lys Ile Ser Thr
65                  70                  75                  80

Ala Pro Ser Ser Pro Pro Pro Tyr Glu Glu
                85                  90

<210> SEQ ID NO 10
<211> LENGTH: 7115
<212> TYPE: DNA
<213> ORGANISM: Artificial Sequence
<220> FEATURE:
<223> OTHER INFORMATION: Junin virus Candid#1 L segment

<400> SEQUENCE: 10
gcgcaccggg atcctaggc gtaacttcat cattaaaatc tcagattctg ctctgagtgt      60
gacttactgc gaagaggcag acaaatgggc aactgcaacg gggcatccaa gtctaaccag    120
ccagactcct caagagccac acagccagcc gcagaattta ggagggtagc tcacagcagt    180
ctatatggta gatataactg taagtgctgc tggtttgctg ataccaattt gataacctgt    240
aatgatcact acctttgttt aaggtgccat cagggtatgt taaggaattc agatctctgc    300
aatatctgct ggaagcccct gcccaccaca atcacagtac cggtggagcc aacagcacca    360
ccaccatagg cagactgcac agggtcagac ccgaccccc gggggccccc catggggacc     420
ccccgtgggg aaccccggg ggtgatgcgc cattagtcaa tgtctttgat ctcgactttg      480
tgcttcagtg gcctgcatgt cacccctttc aatctgaact gcccttgggg atctgatatc    540
agcaggtcat ttaaagatct gctgaatgcc accttgaaat ttgagaattc aaccagtca     600 ccaaatttat caagtgaacg gatcaactgc tcttttgtgta gatcataaac gaggacaaag    660
tcctcttgct gaaataatat tgtttgtgat gttgttttta gataaggcca tagttggctt    720
aataaggttt ccacactatc aatgtcctct agtgctccaa ttgccttgac tatgacatcc    780
ccagacaact caactctata tgttgacaac cttttcattac ctctgtaaaa gataccctct    840
ttcaagacaa gaggttctcc tgggttatct ggcccaatga ggtcatatgc atacttgtta    900
cttagttcag aataaaagtc accaaagttg aacttaacat ggctcagaat attgtcatca    960
tttgtcgcag cgtagcctgc atcaataaac aagccagcta ggtcaaagct tcatggcct   1020 gtgaacaatg gtaggctagc gataaccagt gcaccatcca acaatgagtg gcttccctca   1080
gacccagaaa cacattgact cattgcatcc acattcagct ctaattcagg gtaccgaca    1140 tcatccactc ctagtgaact gacaatggtg taactgtaca ccatctttct tctaagttta    1200
aattttgtcg aaactcgtgt gtgttctact tgaatgatca attttagttt cacagcttct    1260
tggcaagcaa cattgcgcaa cacagtgtgc aggtccatca tgtcttcctg aggcaacaag    1320
gagatgttgt caacagagac accctcaagg aaaaccttga tattatcaaa gctagaaact    1380
acataaccca ttgcaatgtc ttcaacaaac attgctcttg atactttatt attcctaact    1440
gacaaggtaa aatctgtgag ttcagctaga tctacttgac tgtcatcttc tagatctaga    1500
acttcattga accaaaagaa ggatttgaga cacgatgttg acatgactag tgggtttatc    1560
atcgaagata agacaacttg caccatgaag ttcctgcaaa cttgctgtgg gctgatgcca    1620
acttcccaat ttgtatactc tgactgtcta acatgggctg aagcgcaatc actctgtttc    1680
```

```
acaatataaa cattattatc tcttactttc aataagtgac ttataatccc taagttttca    1740
ttcatcatgt ctagagccac acagacatct agaaacttga gtcttccact atccaaagat    1800
ctgttcactt gaagatcatt cataaagggt gccaaatgtt cttcaaatag tttggggtaa    1860
tttcttcgta tagaatgcaa tacatggttc atgcctaatt ggtcttctat ctgtcgtact    1920
gctttgggtt taacagccca gaagaaattc ttattacata agaccagagg ggcctgtgga    1980
ctcttaatag cagaaaacac ccactcccct aactcacagg catttgtcag caccaaagag    2040
aagtaatccc acaaaattgg tttagaaaat tggttaactt ctttaagtga tttttgacag    2100
taaataactt taggctttct ctcacaaatt ccacaaagac atggcattat tcgagtaaat    2160
atgtccttta tatacagaaa tccgccttta ccatccctaa cacacttact ccccatactc    2220
ttacaaaacc caatgaagcc tgaggcaaca gaagactgaa atgcagattt gttgattgac    2280
tctgccaaga tcttcttcac gccttttgtg aaatttcttg acagcctgga ctgtattgtc    2340
cttatcaatg ttggcatctc ttctttctct aacactcttc gacttgtcat gagtttggtc    2400
ctcaagacca acctcaagtc cccaaagctc gctaaattga cccatctgta gtctagagtt    2460
tgtctgattt catcttcact acacccggca tattgcagga atccggataa agcctcatcc    2520
cctcccctgc ttatcaagtt gataaggttt tcctcaaaga ttttgcctct cttaatgtca    2580
ttgaacactt cctcgcgca gttccttata aacattgtct ccttatcatc agaaaaata    2640 gcttcaattt tcctctgtag acggtaccct ctagacccat caacccagtc tttgacatct    2700
tgttcttcaa tagctccaaa cggagtctct ctgtatccag agtatctaat caattggttg    2760
actctaatgg aaatctttga cactatatga gtgctaaccc cattagcaat acattgatca    2820
caaattgtgt ctatggtctc tgacagttgt gttggagttt tacacttaac gttgtgtaga    2880
gcagcagaca caaacttggt gagtaaagga gtctcttcac ccatgacaaa aaatcttgac    2940
ttaaactcag caacaaaagt tcctatcaca ctctttgggc tgataaactt gtttaattta    3000
gaagataaga attcatggaa gcacaccatt tccagcagtt ctgtcctgtc ttgaaacttt    3060
tcatcactaa ggcaaggaat ttttataagg ctaacctggt catcgctgga ggtataagtg    3120
acaggtatca catcatacaa taagtcaagt gcataacaca gaaattgttc agtaattagc    3180
ccatataaat ctgatgtgtt gtgcaagatt ccctggccca tgtccaagac agacattata    3240
tggctgggga cctggtccct tgactgcaga tactggtgaa aaaactcttc accaacacta    3300
gtacagtcac aacccattaa acctaaagat ctcttcaatt tccctacaca gtaggcttct    3360
gcaacattaa ttggaacttc aacgacctta tgaagatgcc atttgagaat gttcattact    3420
ggttcaagat tcacctttgt tctatctctg ggattcttca attctaatgt gtacaaaaaa    3480
gaaaggaaaa gtgctgggct catagttggt ccccatttgg agtggtcata tgaacaggac    3540
aagtcaccat tgttaacagc cattttcata tcacagattg cacgttcgaa ttccttttct    3600
gaattcaagc atgtgtattt cattgaacta cccacagctt ctgagaagtc ttcaactaac    3660
ctggtcatca gcttagtgtt gaggtctccc acatacagtt ctctatttga gccaacctgc    3720
tccttataac ttagtccaaa tttcaagttc cctgtatttg agctgatgct tgtgaactct    3780
gtaggagagt cgtctgaata gaaacataaa ttccgtaggg ctgcatttgt aaaataactt    3840
ttgtctagct tatcagcaat ggcttcagaa ttgctttccc tggtactaag ccgaacctca    3900
tcctttagtc tcagaacttc actggaaaag cccaatctag atctacttct atgctcataa    3960
ctacccaatt tctgatcata atgtccttga attaaaagat acttgaagca ttcaaagaat    4020
```

```
tcatcttctt ggtaggctat tgttgtcaaa ttttttaata acaaacccaa agggcagatg    4080
tcctgcggtg cttcaagaaa ataagtcaat ttaaatggag atagataaac agcatcacat    4140
aactctttat acacatcaga cctgagcaca tctggatcaa aatccttcac ctcatgcatt    4200
gacacctctg ctttaatctc tctcaacact ccaaaagggg cccacaatga ctcaagagac    4260
tctcgctcat caacagatgg attttttgat ttcaacttgg tgatctcaac ttttgtcccc    4320
tcactattag ccatcttggc tagtgtcatt tgtacgtcat ttctaatacc ctcaaaggcc    4380
cttacttgat cctctgttaa actctcatac atcactgata attcttcttg attggttctg    4440
gttcttgaac cggtgctcac aagacctgtt agatttttta atattaagta gtccatggaa    4500
tcaggatcaa gattatacct gccttttgtt ttaaacctct cagccatagt agaaacgcat    4560
gttgaaacaa gtttctcctt atcataaaca gaaagaatat ttccaagttc gtcgagcttg    4620
gggattacca cacttttatt gcttgacaga tccagagctg tgctagtgat gttaggcctg    4680
tagggattgc ttttcagttc acctgtaact ttaagtcttc ctctattgaa gagagaaatg    4740
cagaaggaca aaatctcttt acacactcct ggaatttgag tatctgagga agtcttagcc    4800
tctttggaaa agaatctgtc caatcctctt atcatggtgt cctcttgttc cagtgttaga    4860
ctcccactta gagggggtt tacaacaaca caatcaaact tgactttggg ctcaataaac      4920
ttctcaaaac actttatttg atctgtcagg cgatcaggtg tctctttggt taccaagtga    4980
cacagataac taacatttaa tagatattta aaccttcttg caaagtaaag atctgcatct    5040
tcccttcac ccaaaattgt ctggaaaagt tccacagcca tcctctgaat cagcacctct      5100
gatccagaca tgcagtcgac ccttaacttt gacatcaaat ccacatgatg gatttgattt    5160
gcatatgcca tcaagaaata tcttagacct tgtaaaaatg tctggttcct tttggaaggg    5220
gaacagagta cagctaacac taacaatctt aatattggcc ttgtcattgt catgagttcg    5280
tggctaaaat ccaaccagct ggtcatttcc tcacacattt caattaacac atcctccgaa    5340
aatataggca ggaaaaatct cttttggatca cagtaaaaag agccttgttc ttccaatacc    5400
ccattgatgg atagatagat agaatagcac cttgacttct cacctgtttt ttggtaaaac    5460
aagagaccaa atgtattctt tgtcagatga atctttgta cataacactc tcttagtcta     5520
acattcccaa aatatctaga atactctctt tcattgatta acaatcggga ggaaaatgat    5580
gtcttcatcg agttgaccaa tgcaagggaa atggaggaca aaatcctaaa taatttcttc    5640
tgctcacctt ccactaagct gctgaatggc tgatgtctac agattttctc aaattccttg    5700
ttaatagtat atctcatcac tggtctgtca gaaacaagtg cctgagctaa atcatcaag     5760
ctatccatat cagggtgttt tattagtttt tccagctgtg accagagatc ttgatgagag    5820
ttcttcaatg ttctggaaca cgcttgaacc cacttgggc tggtcatcaa tttcttcctt      5880
attagtttaa tcgcctccag aatatctaga agtctgtcat tgactaacat taacatttgt    5940
ccaacaacta ttcccgcatt tcttaacctt acaattgcat catcatgcgt tttgaaaaga    6000
tcacaaagta aattgagtaa aactaagtcc agaaacagta aagtgtttct cctggtgttg    6060
aaaactttta gaccttcac tttgttacac acggaaaggg cttgaagata acacctctct      6120
acagcatcaa tagatataga attctcatct gactggcttt ccatgttgac ttcatctatt    6180
ggatgcaatg cgatagagta gactacatcc atcaacttgt ttgcacaaaa agggcagctg    6240
ggcacatcac tgtctttgtg gcttcctaat aagatcaagt catttataag cttagacttt    6300
tgtgaaaatt tgaatttccc caactgcttg tcaaaaatct ccttcttaaa ccaaaacctt    6360
aactttatga gttcttctct tatgacagat tctctaatgt ctcctctaac cccaacaaag    6420
```

| | |
|---|---|
| agggattcat ttaacctctc atcataaccc aaagaattct tttcaagca ttcgatgttt | 6480 |
| tctaatccca agctctggtt ttttgtgttg gacaaactat ggatcaatcg ctggtattct | 6540 |
| tgttcttcaa tattaatctc ttgcataaat tttgatttct ttaggatgtc gatcagcaac | 6600 |
| caccgaactc tttcaacaac ccaatcagca aggaatctat tgctgtagct agatctgcca | 6660 |
| tcaaccacag gaaccaacgt aatccctgcc cttagtaggt cggactttag gtttaagagc | 6720 |
| tttgacatgt cactcttcca tttctctca aactcatcag gattgaccct aacaaaggtt | 6780 |
| tccaatagga tgagtgtttt ccctgtgagt ttgaagccat ccggaatgac ttttggaagg | 6840 |
| gtgggacata gtatgccata gtcagacagg atcacatcaa caaacttctg atctgaattg | 6900 |
| atctgacagg cgtgtgcctc acaggactca agctctacta aacttgacag aagtttgaac | 6960 |
| ccttccaaca acagagagct gggggtgatgt tgagataaaa agatgtccct ttggtatgct | 7020 |
| agctcctgtc tttctggaaa atgctttcta ataaggcttt ttatttcatt tactgattcc | 7080 |
| tccatgctca agtgccgcct aggatcctcg gtgcg | 7115 |

```
<210> SEQ ID NO 11
<211> LENGTH: 3411
<212> TYPE: DNA
<213> ORGANISM: Artificial Sequence
<220> FEATURE:
<223> OTHER INFORMATION: Junin virus Candid#1 S segment

<400> SEQUENCE: 11
```

| | |
|---|---|
| gcgcaccggg gatcctaggc gattttggtt acgctataat tgtaactgtt ttctgtttgg | 60 |
| acaacatcaa aaacatccat tgcacaatgg ggcagttcat tagcttcatg caagaaatac | 120 |
| caaccttttt gcaggaggct ctgaacattg ctcttgttgc agtcagtctc attgccatca | 180 |
| ttaagggtat agtgaacttg tacaaaagtg gtttattcca attctttgta ttcctagcgc | 240 |
| ttgcaggaag atcctgcaca gaagaagctt caaaatcgg actgcacact gagttccaga | 300 |
| ctgtgtcctt ctcaatggtg ggtctctttt ccaacaatcc acatgaccta cctttgttgt | 360 |
| gtaccttaaa caagagccat ctttacatta agggggggcaa tgcttcattt cagatcagct | 420 |
| ttgatgatat tgcagtattg ttgccacagt atgatgttat aatacaacat ccagcagata | 480 |
| tgagctggtg ttccaaaagt gatgatcaaa tttggttgtc tcagtggttc atgaatgctg | 540 |
| tgggacatga ttggcatcta gacccaccat ttctgtgtag gaaccgtgca aagacagaag | 600 |
| gcttcatctt tcaagtcaac acctccaaga ctggtgtcaa tggaaattat gctaagaagt | 660 |
| ttaagactgg catgcatcat ttatatagag aatatcctga cccttgcttg aatggcaaac | 720 |
| tgtgcttaat gaaggcacaa cctaccagtt ggcctctcca atgtccactc gaccacgtta | 780 |
| acacattaca cttccttaca agaggtaaaa acattcaact tccaaggagg tccttgaaag | 840 |
| cattcttctc ctggtctttg acagactcat ccggcaagga tacccctgga ggctattgtc | 900 |
| tagaagagtg gatgctcgta gcagccaaaa tgaagtgttt tggcaatact gctgtagcaa | 960 |
| aatgcaattt gaatcatgac tctgaattct gtgacatgtt gaggctcttt gattacaaca | 1020 |
| aaaatgctat caaaacccta aatgatgaaa ctaagaaaca agtaaatctg atggggcaga | 1080 |
| caatcaatgc cctgatatct gacaatttat tgatgaaaaa caaattagg gaactgatga | 1140 |
| gtgtcccta ctgcaattac acaaaatttt ggtatgtcaa ccacacactt tcaggacaac | 1200 |
| actcattacc aagtgctgg ttaataaaaa acaacagcta tttgaacatc tctgacttcc | 1260 |
| gtaatgactg gatattagaa agtgacttct taatttctga aatgctaagc aaagagtatt | 1320 |

| | |
|---|---|
| cggacaggca gggtaaaact cctttgactt tagttgacat ctgtatttgg agcacagtat | 1380 |
| tcttcacagc gtcactcttc cttcacttgg tgggtatacc ctcccacaga cacatcaggg | 1440 |
| gcgaagcatg ccctttgcca cacaggttga acagcttggg tggttgcaga tgtggtaagt | 1500 |
| accccaatct aaagaaacca acagtttggc gtagaggaca ctaagacctc ctgagggtcc | 1560 |
| ccaccagccc gggcactgcc cgggctggtg tggcccccca gtccgcggcc tggccgcgga | 1620 |
| ctggggaggc actgcttaca gtgcataggc tgccttcggg aggaacagca agctcggtgg | 1680 |
| taatagaggt gtaggttcct cctcatagag cttcccatct agcactgact gaaacattat | 1740 |
| gcagtctagc agagcacagt gtggttcact ggaggccaac ttgaagggag tatccttttc | 1800 |
| cctcttttc ttattgacaa ccactccatt gtgatatttg cataagtgac catatttctc | 1860 |
| ccagacctgt tgatcaaact gcctggcttg ttcagatgtg agcttaacat caaccagttt | 1920 |
| aagatctctt cttccatgga ggtcaaacaa cttcctgatg tcatcggatc cttgagtagt | 1980 |
| cacaaccatg tctggaggca gcaagccgat cacgtaacta agaactcctg gcattgcatc | 2040 |
| ttctatgtcc ttcattaaga tgccgtgaga gtgtctgcta ccattttaa acccttctc | 2100 |
| atcatgtggt tttctgaagc agtgaatgta ctgcttacct gcaggttgga ataatgccat | 2160 |
| ctcaacaggg tcagtggctg gtccttcaat gtcgagccaa agggtgttgg tggggtcgag | 2220 |
| tttccccact gcctctctga tgacagcttc ttgtatctct gtcaagttag ccaatctcaa | 2280 |
| attctgaccg ttttttccg gctgtctagg accagcaact ggtttccttg tcagatcaat | 2340 |
| acttgtgttg tcccatgacc tgcctgtgat ttgtgatcta gaaccaatat aaggccaacc | 2400 |
| atcgccagaa agacaaagtt tgtacaaaag gttttcataa ggatttctat tgcctggttt | 2460 |
| ctcatcaata acatgccctt ctcttcgttt aacctgaatg gttgatttta tgagggaaga | 2520 |
| gaagttttct ggggtgactc tgattgtttc caacatgttt ccaccatcaa gaatagatgc | 2580 |
| tccagccttt actgcagctg aaagactgaa gttgtaacca gaaatattga tggagctttc | 2640 |
| atctttagtc acaatctgaa ggcagtcatg ttcctgagtc agtctgtcaa ggtcacttaa | 2700 |
| gtttggatac ttcacagtgt atagaagccc aagtgaggtt aaagcttgta tgacactgtt | 2760 |
| cattgtctca cctccttgaa cagtcatgca tgcaattgtc aatgcaggaa cagagccaaa | 2820 |
| ctgattgttt agctttgaag ggtctttaac atcccatatc ctcaccacac catttccccc | 2880 |
| agtcccttgc tgttgaaatc ccagtgttct caatatctct gatcttttag caagttgtga | 2940 |
| ctgggacaag ttacccatgt aaaccccctg agagcctgtc tctgctcttc ttatcttgtt | 3000 |
| ttttaatttc tcaaggtcag acgccaactc catcagttca tccctcccca gatctcccac | 3060 |
| cttgaaaact gtgtttcgtt gaacactcct catggacatg agtctgtcaa cctctttatt | 3120 |
| caggtccctc aacttgttga ggtcttcttc cccctttta gtctttctga gtgcccgctg | 3180 |
| cacctgtgcc acttggttga agtcgatgct gtcagcaatt agcttggcgt ccttcaaaac | 3240 |
| atctgacttg acagtctgag tgaattggct caaacctctc cttaaggact gagtccatct | 3300 |
| aaagcttgga acctccttgg agtgtgccat gccagaagtt ctggtgattt tgatctagaa | 3360 |
| tagagttgct cagtgaaagt gttagacact atgcctagga tccactgtgc g | 3411 |

<210> SEQ ID NO 12
<211> LENGTH: 558
<212> TYPE: PRT
<213> ORGANISM: Lymphocytic choriomeningitis virus
<220> FEATURE:
<223> OTHER INFORMATION: NP protein of the Clone 13 strain of LCMV
(GenBank Accession No. ABC96002.1; GI:86440166)

```
<400> SEQUENCE: 12

Met Ser Leu Ser Lys Glu Val Lys Ser Phe Gln Trp Thr Gln Ala Leu
1               5                   10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
            35                  40                  45

Asn Val Gln Arg Ile Met Arg Lys Glu Lys Arg Asp Asp Lys Asp Leu
50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
            115                 120                 125

Leu Thr Thr Gln Gln Leu Asp Gln Arg Ser Gln Ile Leu Gln Ile Val
130                 135                 140

Gly Met Arg Lys Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
            180                 185                 190

Asp Val Val Gln Ala Leu Thr Asp Leu Gly Leu Leu Tyr Thr Val Lys
            195                 200                 205

Tyr Pro Asn Leu Asn Asp Leu Glu Arg Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Arg Lys Leu Asn Met Phe
            275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
                325                 330                 335

Glu Lys Pro Ala Val Asn Ser Pro Arg Pro Ala Pro Gly Ala Ala Gly
            340                 345                 350

Pro Pro Gln Val Gly Leu Ser Tyr Ser Gln Thr Met Leu Leu Lys Asp
            355                 360                 365

Leu Met Gly Gly Ile Asp Pro Asn Ala Pro Thr Trp Ile Asp Ile Glu
370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Val Asp Gln Lys Gln Phe
                405                 410                 415
```

-continued

```
Lys Gln Asp Ser Lys Tyr Ser His Gly Met Asp Leu Ala Asp Leu Phe
            420                 425                 430

Asn Ala Gln Pro Gly Leu Thr Ser Val Ile Gly Ala Leu Pro Gln
            435                 440                 445

Gly Met Val Leu Ser Cys Gln Gly Ser Asp Ile Arg Lys Leu Leu
450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys
                500                 505                 510

Glu Ile Thr Pro His Cys Ala Leu Met Asp Cys Ile Ile Phe Glu Ser
            515                 520                 525

Ala Ser Lys Ala Arg Leu Pro Asp Leu Lys Thr Val His Asn Ile Leu
530                 535                 540

Pro His Asp Leu Ile Phe Arg Gly Pro Asn Val Val Thr Leu
545                 550                 555

<210> SEQ ID NO 13
<211> LENGTH: 498
<212> TYPE: PRT
<213> ORGANISM: Lymphocytic choriomeningitis virus
<220> FEATURE:
<223> OTHER INFORMATION: GP protein of the Clone 13 strain of LCMV
      (GenBank Accession No. ABC96001.2; GI:116563462)

<400> SEQUENCE: 13

Met Gly Gln Ile Val Thr Met Phe Glu Ala Leu Pro His Ile Ile Asp
1               5                   10                  15

Glu Val Ile Asn Ile Val Ile Val Leu Ile Val Ile Thr Gly Ile
            20                  25                  30

Lys Ala Val Tyr Asn Phe Ala Thr Cys Gly Ile Phe Ala Leu Ile Ser
            35                  40                  45

Phe Leu Leu Leu Ala Gly Arg Ser Cys Gly Met Tyr Gly Leu Lys Gly
50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Ser His Asn Phe Cys Asn Leu Thr Ser Ala
            115                 120                 125

Phe Asn Lys Lys Thr Phe Asp His Thr Leu Met Ser Ile Val Ser Ser
130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Ala Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
            195                 200                 205

Gly Trp Thr Gly Ser Asp Gly Lys Thr Thr Trp Cys Ser Gln Thr Ser
```

```
            210                 215                 220
Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
    290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
    370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Val Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg

<210> SEQ ID NO 14
<211> LENGTH: 2210
<212> TYPE: PRT
<213> ORGANISM: Lymphocytic choriomeningitis virus
<220> FEATURE:
<223> OTHER INFORMATION: L protein of the Clone 13 strain of LCMV
      (GenBank Accession No. ABC96004.1; GI:86440169)

<400> SEQUENCE: 14

Met Asp Glu Ile Ile Ser Glu Leu Arg Glu Leu Cys Leu Asn Tyr Ile
1               5                   10                  15

Glu Gln Asp Glu Arg Leu Ser Arg Gln Lys Leu Asn Phe Leu Gly Gln
            20                  25                  30

Arg Glu Pro Arg Met Val Leu Ile Glu Gly Leu Lys Leu Leu Ser Arg
        35                  40                  45

Cys Ile Glu Ile Asp Ser Ala Asp Lys Ser Gly Cys Thr His Asn His
    50                  55                  60

Asp Asp Lys Ser Val Glu Thr Ile Leu Val Glu Ser Gly Ile Val Cys
```

```
                65                  70                  75                  80
Pro Gly Leu Pro Leu Ile Ile Pro Asp Gly Tyr Lys Leu Ile Asp Asn
                    85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Arg Glu
        115                 120                 125

Asp Leu Ala Val Ala Gly Val Thr Leu Val Pro Ile Val Asp Gly Arg
    130                 135                 140

Cys Asp Tyr Asp Asn Ser Phe Met Pro Glu Trp Ala Asn Phe Lys Phe
145                 150                 155                 160

Arg Asp Leu Leu Phe Lys Leu Leu Glu Tyr Ser Asn Gln Asn Glu Lys
                165                 170                 175

Val Phe Glu Glu Ser Glu Tyr Phe Arg Leu Cys Glu Ser Leu Lys Thr
            180                 185                 190

Thr Ile Asp Lys Arg Ser Gly Met Asp Ser Met Lys Ile Leu Lys Asp
        195                 200                 205

Ala Arg Ser Thr His Asn Asp Glu Ile Met Arg Met Cys His Glu Gly
    210                 215                 220

Ile Asn Pro Asn Met Ser Cys Asp Asp Val Val Phe Gly Ile Asn Ser
225                 230                 235                 240

Leu Phe Ser Arg Phe Arg Arg Asp Leu Glu Ser Gly Lys Leu Lys Arg
                245                 250                 255

Asn Phe Gln Lys Val Asn Pro Glu Gly Leu Ile Lys Glu Phe Ser Glu
            260                 265                 270

Leu Tyr Glu Asn Leu Ala Asp Ser Asp Asp Ile Leu Thr Leu Ser Arg
        275                 280                 285

Glu Ala Val Glu Ser Cys Pro Leu Met Arg Phe Ile Thr Ala Glu Thr
    290                 295                 300

His Gly His Glu Arg Gly Ser Glu Thr Ser Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Phe Lys Gly Leu Lys Asn Asp Lys His Trp Val Gly
        355                 360                 365

Cys Cys Tyr Ser Ser Val Asn Asp Arg Leu Val Ser Phe His Ser Thr
    370                 375                 380

Lys Glu Glu Phe Ile Arg Leu Leu Arg Asn Arg Lys Lys Ser Lys Val
385                 390                 395                 400

Phe Arg Lys Val Ser Phe Glu Glu Leu Phe Arg Ala Ser Ile Ser Glu
                405                 410                 415

Phe Ile Ala Lys Ile Gln Lys Cys Leu Leu Val Gly Leu Ser Phe
            420                 425                 430

Glu His Tyr Gly Leu Ser Glu His Leu Glu Gln Glu Cys His Ile Pro
        435                 440                 445

Phe Thr Glu Phe Glu Asn Phe Met Lys Ile Gly Ala His Pro Ile Met
    450                 455                 460

Tyr Tyr Thr Lys Phe Glu Asp Tyr Asn Phe Gln Pro Ser Thr Glu Gln
465                 470                 475                 480

Leu Lys Asn Ile Gln Ser Leu Arg Arg Leu Ser Ser Val Cys Leu Ala
                485                 490                 495
```

-continued

```
Leu Thr Asn Ser Met Lys Thr Ser Ser Val Ala Arg Leu Arg Gln Asn
            500                 505                 510
Gln Ile Gly Ser Val Arg Tyr Gln Val Val Glu Cys Lys Glu Val Phe
        515                 520                 525
Cys Gln Val Ile Lys Leu Asp Ser Glu Glu Tyr His Leu Leu Tyr Gln
    530                 535                 540
Lys Thr Gly Glu Ser Ser Arg Cys Tyr Ser Ile Gln Gly Pro Asp Gly
545                 550                 555                 560
His Leu Ile Ser Phe Tyr Ala Asp Pro Lys Arg Phe Phe Leu Pro Ile
                565                 570                 575
Phe Ser Asp Glu Val Leu Tyr Asn Met Ile Asp Ile Met Ile Ser Trp
            580                 585                 590
Ile Arg Ser Cys Pro Asp Leu Lys Asp Cys Leu Thr Asp Ile Glu Val
        595                 600                 605
Ala Leu Arg Thr Leu Leu Leu Met Leu Thr Asn Pro Thr Lys Arg
    610                 615                 620
Asn Gln Lys Gln Val Gln Ser Val Arg Tyr Leu Val Met Ala Ile Val
625                 630                 635                 640
Ser Asp Phe Ser Ser Thr Ser Leu Met Asp Lys Leu Arg Glu Asp Leu
                645                 650                 655
Ile Thr Pro Ala Glu Lys Val Val Tyr Lys Leu Leu Arg Phe Leu Ile
            660                 665                 670
Lys Thr Ile Phe Gly Thr Gly Glu Lys Val Leu Leu Ser Ala Lys Phe
        675                 680                 685
Lys Phe Met Leu Asn Val Ser Tyr Leu Cys His Leu Ile Thr Lys Glu
    690                 695                 700
Thr Pro Asp Arg Leu Thr Asp Gln Ile Lys Cys Phe Glu Lys Phe Phe
705                 710                 715                 720
Glu Pro Lys Ser Gln Phe Gly Phe Val Asn Pro Lys Glu Ala Ile
                725                 730                 735
Thr Pro Glu Glu Glu Cys Val Phe Tyr Glu Gln Met Lys Arg Phe Thr
            740                 745                 750
Ser Lys Glu Ile Asp Cys Gln His Thr Thr Pro Gly Val Asn Leu Glu
        755                 760                 765
Ala Phe Ser Leu Met Val Ser Ser Phe Asn Asn Gly Thr Leu Ile Phe
    770                 775                 780
Lys Gly Glu Lys Lys Leu Asn Ser Leu Asp Pro Met Thr Asn Ser Gly
785                 790                 795                 800
Cys Ala Thr Ala Leu Asp Leu Ala Ser Asn Lys Ser Val Val Val Asn
                805                 810                 815
Lys His Leu Asn Gly Glu Arg Leu Leu Glu Tyr Asp Phe Asn Lys Leu
            820                 825                 830
Leu Val Ser Ala Val Ser Gln Ile Thr Glu Ser Phe Val Arg Lys Gln
        835                 840                 845
Lys Tyr Lys Leu Ser His Ser Asp Tyr Glu Tyr Lys Val Ser Lys Leu
    850                 855                 860
Val Ser Arg Leu Val Ile Gly Ser Lys Gly Glu Glu Thr Gly Arg Ser
865                 870                 875                 880
Glu Asp Asn Leu Ala Glu Ile Cys Phe Asp Gly Glu Glu Thr Ser
                885                 890                 895
Phe Phe Lys Ser Leu Glu Glu Lys Val Asn Thr Thr Ile Ala Arg Tyr
            900                 905                 910
```

```
Arg Arg Gly Arg Arg Ala Asn Asp Lys Gly Asp Gly Glu Lys Leu Thr
        915                 920                 925

Asn Thr Lys Gly Leu His His Leu Gln Leu Ile Leu Thr Gly Lys Met
    930                 935                 940

Ala His Leu Arg Lys Val Ile Leu Ser Glu Ile Ser Phe His Leu Val
945                 950                 955                 960

Glu Asp Phe Asp Pro Ser Cys Leu Thr Asn Asp Asp Met Lys Phe Ile
                965                 970                 975

Cys Glu Ala Val Glu Gly Ser Thr Glu Leu Ser Pro Leu Tyr Phe Thr
            980                 985                 990

Ser Val Ile Lys Asp Gln Cys Gly Leu Asp Glu Met Ala Lys Asn Leu
        995                 1000                1005

Cys Arg Lys Phe Phe Ser Glu Asn Asp Trp Phe Ser Cys Met Lys
    1010                1015                1020

Met Ile Leu Leu Gln Met Asn Ala Asn Ala Tyr Ser Gly Lys Tyr
    1025                1030                1035

Arg His Met Gln Arg Gln Gly Leu Asn Phe Lys Phe Asp Trp Asp
    1040                1045                1050

Lys Leu Glu Glu Asp Val Arg Ile Ser Glu Arg Glu Ser Asn Ser
    1055                1060                1065

Glu Ser Leu Ser Lys Ala Leu Ser Leu Thr Gln Cys Met Ser Ala
    1070                1075                1080

Ala Leu Lys Asn Leu Cys Phe Tyr Ser Glu Glu Ser Pro Thr Ser
    1085                1090                1095

Tyr Thr Ser Val Gly Pro Asp Ser Gly Arg Leu Lys Phe Ala Leu
    1100                1105                1110

Ser Tyr Lys Glu Gln Val Gly Gly Asn Arg Glu Leu Tyr Ile Gly
    1115                1120                1125

Asp Leu Arg Thr Lys Met Phe Thr Arg Leu Ile Glu Asp Tyr Phe
    1130                1135                1140

Glu Ser Phe Ser Ser Phe Phe Ser Gly Ser Cys Leu Asn Asn Asp
    1145                1150                1155

Lys Glu Phe Glu Asn Ala Ile Leu Ser Met Thr Ile Asn Val Arg
    1160                1165                1170

Glu Gly Phe Leu Asn Tyr Ser Met Asp His Ser Lys Trp Gly Pro
    1175                1180                1185

Met Met Cys Pro Phe Leu Phe Leu Met Phe Leu Gln Asn Leu Lys
    1190                1195                1200

Leu Gly Asp Asp Gln Tyr Val Arg Ser Gly Lys Asp His Val Ser
    1205                1210                1215

Thr Leu Leu Thr Trp His Met His Lys Leu Val Glu Val Pro Phe
    1220                1225                1230

Pro Val Val Asn Ala Met Met Lys Ser Tyr Val Lys Ser Lys Leu
    1235                1240                1245

Lys Leu Leu Arg Gly Ser Glu Thr Thr Val Thr Glu Arg Ile Phe
    1250                1255                1260

Arg Gln Tyr Phe Glu Met Gly Ile Val Pro Ser His Ile Ser Ser
    1265                1270                1275

Leu Ile Asp Met Gly Gln Gly Ile Leu His Asn Ala Ser Asp Phe
    1280                1285                1290

Tyr Gly Leu Leu Ser Glu Arg Phe Ile Asn Tyr Cys Ile Gly Val
    1295                1300                1305

Ile Phe Gly Glu Arg Pro Glu Ala Tyr Thr Ser Ser Asp Asp Gln
```

-continued

```
            1310                1315                1320

Ile Thr Leu Phe Asp Arg Arg Leu Ser Asp Leu Val Val Ser Asp
            1325                1330                1335

Pro Glu Glu Val Leu Val Leu Leu Glu Phe Gln Ser His Leu Ser
            1340                1345                1350

Gly Leu Leu Asn Lys Phe Ile Ser Pro Lys Ser Val Ala Gly Arg
            1355                1360                1365

Phe Ala Ala Glu Phe Lys Ser Arg Phe Tyr Val Trp Gly Glu Glu
            1370                1375                1380

Val Pro Leu Leu Thr Lys Phe Val Ser Ala Ala Leu His Asn Val
            1385                1390                1395

Lys Cys Lys Glu Pro His Gln Leu Cys Glu Thr Ile Asp Thr Ile
            1400                1405                1410

Ala Asp Gln Ala Ile Ala Asn Gly Val Pro Val Ser Leu Val Asn
            1415                1420                1425

Ser Ile Gln Arg Arg Thr Leu Asp Leu Leu Lys Tyr Ala Asn Phe
            1430                1435                1440

Pro Leu Asp Pro Phe Leu Leu Asn Thr Asn Thr Asp Val Lys Asp
            1445                1450                1455

Trp Leu Asp Gly Ser Arg Gly Tyr Arg Ile Gln Arg Leu Ile Glu
            1460                1465                1470

Glu Leu Cys Pro Asn Glu Thr Lys Val Val Arg Lys Leu Val Arg
            1475                1480                1485

Lys Leu His His Lys Leu Lys Asn Gly Glu Phe Asn Glu Glu Phe
            1490                1495                1500

Phe Leu Asp Leu Phe Asn Arg Asp Lys Lys Glu Ala Ile Leu Gln
            1505                1510                1515

Leu Gly Asp Leu Leu Gly Leu Glu Glu Asp Leu Asn Gln Leu Ala
            1520                1525                1530

Asp Val Asn Trp Leu Asn Leu Asn Glu Met Phe Pro Leu Arg Met
            1535                1540                1545

Val Leu Arg Gln Lys Val Val Tyr Pro Ser Val Met Thr Phe Gln
            1550                1555                1560

Glu Glu Arg Ile Pro Ser Leu Ile Lys Thr Leu Gln Asn Lys Leu
            1565                1570                1575

Cys Ser Lys Phe Thr Arg Gly Ala Gln Lys Leu Leu Ser Glu Ala
            1580                1585                1590

Ile Asn Lys Ser Ala Phe Gln Ser Cys Ile Ser Ser Gly Phe Ile
            1595                1600                1605

Gly Leu Cys Lys Thr Leu Gly Ser Arg Cys Val Arg Asn Lys Asn
            1610                1615                1620

Arg Glu Asn Leu Tyr Ile Lys Lys Leu Leu Glu Asp Leu Thr Thr
            1625                1630                1635

Asp Asp His Val Thr Arg Val Cys Asn Arg Asp Gly Ile Thr Leu
            1640                1645                1650

Tyr Ile Cys Asp Lys Gln Ser His Pro Glu Ala His Arg Asp His
            1655                1660                1665

Ile Cys Leu Leu Arg Pro Leu Leu Trp Asp Tyr Ile Cys Ile Ser
            1670                1675                1680

Leu Ser Asn Ser Phe Glu Leu Gly Val Trp Val Leu Ala Glu Pro
            1685                1690                1695

Thr Lys Gly Lys Asn Asn Ser Glu Asn Leu Thr Leu Lys His Leu
            1700                1705                1710
```

-continued

Asn Pro Cys Asp Tyr Val Ala Arg Lys Pro Glu Ser Ser Arg Leu
    1715            1720            1725

Leu Glu Asp Lys Val Asn Leu Asn Gln Val Ile Gln Ser Val Arg
    1730            1735            1740

Arg Leu Tyr Pro Lys Ile Phe Glu Asp Gln Leu Leu Pro Phe Met
    1745            1750            1755

Ser Asp Met Ser Ser Lys Asn Met Arg Trp Ser Pro Arg Ile Lys
    1760            1765            1770

Phe Leu Asp Leu Cys Val Leu Ile Asp Ile Asn Ser Glu Ser Leu
    1775            1780            1785

Ser Leu Ile Ser His Val Val Lys Trp Lys Arg Asp Glu His Tyr
    1790            1795            1800

Thr Val Leu Phe Ser Asp Leu Ala Asn Ser His Gln Arg Ser Asp
    1805            1810            1815

Ser Ser Leu Val Asp Glu Phe Val Val Ser Thr Arg Asp Val Cys
    1820            1825            1830

Lys Asn Phe Leu Lys Gln Val Tyr Phe Glu Ser Phe Val Arg Glu
    1835            1840            1845

Phe Val Ala Thr Thr Arg Thr Leu Gly Asn Phe Ser Trp Phe Pro
    1850            1855            1860

His Lys Glu Met Met Pro Ser Glu Asp Gly Ala Glu Ala Leu Gly
    1865            1870            1875

Pro Phe Gln Ser Phe Val Ser Lys Val Val Asn Lys Asn Val Glu
    1880            1885            1890

Arg Pro Met Phe Arg Asn Asp Leu Gln Phe Gly Phe Gly Trp Phe
    1895            1900            1905

Ser Tyr Arg Met Gly Asp Val Val Cys Asn Ala Ala Met Leu Ile
    1910            1915            1920

Arg Gln Gly Leu Thr Asn Pro Lys Ala Phe Lys Ser Leu Lys Asp
    1925            1930            1935

Leu Trp Asp Tyr Met Leu Asn Tyr Thr Lys Gly Val Leu Glu Phe
    1940            1945            1950

Ser Ile Ser Val Asp Phe Thr His Asn Gln Asn Thr Asp Cys
    1955            1960            1965

Leu Arg Lys Phe Ser Leu Ile Phe Leu Val Arg Cys Gln Leu Gln
    1970            1975            1980

Asn Pro Gly Val Ala Glu Leu Leu Ser Cys Ser His Leu Phe Lys
    1985            1990            1995

Gly Glu Ile Asp Arg Arg Met Leu Asp Glu Cys Leu His Leu Leu
    2000            2005            2010

Arg Thr Asp Ser Val Phe Lys Val Asn Asp Gly Val Phe Asp Ile
    2015            2020            2025

Arg Ser Glu Glu Phe Glu Asp Tyr Met Glu Asp Pro Leu Ile Leu
    2030            2035            2040

Gly Asp Ser Leu Glu Leu Leu Leu Gly Ser Lys Arg Ile Leu
    2045            2050            2055

Asp Gly Ile Arg Ser Ile Asp Phe Glu Arg Val Gly Pro Glu Trp
    2060            2065            2070

Glu Pro Val Pro Leu Thr Val Lys Met Gly Ala Leu Phe Glu Gly
    2075            2080            2085

Arg Asn Leu Val Gln Asn Ile Ile Val Lys Leu Glu Thr Lys Asp
    2090            2095            2100

```
Met Lys Val Phe Leu Ala Gly Leu Glu Gly Tyr Glu Lys Ile Ser
    2105                2110                2115

Asp Val Leu Gly Asn Leu Phe Leu His Arg Phe Arg Thr Gly Glu
    2120                2125                2130

His Leu Leu Gly Ser Glu Ile Ser Val Ile Leu Gln Glu Leu Cys
    2135                2140                2145

Ile Asp Arg Ser Ile Leu Leu Ile Pro Leu Ser Leu Leu Pro Asp
    2150                2155                2160

Trp Phe Ala Phe Lys Asp Cys Arg Leu Cys Phe Ser Lys Ser Arg
    2165                2170                2175

Ser Thr Leu Met Tyr Glu Thr Val Gly Gly Arg Phe Arg Leu Lys
    2180                2185                2190

Gly Arg Ser Cys Asp Asp Trp Leu Gly Gly Ser Val Ala Glu Asp
    2195                2200                2205

Ile Asp
    2210

<210> SEQ ID NO 15
<211> LENGTH: 90
<212> TYPE: PRT
<213> ORGANISM: Lymphocytic choriomeningitis virus
<220> FEATURE:
<223> OTHER INFORMATION: Z protein of the Clone 13 strain of LCMV
      (GenBank Accession No. ABC96003.1; GI:86440168)

<400> SEQUENCE: 15

Met Gly Gln Gly Lys Ser Arg Glu Glu Lys Gly Thr Asn Ser Thr Asn
1               5                   10                  15

Arg Ala Glu Ile Leu Pro Asp Thr Thr Tyr Leu Gly Pro Leu Ser Cys
                20                  25                  30

Lys Ser Cys Trp Gln Lys Phe Asp Ser Leu Val Arg Cys His Asp His
                35                  40                  45

Tyr Leu Cys Arg His Cys Leu Asn Leu Leu Ser Val Ser Asp Arg
    50                  55                  60

Cys Pro Leu Cys Lys Tyr Pro Leu Pro Thr Arg Leu Lys Ile Ser Thr
65                  70                  75                  80

Ala Pro Ser Ser Pro Pro Tyr Glu Glu
                85                  90

<210> SEQ ID NO 16
<211> LENGTH: 498
<212> TYPE: PRT
<213> ORGANISM: Lymphocytic choriomeningitis virus
<220> FEATURE:
<223> OTHER INFORMATION: GP protein of the WE strain of LCMV

<400> SEQUENCE: 16

Met Gly Gln Ile Val Thr Met Phe Glu Ala Leu Pro His Ile Ile Asp
1               5                   10                  15

Glu Val Ile Asn Ile Val Ile Val Leu Ile Ile Ile Thr Ser Ile
                20                  25                  30

Lys Ala Val Tyr Asn Phe Ala Thr Cys Gly Ile Leu Ala Leu Val Ser
                35                  40                  45

Phe Leu Phe Leu Ala Gly Arg Ser Cys Gly Met Tyr Gly Leu Asn Gly
    50                  55                  60

Pro Asp Ile Tyr Lys Gly Val Tyr Gln Phe Lys Ser Val Glu Phe Asp
65                  70                  75                  80

Met Ser His Leu Asn Leu Thr Met Pro Asn Ala Cys Ser Ala Asn Asn
```

```
                    85                  90                  95
Ser His His Tyr Ile Ser Met Gly Ser Ser Gly Leu Glu Leu Thr Phe
                    100                 105                 110

Thr Asn Asp Ser Ile Leu Asn His Asn Phe Cys Asn Leu Thr Ser Ala
                    115                 120                 125

Phe Asn Lys Lys Thr Phe Asp His Thr Leu Met Ser Ile Val Ser Ser
        130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                    165                 170                 175

Pro Gln Ser Ala Ile Ser Gln Cys Arg Thr Phe Arg Gly Arg Val Leu
                    180                 185                 190

Asp Met Phe Arg Thr Ala Phe Gly Gly Lys Tyr Met Arg Ser Gly Trp
                    195                 200                 205

Gly Trp Ala Gly Ser Asp Gly Lys Thr Thr Trp Cys Ser Gln Thr Ser
        210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                    245                 250                 255

Thr Lys Phe Leu Thr Arg Arg Leu Ala Gly Thr Phe Thr Trp Thr Leu
                    260                 265                 270

Ser Asp Ser Ser Gly Val Glu Asn Pro Gly Gly Tyr Cys Leu Thr Lys
                    275                 280                 285

Trp Met Ile Leu Ala Ala Glu Leu Lys Cys Phe Gly Asn Thr Ala Val
        290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                    325                 330                 335

Glu Ser Ala Leu His Val Phe Lys Thr Thr Val Asn Ser Leu Ile Ser
                    340                 345                 350

Asp Gln Leu Leu Met Arg Asn His Leu Arg Asp Leu Met Gly Val Pro
                    355                 360                 365

Tyr Cys Asn Tyr Ser Lys Phe Trp Tyr Leu Glu His Ala Lys Thr Gly
        370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                    405                 410                 415

Ile Thr Glu Met Leu Arg Lys Asp Tyr Ile Lys Arg Gln Gly Ser Thr
                    420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
        450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                    485                 490                 495

Arg Arg
```

```
<210> SEQ ID NO 17
<211> LENGTH: 35
<212> TYPE: DNA
<213> ORGANISM: Artificial Sequence
<220> FEATURE:
<223> OTHER INFORMATION: WE specific primer

<400> SEQUENCE: 17
aatcgtctct aaggatgggt cagattgtga caatg                         35

<210> SEQ ID NO 18
<211> LENGTH: 35
<212> TYPE: DNA
<213> ORGANISM: Artificial Sequence
<220> FEATURE:
<223> OTHER INFORMATION: WE specific fusion-primer carrying an overhang
      complementary to the WET-specific primer

<400> SEQUENCE: 18
aatcgtctct aaggatgggt cagattgtga caatg                         35

<210> SEQ ID NO 19
<211> LENGTH: 37
<212> TYPE: DNA
<213> ORGANISM: Artificial Sequence
<220> FEATURE:
<223> OTHER INFORMATION: WE specific primer

<400> SEQUENCE: 19
ctcggtgatc atgttatctg cttcttgttc gatttga                       37

<210> SEQ ID NO 20
<211> LENGTH: 34
<212> TYPE: DNA
<213> ORGANISM: Artificial Sequence
<220> FEATURE:
<223> OTHER INFORMATION: WE specific fusion-primer complementary to the
      WE-sequence

<400> SEQUENCE: 20
aatcgtctct ttctttatct cctcttccag atgg                          34

<210> SEQ ID NO 21
<211> LENGTH: 23
<212> TYPE: DNA
<213> ORGANISM: Artificial Sequence
<220> FEATURE:
<223> OTHER INFORMATION: Primer specific for LCMV NP

<400> SEQUENCE: 21
ggctcccaga tctgaaaact gtt                                      23

<210> SEQ ID NO 22
<211> LENGTH: 22
<212> TYPE: DNA
<213> ORGANISM: Artificial Sequence
<220> FEATURE:
<223> OTHER INFORMATION: NP- and GP-specific primers; NP-specific: same
      as in RT reaction, GP- specific: 5 prime end

<400> SEQUENCE: 22
gctggcttgt cactaatggc tc                                       22
```

US 11,266,727 B2

ARENAVIRUS PARTICLES AS CANCER VACCINES

This application is a U.S. National Stage Application under 35 U.S.C. § 371 of International Patent Application No. PCT/EP2016/076668, filed Nov. 4, 2016, which claims the benefit of priority of U.S. Provisional Application No. 62/254,654, filed Nov. 12, 2015, and U.S. Provisional Application No. 62/254,651, filed Nov. 12, 2015, the entire contents of which are each incorporated herein by reference.

The instant application contains a Sequence Listing which has been submitted in ASCII format via EFS-Web and is hereby incorporated by reference in its entirety. Said ASCII copy, created on Nov. 2, 2016, is named 13194-017-228_Sequence_Listing.txt and is 112,465 bytes in size.

1. INTRODUCTION

The present application relates generally to genetically modified arenaviruses that are suitable vaccines against neoplastic diseases, such as cancer. The arenaviruses described herein may be suitable for vaccines and/or treatment of neoplastic diseases and/or for the use in immunotherapies. In particular, provided herein are methods and compositions for treating a neoplastic disease by administering a genetically modified arenavirus in combination with an immune checkpoint inhibitor, wherein the arenavirus has been engineered to include a nucleotide sequence encoding a tumor antigen, tumor associated antigen or antigenic fragment thereof.

2. BACKGROUND

2.1 Lymphocytic Choriomeningitis Virus Research and Human Disease

Lymphocytic choriomeningitis virus (LCMV), a member of the family arenaviridae, is a prototypic mouse model virus in research on viral infections. Since its isolation in the 1930s (Rivers and McNair Scott, 1935, Science, 81(2105): 439-440) studies using this virus have uncovered many key concepts in viral immunology and pathogenesis (summarized in Zinkernagel, 2002, Curr Top Microbiol Immunol, 263:1-5; Oldstone, 2002, Curr Top Microbiol Immunol, 263:83-117). LCMV has been extensively used to investigate viral molecular biology and immune responses particularly in the context of persistent infection. The natural hosts of LCMV are mice, however, several reports revealed that LCMV might also be a neglected human pathogen (Barton, 1996, Clin. Infect. Dis, 22(1):197; Wright et al., 1997, Pediatrics 100(1): E9). Moreover, numerous other members of the arenavirus family have been found in rodent populations around the world. In addition to the Old World arenavirus Lassa virus (LASV), which can be found in Africa, several New World arenaviruses like Junin, Guanarito or Machupo are prevalent in diverse rodent populations of South America (Johnson et al., 1966, Am J Trop Med Hyg, 15(1): 103-106; Tesh et al., 1993, Am J Trop Med Hyg 49(2):227-235; Mills et al., 1994, Trop Med Hyg 51(5): 554-562). Upon transmission to humans, many of those viruses can cause viral hemorrhagic fever associated with high mortality (Geisbert and Jahrling, 2004, Nat Med 10(12 Suppl): S110-121).

2.2 Genomic Organization of Lymphocytic Choriomeningitis Virus

Arenaviruses are enveloped viruses. Their genome consists of two segments of single-stranded RNA of negative sense (L: 7.2 kb, S: 3.4 kb). Each segment encodes for two viral genes in opposite orientations. The short segment (S segment) encodes the viral glycoprotein (GP) precursor (GP-C; 75 kDa) and the nucleoprotein (NP; 63 kDa) (Salvato et al., 1988, Virology 164(2): 517-522). The long segment (L segment) expresses the RNA-dependent RNA polymerase (RdRp; L protein; approximately 200 kDa) and the matrix protein Z (protein Z), a RING finger protein (11 kDa) (FIG. 1A) (Salvato et al., 1988, Virology 164(2): 517-522). The GP precursor GP-C is post-translationally cleaved into GP-1 and GP-2, which remain non-covalently associated (Buchmeier and Oldstone 1979, Virology 99(1): 111-120). Trimers of GP-1 and GP-2 are assembled as spikes on the surface of virions and are essential for mediating entry into the host cells by interaction with the cellular surface receptors. Binding and entry of the virus into host cells was long claimed to be mediated by interaction of the LCMV GP with the cellular receptor α-Dystroglycan as the only cellular receptor for LCMV (Cao et al., 1998, Science, 282(5396):2079-2081). Only very recently three additional human molecules (Axl and Tyro3 from the TAM family and dendritic cell-specific intracellular adhesion molecule 3-grabbing nonintegrin) were postulated as additional receptors for LCMV and LASV, a close relative of LCMV, which enable entry of LCMV into cells independently of α-Dystroglycan (Shimojima and Kawaoka 2012, J Vet Med, 74(10): 1363-1366; Shimojima et al., 2012, J Virol 86(4):2067-2078). NP binds to the viral RNA, forming the nucleocapsid, which serves as a template for the viral L protein. The nucleocapsid associated with the viral L protein forms the so-called ribonucleoprotein complex, which is active both in replication and transcription and represents the minimum unit of viral infectivity. It has been shown, that NP and the L protein are the minimal trans-acting factors necessary for viral RNA transcription and replication (Lee et al., 2000, J Virol 74(8): 3470-3477). The two genes on each segment are separated by a non-coding intergenic region (IGR) and flanked by 5' and 3' untranslated regions (UTR). The IGR forms a stable hairpin structure and has been shown to be involved in structure-dependent termination of viral mRNA transcription (Pinschewer et al., 2005, J Virol 79(7): 4519-4526). The terminal nucleotides of the UTR show a high degree of complementarity, resulting in the formation of secondary structures. These panhandle structures are known to serve as the viral promoter for transcription and replication, and their analysis by site-directed mutagenesis has revealed sequence- and structure-dependence, tolerating not even minor sequence changes (Perez and de la Torre, 2003, Virol 77(2): 1184-1194).

2.3 Reverse Genetic System

Isolated and purified RNAs of negative-strand viruses like LCMV cannot directly serve as mRNA i.e., cannot be translated when introduced into cells. Consequently transfection of cells with viral RNA does not lead to production of infectious viral particles. In order to generate infectious viral particles of negative-stranded RNA viruses from cDNA in cultured permissive cells, the viral RNA segment(s) must be trans-complemented with the minimal factors required for transcription and replication. With the help of a minigenome system which has been published several years ago, viral cis-acting elements and transacting factors involved in transcription, replication and formation of viral particles could finally be analyzed (Lee et al., 2000, J Virol 74(8): 3470-3477; Lee et al., 2002, J Virol 76(12): 6393-6397; Perez and de la Torre 2003, J Virol 77(2): 1184-1194;

Pinschewer et al., 2003, J Virol 77(6): 3882-3887; Pinschewer et al., 2005, J Virol 79(7): 4519-4526.). Also for other arenaviruses like LASV and Tacaribe virus reverse genetic systems have been established (Lopez et al., 2001, J Virol 75(24): 12241-12251; Hass et al., 2004, J Virol 78(24): 13793-13803). Two publications showed the recovery of infectious LCMV entirely from cDNA using pol-I/-II or T7/pol-II-driven plasmids, respectively (referred to as "viral rescue") (Flatz et al., 2006, Proc Natl Acad Sci USA 103(12): 4663-4668; Sanchez and de la Torre, 2006, Virology 350(2): 370-380).

2.4 Recombinant LCMV Expressing Genes of Interest

The generation of recombinant negative-stranded RNA viruses expressing foreign genes of interest has been pursued for a long time. Different strategies have been published for other viruses (Garcia-Sastre et al., 1994, J Virol 68(10): 6254-6261; Percy et al., 1994, J Virol 68(7): 4486-4492; Flick and Hobom, 1999, Virology 262(1): 93-103; Machado et al., 2003, Virology 313(1): 235-249). In the past it has been shown that it is possible to introduce additional foreign genes into the genome of bi-segmented LCMV particles (Emonet et al., 2009, PNAS, 106(9):3473-3478). Two foreign genes of interest were inserted into the bi-segmented genome of LCMV, resulting in tri-segmented LCMV particles (r3LCMV) with two S segments and one L segment. In the tri-segmented virus, published by Emonet et al., (2009), both NP and GP were kept in their respective natural position in the S segment and thus were expressed under their natural promoters in the flanking UTR.

2.5 Replication-Deficient Arenavirus

Recently, it has been shown that an infectious arenavirus particle can be engineered to contain a genome with the ability to amplify and express its genetic material in infected cells but unable to produce further progeny in normal, not genetically engineered cells (i.e., an infectious, replication-deficient arenavirus particle) (International Publication No.: WO 2009/083210 A1 and International Publication No.: WO 2014/140301 A1).

2.6 Replication-Deficient Arenavirus Vectors Expressing Genes of Interest

The use of infectious, replication-deficient arenaviruses as vectors for the expression of antigens has been reported (see Flatz et. al., 2010, Nat. Med., 16(3):339-345; Flatz et al., 2012, J. Virol., 86(15), 7760-7770). These infectious, replication-deficient arenaviruses can infect a host cell, i.e., attach to a host cell and release their genetic material into the host cell. However, they are replication-deficient, i.e., the arenavirus is unable to produce further infectious progeny particles in a non-complementing cell, due to a deletion or functional inactivation of an open reading frame (ORF) encoding a viral protein, such as the GP protein. Instead, the ORF is substituted with a nucleotide sequence of an antigen of interest. In Flatz et al. 2010, the authors used infectious, replication-deficient arenaviruses as vectors to express OVA (SIINFEKL epitope). In Flatz et al. 2012, the authors used replication deficient arenaviruses as vectors to express HIV/SIV Env.

3. SUMMARY OF THE INVENTION

Provided herein are methods and compositions for treating a neoplastic disease using an arenavirus particle comprising a nucleotide sequence encoding a tumor antigen, tumor associated antigen or antigenic fragment thereof. Also provided herein are methods and compositions for treating a neoplastic disease using an immune checkpoint inhibitor. Such an immune check point inhibitor can inhibit, decrease or interfere with the activity of a negative checkpoint regulator. Thus, in certain embodiments, provided herein are methods for treating a neoplastic disease using an arenavirus particle comprising a nucleotide sequence encoding a tumor antigen, tumor associated antigen or antigenic fragment thereof, and an immune checkpoint inhibitor that inhibits, decreases or interferes with the activity of a negative checkpoint regulator. Also, in certain embodiments, provided herein are compositions comprising an arenavirus particle comprising a nucleotide sequence encoding a tumor antigen, tumor associated antigen or antigenic fragment thereof, and an immune checkpoint inhibitor that inhibits, decreases or interferes with the activity of a negative checkpoint regulator.

In certain embodiments, the arenavirus particle provided herein is engineered to contain an arenavirus genomic segment having a nucleotide sequence encoding a tumor antigen, tumor associated antigen or antigenic fragment thereof and at least one arenavirus open reading frame ("ORF") in a position other than the wild-type position of the ORF. In certain embodiments, the arenavirus particle provided herein is an infectious, replication deficient arenavirus particle. In other embodiments, the arenavirus particle provided herein is a tri-segmented arenavirus particle, which can be replication-deficient or replication-competent. In still other embodiments, the tri-segmented arenavirus particle provided herein, when propagated, does not result in a replication-competent bi-segmented viral particle.

3.1 Arenavirus Particles Having Non-Natural Open Reading Frame

In certain embodiments, provided herein are arenaviruses with rearrangements of their ORFs in their genomes and a nucleotide sequence encoding a tumor antigen, tumor associated antigen or an antigenic fragment thereof provided herein. In a particular embodiment, an arenavirus particle provided herein includes an arenavirus genomic segment that has been engineered to carry an arenavirus ORF in a position other than the wild-type position. Thus, in certain particular embodiments, provided herein is an arenavirus genomic segment comprising: a nucleotide sequence encoding a tumor antigen, tumor associated antigen or an antigenic fragment thereof; and at least one arenavirus ORF in a position other than the wild-type position of said ORF, wherein the ORF encodes the glycoprotein ("GP"), the nucleoprotein ("NP"), the matrix protein Z ("Z protein") or the RNA dependent RNA polymerase L ("L protein") of an arenavirus particle. Also provided herein is an arenavirus particle that has been engineered to contain such an arenavirus genomic segment.

In certain embodiments, an arenavirus particle provided herein is infectious, i.e., it is capable of entering into or injecting its genetic material into a host cell. In certain more specific embodiments, an arenavirus particle as provided herein is infectious, i.e., is capable of entering into or injecting its genetic material into a host cell followed by amplification and expression of its genetic information inside the host cell. In certain embodiments, the arenavirus particle provided herein is engineered to be an infectious, replication-deficient arenavirus particle, i.e., it contains a genome with the ability to amplify and express its genetic information in infected cells but unable to produce further infectious progeny particles in non-complementing cells.

The tumor antigen or tumor associated antigen encoded by the nucleotide sequence included within an arenavirus genomic segment or arenavirus particle provided herein can be one or more of the tumor antigens or tumor associated antigens selected from the group consisting of oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pm1-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triosephosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyp1B1, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMWMAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysis, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin αvβ3 (CD61), galactin, or Ral-B, CD123, CLL-1, CD38, CS-1, CD138, and ROR1. In certain embodiments, the nucleotide sequence encodes two, three, four, five, six, seven, eight, nine, ten or more tumor antigens, tumor associated antigens or antigenic fragments thereof. In certain embodiments, an antigenic fragment of a tumor antigen or tumor associated antigen provided herein is encoded by the nucleotide sequence included within the arenavirus.

Accordingly, in certain embodiments, provided herein is an arenavirus genomic segment comprising a nucleotide sequence encoding a tumor antigen, tumor associated antigen or an antigenic fragment thereof provided herein. In certain embodiments, the genomic segment is engineered to carry an arenavirus ORF in a position other than the wild-type position of the ORF. In some embodiments, the arenavirus genomic segment is selected from the group consisting of:

(i) an S segment, wherein the ORF encoding the NP is under control of an arenavirus 5' UTR;
(ii) an S segment, wherein the ORF encoding the Z protein is under control of an arenavirus 5' UTR;
(iii) an S segment, wherein the ORF encoding the L protein is under control of an arenavirus 5' UTR;
(iv) an S segment, wherein the ORF encoding the GP is under control of an arenavirus 3' UTR;
(v) an S segment, wherein the ORF encoding the L protein is under control of an arenavirus 3' UTR;
(vi) an S segment, wherein the ORF encoding the Z protein is under control of an arenavirus 3' UTR;
(vii) an L segment, wherein the ORF encoding the GP is under control of an arenavirus 5' UTR;
(viii) an L segment, wherein the ORF encoding the NP is under control of an arenavirus 5' UTR;
(ix) an L segment, wherein the ORF encoding the L protein is under control of an arenavirus 5' UTR;
(x) an L segment, wherein the ORF encoding the GP is under control of an arenavirus 3' UTR;
(xi) an L segment, wherein the ORF encoding the NP is under control of an arenavirus 3' UTR; and
(xii) an L segment, wherein the ORF encoding the Z protein is under control of an arenavirus 3' UTR.

In certain embodiments, the arenavirus 3' UTR is the 3' UTR of the arenavirus S segment or the arenavirus L segment. In certain embodiments, the arenavirus 5' UTR is the 5' UTR of the arenavirus S segment or the arenavirus L segment.

In certain embodiments, the arenavirus particle provided herein comprises a second arenavirus genomic segment so that the arenavirus particle comprises an S segment and an L segment.

In certain embodiments, an arenavirus particle provided herein is infectious, i.e., it is capable of entering into or injecting its genetic material into a host cell. In certain more specific embodiments, an arenavirus particle as provided herein is infectious, i.e., is capable of entering into or injecting its genetic material into a host cell followed by amplification and expression of its genetic information inside the host cell. In certain embodiments, the arenavirus particle is an infectious, replication-deficient arenavirus particle engineered to contain a genome with the ability to amplify and express its genetic information in infected cells but unable to produce further infectious progeny particles in non-complementing cells. In certain embodiments, the arenavirus particle is replication-competent and able to produce further infectious progeny particles in normal, not genetically engineered cells. In certain more specific embodiments, such a replication-competent particle is attenuated relative to the wild type virus from which the replication-competent particle is derived.

In certain embodiments, an arenavirus genomic segment provided herein, including an arenavirus particle comprising the arenavirus genomic segment, comprises at least one arenavirus ORF that is at least partially removed or functionally inactivated. The ORF can encode the GP, NP, Z protein, or L protein of an arenavirus particle. Additionally, in certain embodiments, at least one ORF encoding the GP, NP, Z protein, or L protein is removed and replaced with a nucleotide sequence encoding a tumor antigen, tumor associated antigen or an antigenic fragment thereof provided herein. In certain embodiments, only one of the four ORFs encoding GP, NP, Z protein, and L protein is removed. Thus, in certain embodiments, the ORF encoding GP is removed. In certain embodiments, the ORF encoding NP is removed. In certain embodiments, the ORF encoding Z protein is removed. In certain embodiments, the ORF encoding L protein is removed.

In certain embodiments, a bi-segmented infectious, replication-deficient arenavirus particle provided herein comprises at least one arenavirus ORF that is at least partially removed or functionally inactivated. The ORF can encode GP, NP, Z protein, or L protein. Additionally, in certain embodiments, at least one ORF encoding the GP, NP, Z protein, or L protein is removed and replaced with a nucleotide sequence encoding a tumor antigen, tumor associated antigen or an antigenic fragment thereof provided herein. In certain embodiments, only one of the four ORFs encoding GP, NP, Z protein and L protein is removed. Thus, in certain embodiments, the ORF encoding GP is removed. In certain embodiments, the ORF encoding NP is removed. In certain embodiments, the ORF encoding Z protein is removed. In certain embodiments, the ORF encoding L protein is removed.

In certain embodiments, a bi-segmented infectious, replication-deficient arenavirus particle comprising a nucleotide sequence encoding a tumor antigen, tumor associated antigen or antigenic fragment thereof as provided herein further comprises at least one nucleotide sequence encoding at least one immunomodulatory peptide, polypeptide or protein. In certain embodiments, the immunomodulatory peptide, polypeptide or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; *Mycobacterium tuberculosis* Heat shock protein 70 or an antigenic fragment thereof; Herpes simplex virus 1 protein VP22 or an antigenic fragment thereof; CD40 ligand or an antigenic fragment thereof; or Fms-related tyrosine kinase 3 (Flt3) ligand or an antigenic fragment thereof.

In certain embodiments, an arenavirus particle provided herein is derived from a specific arenavirus species, such as lymphocytic choriomeningitis virus ("LCMV") or Junin virus ("JUNV"). In other words, the genomic information encoding the arenavirus particle is derived from a specific species of arenavirus. Thus, in certain embodiments, the arenavirus particle is derived from LCMV. In other embodiments, the arenavirus particle is derived from JUNV. Additionally, is specific embodiments, the LCMV is MP strain, WE strain, Armstrong strain, or Armstrong Clone 13 strain. In other specific embodiments, the JUNV is JUNV vaccine Candid #1 strain, or JUNV vaccine XJ Clone 3 strain.

3.2 Tri-Segmented Arenaviruses

In certain embodiments, provided herein are tri-segmented arenavirus particles comprising a nucleotide sequence encoding a tumor antigen, tumor associated antigen or an antigenic fragment thereof provided herein. Thus, in certain embodiments, an arenavirus particle provided herein can comprise one L segment and two S segments or two L segments and one S segment. In certain embodiments, the tri-segmented arenavirus particle provided herein does not recombine into a replication-competent bi-segmented arenavirus particle. Accordingly, in certain embodiments, propagation of the tri-segmented arenavirus particle does not result in a replication-competent bi-segmented particle after 70 days of persistent infection in mice lacking type I interferon receptor, type II interferon receptor and recombination activating gene 1 (RAG1) and having been infected with $10^4$ PFU of the tri-segmented arenavirus particle. The tri-segmented arenavirus particles provided herein, in certain embodiments, can be engineered to improve genetic stability and ensure lasting transgene expression. Moreover, in certain embodiments, inter-segmental recombination of the two S segments or two L segments, uniting two arenavirus ORFs on only one instead of two separate segments, abrogates viral promoter activity.

In certain embodiments, a tri-segmented arenavirus particle, as provided herein, is infectious, i.e., it is capable of entering into or injecting its genetic material into a host cell. In certain more specific embodiments, a tri-segmented arenavirus particle as provided herein is infectious, i.e., is capable of entering into or injecting its genetic material into a host cell followed by amplification and expression of its genetic information inside the host cell. In certain embodiments, the tri-segmented arenavirus particle is an infectious, replication-deficient arenavirus particle engineered to contain a genome with the ability to amplify and express its genetic information in infected cells but unable to produce further infectious progeny particles in non-complementing cells. In certain embodiments, the tri-segmented arenavirus particle is replication-competent and able to produce further infectious progeny particles in normal, not genetically engineered cells. In certain more specific embodiments, such a replication-competent particle is attenuated relative to the wild type virus from which the replication-competent particle is derived.

The tumor antigen or tumor associated antigen encoded by the nucleotide sequence included within a tri-segmented arenavirus particle provided herein can be one or more of the tumor antigens or tumor associated antigens selected from the group consisting of oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (Ep-CAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pm1-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triosephosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyp1B1, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMWMAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysis, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin αvβ3 (CD61), galactin, or Ral-B, CD123, CLL-1, CD38, CS-1, CD138, and ROR1. In certain embodiments, the nucleotide sequence encodes two, three, four, five, six, seven, eight, nine, ten or more tumor antigens, tumor associated antigens or antigenic fragments thereof. In certain embodiments, an antigenic fragment of a tumor antigen or tumor associated antigen provided herein is encoded by the nucleotide sequence included within the tri-segmented arenavirus.

In certain embodiments, provided herein are tri-segmented arenaviruses with rearrangements of their ORFs in their genomes and a nucleotide sequence encoding a tumor antigen, tumor associated antigen or an antigenic fragment thereof provided herein. In a particular embodiment, a tri-segmented arenavirus particle provided herein has been engineered to carry an arenavirus ORF in a position other than the wild-type position. Thus, in certain particular embodiments, provided herein is a tri-segmented arenavirus comprising: a nucleotide sequence encoding a tumor antigen, tumor associated antigen or an antigenic fragment thereof; and at least one arenavirus ORF in a position other than the wild-type position of said ORF, wherein the ORF encodes the GP, NP, Z protein or L protein of an arenavirus particle.

In certain embodiments, one of the two S segments included in the tri-segmented arenavirus particle provided herein is selected from the group consisting of:

(i) an S segment, wherein the ORF encoding the NP is under control of an arenavirus 5' UTR
(ii) an S segment, wherein the ORF encoding the Z protein is under control of an arenavirus 5' UTR;
(iii) an S segment, wherein the ORF encoding the L protein is under control of an arenavirus 5' UTR;
(iv) an S segment, wherein the ORF encoding the GP is under control of an arenavirus 3' UTR;
(v) an S segment, wherein the ORF encoding the L protein is under control of an arenavirus 3' UTR; and
(vi) an S segment, wherein the ORF encoding the Z protein is under control of an arenavirus 3' UTR.

In certain embodiments, one of the two L segments included in the tri-segmented arenavirus particle provided herein is selected from the group consisting of:

(i) an L segment, wherein the ORF encoding the GP is under control of an arenavirus 5' UTR;
(ii) an L segment, wherein the ORF encoding the NP is under control of an arenavirus 5' UTR;
(iii) an L segment, wherein the ORF encoding the L protein is under control of an arenavirus 5' UTR;
(iv) an L segment, wherein the ORF encoding the GP is under control of an arenavirus 3' UTR;
(v) an L segment, wherein the ORF encoding the NP is under control of an arenavirus 3' UTR; and
(vi) an L segment, wherein the ORF encoding the Z protein is under control of an arenavirus 3' UTR.

In certain embodiments, the tri-segmented arenavirus particle 3' UTR is the 3' UTR of the arenavirus S segment or the arenavirus L segment. In other embodiments, the tri-segmented arenavirus particle 5' UTR is the 5' UTR of the arenavirus S segment or the arenavirus L segment.

In certain embodiments, the two S segments comprise: (i) one or two nucleotide sequences each encoding a tumor antigen, tumor associated antigen or an antigenic fragment thereof; or (ii) one or two duplicated arenavirus ORFs; or (iii) one nucleotide sequence encoding a tumor antigen, tumor associated antigen or an antigenic fragment thereof and one duplicated arenavirus ORF.

In certain embodiments, the two L segments comprise (i) one or two nucleotide sequences each encoding a tumor antigen, tumor associated antigen or an antigenic fragment thereof; or (ii) one or two duplicated arenavirus ORFs; or (iii) one nucleotide sequence encoding a tumor antigen, tumor associated antigen or an antigenic fragment thereof and one duplicated arenavirus ORF.

In certain embodiments, a tri-segmented arenavirus particle provided herein, comprises at least one arenavirus ORF that is at least partially removed or functionally inactivated.

The ORF can encode the GP, NP, Z protein, or L protein of an arenavirus particle. Additionally, in certain embodiments, at least one ORF encoding the GP, NP, Z protein, or L protein is removed and replaced with a nucleotide sequence encoding a tumor antigen, tumor associated antigen or an antigenic fragment thereof provided herein. In certain embodiments, only one of the four ORFs encoding GP, NP, Z protein, and L protein is removed. Thus, in certain embodiments, the ORF encoding GP is removed. In certain embodiments, the ORF encoding NP is removed. In certain embodiments, the ORF encoding Z protein is removed. In certain embodiments, the ORF encoding L protein is removed.

In certain embodiments, a tri-segmented arenavirus particle provided herein is derived from a specific arenavirus species, such as lymphocytic choriomeningitis virus ("LCMV") or Junin virus ("JUNV"). In other words, the genomic information encoding the tri-segmented arenavirus particle is derived from a specific species of arenavirus. Thus, in certain embodiments, the tri-segmented arenavirus particle is derived from LCMV. In other embodiments, the tri-segmented arenavirus particle is derived from JUNV. Additionally, is specific embodiments, the LCMV is MP strain, WE strain, Armstrong strain, or Armstrong Clone 13 strain. In other specific embodiments, the JUNV is JUNV vaccine Candid #1 strain, or JUNV vaccine XJ Clone 3 strain

3.3 Methods for Treating a Neoplastic Disease

In certain embodiments, provided herein are methods of treating a neoplastic disease in a subject. Such methods can include administering to a subject in need thereof an arenavirus particle, including a tri-segmented arenavirus particle, provided herein and an immune checkpoint inhibitor provided herein.

In certain embodiments, the arenavirus particle used in the methods is an infectious, replication-deficient arenavirus particle provided herein. In certain embodiments, the arenavirus particle used in the methods is a tri-segmented arenavirus particle provided herein, including an infectious, replication-deficient tri-segmented arenavirus particle or a replication-competent tri-segmented arenavirus particle. Thus, in certain embodiments, the arenavirus particle, including a tri-segmented arenavirus particle, used in the methods is replication-deficient, wherein the arenavirus particle is engineered to contain a genome comprising: (1) a nucleotide sequence encoding a tumor antigen, tumor associated antigen or an antigenic fragment thereof; and (2) the ability to amplify and express its genetic information in infected cells but unable to produce further infectious progeny particles in non-complementing cells. Moreover, in certain embodiments, a tri-segmented arenavirus particle used in the methods is replication-competent, wherein the tri-segmented arenavirus particle is engineered to contain a genome comprising: (1) a nucleotide sequence encoding a tumor antigen, tumor associated antigen or an antigenic fragment thereof; (2) the ability to amplify and express its genetic information in infected cells; and (3) the ability to produce further infectious progeny particles in normal, not genetically engineered cells. In certain embodiments, the immune checkpoint inhibitor inhibits, decreases or interferes with the activity of a negative checkpoint regulator. In certain embodiments, the arenavirus particle used in the methods is a bi-segmented infectious, replication-deficient arenavirus particle. Thus, in certain embodiments, the infectious, replication-deficient arenavirus particle used in the methods is engineered to contain a genome comprising: (1) a nucleotide sequence encoding a tumor antigen, tumor associated antigen or an antigenic fragment thereof; and (2) the ability to amplify and express its genetic information in infected cells but unable to produce further infectious progeny particles in non-complementing cells. In certain embodiments, the immune checkpoint inhibitor inhibits, decreases or interferes with the activity of a negative checkpoint regulator.

In certain embodiments, the tumor antigen or tumor associated antigen encoded by the nucleotide sequence included within an arenavirus particle, including a tri-segmented arenavirus particle, provided herein can be one or more of the tumor antigens or tumor associated antigens selected from the group consisting of oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pml-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triosephosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyp1B1, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMWMAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysis, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin αvβ3 (CD61), galactin, or Ral-B, CD123, CLL-1, CD38, CS-1, CD138, and ROR1. In certain embodiments, the nucleotide sequence encodes two, three, four, five, six, seven, eight, nine, ten or more tumor antigen, tumor associated antigens or antigenic fragments thereof. In certain embodiments, a tumor antigen, tumor associated antigen or an antigenic fragment thereof, provided herein is encoded by the nucleotide sequence included within the arenavirus, including a tri-segmented arenavirus.

In certain embodiments, provided herein are methods for treating a neoplastic disease in a subject by administering an immune checkpoint inhibitor that inhibits, decreases or interferes with the activity of a negative checkpoint regulator. In certain embodiments, the negative checkpoint regulator is selected from the group consisting of Cytotoxic T-lymphocyte antigen-4 (CTLA-4), CD80, CD86, Programmed cell death 1 (PD-1), Programmed cell death ligand 1 (PD-L1), Programmed cell death ligand 2 (PD-L2), Lymphocyte activation gene-3 (LAG-3; also known as CD223), Galectin-3, B and T lymphocyte attenuator (BTLA), T-cell membrane protein 3 (TIM3), Galectin-9 (GAL9), B7-H1, B7-H3, B7-H4, T-Cell immunoreceptor with Ig and ITIM domains (TIGIT/Vstm3/WUCAM/VSIG9), V-domain Ig suppressor of T-Cell activation (VISTA), Glucocorticoid-induced tumor necrosis factor receptor-related (GITR) protein, Herpes Virus Entry Mediator (HVEM), OX40, CD27, CD28, CD137. CGEN-15001T, CGEN-15022, CGEN-15027, CGEN-15049, CGEN-15052, and CGEN-15092.

In certain embodiments, the subject that is treated using the methods provided herein is suffering from, is susceptible to, or is at risk for a neoplastic disease. Thus, in some embodiments, the subject is suffering from a neoplastic disease. In some embodiments, the subject is susceptible to a neoplastic disease. In some embodiments, the subject is at risk for a neoplastic disease. In certain embodiments, the neoplastic disease that a subject treatable by the methods provided herein is selected from the group consisting of acute lymphoblastic leukemia; acute lymphoblastic lymphoma; acute lymphocytic leukaemia; acute myelogenous leukemia; acute myeloid leukemia (adult/childhood); adrenocortical carcinoma; AIDS-related cancers; AIDS-related lymphoma; anal cancer; appendix cancer; astrocytomas; atypical teratoid/rhabdoid tumor; basal-cell carcinoma; bile duct cancer, extrahepatic (cholangiocarcinoma); bladder cancer; bone osteosarcoma/malignant fibrous histiocytoma; brain cancer (adult/childhood); brain tumor, cerebellar astrocytoma (adult/childhood); brain tumor, cerebral astrocytoma/malignant glioma brain tumor; brain tumor, ependymoma; brain tumor, medulloblastoma; brain tumor, supratentorial primitive neuroectodermal tumors; brain tumor, visual pathway and hypothalamic glioma; brainstem glioma; breast cancer; bronchial adenomas/carcinoids; bronchial tumor; Burkitt lymphoma; cancer of childhood; carcinoid gastrointestinal tumor; carcinoid tumor; carcinoma of adult, unknown primary site; carcinoma of unknown primary; central nervous system embryonal tumor; central nervous system lymphoma, primary; cervical cancer; childhood adrenocortical carcinoma; childhood cancers; childhood cerebral astrocytoma; chordoma, childhood; chronic lymphocytic leukemia; chronic myelogenous leukemia; chronic myeloid leukemia; chronic myeloproliferative disorders; colon cancer; colorectal cancer; craniopharyngioma; cutaneous T-cell lymphoma; desmoplastic small round cell tumor; emphysema; endometrial cancer; ependymoblastoma; ependymoma; esophageal cancer; ewing's sarcoma in the Ewing family of tumors; extracranial germ cell tumor; extragonadal germ cell tumor; extrahepatic bile duct cancer; gallbladder cancer; gastric (stomach) cancer; gastric carcinoid; gastrointestinal carcinoid tumor; gastrointestinal stromal tumor; germ cell tumor: extracranial, extragonadal, or ovarian gestational trophoblastic tumor; gestational trophoblastic tumor, unknown primary site; glioma; glioma of the brain stem; glioma, childhood visual pathway and hypothalamic; hairy cell leukemia; head and neck cancer; heart cancer; hepatocellular (liver) cancer; hodgkin lymphoma; hypopharyngeal cancer; hypothalamic and visual pathway glioma; intraocular melanoma; islet cell carcinoma (endocrine pancreas); Kaposi Sarcoma; kidney cancer (renal cell cancer); langerhans cell histiocytosis; laryngeal cancer; lip and oral cavity cancer; liposarcoma; liver cancer (primary); lung cancer, non-small cell; lung cancer, small cell; lymphoma, primary central nervous system; macroglobulinemia, Waldenström; male breast cancer; malignant fibrous histiocytoma of bone/osteosarcoma; medulloblastoma; medulloepithelioma; melanoma; melanoma, intraocular (eye); merkel cell cancer; merkel cell skin carcinoma; mesothelioma; mesothelioma, adult malignant; metastatic squamous neck cancer with occult primary; mouth cancer; multiple endocrine neoplasia syndrome; multiple myeloma/plasma cell neoplasm; mycosis fungoides, myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma, non-small cell lung cancer; non-hodgkin lymphoma; oligodendroglioma; oral cancer; oral cavity cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; papillomatosis; paranasal sinus and nasal cavity cancer; parathyroid cancer; penile cancer; pharyngeal cancer; pheochromocytoma; pineal astrocytoma; pineal germinoma; pineal parenchymal tumors of intermediate differentiation; pineoblastoma and supratentorial primitive neuroectodermal tumors; pituary tumor; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; respiratory tract carcinoma involving the NUT gene on chromosome 15; retinoblastoma; rhabdomyosarcoma, childhood; salivary gland cancer; sarcoma, Ewing family of tumors; Sézary syndrome; skin cancer (melanoma); skin cancer (non-melanoma); small cell lung cancer; small intestine cancer soft tissue sarcoma; soft tissue sarcoma; spinal cord tumor; squamous cell carcinoma; squamous neck cancer with occult primary, metastatic; stomach (gastric) cancer; supratentorial primitive neuroectodermal tumor; T-cell lymphoma, cutaneous (Mycosis Fungoides and Sézary syndrome); testicular cancer; throat cancer; thymoma; thymoma and thymic carcinoma; thyroid cancer; thyroid cancer, childhood; transitional cell cancer of the renal pelvis and ureter; urethral cancer; uterine cancer, endometrial; uterine sarcoma; vaginal cancer; vulvar cancer; and Wilms Tumor.

In certain embodiments, the arenavirus particle, including a tri-segmented arenavirus, provided herein and an immune checkpoint inhibitor provided herein, which are used in the methods provided herein, can be administered in a variety of different combinations. Thus, in certain embodiments, the arenavirus particle and the immune checkpoint inhibitor are co-administered simultaneously. In other embodiments, the arenavirus particle is administered prior to administration of the immune checkpoint inhibitor. In still other embodiments, the arenavirus particle is administered after administration of the immune checkpoint inhibitor. The interval between administration of the arenavirus particle and the immune checkpoint inhibitor can be hours, days, weeks or months. Thus, in some embodiments, the interval is about 1 hour, about 2 hours, about 3 hours, about 4 hours, about 5 hours, about 6 hours, about 7 hours, about 8 hours, about 9 hours, about 10 hours, about 11 hours, about 12 hours, about 1 day, about 2 days, about 3 days, about 4 days, about 5 days, about 6 days, about 1 week, about 8 days, about 9 days, about 10 days, about 11 days, about 12 days, about 13 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 1 month, about 2 months, about 3 months, about 4 months, about 5 months, about 6 months, or more.

In certain embodiments, the method provided herein includes administering an arenavirus particle, including a tri-segmented arenavirus, provided herein and the immune checkpoint inhibitor provided herein in a therapeutically effective amount. Thus, in certain embodiments, provided herein is a method for treating a neoplastic disease in a subject comprising, administering to a subject in need thereof a therapeutically effective amount of an arenavirus particle and a therapeutically effective amount of an immune checkpoint inhibitor, wherein the arenavirus particle is engineered to contain a genomic segment comprising: a nucleotide sequence encoding a tumor antigen, tumor associated antigen or an antigenic fragment thereof; and at least one arenavirus ORF in a position other than the wild-type position of the ORF, wherein the ORF encodes the GP, NP, Z protein or L protein of the arenavirus particle, and wherein the immune checkpoint inhibitor inhibits, decreases or interferes with the activity of a negative checkpoint regulator.

In certain embodiments, provided herein is a method for treating a neoplastic disease in a subject comprising, administering to a subject in need thereof a therapeutically effective amount of a bi-segmented infectious, replication-deficient arenavirus particle and a therapeutically effective amount of an immune checkpoint inhibitor, wherein the arenavirus particle is engineered to contain a genome comprising: a nucleotide sequence encoding a tumor antigen, tumor associated antigen or an antigenic fragment thereof and the ability to amplify and express its genetic information in infected cells but unable to produce further infectious progeny particles in non-complementing cells, and wherein the immune checkpoint inhibitor inhibits, decreases or interferes with the activity of a negative checkpoint regulator.

In certain embodiments, provided herein are methods of treating a neoplastic disease in a subject comprising, administering to the subject two or more arenaviruses, including a tri-segmented arenavirus, provided herein expressing a tumor antigen, tumor associated antigen or antigenic fragment thereof. In a more specific embodiment, the method provided herein includes administering to the subject a first arenavirus particle, and administering to the subject, after a period of time, a second arenavirus particle. In still another embodiment, the first arenavirus particle and the second arenavirus particle are derived from different arenavirus species and/or comprise nucleotide sequences encoding different tumor antigen, tumor associated antigens or antigenic fragments thereof.

In certain embodiments, a method described herein includes administering to a subject in need thereof an arenavirus particle encoding a neoantigen in combination with an immune checkpoint inhibitor. In some embodiments, the neoantigen is ADP-dependent glucokinase (Adpgk) having a R203M mutation. In some embodiments, the subject has colon cancer. In some embodiments, the immune checkpoint inhibitor is an antibody that binds to or inhibits activity of Programmed cell death 1 ("PD1"). Accordingly, in one embodiment, disclosed herein is a method for treating colon cancer in a subject comprising administering to a subject in need thereof an arenavirus particle and an immune checkpoint inhibitor, wherein the arenavirus particle is engineered to contain an arenavirus genomic segment comprising: (i) a nucleotide sequence encoding a neoantigen or an antigenic fragment thereof; and (ii) at least one arenavirus ORF in a position other than the wild-type position of the ORF, wherein the ORF encodes the GP, the NP, the Z protein or the L protein of the arenavirus particle, wherein the neoantigen is Adpgk having a R203M mutation, the immune checkpoint inhibitor is an antibody that binds to or inhibits PD1, the arenavirus particle is derived from LCMV and is a tri-segmented arenavirus particle comprising one L segment and two S segments, and wherein, in one of the two S segments the ORF encoding the GP is under control of an arenavirus 3' UTR, and each of the two S segments comprise a nucleotide sequence encoding the neoantigen or antigenic fragment thereof.

In certain embodiments, a method described herein includes administering to a subject in need thereof an arenavirus particle encoding a melanoma antigen in combination with an immune checkpoint inhibitor. In some embodiments, the melanoma antigen is glycoprotein 100 ("GP100"), tyrosinase-related protein 1 ("TRP1") or tyrosinase-related protein 2 ("TRP2"). In some embodiments, the subject has melanoma. In some embodiments, the immune checkpoint inhibitor is an antibody that binds to or inhibits activity of PD1. Accordingly, in one embodiment, disclosed herein is a method for treating melanoma in a subject comprising administering to a subject in need thereof an arenavirus particle and an immune checkpoint inhibitor, wherein the arenavirus particle is engineered to contain an arenavirus genomic segment comprising: (i) a nucleotide sequence encoding a melanoma antigen or an antigenic fragment thereof; and (ii) at least one arenavirus ORF in a position other than the wild-type position of the ORF, wherein the ORF encodes the GP, the NP, the Z protein or the L protein of the arenavirus particle, wherein the melanoma antigen is selected from the group consisting of GP100, TRP1 and TRP2, the immune checkpoint inhibitor is an antibody that binds to or inhibits PD1, the arenavirus particle is derived from LCMV and is a tri-segmented arenavirus particle comprising one L segment and two S segments, and wherein, in one of the two S segments the ORF encoding the GP is under control of an arenavirus 3'

UTR, and each of the two S segments comprise a nucleotide sequence encoding the melanoma antigen or antigenic fragment thereof.

In certain embodiments, provided herein is the use of an arenavirus particle and an immune checkpoint inhibitor as described herein in a method of treatment of a neoplastic disease in a subject as described herein.

3.4 Pharmaceutical Compositions and Kits

In certain embodiments, provided herein are compositions, e.g., pharmaceutical, immunogenic or vaccine compositions, comprising an arenavirus particle, including a tri-segmented arenavirus particle, provided herein, an immune checkpoint inhibitor provided herein, and a pharmaceutically acceptable carrier. Thus, in some embodiments, provided herein is a pharmaceutical composition comprising an arenavirus particle as provided herein, an immune checkpoint inhibitor as provided herein and a pharmaceutically acceptable carrier.

In certain embodiments, the arenavirus particle contained within the compositions is an infectious, replication-deficient arenavirus particle provided herein. In certain embodiments, the arenavirus particle contained within the compositions is a tri-segmented arenavirus particle provided herein, including an infectious, replication-deficient tri-segmented arenavirus particle or a replication-competent tri-segmented arenavirus particle. Thus, in certain embodiments, the compositions providing herein, including a pharmaceutical, immunogenic or vaccine composition, comprise an arenavirus particle, including a tri-segmented arenavirus particle, that is replication-deficient, wherein the arenavirus particle is engineered to contain a genome comprising: (1) a nucleotide sequence encoding a tumor antigen, tumor associated antigen or an antigenic fragment thereof; and (2) the ability to amplify and express its genetic information in infected cells but unable to produce further infectious progeny particles in non-complementing cells. Moreover, in certain embodiments, the compositions providing herein, including a pharmaceutical, immunogenic or vaccine composition, comprise a tri-segmented arenavirus particle that is replication-competent, wherein the tri-segmented arenavirus particle is engineered to contain a genome comprising: (1) a nucleotide sequence encoding a tumor antigen, tumor associated antigen or an antigenic fragment thereof; (2) the ability to amplify and express its genetic information in infected cells; and (3) the ability to produce further infectious progeny particles in normal, not genetically engineered cells. In certain embodiments, the immune checkpoint inhibitor inhibits, decreases or interferes with the activity of a negative checkpoint regulator.

Thus, in some embodiments, provided herein is a pharmaceutical composition comprising a bi-segmented infectious, replication-deficient arenavirus particle as provided herein, an immune checkpoint inhibitor as provided herein and a pharmaceutically acceptable carrier. In specific certain embodiments, the arenavirus particle is engineered to contain a genome comprising: (1) a nucleotide sequence encoding a tumor antigen, tumor associated antigen or an antigenic fragment thereof; and (2) the ability to amplify and express its genetic information in infected cells but unable to produce further infectious progeny particles in non-complementing cells. In still further embodiments, the immune checkpoint inhibitor inhibits, decreases or interferes with the activity of a negative checkpoint regulator.

In certain embodiments, the tumor antigen or tumor associated antigen encoded by the nucleotide sequence included within an arenavirus particle provided herein can be one or more of the tumor antigens or tumor associated antigens selected from the group consisting of oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pml-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triosephosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyp1B1, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMWMAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysis, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin $\alpha v\beta 3$ (CD61), galactin, or Ral-B, CD123, CLL-1, CD38, CS-1, CD138, and ROR1. In certain embodiments, the nucleotide sequence encodes two, three, four, five, six, seven, eight, nine, ten or more tumor antigen, tumor associated antigens or antigenic fragments thereof. In certain embodiments, an antigenic fragment of a tumor antigen or tumor associated antigen provided herein is encoded by the nucleotide sequence included within the arenavirus.

In certain embodiments, the composition provided herein, including a pharmaceutical, immunogenic or vaccine composition, includes an immune checkpoint inhibitor that inhibits, decreases or interferes with the activity of a negative checkpoint regulator. In certain embodiments, the negative checkpoint regulator is selected from the group consisting of Cytotoxic T-lymphocyte antigen-4 (CTLA-4), CD80, CD86, Programmed cell death 1 (PD-1), Programmed cell death ligand 1 (PD-L1), Programmed cell death ligand 2 (PD-L2), Lymphocyte activation gene-3 (LAG-3; also known as CD223), Galectin-3, B and T lymphocyte attenuator (BTLA), T-cell membrane protein 3 (TIM3), Galectin-9 (GAL9), B7-H1, B7-H3, B7-H4, T-Cell immunoreceptor with Ig and ITIM domains (TIGIT/Vstm3/WUCAM/VSIG9), V-domain Ig suppressor of T-Cell activation (VISTA), Glucocorticoid-induced tumor necrosis factor receptor-related (GITR) protein, Herpes Virus Entry Mediator (HVEM), OX40, CD27, CD28, CD137. CGEN-15001T, CGEN-15022, CGEN-15027, CGEN-15049, CGEN-15052, and CGEN-15092.

In certain embodiments, the compositions provided herein, a pharmaceutical, immunogenic or vaccine composition, can be used in the methods described herein. Thus, in certain embodiments, the compositions can be used for the treatment of a neoplastic disease. In specific certain embodiments, the compositions provided herein can be used for the treatment of a neoplastic disease selected from the group consisting of acute lymphoblastic leukemia; acute lymphoblastic lymphoma; acute lymphocytic leukaemia; acute myelogenous leukemia; acute myeloid leukemia (adult/childhood); adrenocortical carcinoma; AIDS-related cancers; AIDS-related lymphoma; anal cancer; appendix cancer; astrocytomas; atypical teratoid/rhabdoid tumor; basal-cell carcinoma; bile duct cancer, extrahepatic (cholangiocarcinoma); bladder cancer; bone osteosarcoma/malignant fibrous histiocytoma; brain cancer (adult/childhood); brain tumor, cerebellar astrocytoma (adult/childhood); brain tumor, cerebral astrocytoma/malignant glioma brain tumor; brain tumor, ependymoma; brain tumor, medulloblastoma; brain tumor, supratentorial primitive neuroectodermal tumors; brain tumor, visual pathway and hypothalamic glioma; brainstem glioma; breast cancer; bronchial adenomas/carcinoids; bronchial tumor; Burkitt lymphoma; cancer of childhood; carcinoid gastrointestinal tumor; carcinoid tumor; carcinoma of adult, unknown primary site; carcinoma of unknown primary; central nervous system embryonal tumor; central nervous system lymphoma, primary; cervical cancer; childhood adrenocortical carcinoma; childhood cancers; childhood cerebral astrocytoma; chordoma, childhood; chronic lymphocytic leukemia; chronic myelogenous leukemia; chronic myeloid leukemia; chronic myeloproliferative disorders; colon cancer; colorectal cancer; craniopharyngioma; cutaneous T-cell lymphoma; desmoplastic small round cell tumor; emphysema; endometrial cancer; ependymoblastoma; ependymoma; esophageal cancer; ewing's sarcoma in the Ewing family of tumors; extracranial germ cell tumor; extragonadal germ cell tumor; extrahepatic bile duct cancer; gallbladder cancer; gastric (stomach) cancer; gastric carcinoid; gastrointestinal carcinoid tumor; gastrointestinal stromal tumor; germ cell tumor: extracranial, extragonadal, or ovarian gestational trophoblastic tumor; gestational trophoblastic tumor, unknown primary site; glioma; glioma of the brain stem; glioma, childhood visual pathway and hypothalamic; hairy cell leukemia; head and neck cancer; heart cancer; hepatocellular (liver) cancer; hodgkin lymphoma; hypopharyngeal cancer; hypothalamic and visual pathway glioma; intraocular melanoma; islet cell carcinoma (endocrine pancreas); Kaposi Sarcoma; kidney cancer (renal cell cancer); langerhans cell histiocytosis; laryngeal cancer; lip and oral cavity cancer; liposarcoma; liver cancer (primary); lung cancer, non-small cell; lung cancer, small cell; lymphoma, primary central nervous system; macroglobulinemia, Waldenström; male breast cancer; malignant fibrous histiocytoma of bone/osteosarcoma; medulloblastoma; medulloepithelioma; melanoma; melanoma, intraocular (eye); merkel cell cancer; merkel cell skin carcinoma; mesothelioma; mesothelioma, adult malignant; metastatic squamous neck cancer with occult primary; mouth cancer; multiple endocrine neoplasia syndrome; multiple myeloma/plasma cell neoplasm; mycosis fungoides, myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma, non-small cell lung cancer; non-hodgkin lymophoma; oligodendroglioma; oral cancer; oral cavity cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; papillomatosis; paranasal sinus and nasal cavity cancer; parathyroid cancer; penile cancer; pharyngeal cancer; pheochromocytoma; pineal astrocytoma; pineal germinoma; pineal parenchymal tumors of intermediate differentiation; pineoblastoma and supratentorial primitive neuroectodermal tumors; pituary tumor; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; respiratory tract carcinoma involving the NUT gene on chromosome 15; retinoblastoma; rhabdomyosarcoma, childhood; salivary gland cancer; sarcoma, Ewing family of tumors; Sézary syndrome; skin cancer (melanoma); skin cancer (non-melanoma); small cell lung cancer; small intestine cancer soft tissue sarcoma; soft tissue sarcoma; spinal cord tumor; squamous cell carcinoma; squamous neck cancer with occult primary, metastatic; stomach (gastric) cancer; supratentorial primitive neuroectodermal tumor; T-cell lymphoma, cutaneous (Mycosis Fungoides and Sézary syndrome); testicular cancer; throat cancer; thymoma; thymoma and thymic carcinoma; thyroid cancer; thyroid cancer, childhood; transitional cell cancer of the renal pelvis and ureter; urethral cancer; uterine cancer, endometrial; uterine sarcoma; vaginal cancer; vulvar cancer; and Wilms Tumor.

Also provided herein are kits that can be used to perform the methods described herein. Thus, in certain embodiments, the kit provided herein includes one or more containers and instructions for use, wherein the one or more containers comprise a composition (e.g., pharmaceutical, immunogenic or vaccine composition) provided herein. In other certain embodiments, a kit provided herein includes containers that each contains the active ingredients for performing the methods described herein. Thus, in certain embodiments, the kit provided herein includes two or more containers and instructions for use, wherein one of the containers comprises an arenavirus particle, including a tri-segmented arenavirus particle, provided herein and another container comprises an immune checkpoint inhibitor provided herein. In a specific embodiment, a kit provided herein includes two or more containers and instructions for use, wherein one of the containers comprises an arenavirus particle, including a tri-segmented arenavirus particle, provided herein and another container comprises an immune checkpoint inhibitor provided herein, wherein the arenavirus particle is engineered to contain a genome comprising: a nucleotide sequence encoding a tumor antigen, tumor associated antigen or an antigenic fragment thereof; and the ability to amplify and express its genetic information in infected cells but unable to produce further infectious progeny particles in non-complementing cells. Moreover, in certain embodiments, one of the containers comprises a tri-segmented arenavirus particle that is engineered to contain a genome comprising: a nucleotide sequence encoding a tumor antigen, tumor associated antigen or an antigenic fragment thereof; the ability to amplify and express its genetic information in infected cells; and the ability to produce further infectious progeny particles in normal, not genetically engineered cells. In certain embodiments, the kit provided herein includes two or more containers and instructions for use, wherein one of the containers comprises a bi-segmented infectious, replication-deficient arenavirus particle provided herein and another container comprises an immune checkpoint inhibitor provided herein. In a specific embodiment, a kit provided herein includes two or more containers and instructions for use, wherein one of the containers comprises a bi-segmented infectious, replication-deficient arenavirus particle provided herein and another container comprises an immune checkpoint inhibitor provided herein, wherein the arenavirus particle is engineered to contain a genome comprising: a nucleotide sequence encoding a tumor antigen, tumor associated antigen or an antigenic fragment thereof; and the ability to amplify and express its genetic information in infected cells but unable to produce further infectious progeny particles in non-complementing cells. In certain embodiments, the immune checkpoint inhibitor inhibits, decreases or interferes with the activity of a negative checkpoint regulator.

3.5 Conventions and Abbreviations

| Abbreviation | Convention |
|---|---|
| APC | Antigen presenting cell |
| C-cell | Complementing cell line |
| CD4 | Cluster of differentiation 4 |
| CD8 | Cluster of differentiation 8 |
| CMI | cell-mediated immunity |
| GP | Glycoprotein |
| GS-plasmid | Plasmid expressing genome segments |
| IGR | Intergenic region |
| JUNV | Junin virus |
| L protein | RNA-dependent RNA polymerase |
| L segment | Long segment |
| LCMV | Lymphocytic choriomeningitis virus |
| MHC | Major Histocompatibility Complex |
| NP | Nucleoprotein |

-continued

| Abbreviation | Convention |
|---|---|
| ORF | Open reading frame |
| S segment | Short segment |
| TF-plasmid | Plasmid expressing transacting factors |
| UTR | Untranslated region |
| Z protein | Matrix protein Z |

4. BRIEF DESCRIPTION OF THE FIGURES

FIG. 1: Schematic representation of the genomic organization of bi- and tri-segmented LCMV. The bi-segmented genome of wild-type LCMV consists of one S segment encoding the GP and NP and one L segment encoding the Z protein and the L protein (i). Both segments are flanked by the respective 5' and 3' UTRs. The genome of recombinant tri-segmented LCMVs (r3LCMV) consists of one L and two S segments with one position where to insert a gene of interest (here GFP, which can alternatively be a tumor antigen, tumor associated antigen or antigenic fragment thereof as described herein) into each one of the S segments. r3LCMV-GFP$^{natural}$ (nat) has all viral genes in their natural position (ii), whereas the GP ORF in r3LCMV-GFP$^{artificial}$ (art) is artificially juxtaposed to and expressed under control of the 3' UTR (iii).

FIG. 2: The genome of wild type arenaviruses consists of a short (1; ~3.4 kb) and a large (2; ~7.2 kb) RNA segment. The short segment carries open reading frames encoding the nucleoprotein (3) and glycoprotein (4). The large segment encodes the RNA-dependent RNA polymerase L (5) and the matrix protein Z (6). Wild type arenaviruses can be rendered replication-deficient vaccine vectors by deleting the glycoprotein gene and inserting, instead of the glycoprotein gene, a tumor antigen, tumor associated antigen, or antigenic fragment thereof described herein (7) against which immune responses are to be induced.

FIGS. 3A-3B depict exemplary results of a MC-38 OVA mouse cancer model (C57BL/6 mice, implanted with MC-38 OVADim tumor cells) treated with a tri-segmented replication competent arenavirus vector encoding an OVA antigen (r3LCMV-OVA) and an anti-PD1 antibody (aPD1) on tumor growth (FIG. 3A) and percent survival (FIG. 3B). Symbols represent the mean±SEM of five (untreated) or six (other groups) mice per group.

FIGS. 4A-4C depict exemplary results of a MC-38 mouse cancer model (C57BL/6 mice, implanted with MC-38 tumor cells) treated with a tri-segmented replication competent (r3LCMV) or bi-segmented replication-deficient (r2LCMV) arenavirus vector encoding an Adpgk$^{mut}$ antigen (Adpgk$^{mut}$), and an anti-PD1 antibody (u-PD-1 or PD1) on the induction of AdpgK$^{mut}$ antigen specific CD8+ cytotoxic T-cells (FIG. 4A), tumor growth (FIG. 4B) and percent survival (FIG. 4C).

FIG. 5A graphically represents an exemplary treatment regimen of a melanoma mouse model.

FIGS. 5B-5D depict exemplary results of a melanoma mouse model (C57BL/6 mice injected with B16F10 melanoma cells) treated with tri-segmented replication competent (r3LCMV) or bi-segmented replication-deficient (rLCMV) arenavirus vectors encoding melanoma antigens, and an anti-PD1 antibody (α-PD-1) using the treatment regimen of FIG. 5A on tumor growth (FIG. 5B), percent of animal survival (FIG. 5C) and days of survival (FIG. 5D). Gr.1 indicates group treated with r3LCMV and α-PD-1. Gr.2 indicates group treated with rLCMV and α-PD-1. Gr.3 indicates group treated with buffer and α-PD-1. Gr.4 indicates group treated with r3LCMV only. Gr.5 indicates group treated with rLCMV only. Gr.6 indicates treated with buffer only. Symbols represent the mean±SEM of five mice per group.

5. DETAILED DESCRIPTION OF THE INVENTION

Provided herein are immunotherapies for treating a neoplastic disease, such as cancer. The term "neoplastic" or "neoplasm" refers to an abnormal new growth of cells or tissue. This abnormal new growth can form a mass, also known as a tumor or neoplasia. A neoplasm includes a benign neoplasm, an in situ neoplasm, a malignant neoplasm, and a neoplasm of uncertain or unknown behavior. In certain embodiments, the neoplastic disease treated using the methods and compositions described herein is cancer.

The immunotherapies provided herein include various methods and compositions. More specifically, provided herein are arenavirus particles or viral vectors that comprise a nucleotide sequence encoding tumor antigen, tumor associated antigen or antigenic fragment thereof. These genetically modified viruses can be administered to a subject for the treatment of a neoplastic disease, such as cancer. Detailed descriptions of the arenaviruses provided herein, including the nucleotide sequences encoding a tumor antigen, tumor associated antigen or antigenic fragment thereof can be found in Sections 5.1, 5.2, 5.3, and 5.4. Additionally, methods for generation of arenavirus particles or viral vectors for use in the methods and compositions described herein are described in more detail in Sections 5.5 and 5.6.

In addition to administering arenavirus particles or viral vectors to a subject, the immunotherapies for treating a neoplastic disease provided herein can include an immune checkpoint modulator. The term "immune checkpoint modulator" (also referred to as "checkpoint modulator" or as "checkpoint regulator") refers to a molecule or to a compound that modulates (e.g., totally or partially reduces, inhibits, interferes with, activates, stimulates, increases, reinforces or supports) the function of one or more checkpoint molecules. Thus, an immune checkpoint modulator may be an immune checkpoint inhibitor or an immune checkpoint activator.

An "immune checkpoint inhibitor" refers to a molecule that inhibits, decreases or interferes with the activity of a negative checkpoint regulator. In certain embodiments, immune checkpoint inhibitors for use with the methods and compositions disclosed herein can inhibit the activity of a negative checkpoint regulator directly, or decrease the expression of a negative checkpoint regulator, or interfere with the interaction of a negative checkpoint regulator and a binding partner (e.g., a ligand). Immune checkpoint inhibitors for use with the methods and compositions disclosed herein include a protein, a polypeptide, a peptide, an antisense oligonucleotide, an antibody, an antibody fragment, or an inhibitory RNA molecule that targets the expression of a negative checkpoint regulator.

A "negative checkpoint regulator" refers to a molecule that down-regulates immune responses (e.g., T-cell activation) by delivery of a negative signal to T-cells following their engagement by ligands or counter-receptors. Exemplary functions of a negative-checkpoint regulator are to prevent out-of-proportion immune activation, minimize collateral damage, and/or maintain peripheral self-tolerance. In certain embodiments, a negative checkpoint regulator is a ligand or receptor expressed by an antigen presenting cell. In certain embodiments, a negative checkpoint regulator is a ligand or receptor expressed by a T-cell. In certain embodiments, a negative checkpoint regulator is a ligand or receptor expressed by both an antigen presenting cell and a T-cell.

Thus, in certain embodiments, provided herein are methods and compositions for treating a neoplastic disease using an arenavirus particle or viral vector comprising a nucleotide sequence encoding a tumor antigen, tumor associated antigen or antigenic fragment thereof and an immune checkpoint inhibitor. Such an immune check point inhibitor can inhibit, decrease or interfere with the activity of a negative checkpoint regulator. Thus, in certain embodiments, provided herein are methods for treating a neoplastic disease using an arenavirus particle or viral vector comprising a nucleotide sequence encoding a tumor antigen, tumor associated antigen or antigenic fragment thereof, and an immune checkpoint inhibitor that inhibits, decreases or interferes with the activity of a negative checkpoint regulator. Also, in certain embodiments, provided herein are compositions comprising an arenavirus particle or viral vector comprising a nucleotide sequence encoding a tumor antigen, tumor associated antigen or antigenic fragment thereof, and an immune checkpoint inhibitor that inhibits, decreases or interferes with the activity of a negative checkpoint regulator. In certain embodiments, the arenavirus particle or viral vector provided herein is engineered to contain an arenavirus genomic segment having a nucleotide sequence encoding a tumor antigen, tumor associated antigen or antigenic fragment thereof and at least one arenavirus open reading frame ("ORF") in a position other than the wild-type position of the ORF. In certain embodiments, the arenavirus particle or viral vector provided herein is an infectious, replication deficient arenavirus particle or viral vector. In other embodiments, the arenavirus particle provided herein is a tri-segmented arenavirus particle or viral vector, which can be replication-deficient or replication-competent. In still other embodiments, the tri-segmented arenavirus particle or viral vector provided herein, when propagated, does not result in a replication-competent bi-segmented viral particle. Methods and compositions for using an arenavirus particle or viral vector and an immune checkpoint inhibitor provided herein are described in more detail in Sections 5.8 and 5.9.

5.1 Arenaviruses with an Open Reading Frame in a Non-Natural Position

Provided herein are arenaviruses with rearrangements of their ORFs and a nucleotide sequence encoding a tumor antigen, tumor associated antigen or an antigenic fragment thereof provided herein. In certain embodiments, such arenaviruses are replication-competent and infectious. Thus, in certain embodiments, provided herein is an arenavirus genomic segment, wherein the arenavirus genomic segment is engineered to carry an arenavirus ORF in a position other than the position in which the respective gene is found in viruses isolated from the wild, such as LCMV-MP (referred to herein as "wild-type position") of the ORF (i.e., a non-natural position) and a nucleotide sequence encoding a tumor antigen, tumor associated antigen or an antigenic fragment thereof provided herein.

The wild-type arenavirus genomic segments and ORFs are known in the art. In particular, the arenavirus genome consists of an S segment and an L segment. The S segment carries the ORFs encoding the GP and the NP. The L segment encodes the L protein and the Z protein. Both segments are flanked by the respective 5' and 3' UTRs.

In certain embodiments, an arenavirus genomic segment can be engineered to carry two or more arenavirus ORFs in a position other than the wild-type position. In other embodiments, the arenavirus genomic segment can be engineered to carry two arenavirus ORFs, or three arenavirus ORFs, or four arenavirus ORFs in a position other than the wild-type position.

In certain embodiments, an arenavirus genomic segment provided herein can be:
(i) an arenavirus S segment, wherein the ORF encoding the NP is under control of an arenavirus 5' UTR;
(ii) an arenavirus S segment, wherein the ORF encoding the Z protein is under control of an arenavirus 5' UTR;
(iii) an arenavirus S segment, wherein the ORF encoding the L protein is under control of an arenavirus 5' UTR;
(iv) an arenavirus S segment, wherein the ORF encoding the GP is under control of an arenavirus 3' UTR;
(v) an arenavirus S segment, wherein the ORF encoding the L protein is under control of an arenavirus 3' UTR;
(vi) an arenavirus S segment, wherein the ORF encoding the Z protein is under control of an arenavirus 3' UTR;
(vii) an arenavirus L segment, wherein the ORF encoding the GP is under control of an arenavirus 5' UTR;
(viii) an arenavirus L segment, wherein the ORF encoding the NP is under control of an arenavirus 5' UTR;
(ix) an arenavirus L segment, wherein the ORF encoding the L protein is under control of an arenavirus 5' UTR;
(x) an arenavirus L segment, wherein the ORF encoding the GP is under control of an arenavirus 3' UTR;
(xi) an arenavirus L segment, wherein the ORF encoding the NP is under control of an arenavirus 3' UTR; and
(xii) an arenavirus L segment, wherein the ORF encoding the Z protein is under control of an arenavirus 3' UTR.

In certain embodiments, the ORF that is in the non-natural position of the arenavirus genomic segment described herein can be under the control of an arenavirus 3' UTR or an arenavirus 5' UTR. In more specific embodiments, the arenavirus 3' UTR is the 3' UTR of the arenavirus S segment. In another specific embodiment, the arenavirus 3' UTR is the 3'UTR of the arenavirus L segment. In more specific embodiments, the arenavirus 5' UTR is the 5' UTR of the arenavirus S segment. In other specific embodiments, the 5' UTR is the 5' UTR of the L segment.

In other embodiments, the ORF that is in the non-natural position of the arenavirus genomic segment described herein can be under the control of the arenavirus conserved terminal sequence element (the 5'- and 3'-terminal 19-20-nt regions) (see e.g., Perez & de la Torre, 2003, J Virol. 77(2): 1184-1194).

In certain embodiments, the ORF that is in the non-natural position of the arenavirus genomic segment can be under the control of the promoter element of the 5' UTR (see e.g., Albarino et al., 2011, J Virol., 85(8):4020-4). In another embodiment, the ORF that is in the non-natural position of the arenavirus genomic segment can be under the control of the promoter element of the 3' UTR (see e.g., Albarino et al., 2011, J Virol., 85(8):4020-4). In more specific embodiments, the promoter element of the 5' UTR is the 5' UTR promoter element of the S segment or the L segment. In another specific embodiment, the promoter element of the 3' UTR is the 3' UTR the promoter element of the S segment or the L segment.

In certain embodiments, the ORF that is in the non-natural position of the arenavirus genomic segment can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment or L segment.

Also provided herein, is an arenavirus particle comprising a first genomic segment that has been engineered to carry an ORF in a position other than the wild-type position of the ORF and a second arenavirus genomic segment so that the arenavirus particle comprises an S segment and an L segment. In specific embodiments, the ORF in a position other than the wild-type position of the ORF is one of the arenavirus ORFs.

In certain specific embodiments, the arenavirus particle can comprise a full complement of all four arenavirus ORFs. In specific embodiments, the second arenavirus genomic segment has been engineered to carry an ORF in a position other than the wild-type position of the ORF. In another specific embodiment, the second arenavirus genomic segment can be the wild-type genomic segment (i.e., comprises the ORFs on the segment in the wild-type position).

In certain embodiments, the first arenavirus genomic segment is an L segment and the second arenavirus genomic segment is an S segment. In other embodiments, the first arenavirus genomic segment is an S segment and the second arenavirus genomic segment is an L segment.

Non-limiting examples of the arenavirus particle comprising a genomic segment with an ORF in a position other than the wild-type position of the ORF and a second genomic segment are illustrated in Table 1.

TABLE 1

| Arenavirus particle | | | |
|---|---|---|---|
| Position 1 | Position 2 | Position 3 | Position 4 |
| GP | NP | L | Z |
| GP | Z | L | NP |
| GP | Z | NP | L |
| GP | L | NP | Z |
| GP | L | Z | NP |
| NP | GP | L | Z |
| NP | GP | Z | L |
| NP | L | GP | Z |
| NP | L | Z | GP |
| NP | Z | GP | L |
| NP | Z | L | GP |
| Z | GP | L | NP |
| Z | GP | NP | L |
| Z | NP | GP | L |
| Z | NP | L | GP |
| Z | L | NP | GP |
| Z | L | GP | NP |
| L | NP | GP | Z |
| L | NP | Z | GP |
| L | GP | Z | NP |
| L | GP | NP | Z |
| L | Z | NP | GP |
| L | Z | GP | NP |

*Position 1 is under the control of an arenavirus S segment 5' UTR; Position 2 is under the control of an arenavirus S segment 3' UTR; Position 3 is under the control of an arenavirus L segment 5' UTR; Position 4 is under the control of an arenavirus L segment 3' UTR.

Also provided herein, is a cDNA of the arenavirus genomic segment engineered to carry an ORF in a position other than the wild-type position of the ORF and a nucleotide sequence encoding a tumor antigen, tumor associated antigen or an antigenic fragment thereof provided herein. In more specific embodiments, provided herein is a cDNA or a set of cDNAs of an arenavirus genome as set forth in Table 1.

In certain embodiments, a cDNA of the arenavirus genomic segment that is engineered to carry an ORF in a position other than the wild-type position of the ORF is part of or incorporated into a DNA expression vector. In a specific embodiment, a cDNA of the arenavirus genomic segment that is engineered to carry an ORF in a position other than the wild-type position of the ORF is part of or incorporated into a DNA expression vector that facilitates production of an arenavirus genomic segment as described herein. In another embodiment, a cDNA described herein can be incorporated into a plasmid. More detailed description of the cDNAs or nucleic acids and expression systems are provided is Section 5.7. Techniques for the production of a cDNA are routine and conventional techniques of molecular biology and DNA manipulation and production. Any cloning technique known to the skilled artesian can be used. Such as techniques are well known and are available to the skilled artesian in laboratory manuals such as, Sambrook and Russell, Molecular Cloning: A laboratory Manual, $3^{rd}$ edition, Cold Spring Harbor Laboratory N.Y. (2001).

In certain embodiments, the cDNA of the arenavirus genomic segment that is engineered to carry an ORF in a position other than the wild-type position of the ORF and a nucleotide sequence encoding a tumor antigen, tumor associated antigen or an antigenic fragment thereof provided herein is introduced (e.g., transfected) into a host cell. Thus, in some embodiments provided herein, is a host cell comprising a cDNA of the arenavirus genomic segment that is engineered to carry an ORF in a position other than the wild-type position of the ORF (i.e., a cDNA of the genomic segment) and a nucleotide sequence encoding a tumor antigen, tumor associated antigen or an antigenic fragment thereof provided herein. In other embodiments, the cDNA described herein is part of or can be incorporated into a DNA expression vector and introduced into a host cell. Thus, in some embodiments provided herein is a host cell comprising a cDNA described herein that is incorporated into a vector. In other embodiments, the arenavirus genomic segment described herein is introduced into a host cell.

In certain embodiments, described herein is a method of producing the arenavirus genomic segment comprising a nucleotide sequence encoding a tumor antigen, tumor associated antigen or an antigenic fragment thereof provided herein, wherein the method comprises transcribing the cDNA of the arenavirus genomic segment. In certain embodiments, a viral polymerase protein can be present during transcription of the arenavirus genomic segment in vitro or in vivo.

In certain embodiments transcription of the arenavirus genomic segment is performed using a bi-directional promoter. In other embodiments, transcription of the arenavirus genomic segment is performed using a bi-directional expression cassette (see e.g., Ortiz-Riaño et al., 2013, J Gen Virol., 94(Pt 6): 1175-1188). In more specific embodiments the bi-directional expression cassette comprises both a polymerase I and a polymerase II promoter reading from opposite sides into the two termini of the inserted arenavirus genomic segment, respectively. In yet more specific embodiments the bi-directional expression cassette with pol-I and pol-II promoters read from opposite sides into the L segment and S segment In other embodiments, transcription of the cDNA of the arenavirus genomic segment described herein comprises a promoter. Specific examples of promoters include an RNA polymerase I promoter, an RNA polymerase II promoter, an RNA polymerase III promoter, a T7 promoter, an SP6 promote or a T3 promoter.

In certain embodiments, the method of producing the arenavirus genomic segment can further comprise introducing into a host cell the cDNA of the arenavirus genomic segment comprising a nucleotide sequence encoding a tumor antigen, tumor associated antigen or an antigenic fragment thereof provided herein. In certain embodiments, the method of producing the arenavirus genomic segment can further comprise introducing into a host cell the cDNA of the arenavirus genomic segment comprising a nucleotide sequence encoding a tumor antigen, tumor associated antigen or an antigenic fragment thereof provided herein, wherein the host cell expresses all other components for production of the arenavirus genomic segment; and purifying the arenavirus genomic segment from the supernatant of the host cell. Such methods are well-known to those skilled in the art.

Provided herein are cell lines, cultures and methods of culturing cells infected with nucleic acids, vectors, and compositions provided herein. More detailed description of nucleic acids, vector systems and cell lines described herein is provided in Section 5.7.

In certain embodiments, the arenavirus particle as described herein results in an infectious and replication competent arenavirus particle. In specific embodiments, the arenavirus particle described herein is attenuated. In a particular embodiment, the arenavirus particle is attenuated such that the virus remains, at least partially, able to spread and can replicate in vivo, but can only generate low viral loads resulting in subclinical levels of infection that are non-pathogenic. Such attenuated viruses can be used as an immunogenic composition. Provided herein, are immunogenic compositions that comprise an arenavirus with an ORF in a non-natural position as described in Section 5.9.

5.1.1 Replication-Defective Arenavirus Particle with an Open Reading Frame in a Non-Natural Position In certain embodiments, provided herein is an arenavirus particle in which (i) an ORF is in a position other than the wild-type position of the ORF; and (ii) an ORF encoding GP, NP, Z protein, and L protein has been removed or functionally inactivated such that the resulting virus cannot produce further infectious progeny virus particles. An arenavirus particle comprising a genetically modified genome in which one or more ORFs has been deleted or functionally inactivated can be produced in complementing cells (i.e., cells that express the arenavirus ORF that has been deleted or functionally inactivated). The genetic material of the resulting arenavirus particle can be transferred upon infection of a host cell into the host cell, wherein the genetic material can be expressed and amplified. In addition, the genome of the genetically modified arenavirus particle described herein can encode a heterologous ORF from an organism other than an arenavirus particle.

In certain embodiments, an ORF of the arenavirus is deleted or functionally inactivated and replaced with a nucleotide sequence encoding a tumor antigen or tumor associated antigen as described herein. In a specific embodiment, the ORF that encodes the glycoprotein GP of the arenavirus is deleted or functionally inactivated. In certain embodiments, functional inactivation of a gene eliminates any translation product. In certain embodiments, functional inactivation refers to a genetic alteration that allows some translation, the translation product, however, is not longer functional and cannot replace the wild type protein.

In certain embodiments, at least one of the four ORFs encoding GP, NP, Z protein, and L protein is removed and replaced with a nucleotide sequence encoding a tumor antigen, tumor associated antigen or an antigenic fragment thereof provided herein. In another embodiment, at least one ORF, at least two ORFs, at least three ORFs, or at least four ORFs encoding GP, NP, Z protein and L protein can be removed and replaced with a nucleotide sequence encoding a tumor antigen, tumor associated antigen or an antigenic fragment thereof provided herein. In specific embodiments, only one of the four ORFs encoding GP, NP, Z protein, and L protein is removed and replaced with a nucleotide sequence encoding a tumor antigen, tumor associated antigen or an antigenic fragment thereof provided herein. In more specific embodiments, the ORF that encodes GP of the arenavirus genomic segment is removed. In another specific embodiment, the ORF that encodes the NP of the arenavirus genomic segment is removed. In more specific embodiments, the ORF that encodes the Z protein of the arenavirus genomic segment is removed. In yet another specific embodiment, the ORF encoding the L protein is removed.

Thus, in certain embodiments, the arenavirus particle provided herein comprises a genomic segment that (i) is engineered to carry an ORF in a non-natural position; (ii) an ORF encoding GP, NP, Z protein, or L protein is removed; (iii) the ORF that is removed is replaced with a nucleotide sequence encoding a tumor antigen, tumor associated antigen or an antigenic fragment thereof provided herein.

In certain embodiments, the fragment of the tumor antigen or tumor associated antigen is antigenic when it is capable of (i) eliciting an antibody immune response in a host (e.g., mouse, rabbit, goat, donkey or human) wherein the resulting antibodies bind specifically to an immunogenic protein expressed in or on a neoplastic cell (e.g., a cancer cell); and/or (ii) eliciting a specific T cell immune response.

In certain embodiments, the nucleotide sequence encoding an antigenic fragment provided herein is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the nucleotide sequence encoding an antigenic fragment provided herein is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides in length. In some embodiments, the nucleotide sequence encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length, 1250 to 1500 amino acids in length, 1500 to 1750 amino acids in length, 1750 to 2000 amino acids in length, 2000 to 2500 amino acids in length, or more than 2500 or more amino acids in length. In some embodiments, the nucleotide sequence encodes a polypeptide that does not exceed 2500 amino acids in length. In specific embodiments the nucleotide sequence does not contain a stop codon. In certain embodiments, the nucleotide sequence is codon-optimized. In certain embodiments the nucleotide composition, nucleotide pair composition or both can be optimized. Techniques for such optimizations are known in the art and can be applied to optimize a nucleotide sequence encoding a tumor antigen, tumor associated antigen or an antigenic fragment thereof provided herein.

In certain embodiments, the growth and infectivity of the arenavirus particle is not affected by the nucleotide sequence encoding a tumor antigen, tumor associated antigen or an antigenic fragment thereof provided herein.

Techniques known to one skilled in the art may be used to produce an arenavirus particle comprising an arenavirus genomic segment engineered to carry an arenavirus ORF in a position other than the wild-type position and a nucleotide sequence encoding a tumor antigen, tumor associated antigen or an antigenic fragment thereof provided herein. For example, reverse genetics techniques may be used to generate such arenavirus particle. In other embodiments, the replication-defective arenavirus particle (i.e., the arenavirus genomic segment engineered to carry an arenavirus ORF in a position other than the wild-type position, wherein an ORF encoding GP, NP, Z protein, L protein, has been deleted) can be produced in a complementing cell.

In certain embodiments, an arenavirus particle or arenavirus genomic segment provided herein comprising a nucleotide sequence encoding a tumor antigen, tumor associated antigen or antigenic fragment thereof as provided herein further comprises at least one nucleotide sequence encoding at least one immunomodulatory peptide, polypeptide or protein. In certain embodiments, the immunomodulatory peptide, polypeptide or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; *Mycobacterium tuberculosis* Heat shock protein 70 or an antigenic fragment thereof; Herpes simplex virus 1 protein VP22 or an antigenic fragment thereof; CD40 ligand or an antigenic fragment thereof; or Fms-related tyrosine kinase 3 (Flt3) ligand or an antigenic fragment thereof.

In certain embodiments, the arenavirus genomic segment or the arenavirus particle used according to the present application can be Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus.

In certain embodiments, the arenavirus particle as described herein is suitable for use as a vaccine and methods of using such arenavirus particle in a vaccination and treatment for a neoplastic disease, for example, cancer, is provided. More detailed description of the methods of using the arenavirus particle described herein is provided in Section 5.8

In certain embodiments, the arenavirus particle as described herein is suitable for use as a pharmaceutical composition and methods of using such arenavirus particle in a vaccination and treatment for a neoplastic disease, for example, cancer, is provided. More detailed description of the methods of using the arenavirus particle described herein is provided in Section 5.9.

5.2 Tri-Segmented Arenavirus Particle

Provided herein are tri-segmented arenavirus particles with rearrangements of their ORFs and a nucleotide sequence encoding a tumor antigen, tumor associated antigen or an antigenic fragment thereof provided herein. In one aspect, provided herein is a tri-segmented arenavirus particle comprising one L segment and two S segments or two L segments and one S segment. In certain embodiments, the tri-segmented arenavirus particle does not recombine into a replication competent bi-segmented arenavirus particle. More specifically, in certain embodiments, two of the genomic segments (e.g., the two S segments or the two L segments, respectively) cannot recombine in a way to yield a single viral segment that could replace the two parent segments. In specific embodiments, the tri-segmented arenavirus particle comprises an ORF in a position other than the wild-type position of the ORF and a nucleotide sequence encoding a tumor antigen, tumor associated antigen or an antigenic fragment thereof provided herein. In yet another specific embodiment, the tri-segmented arenavirus particle comprises all four arenavirus ORFs. Thus, in certain embodiments, the tri-segmented arenavirus particle is replication competent and infectious. In other embodiments, the tri-segmented arenavirus particle lacks one of the four arenavirus ORFs. Thus, in certain embodiments, the tri-segmented arenavirus particle is infectious but unable to produce further infectious progeny in non-complementing cells.

In certain embodiments, the ORF encoding GP, NP, Z protein, or the L protein of the tri-segmented arenavirus particle described herein can be under the control of an arenavirus 3' UTR or an arenavirus 5' UTR. In more specific embodiments, the tri-segmented arenavirus 3' UTR is the 3' UTR of an arenavirus S segment(s). In another specific embodiment, the tri-segmented arenavirus 3' UTR is the 3' UTR of a tri-segmented arenavirus L segment(s). In more specific embodiments, the tri-segmented arenavirus 5' UTR is the 5' UTR of an arenavirus S segment(s). In other specific embodiments, the 5' UTR is the 5' UTR of the L segment(s).

In other embodiments, the ORF encoding GP, NP, Z protein, or the L protein of tri-segmented arenavirus particle described herein can be under the control of the arenavirus conserved terminal sequence element (the 5'- and 3'-terminal 19-20-nt regions) (see e.g., Perez & de la Torre, 2003, J Virol. 77(2): 1184-1194).

In certain embodiments, the ORF encoding GP, NP, Z protein or the L protein of the tri-segmented arenavirus particle can be under the control of the promoter element of the 5' UTR (see e.g., Albarino et al., 2011, J Virol., 85(8): 4020-4). In another embodiment, the ORF encoding GP, NP Z protein, L protein of the tri-segmented arenavirus particle can be under the control of the promoter element of the 3' UTR (see e.g., Albarino et al., 2011, J Virol., 85(8):4020-4). In more specific embodiments, the promoter element of the 5' UTR is the 5' UTR promoter element of the S segment(s) or the L segment(s). In another specific embodiment, the promoter element of the 3' UTR is the 3' UTR the promoter element of the S segment(s) or the L segment(s).

In certain embodiments, the ORF that encoding GP, NP, Z protein or the L protein of the tri-segmented arenavirus particle can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment(s) or L segment(s).

Also provided herein, is a cDNA of the tri-segmented arenavirus particle comprising a nucleotide sequence encoding a tumor antigen, tumor associated antigen or an antigenic fragment thereof provided herein. In more specific embodiments, provided herein is a DNA nucleotide sequence or a set of DNA nucleotide sequences encoding a tri-segmented arenavirus particle as set forth in Table 2 or Table 3.

In certain embodiments, the nucleic acids encoding the tri-segmented arenavirus genome are part of or incorporated into one or more DNA expression vectors. In a specific embodiment, nucleic acids encoding the genome of the tri-segmented arenavirus particle are part of or incorporated into one or more DNA expression vectors that facilitate production of a tri-segmented arenavirus particle as described herein. In another embodiment, a cDNA described herein can be incorporated into a plasmid. More detailed description of the cDNAs and expression systems are provided is Section 5.7. Techniques for the production of a cDNA routine and conventional techniques of molecular biology and DNA manipulation and production. Any cloning technique known to the skilled artesian can be used. Such techniques are well known and are available to the skilled artesian in laboratory manuals such as, Sambrook and Russell, Molecular Cloning: A laboratory Manual, $3^{rd}$ edition, Cold Spring Harbor Laboratory N.Y. (2001).

In certain embodiments, the cDNA of the tri-segmented arenavirus comprising a nucleotide sequence encoding a tumor antigen, tumor associated antigen or an antigenic fragment thereof provided herein is introduced (e.g., transfected) into a host cell. Thus, in some embodiments provided herein, is a host cell comprising a cDNA of the tri-segmented arenavirus particle (i.e., a cDNA of the genomic segments of the tri-segmented arenavirus particle) and a nucleotide sequence encoding a tumor antigen, tumor associated antigen or an antigenic fragment thereof provided herein. In other embodiments, the cDNA described herein that is part of or can be incorporated into a DNA expression vector and introduced into a host cell. Thus, in some embodiments provided herein is a host cell comprising a cDNA described herein that is incorporated into a vector. In other embodiments, the tri-segmented arenavirus genomic segments (i.e., the L segment and/or S segment or segments) described herein is introduced into a host cell.

In certain embodiments, described herein is a method of producing the tri-segmented arenavirus particle, wherein the method comprises transcribing the cDNA of the tri-segmented arenavirus particle comprising a nucleotide sequence encoding a tumor antigen, tumor associated antigen or an antigenic fragment thereof provided herein. In certain embodiments, a viral polymerase protein can be present during transcription of the tri-segmented arenavirus particle in vitro or in vivo. In certain embodiments, transcription of the arenavirus genomic segment is performed using a bi-directional promoter.

In other embodiments, transcription of the arenavirus genomic segment is performed using a bi-directional expression cassette (see e.g., Ortiz-Riaño et al., 2013, J Gen Virol., 94(Pt 6): 1175-1188). In more specific embodiments the bi-directional expression cassette comprises both a polymerase I and a polymerase II promoter reading from opposite sides into the two termini of the inserted arenavirus genomic segment, respectively.

In other embodiments, transcription of the cDNA of the arenavirus genomic segment described herein comprises a promoter. Specific examples of promoters include an RNA polymerase I promoter, an RNA polymerase II promoter, an RNA polymerase III promoter, a T7 promoter, an SP6 promoter or a T3 promoter.

In certain embodiments, the method of producing the tri-segmented arenavirus particle can further comprise introducing into a host cell the cDNA of the tri-segmented arenavirus particle comprising a nucleotide sequence encoding a tumor antigen, tumor associated antigen or an antigenic fragment thereof provided herein. In certain embodiments, the method of producing the tri-segmented arenavirus particle can further comprise introducing into a host cell the cDNA of the tri-segmented arenavirus particle that comprises a nucleotide sequence encoding a tumor antigen, tumor associated antigen or an antigenic fragment thereof provided herein, wherein the host cell expresses all other components for production of the tri-segmented arenavirus particle; and purifying the tri-segmented arenavirus particle from the supernatant of the host cell. Such methods are well-known to those skilled in the art.

Provided herein are cell lines, cultures and methods of culturing cells infected with nucleic acids, vectors, and compositions provided herein. More detailed description of nucleic acids, vector systems and cell lines described herein is provided in Section 5.7.

In certain embodiments, the tri-segmented arenavirus particle as described herein results in a infectious and replication competent arenavirus particle. In specific embodiments, the arenavirus particle described herein is attenuated. In a particular embodiment, the tri-segmented arenavirus particle is attenuated such that the virus remains, at least partially, replication-competent and can replicate in vivo, but can only generate low viral loads resulting in subclinical levels of infection that are non-pathogenic. Such attenuated viruses can be used as an immunogenic composition.

In certain embodiments, the tri-segmented arenavirus particle has the same tropism as the bi-segmented arenavirus particle.

Also provided herein, are compositions that comprise the tri-segmented arenavirus particle as described in Section 5.8 and 5.9.

5.2.1 Tri-Segmented Arenavirus Particle Comprising One L Segment and Two S Segments In one aspect, provided herein is a tri-segmented arenavirus particle comprising one L segment and two S segments. In certain embodiments, propagation of the tri-segmented arenavirus particle comprising one L segment and two S segments does not result in a replication-competent bi-segmented viral particle. In specific embodiments, propagation of the tri-segmented arenavirus particle comprising one L segment and two S segments does not result in a replication-competent bi-segmented viral particle after at least 10 days, at least 20 days, at least 30 days, at least 40 days, at least 50 days, at least 60 days, at least 70 days, at least 80 days, at least 90 days, or at least 100 days of persistent infection in mice lacking type I interferon receptor, type II interferon receptor and recombination activating gene (RAG1), and having been infected with $10^4$ PFU of the tri-segmented arenavirus particle (see Section 5.10.14). In other embodiments, propagation of the tri-segmented arenavirus particle comprising one L segment and two S segments does not result in a replication-competent bi-segmented viral particle after at least 10 passages, at least 20 passages, at least 30 passages, at least 40 passages, or at least 50 passages.

The tri-segmented arenavirus particle with all viral genes in their respective wild-type position is known in the art (e.g., Emonet et al., 2011 J. Virol., 85(4):1473; Popkin et al., 2011, J. Virol, 85(15):7928). In particular, the tri-segmented arenavirus genome consists of one L segment and two S segments, in which a nucleotide sequence encoding a tumor antigen, tumor associated antigen or an antigenic fragment thereof provided herein is inserted into one position on each S segment. More specifically, one S segment encodes GP and a tumor antigen, tumor associated antigen or an antigenic fragment thereof, respectively. The other S segment encodes a tumor antigen, a tumor associated antigen or an antigenic fragment thereof and NP, respectively. The L segment encodes the L protein and Z protein. All segments are flanked by the respective 5' and 3' UTRs.

In certain embodiments, inter-segmental recombination of the two S segments of the tri-segmented arenavirus particle, provided herein, that unities the two arenaviral ORFs on one instead of two separate segments results in a non functional promoter (i.e., a genomic segment of the structure: 5' UTR-----------5' UTR or a 3' UTR-----------3' UTR), wherein each UTR forming one end of the genome is an inverted repeat sequence of the other end of the same genome.

In certain embodiments, the tri-segmented arenavirus particle comprising one L segment and two S segments has been engineered to carry an arenavirus ORF in a position other than the wild-type position of the ORF and a nucleotide sequence encoding a tumor antigen, tumor associated antigen or an antigenic fragment thereof provided herein. In other embodiments, the tri-segmented arenavirus particle comprising one L segment and two S segments has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus particle comprising one L segment and two S segments comprises a full complement of all four arenavirus ORFs. Thus, in some embodiments, the tri-segmented arenavirus particle is an infectious and replication competent tri-segmented arenavirus particle. In specific embodiments, the two S segments of the tri-segmented arenavirus particle have been engineered to carry one of their ORFs in a position other than the wild-type position. In more specific embodiments, the two S segments comprise a full complement of the S segment ORF's. In certain specific embodiments, the L segment has been engineered to carry an ORF in a position other than the wild-type position or the L segment can be the wild-type genomic segment.

In certain embodiments, one of the two S segments can be:

(i) an arenavirus S segment, wherein the ORF encoding the Z protein is under control of an arenavirus 5' UTR;
(ii) an arenavirus S segment, wherein the ORF encoding the L protein is under control of an arenavirus 5' UTR;
(iii) an arenavirus S segment, wherein the ORF encoding the NP is under control of an arenavirus 5' UTR;
(iv) an arenavirus S segment, wherein the ORF encoding the GP is under control of an arenavirus 3' UTR;
(v) an arenavirus S segment, wherein the ORF encoding the L is under control of an arenavirus 3' UTR; and
(vi) an arenavirus S segment, wherein the ORF encoding the Z protein is under control of an arenavirus 3' UTR.

In certain embodiments, the tri-segmented arenavirus particle comprising one L segment and two S segments can comprise a duplicate ORF (i.e., two wild-type S segment ORFs e.g., GP or NP). In specific embodiments, the tri-segmented arenavirus particle comprising one L segment and two S segments can comprise one duplicate ORF (e.g., (GP, GP)) or two duplicate ORFs (e.g., (GP, GP) and (NP, NP)).

Table 2A, below, is an illustration of the genome organization of a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombed S segment is made up of two 3'UTRs instead of a 3' UTR and a 5' UTR).

TABLE 2A

Tri-segmented arenavirus particle comprising one L segment and two S segments

| Position 1 | Position 2 | Position 3 | Position 4 | Position 5 | Position 6 |
|---|---|---|---|---|---|
| *ORF | GP | *ORF | NP | Z | L |
| *ORF | NP | *ORF | GP | Z | L |
| *ORF | NP | *ORF | GP | L | Z |
| *ORF | NP | *ORF | Z | L | GP |
| *ORF | NP | Z | GP | *ORF | Z |
| *ORF | NP | Z | GP | Z | *ORF |
| *ORF | NP | *ORF | L | Z | GP |
| *ORF | L | *ORF | NP | Z | GP |
| *ORF | L | Z | NP | *ORF | GP |
| *ORF | L | *ORF | GP | Z | NP |
| *ORF | L | Z | GP | *ORF | NP |
| *ORF | Z | L | NP | *ORF | GP |
| *ORF | Z | *ORF | GP | L | NP |
| *ORF | Z | L | GP | *ORF | NP |
| L | GP | *ORF | NP | *ORF | Z |
| L | GP | *ORF | *ORF | Z | NP |
| L | GP | *ORF | Z | *ORF | NP |
| L | *ORF | Z | GP | *ORF | NP |
| L | GP | *ORF | NP | *ORF | Z |
| L | GP | *ORF | Z | *ORF | NP |
| L | GP | Z | NP | *ORF | *ORF |
| L | GP | Z | NP | *ORF | *ORF |
| L | *ORF | Z | NP | *ORF | GP |
| L | NP | *ORF | Z | *ORF | GP |
| L | NP | Z | *ORF | GP | *ORF |
| L | *ORF | Z | *ORF | GP | NP |
| L | NP | Z | GP | *ORF | *ORF |
| L | NP | *ORF | Z | *ORF | GP |
| L | *ORF | Z | NP | *ORF | GP |
| L | Z | *ORF | GP | *ORF | NP |
| L | Z | *ORF | NP | *ORF | GP |
| Z | GP | *ORF | NP | *ORF | L |
| Z | GP | *ORF | *ORF | L | NP |
| Z | GP | *ORF | L | *ORF | NP |
| Z | *ORF | L | GP | *ORF | NP |
| Z | GP | *ORF | NP | *ORF | L |
| Z | GP | *ORF | L | *ORF | NP |
| Z | GP | L | NP | *ORF | *ORF |
| Z | GP | L | NP | *ORF | *ORF |
| Z | *ORF | L | NP | *ORF | GP |
| Z | NP | *ORF | *ORF | L | GP |
| Z | NP | *ORF | GP | *ORF | L |
| Z | NP | *ORF | *ORF | L | GP |
| Z | NP | *ORF | L | *ORF | GP |
| Z | NP | L | GP | *ORF | *ORF |
| Z | *ORF | L | GP | *ORF | NP |
| Z | NP | *ORF | GP | *ORF | L |
| Z | NP | *ORF | L | *ORF | GP |
| Z | *ORF | L | NP | *ORF | GP |
| Z | L | *ORF | GP | *ORF | NP |

Position 1 is under the control of an arenavirus S segment 5' UTR; Position 2 is under the control of an arenavirus S segment 3' UTR; Position 3 is under the control of an arenavirus S segment 5' UTR; Position 4 under the control of an arenavirus S segment 3' UTR; Position 5 is under the control of an arenavirus L segment 5' UTR; Position 6 is under the control of an arenavirus L segment 3' UTR.
*ORF indicates that a nucleotide sequence encoding a tumor antigen, tumor associated antigen or an antigenic fragment thereof provided herein has been inserted.

In certain embodiments, the IGR between position one and position two can be an arenavirus S segment or L segment IGR; the IGR between position three and four can be an arenavirus S segment or L segment IGR; and the IGR between the position five and six can be an arenavirus L segment IGR. In a specific embodiment, the IGR between position one and position two can be an arenavirus S segment IGR; the IGR between position three and four can be an arenavirus S segment IGR; and the IGR between the position five and six can be an arenavirus L segment IGR. In certain embodiments, other combinations are also possible. For example, a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombed S segment is made up of two 5'UTRs instead of a 3' UTR and a 5' UTR).

In certain embodiments, intersegmental recombination of an S segment and an L segment in the tri-segmented arenavirus particle comprising one L segment and two S segments, restores a functional segment with two viral genes on only one segment instead of two separate segments. In other embodiments, intersegmental recombination of an S segment and an L segment in the tri-segmented arenavirus particle comprising one L segment and two S segments does not result in a replication-competent bi-segmented viral particle.

Table 2B, below, is an illustration of the genome organization of a tri-segmented arenavirus particle comprising one L segment and two S segments, wherein intersegmental recombination of an S segment and an L segment in the tri-segmented arenavirus genome does not result in a replication-competent bi-segmented viral particle and abrogates arenaviral promoter activity (i.e., the resulting recombed S segment is made up of two 3'UTRs instead of a 3' UTR and a 5' UTR).

TABLE 2B

Tri-segmented arenavirus particle comprising one L segment and two S segments

| Position 1 | Position 2 | Position 3 | Position 4 | Position 5 | Position 6 |
|---|---|---|---|---|---|
| L | GP | *ORF | NP | Z | *ORF |
| L | GP | Z | *ORF | *ORF | NP |
| L | GP | *ORF | NP | Z | *ORF |
| L | GP | Z | *ORF | *ORF | NP |
| L | NP | *ORF | GP | Z | *ORF |
| L | NP | Z | *ORF | *ORF | GP |
| L | NP | *ORF | GP | Z | *ORF |
| L | NP | Z | *ORF | *ORF | GP |
| Z | GP | *ORF | NP | L | *ORF |
| Z | GP | L | *ORF | *ORF | NP |
| Z | GP | *ORF | NP | L | *ORF |
| Z | NP | L | *ORF | *ORF | GP |
| Z | NP | *ORF | GP | L | *ORF |
| Z | NP | L | *ORF | *ORF | GP |

Position 1 is under the control of an arenavirus S segment 5' UTR; Position 2 is under the control of an arenavirus S segment 3' UTR; Position 3 is under the control of an arenavirus S segment 5' UTR; Position 4 under the control of an arenavirus S segment 3' UTR; Position 5 is under the control of an arenavirus L segment 5' UTR; Position 6 is under the control of an arenavirus L segment 3' UTR.
*ORF indicates that a nucleotide sequence encoding a tumor antigen, tumor associated antigen or an antigenic fragment thereof provided herein has been inserted.

In certain embodiments, the IGR between position one and position two can be an arenavirus S segment or L segment IGR; the IGR between position three and four can be an arenavirus S segment or L segment IGR; and the IGR between the position five and six can be an arenavirus L segment IGR. In a specific embodiment, the IGR between position one and position two can be an arenavirus S segment IGR; the IGR between position three and four can be an arenavirus S segment IGR; and the IGR between the position five and six can be an arenavirus L segment IGR. In certain embodiments, other combinations are also possible. For example, a tri-segmented arenavirus particle comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 5'UTRs instead of a 3' UTR and a 5' UTR).

In certain embodiments, one of skill in the art could construct an arenavirus genome with an organization as illustrated in Table 2A or 2B and as described herein, and then use an assay as described in Section 5.10 to determine whether the tri-segmented arenavirus particle is genetically stable, i.e., does not result in a replication-competent bi-segmented viral particle as discussed herein.

5.2.2 Tri-Segmented Arenavirus Particle Comprising Two L Segments and One S Segment In one aspect, provided herein is a tri-segmented arenavirus particle comprising two L segments and one S segment. In certain embodiments, propagation of the tri-segmented arenavirus particle comprising two L segments and one S segment does not result in a replication-competent bi-segmented viral particle. In specific embodiments, propagation of the tri-segmented arenavirus particle comprising two L segments and one S segment does not result in a replication-competent bi-segmented viral particle after at least 10 days, at least 20 days, at least 30 days, at least 40 days, or at least 50 days, at least 60 days, at least 70 days, at least 80 days, at least 90 days, at least 100 days of persistent in mice lacking type I interferon receptor, type II interferon receptor and recombination activating gene (RAG1), and having been infected with $10^4$ PFU of the tri-segmented arenavirus particle (see Section 5.10.14). In other embodiments, propagation of the tri-segmented arenavirus particle comprising two L segments and one S segment does not result in a replication-competent bi-segmented viral particle after at least 10 passages, 20 passages, 30 passages, 40 passages, or 50 passages.

In certain embodiments, inter-segmental recombination of the two L segments of the tri-segmented arenavirus particle, provided herein, that unities the two arenaviral ORFs on one instead of two separate segments results in a non functional promoter (i.e., a genomic segment of the structure: 5' UTR-----------5' UTR or a 3' UTR-----------3' UTR), wherein each UTR forming one end of the genome is an inverted repeat sequence of the other end of the same genome.

In certain embodiments, the tri-segmented arenavirus particle comprising two L segments and one S segment has been engineered to carry an arenavirus ORF in a position other than the wild-type position of the ORF and a nucleotide sequence encoding a tumor antigen, tumor associated antigen or an antigenic fragment thereof provided herein. In other embodiments, the tri-segmented arenavirus particle comprising two L segments and one S segment has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus particle comprising two L segments and one S segment comprises a full complement of all four arenavirus ORFs. Thus, in some embodiments, the tri-segmented arenavirus particle is an infectious and replication competent tri-segmented arenavirus particle. In specific embodiments, the two L segments of the tri-segmented arenavirus particle have been engineered to carry one of their ORFs in a position other than the wild-type position. In more specific embodiments, the two L segments comprise a full complement of the L segment ORF's. In certain specific embodiments, the S segment has been engineered to carry one of their ORFs in a position other than the wild-type position or the S segment can be the wild-type genomic segment.

In certain embodiments, one of the two L segments can be:
(i) an L segment, wherein the ORF encoding the GP is under control of an arenavirus 5' UTR;
(ii) an L segment, wherein the ORF encoding NP is under control of an arenavirus 5' UTR;
(iii) an L segment, wherein the ORF encoding the L protein is under control of an arenavirus 5' UTR;
(iv) an L segment, wherein the ORF encoding the GP is under control of an arenavirus 3' UTR;
(v) an L segment, wherein the ORF encoding the NP is under control of an arenavirus 3' UTR; and
(vi) an L segment, wherein the ORF encoding the Z protein is under control of an arenavirus 3' UTR.

In certain embodiments, the tri-segmented arenavirus particle comprising one L segment and two S segments can comprise a duplicate ORF (i.e., two wild-type L segment ORFs e.g., Z protein or L protein). In specific embodiments, the tri-segmented arenavirus particle comprising two L segments and one S segment can comprise one duplicate ORF (e.g., (Z protein, Z protein)) or two duplicate ORFs (e.g., (Z protein, Z protein) and (L protein, L protein)).

Table 3, below, is an illustration of the genome organization of a tri-segmented arenavirus particle comprising two L segments and one S segment, wherein intersegmental recombination of the two L segments in the tri-segmented arenavirus genome does not result in a replication-competent bi-segmented viral particle and abrogates arenaviral promoter activity (i.e., the S segment is made up of two 3'UTRs instead of a 3' UTR and a 5' UTR). Based on Table 3 similar combinations could be predicted for generating an arenavirus particle made up of two 5' UTRs instead of a 3' UTR and a 5' UTR.

TABLE 3

Tri-segmented arenavirus particle comprising two L segments and one S segment

| Position 1 | Position 2 | Position 3 | Position 4 | Position 5 | Position 6 |
|---|---|---|---|---|---|
| ORF* | Z | ORF* | L | NP | GP |
| ORF* | Z | ORF* | L | GP | NP |
| ORF* | Z | GP | L | ORF* | NP |
| ORF* | Z | ORF* | GP | NP | L |
| ORF* | Z | GP | ORF* | NP | L |
| ORF* | Z | NP | ORF* | GP | L |
| ORF* | ORF* | NP | Z | GP | L |
| ORF* | Z | GP | NP | ORF* | L |
| ORF* | Z | NP | GP | ORF* | L |
| ORF* | L | ORF* | Z | NP | GP |
| ORF* | L | ORF* | Z | GP | NP |
| ORF* | L | ORF* | GP | NP | Z |
| ORF* | L | GP | Z | ORF* | NP |
| ORF* | L | ORF* | GP | NP | Z |
| ORF* | L | NP | Z | ORF* | GP |
| ORF* | L | GP | NP | ORF* | Z |
| ORF* | L | NP | GP | ORF* | Z |
| ORF* | GP | ORF* | L | NP | Z |
| ORF* | GP | NP | L | ORF* | Z |
| ORF* | GP | ORF* | Z | NP | L |
| ORF* | GP | NP | Z | ORF* | L |
| ORF* | NP | ORF* | L | GP | Z |

TABLE 3-continued

Tri-segmented arenavirus particle comprising
two L segments and one S segment

| Position 1 | Position 2 | Position 3 | Position 4 | Position 5 | Position 6 |
|---|---|---|---|---|---|
| ORF* | NP | GP | L | ORF* | Z |
| ORF* | NP | GP | Z | ORF* | L |
| ORF* | NP | ORF* | Z | GP | L |
| ORF* | L | ORF* | Z | NP | GP |
| ORF* | L | ORF* | Z | GP | NP |
| ORF* | L | ORF* | NP | GP | Z |
| ORF* | L | ORF* | GP | NP | Z |
| ORF* | L | NP | Z | ORF* | GP |
| ORF* | Z | ORF* | GP | NP | L |
| ORF* | Z | GP | L | ORF* | NP |
| ORF* | Z | NP | GP | ORF* | L |
| ORF* | Z | GP | NP | ORF* | L |
| ORF* | GP | ORF* | L | NP | Z |
| ORF* | GP | ORF* | L | Z | NP |
| ORF* | GP | ORF* | Z | GP | L |
| ORF* | GP | NP | L | ORF* | Z |
| GP | L | ORF* | Z | ORF* | NP |
| GP | L | ORF* | NP | ORF* | Z |
| GP | Z | ORF* | L | ORF* | NP |
| GP | Z | ORF* | L | ORF* | NP |
| GP | Z | ORF* | NP | ORF* | L |
| GP | NP | ORF* | Z | ORF* | L |
| NP | L | ORF* | Z | ORF* | GP |
| NP | L | ORF* | GP | ORF* | Z |
| NP | L | ORF* | Z | ORF* | GP |

*Position 1 is under the control of an arenavirus L segment 5' UTR; position 2 is under the control of an arenavirus L segment 3' UTR; position 3 is under the control of an arenavirus L segment 5' UTR; position 4 is under the control of an arenavirus L segment 3' UTR; position 5 is under the control of an arenavirus S segment 5' UTR; position 6 is under the control of an arenavirus S segment 3' UTR.
*ORF indicates that a nucleotide sequence encoding a tumor antigen, tumor associated antigen or an antigenic fragment thereof provided herein has been inserted.

In certain embodiments, the IGR between position one and position two can be an arenavirus S segment or L segment IGR; the IGR between position three and four can be an arenavirus S segment or L segment IGR; and the IGR between the position five and six can be an arenavirus S segment IGR. In a specific embodiment, the IGR between position one and position two can be an arenavirus L segment IGR; the IGR between position three and four can be an arenavirus L segment IGR; and the IGR between the position five and six can be an arenavirus S segment IGR. In certain embodiments, other combinations are also possible.

In certain embodiments, intersegmental recombination of an L segment and an S segment from the tri-segmented arenavirus particle comprising two L segments and one S segment restores a functional segment with two viral genes on only one segment instead of two separate segments. In other embodiments, intersegmental recombination of an L segment and an S segment in the tri-segmented arenavirus particle comprising two L segments and one S segment does not result in a replication-competent bi-segmented viral particle.

Table 3B, below, is an illustration of the genome organization of a tri-segmented arenavirus particle comprising two L segments and one S segment, wherein intersegmental recombination of an L segment and an S segment in the tri-segmented arenavirus genome does not result in a replication-competent bi-segmented viral particle and abrogates arenaviral promoter activity (i.e., the resulting recombined S segment is made up of two 3'UTRs instead of a 3' UTR and a 5' UTR).

TABLE 3B

Tri-segmented arenavirus particle comprising
two L segments and one S segment

| Position 1 | Position 2 | Position 3 | Position 4 | Position 5 | Position 6 |
|---|---|---|---|---|---|
| NP | Z | *ORF | GP | L | *ORF |
| NP | Z | GP | *ORF | *ORF | L |
| NP | Z | *ORF | GP | L | *ORF |
| NP | Z | GP | *ORF | *ORF | L |
| NP | L | *ORF | GP | Z | *ORF |
| NP | L | GP | *ORF | *ORF | Z |
| NP | L | *ORF | GP | Z | *ORF |
| NP | L | GP | *ORF | *ORF | Z |
| GP | Z | *ORF | NP | L | *ORF |
| GP | Z | NP | *ORF | *ORF | L |
| GP | Z | *ORF | NP | L | *ORF |
| GP | L | NP | *ORF | *ORF | Z |
| GP | L | *ORF | NP | Z | *ORF |
| GP | L | NP | *ORF | *ORF | Z |

*Position 1 is under the control of an arenavirus L segment 5' UTR; position 2 is under the control of an arenavirus L segment 3' UTR; position 3 is under the control of an arenavirus L segment 5' UTR; position 4 is under the control of an arenavirus L segment 3' UTR; position 5 is under the control of an arenavirus S segment 5' UTR; position 6 is under the control of an arenavirus S segment 3' UTR.
*ORF indicates that a nucleotide sequence encoding a tumor antigen, tumor associated antigen or an antigenic fragment thereof provided herein has been inserted.

In certain embodiments, the IGR between position one and position two can be an arenavirus S segment or L segment IGR; the IGR between position three and four can be an arenavirus S segment or L segment IGR; and the IGR between the position five and six can be an arenavirus S segment IGR. In a specific embodiment, the IGR between position one and position two can be an arenavirus L segment IGR; the IGR between position three and four can be an arenavirus L segment IGR; and the IGR between the position five and six can be an arenavirus S segment IGR. In certain embodiments, other combinations are also possible.

In certain embodiments, one of skill in the art could construct an arenavirus genome with an organization as illustrated in Table 3A or 3B and as described herein, and then use an assay as described in Section 5.10 to determine whether the tri-segmented arenavirus particle is genetically stable, i.e., does not result in a replication-competent bi-segmented viral particle as discussed herein.

5.2.3 Replication-Defective Tri-Segmented Arenavirus Particle

In certain embodiments, provided herein is a tri-segmented arenavirus particle in which (i) an ORF is in a position other than the wild-type position of the ORF; and (ii) an ORF encoding GP, NP, Z protein, or L protein has been removed or functionally inactivated such that the resulting virus cannot produce further infectious progeny virus particles (i.e., is replication defective). In certain embodiments, the third arenavirus segment can be an S segment. In other embodiments, the third arenavirus segment can be an L segment. In more specific embodiments, the third arenavirus segment can be engineered to carry an ORF in a position other than the wild-type position of the ORF or the third arenavirus segment can be the wild-type arenavirus genomic segment. In yet more specific embodiments, the third arenavirus segment lacks an arenavirus ORF encoding GP, NP, Z protein, or the L protein.

In certain embodiments, a tri-segmented genomic segment could be a S or a L segment hybrid (i.e., a genomic segment that can be a combination of the S segment and the L segment). In other embodiments, the hybrid segment is an S segment comprising an L segment IGR. In another embodiment, the hybrid segment is an L segment comprising an S segment IGR. In other embodiments, the hybrid segment is an S segment UTR with and L segment IGR. In another embodiment, the hybrid segment is an L segment UTR with an S segment IGR. In specific embodiments, the hybrid segment is an S segment 5' UTR with an L segment IGR or an S segment 3' UTR with an L segment IGR. In other specific embodiments, the hybrid segment is an L segment 5' UTR with an S segment IGR or an L segment 3' UTR with an S segment IGR.

A tri-segmented arenavirus particle comprising a genetically modified genome in which one or more ORFs has been deleted or functionally inactivated can be produced in complementing cells (i.e., cells that express the arenavirus ORF that has been deleted or functionally inactivated). The genetic material of the resulting arenavirus particle can be transferred upon infection of a host cell into the host cell, wherein the genetic material can be expressed and amplified. In addition, the genome of the genetically modified arenavirus particle described herein can include a nucleotide sequence encoding a tumor antigen, tumor associated antigen or an antigenic fragment thereof provided herein.

In certain embodiments, at least one of the four ORFs encoding GP, NP, Z protein, and L protein is removed and replaced with a nucleotide sequence encoding a tumor antigen, tumor associated antigen or an antigenic fragment thereof provided herein. In another embodiment, at least one ORF, at least two ORFs, at least three ORFs, or at least four ORFs encoding GP, NP, Z protein and L protein can be removed and replaced with a nucleotide sequence encoding a tumor antigen, tumor associated antigen or an antigenic fragment thereof provided herein. In specific embodiments, only one of the four ORFs encoding GP, NP, Z protein, and L protein is removed and replaced with a nucleotide sequence encoding a tumor antigen, tumor associated antigen or an antigenic fragment thereof provided herein. In more specific embodiments, the ORF that encodes GP of the arenavirus genomic segment is removed. In another specific embodiment, the ORF that encodes the NP of the arenavirus genomic segment is removed. In more specific embodiments, the ORF that encodes the Z protein of the arenavirus genomic segment is removed. In yet another specific embodiment, the ORF encoding the L protein is removed.

In certain embodiments, provided herein is a tri-segmented arenavirus particle comprising one L segment and two S segments in which (i) an ORF is in a position other than the wild-type position of the ORF; and (ii) an ORF encoding GP or NP has been removed or functionally inactivated, such that the resulting virus is replication-defective and not infectious. In a specific embodiment, one ORF is removed and replaced with a nucleotide sequence encoding a tumor antigen, tumor associated antigen or an antigenic fragment thereof provided herein. In another specific embodiment, two ORFs are removed and replaced with a nucleotide sequence encoding a tumor antigen, tumor associated antigen or an antigenic fragment thereof provided herein. In other specific embodiments, three ORFs are removed and replaced with a nucleotide sequence encoding a tumor antigen, tumor associated antigen or an antigenic fragment thereof provided herein. In specific embodiments, the ORF encoding GP is removed and replaced with a nucleotide sequence encoding a tumor antigen, tumor associated antigen or an antigenic fragment thereof provided herein. In other specific embodiments, the ORF encoding NP is removed and replaced with a nucleotide sequence encoding a tumor antigen, tumor associated antigen or an antigenic fragment thereof provided herein. In yet more specific embodiments, the ORF encoding NP and the ORF encoding GP are removed and replaced with one or two nucleotide sequences encoding tumor antigens, tumor associated antigens or antigenic fragments thereof provided herein. Thus, in certain embodiments the tri-segmented arenavirus particle comprises (i) one L segment and two S segments; (ii) an ORF in a position other than the wild-type position of the ORF; (iii) one or more nucleotide sequences encoding tumor antigens, tumor associated antigens or an antigenic fragments thereof provided herein.

In certain embodiments, provided herein is a tri-segmented arenavirus particle comprising two L segments and one S segment in which (i) an ORF is in a position other than the wild-type position of the ORF; and (ii) an ORF encoding the Z protein, and/or the L protein has been removed or functionally inactivated, such that the resulting virus replication-defective and not infectious. In a specific embodiment, one ORF is removed and replaced with a nucleotide sequence encoding a tumor antigen, tumor associated antigen or an antigenic fragment thereof provided herein. In another specific embodiment, two ORFs are removed and replaced with a nucleotide sequence encoding a tumor antigen, tumor associated antigen or an antigenic fragment thereof provided herein. In specific embodiments, the ORF encoding the Z protein is removed and replaced with a nucleotide sequence encoding a tumor antigen, tumor associated antigen or an antigenic fragment thereof provided herein. In other specific embodiments, the ORF encoding the L protein is removed and replaced with a nucleotide sequence encoding a tumor antigen, tumor associated antigen or an antigenic fragment thereof provided herein. In yet more specific embodiments, the ORF encoding the Z protein and the ORF encoding the L protein is removed and replaced with a nucleotide sequence encoding a tumor antigen, tumor associated antigen or an antigenic fragment thereof provided herein. Thus, in certain embodiments the tri-segmented arenavirus particle comprises (i) two L segments and one S segment; (ii) an ORF in a position other than the wild-type position of the ORF; (iii) a nucleotide sequence encoding a tumor antigen, tumor associated antigen or an antigenic fragment thereof provided herein.

Thus, in certain embodiments, the tri-segmented arenavirus particle provided herein comprises a tri-segmented arenavirus particle (i.e., one L segment and two S segments or two L segments and one S segment) that i) is engineered to carry an ORF in a non-natural position; ii) an ORF encoding GP, NP, Z protein, or L protein is removed); iii) the ORF that is removed is replaced with one or more nucleotide sequences encoding tumor antigens, tumor associated antigens or antigenic fragments thereof provided herein.

In certain embodiments, the nucleotide sequence encoding an antigenic fragment provided herein is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the nucleotide sequence encoding an antigenic fragment provided herein is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides in length. In some embodiments, the nucleotide sequence encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length, 1250 to 1500 amino acids in length, 1500 to 1750 amino acids in length, 1750 to 2000 amino acids in length, 2000 to 2500 amino acids in length, or more than 2500 or more amino acids in length. In some embodiments, the nucleotide sequence encodes a polypeptide that does not exceed 2500 amino acids in length. In specific embodiments the nucleotide sequence does not contain a stop codon. In certain embodiments, the nucleotide sequence is codon-optimized. In certain embodiments the nucleotide composition, nucleotide pair composition or both can be optimized. Techniques for such optimizations are known in the art and can be applied to optimize a nucleotide sequence encoding a tumor antigen, tumor associated antigen or an antigenic fragment thereof provided herein.

Any nucleotide sequence encoding a tumor antigen, tumor associated antigen or an antigenic fragment thereof provided herein may be included in the tri-segmented arenavirus particle. In one embodiment, the a nucleotide sequence encoding a tumor antigen, tumor associated antigen or an antigenic fragment thereof provided herein is capable of eliciting an immune response.

In certain embodiments, the growth and infectivity of the arenavirus particle is not affected by the nucleotide sequence encoding a tumor antigen, tumor associated antigen or an antigenic fragment thereof provided herein.

Techniques known to one skilled in the art may be used to produce an arenavirus particle comprising an arenavirus genomic segment engineered to carry an arenavirus ORF in a position other than the wild-type position and a nucleotide sequence encoding a tumor antigen, tumor associated antigen or an antigenic fragment thereof provided herein. For example, reverse genetics techniques may be used to generate such arenavirus particle. In other embodiments, the replication-defective arenavirus particle (i.e., the arenavirus genomic segment engineered to carry an arenavirus ORF in a position other than the wild-type position, wherein an ORF encoding GP, NP, Z protein, L protein, has been deleted) can be produced in a complementing cell.

In certain embodiments, a tri-segmented arenavirus particle provided herein comprising a nucleotide sequence encoding a tumor antigen, tumor associated antigen or antigenic fragment thereof as provided herein further comprises at least one nucleotide sequence encoding at least one immunomodulatory peptide, polypeptide or protein. In certain embodiments, the immunomodulatory peptide, polypeptide or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; *Mycobacterium tuberculosis* Heat shock protein 70 or an antigenic fragment thereof; Herpes simplex virus 1 protein VP22 or an antigenic fragment thereof; CD40 ligand or an antigenic fragment thereof; or Fms-related tyrosine kinase 3 (Flt3) ligand or an antigenic fragment thereof.

Arenaviruses for use with the methods and compositions provided herein can be Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus.

In certain embodiments, the tri-segmented arenavirus particle as described herein is suitable for use as a vaccine and methods of using such arenavirus particle in a vaccination and treatment for a neoplastic disease, for example, cancer, is provided. More detailed description of the methods of using the arenavirus particle described herein is provided in Section 5.8

In certain embodiments, the tri-segmented arenavirus particle as described herein is suitable for use as a pharmaceutical composition and methods of using such arenavirus particle in a vaccination and treatment for a neoplastic disease, for example, cancer, is provided. More detailed description of the methods of using the arenavirus particle described herein is provided in Section 5.9.

5.3 Infectious, Replication-Deficient Arenavirus Particles

A genetically modified arenavirus provided herein includes where the arenavirus:
- is infectious;
- cannot form infectious progeny virus in a non-complementary cell (i.e., a cell that does not express the functionality that is missing from the replication-deficient arenavirus and causes it to be replication-deficient);
- is capable of replicating its genome and expressing its genetic information; and
- encodes a tumor antigen, tumor associated antigen or an antigenic fragment thereof.

A genetically modified arenavirus described herein is infectious, i.e., it can attach to a host cell and release its genetic material into the host cell. A genetically modified arenavirus described herein is replication-deficient, i.e., the arenavirus is unable to produce further infectious progeny particles in a non-complementing cell. In particular, the genome of the arenavirus is modified (e.g., by removal or functional inactivation of an ORF) such that a virus carrying the modified genome can no longer produce infectious progeny viruses. A non-complementing cell is a cell that does not provide the functionality that has been eliminated from the replication-deficient arenavirus by modification of the virus genome (e.g., if the ORF encoding the GP protein is removed or functionally inactivated, a non-complementing cell does not provide the GP protein). However, a genetically modified arenavirus provided herein is capable of producing infectious progeny viruses in complementing cells. Complementing cells are cells that provide (in trans) the functionality that has been eliminated from the replication-deficient arenavirus by modification of the virus genome (e.g., if the ORF encoding the GP protein is removed or functionally inactivated, a complementing cell does provide the GP protein). Expression of the complementing functionality (e.g., the GP protein) can be accomplished by any method known to the skilled artisan (e.g., transient or stable expression). A genetically modified arenavirus described herein can amplify and express its genetic information in a cell that has been infected by the virus. A genetically modified arenavirus provided herein can comprise a nucleotide sequence that encodes a tumor antigen, tumor associated antigen or an antigenic fragment thereof such as, but not limited to, the tumor antigen, tumor associated antigen or an antigenic fragment thereof described in Section 5.4.

In certain embodiments, provided herein is a genetically modified arenavirus in which an ORF of the arenavirus genome is removed or functionally inactivated such that the resulting virus cannot produce further infectious progeny virus particles in non-complementing cells. An arenavirus particle comprising a genetically modified genome in which an ORF is removed or functionally inactivated can be produced in complementing cells (i.e., in cells that express the arenaviral ORF that has been removed or functionally inactivated). The genetic material of the resulting arenavirus particles can be transferred upon infection of a host cell into the host cell, wherein the genetic material can be expressed and amplified. In addition, the genome of the genetically modified arenavirus particles provided herein encodes a tumor antigen, tumor associated antigen or antigenic fragment thereof that can be expressed in the host cell.

In certain embodiments, an ORF of the arenavirus is deleted or functionally inactivated and replaced with a nucleotide encoding a tumor antigen or tumor associated antigen as described herein. In a specific embodiment, the ORF that encodes the glycoprotein GP of the arenavirus is deleted or functionally inactivated. In certain embodiments, functional inactivation of a gene eliminates any translation product. In certain embodiments, functional inactivation refers to a genetic alteration that allows some translation, the translation product, however, is not longer functional and cannot replace the wild type protein.

In certain embodiments, the ORF that encodes the glycoprotein (GP) of the arenavirus is deleted to generate a replication-deficient arenavirus for use in the methods and compositions provided herein. In a specific embodiment, the replication-deficient arenavirus comprises a genomic segment comprising a nucleotide sequence encoding a tumor antigen, tumor associated antigen or antigenic fragment thereof. Thus, in certain embodiments, a genetically modified arenavirus particle provided herein comprises a genomic segment that a) has a deletion or functional inactivation of an ORF that is present in the wild type form of the genomic segment; and b) encodes (either in sense or antisense) a tumor antigen, tumor associated antigen or antigenic fragment thereof.

In certain embodiments, the antigen encoded by the nucleotide that is inserted into the genome of replication-deficient arenavirus can encode, for example, a tumor antigen, tumor associated antigen or antigenic fragment thereof or combinations of tumor antigens, tumor associated antigens or antigenic fragments thereof including, but not limited to, oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pml-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triosephosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyplBl, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMW-MAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysis, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin αvβ3 (CD61), galactin, or Ral-B, CD123, CLL-1, CD38, CS-1, CD138, and ROR1. A detailed description of the antigens described herein is provided in Section 5.4.

Arenaviruses for use with the methods and compositions provided herein can be Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus.

The wild type arenavirus genome consists of a short (~3.4 kb) and a large (~7.2 kb) RNA segment. The short segment carries the ORFs encoding the nucleoprotein NP and glycoprotein GP genes. The large segment comprises the RNA-dependent RNA polymerase L and the matrix protein Z genes. Wild type arenaviruses can be rendered replication-deficient to generate vaccine vectors by substituting the glycoprotein gene for one or more tumor antigens, tumor associated antigens or antigenic fragments thereof, against which immune responses are to be induced.

Infectious, replication-deficient arenavirus particles expressing a tumor antigen, tumor associated antigen, or antigenic fragment thereof, or a combination of tumor antigens, tumor associated antigens or antigenic fragments thereof as described herein, can be used to treat (in an immunotherapeutic manner) subjects having a neoplastic disease described herein.

Arenavirus disease and immunosuppression in wild type arenavirus infection are known to result from unchecked viral replication. By abolishing replication, i.e., the ability to produce infectious progeny virus particles, of arenavirus particles by deleting from their genome, e.g., the Z gene which is required for particle release, or the GP gene which is required for infection of target cells, the total number of infected cells can be limited by the inoculum administered, e.g., to a vaccine recipient, or accidentally transmitted to personnel involved in medical or biotechnological applications, or to animals. Therefore, abolishing replication of arenavirus particles prevents pathogenesis as a result of intentional or accidental transmission of vector particles. In this invention, one important aspect consists in exploiting the above necessity of abolishment of replication in a beneficial way for the purpose of expressing tumor antigens, tumor associated antigens or antigenic fragments thereof. In certain embodiments, an arenavirus particle is rendered replication deficient by genetic modification of its genome. Such modifications to the genome can include:

- deletion of an ORF (e.g., the ORF encoding the GP, NP, L, or Z protein);
- functional inactivation of an ORF (e.g., the ORF encoding the GP, NP, L, or Z protein). For example, this can be achieved by introducing a missense or a nonsense mutation;
- change of the sequence of the ORF (e.g., the exchange of an S1P cleavage site with the cleavage site of another protease);
- mutagenesis of one of the 5' or 3' termini of one of the genomic segments;
- mutagenesis of an intergenic region (i.e., of the L or the S genomic segment).

In certain embodiments, a bi-segmented infectious, replication-deficient arenavirus expressing a tumor antigen, tumor associated antigen or antigenic fragment thereof described herein is a Lymphocytic choriomeningitis virus (LCMV) wherein the S segment of the virus is modified by substituting the ORF encoding the GP protein with an ORF encoding a tumor antigen, tumor associated antigen or antigenic fragment thereof.

In certain embodiments, a wild type arenavirus vector genome can be designed to retain at least the essential regulatory elements on the 5' and 3' untranslated regions (UTRs) of both segments, and/or also the intergenic regions (IGRs). Without being bound by theory, the minimal trans-acting factors for gene expression in infected cells remain in the vector genome as ORFs that can be expressed, yet they can be placed differently in the genome and can be placed under control of a different promoter than naturally, or can be expressed from internal ribosome entry sites. In certain embodiments, the nucleic acid encoding a tumor antigen, tumor associated antigen or antigenic fragment thereof is transcribed from one of the endogenous arenavirus promoters (i.e., 5' UTR, 3' UTR of the S segment, 5' UTR, 3' UTR of the L segment). In other embodiments, the nucleic acid encoding a tumor antigen, tumor associated antigen or antigenic fragment thereof is expressed from a heterologous introduced promoter sequences that can be read by the viral RNA-dependent RNA polymerase, by cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. In certain embodiments, ribonucleic acids coding for a tumor antigen, tumor associated antigen or antigenic fragment thereof are transcribed and translated either by themselves or as read-through by fusion to arenavirus protein ORFs, and expression of proteins in the host cell may be enhanced by introducing in the viral transcript sequence at the appropriate place(s) one or more, e.g., two, three or four, internal ribosome entry sites.

In certain embodiments, the vector generated to encode one or more tumor antigens, tumor associated antigens or antigenic fragments thereof may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, the vector generated to encode one or more tumor antigens, tumor associated antigens or antigenic fragments thereof may be based on LCMV Clone 13. In other embodiments, the vector generated to encode one or more tumor antigens, tumor associated antigens or antigenic fragments thereof may be based on LCMV MP strain.

In certain embodiments, the vector generated to encode one or more tumor antigens, tumor associated antigens or antigenic fragments thereof may be based on a specific strain of Junin virus. Strains of Junin virus include vaccine strains XJ13, XJ #44, and Candid #1 as well as IV4454, a human isolate. In certain embodiments, the vector generated to encode one or more tumor antigens, tumor associated antigens or antigenic fragments thereof is based on Junin virus Candid #1 strain.

5.4 Tumor Antigens, Tumor Associated Antigens and Antigenic Fragments

In certain embodiments, a tumor antigen or tumor associated antigen for use with the methods and compositions described herein is an immunogenic protein expressed in or on a neoplastic cell or tumor, such as a cancer cell or malignant tumor. In certain embodiments, a tumor antigen or tumor associated antigen for use with the methods and compositions described herein is a non-specific, mutant, overexpressed or abnormally expressed protein, which can be present on both a neoplastic cell or tumor and a normal cell or tissue. In certain embodiments, a tumor antigen or tumor associated antigen for use with the methods and compositions described herein is a tumor-specific antigen which is restricted to tumor cells. In certain embodiments, a tumor antigen for use with the methods and compositions described herein is a cancer-specific antigen which is restricted to cancer cells.

In certain embodiments, a tumor antigen or tumor associated antigen can exhibit one, two, three, or more, including all, of the following characteristics: overexpressed/accumulated (i.e., expressed by both normal and neoplastic tissue, but highly expressed in neoplasia), oncofetal (i.e., usually only expressed in fetal tissues and in cancerous somatic cells), oncoviral or oncogenic viral (i.e., encoded by tumorigenic transforming viruses), cancer-testis (i.e., expressed only by cancer cells and adult reproductive tissues, e.g., the testis), lineage-restricted (i.e., expressed largely by a single cancer histotype), mutated (i.e., only expressed in neoplastic tissue as a result of genetic mutation or alteration in transcription), post-translationally altered (e.g., tumor-associated alterations in glycosylation), or idiotypic (i.e., developed from malignant clonal expansions of B or T lymphocytes).

In certain embodiments, the tumor antigen or tumor associated antigen for use with the methods and compositions described herein includes antigens from neoplastic diseases including acute lymphoblastic leukemia; acute lymphoblastic lymphoma; acute lymphocytic leukaemia; acute myelogenous leukemia; acute myeloid leukemia (adult/childhood); adrenocortical carcinoma; AIDS-related cancers; AIDS-related lymphoma; anal cancer; appendix cancer; astrocytomas; atypical teratoid/rhabdoid tumor; basal-cell carcinoma; bile duct cancer, extrahepatic (cholangiocarcinoma); bladder cancer; bone osteosarcoma/malignant fibrous histiocytoma; brain cancer (adult/childhood); brain tumor, cerebellar astrocytoma (adult/childhood); brain tumor, cerebral astrocytoma/malignant glioma brain tumor; brain tumor, ependymoma; brain tumor, medulloblastoma; brain tumor, supratentorial primitive neuroectodermal tumors; brain tumor, visual pathway and hypothalamic glioma; brainstem glioma; breast cancer; bronchial adenomas/carcinoids; bronchial tumor; Burkitt lymphoma; cancer of childhood; carcinoid gastrointestinal tumor; carcinoid tumor; carcinoma of adult, unknown primary site; carcinoma of unknown primary; central nervous system embryonal tumor; central nervous system lymphoma, primary; cervical cancer; childhood adrenocortical carcinoma; childhood cancers; childhood cerebral astrocytoma; chordoma, childhood; chronic lymphocytic leukemia; chronic myelogenous leukemia; chronic myeloid leukemia; chronic myeloproliferative disorders; colon cancer; colorectal cancer; craniopharyngioma; cutaneous T-cell lymphoma; desmoplastic small round cell tumor; emphysema; endometrial cancer; ependymoblastoma; ependymoma; esophageal cancer; ewing's sarcoma in the Ewing family of tumors; extracranial germ cell tumor; extragonadal germ cell tumor; extrahepatic bile duct cancer; gallbladder cancer; gastric (stomach) cancer; gastric carcinoid; gastrointestinal carcinoid tumor; gastrointestinal stromal tumor; germ cell tumor: extracranial, extragonadal, or ovarian gestational trophoblastic tumor; gestational trophoblastic tumor, unknown primary site; glioma; glioma of the brain stem; glioma, childhood visual pathway and hypothalamic; hairy cell leukemia; head and neck cancer; heart cancer; hepatocellular (liver) cancer; hodgkin lymphoma; hypopharyngeal cancer; hypothalamic and visual pathway glioma; intraocular melanoma; islet cell carcinoma (endocrine pancreas); Kaposi Sarcoma; kidney cancer (renal cell cancer); langerhans cell histiocytosis; laryngeal cancer; lip and oral cavity cancer; liposarcoma; liver cancer (primary); lung cancer, non-small cell; lung cancer, small cell; lymphoma, primary central nervous system; macroglobulinemia, Waldenström; male breast cancer; malignant fibrous histiocytoma of bone/osteosarcoma; medulloblastoma; medulloepithelioma; melanoma; melanoma, intraocular (eye); merkel cell cancer; merkel cell skin carcinoma; mesothelioma; mesothelioma, adult malignant; metastatic squamous neck cancer with occult primary; mouth cancer; multiple endocrine neoplasia syndrome; multiple myeloma/plasma cell neoplasm; mycosis fungoides, myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma, non-small cell lung cancer; non-hodgkin lymophoma; oligodendroglioma; oral cancer; oral cavity cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; papillomatosis; paranasal sinus and nasal cavity cancer; parathyroid cancer; penile cancer; pharyngeal cancer; pheochromocytoma; pineal astrocytoma; pineal germinoma; pineal parenchymal tumors of intermediate differentiation; pineoblastoma and supratentorial primitive neuroectodermal tumors; pituary tumor; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; respiratory tract carcinoma involving the NUT gene on chromosome 15; retinoblastoma; rhabdomyosarcoma, childhood; salivary gland cancer; sarcoma, Ewing family of tumors; Sézary syndrome; skin cancer (melanoma); skin cancer (non-melanoma); small cell lung cancer; small intestine cancer soft tissue sarcoma; soft tissue sarcoma; spinal cord tumor; squamous cell carcinoma; squamous neck cancer with occult primary, metastatic; stomach (gastric) cancer; supratentorial primitive neuroectodermal tumor; T-cell lymphoma, cutaneous (Mycosis Fungoides and Sézary syndrome); testicular cancer; throat cancer; thymoma; thymoma and thymic carcinoma; thyroid cancer; thyroid cancer, childhood; transitional cell cancer of the renal pelvis and ureter; urethral cancer; uterine cancer, endometrial; uterine sarcoma; vaginal cancer; vulvar cancer; and Wilms Tumor.

In certain embodiments, the tumor antigen or tumor associated antigen for use with the methods and compositions described herein includes oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-

AML, ETV6-AML1 fusion protein, FLT3-ITD, FN1, GPNMB, LDLR-fucosyltransferaseAS fusion protein, NFYC, OGT, OS-9, pml-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triosephosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyp1B1, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMW-MAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysin, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin αvβ3 (CD61), galactin, or Ral-B, CD123, CLL-1, CD38, CS-1, CD138, and ROR1.

In certain embodiments, the tumor antigen or tumor associated antigen for use with the methods and compositions described herein includes oncogenic viral antigens, wherein the oncogenic virus antigens are antigens of human papillomavirus (HPV), antigens of Kaposi's sarcoma-associated herpesvirus, such as latency-associated nuclear antigen, antigens of Epstein-Barr virus, such as EBV-EA, EBV-MA, or EBV-VCA, antigens of Merkel cell polyomavirus, such as MCV T antigen, or antigens of human T-lymphotropic virus, such as HTLV-1 Tax antigen.

In certain embodiments, the tumor antigen or tumor associated antigen is a neoantigen. A "neoantigen," as used herein, means an antigen that arises by mutation in a tumor cell and such an antigen is not generally expressed in normal cells or tissue. Without being bound by theory, because healthy tissues generally do not posses these antigens, neoantigens represent a preferred target. Additionally, without being bound by theory, in the context of the present invention, since the T cells that recognize the neoantigen may not have undergone negative thymic selection, such cells can have high avidity to the antigen and mount a strong immune response against tumors, while lacking the risk to induce destruction of normal tissue and autoimmune damage. In certain embodiments, the neoantigen is an MHC class I-restricted neoantigen. In certain embodiments, the neoantigen is an MHC class II-restricted neoantigen. In certain embodiments, a mutation in a tumor cell of the patient results in a novel protein that produces the neoantigen.

In certain embodiments, the tumor antigen or tumor associated antigen can be an antigen ortholog, e.g., a mammalian (i.e., non-human primate, pig, dog, cat, or horse) to a human tumor antigen or tumor associated antigen.

In certain embodiments, an antigenic fragment of a tumor antigen or tumor associated antigen described herein is encoded by the nucleotide sequence included within the arenavirus. In certain embodiments, a fragment is antigenic when it is capable of (i) eliciting an antibody immune response in a host (e.g., mouse, rabbit, goat, donkey or human) wherein the resulting antibodies bind specifically to an immunogenic protein expressed in or on a neoplastic cell (e.g., a cancer cell); and/or (ii) eliciting a specific T cell immune response.

In certain embodiments, the nucleotide sequence encoding antigenic fragment of a tumor antigen or tumor associated antigen is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the nucleotide sequence is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides in length. In some embodiments, the nucleotide sequence encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length, 1250 to 1500 amino acids in length, 1500 to 1750 amino acids in length, 1750 to 2000 amino acids in length, 2000 to 2500 amino acids in length, or more than 2500 or more amino acids in length. In some embodiments, the nucleotide sequence encodes a polypeptide that does not exceed 2500 amino acids in length. In specific embodiments the nucleotide sequence does not contain a stop codon. In certain embodiments, the nucleotide sequence is codon-optimized. In certain embodiments the nucleotide composition, nucleotide pair composition or both can be optimized. Techniques for such optimizations are known in the art and can be applied to optimize a nucleotide sequence of a tumor antigen or tumor associated antigen.

In certain embodiments, the arenavirus genomic segment, the arenavirus particle or the tri-segmented arenavirus particle can comprise one or more nucleotide sequences encoding tumor antigens, tumor associated antigens, or antigenic fragments thereof. In other embodiments, the arenavirus genomic segment, the arenavirus particle or the tri-segmented arenavirus particle can comprise at least one nucleotide sequence encoding a tumor antigen, tumor associated antigen, or antigenic fragment thereof, at least two nucleotide sequences encoding tumor antigens, tumor associated antigens, or antigenic fragments thereof, at least three nucleotide sequences encoding tumor antigens, tumor associated antigens, or antigenic fragments thereof, or more nucleotide sequences encoding tumor antigens, tumor associated antigens, or antigenic fragments thereof.

Nucleic acid sequences encoding a tumor antigen, tumor associated antigen, or antigenic fragment thereof can be introduced in the genome of a bi-segmented infectious, replication-deficient arenavirus by substitution of the nucleic acid sequence of the ORF of glycoprotein GP, the matrix protein Z, the nucleoprotein NP, or the polymerase protein L. In other embodiments, the nucleic acid sequence encoding the a tumor antigen, tumor associated antigen, or antigenic fragment thereof is fused to the ORF of glycoprotein GP, the matrix protein Z, the nucleoprotein NP, or the polymerase protein L. The nucleotide sequence encoding the a tumor antigen, tumor associated antigen, or antigenic fragment thereof, once inserted into the genome of a bi-segmented infectious, replication-deficient arenavirus, can be transcribed and/or expressed under control of the four arenavirus promoters (5' UTR and 3' UTR of the S segment, and 5' UTR and 3' UTR of the L segment), as well as ribonucleic acids that can be inserted with regulatory elements that can be read by the viral RNA-dependent RNA polymerase, cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. The nucleic acids encoding the a tumor antigen, tumor associated antigen, or antigenic fragment thereof can be transcribed and/or expressed either by themselves or as read-through by fusion to arenavirus ORFs and genes, respectively, and/or in combination with one or more, e.g., two, three or four, internal ribosome entry sites.

In certain embodiments, an arenavirus particle comprising a nucleotide sequence encoding a tumor antigen, tumor associated antigen or antigenic fragment thereof as provided herein further comprises at least one nucleotide sequence encoding at least one immunomodulatory peptide, polypeptide or protein. In certain embodiments, the immunomodulatory peptide, polypeptide or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; *Mycobacterium tuberculosis* Heat shock protein 70 or an antigenic fragment thereof; Herpes simplex virus 1 protein VP22 or an antigenic fragment thereof; CD40 ligand or an antigenic fragment thereof; or Fms-related tyrosine kinase 3 (Flt3) ligand or an antigenic fragment thereof.

In certain embodiments, an arenavirus particle provided herein comprises a genomic segment that a) has a removal or functional inactivation of an ORF that is present in the wild type form of the genomic segment; and b) encodes (either in sense or antisense): (i) one or more tumor antigen, tumor associated antigen or an antigenic fragment thereof provided herein, and (ii) one or more immunomodulatory peptide, polypeptide or protein provided herein.

In certain embodiments, the nucleotide sequence encoding the tumor antigen, tumor associated antigen or an antigenic fragment thereof provided herein, and the nucleotide sequence encoding the immunomodulatory peptide, polypeptide or protein provided herein, are on the same position of the viral genome. In certain embodiments, the nucleotide sequence encoding the tumor antigen, tumor associated antigen or an antigenic fragment thereof provided herein, and the nucleotide sequence encoding the immunomodulatory peptide, polypeptide or protein provided herein, are on different positions of the viral genome.

In certain embodiments, the nucleotide sequence encoding the tumor antigen, tumor associated antigen or an antigenic fragment thereof provided herein, and the nucleotide sequence encoding the immunomodulatory peptide, polypeptide or protein provided herein, are separated via a spacer sequence. In certain embodiments, the sequence encoding the tumor antigen, tumor associated antigen or an antigenic fragment thereof provided herein, and the nucleotide sequence encoding the immunomodulatory peptide, polypeptide or protein provided herein, are separated by an internal ribosome entry site, or a sequence encoding a protease cleavage site. In certain embodiments, the nucleotide sequence encoding the tumor antigen, tumor associated antigen or an antigenic fragment thereof provided herein, and the nucleotide sequence encoding the immunomodulatory peptide, polypeptide or protein provided herein, are separated by a nucleotide sequence encoding a linker or a self-cleaving peptide. Any linker peptide or self-cleaving peptide known to the skilled artisan can be used with the compositions and methods provided herein. A non-limiting example of a peptide linker is GSG. Non-limiting examples of a self-cleaving peptide are Porcine teschovirus-1 2A peptide, Thoseaasignavirus 2A peptide, or Foot-and-mouth disease virus 2A peptide.

In certain embodiments, the tumor antigen, tumor associated antigen or an antigenic fragment thereof provided herein, and the immunomodulatory peptide, polypeptide or protein provided herein, are directly fused together. In certain embodiments, the tumor antigen, tumor associated antigen or an antigenic fragment thereof provided herein, and the immunomodulatory peptide, polypeptide or protein provided herein, are fused together via a peptide linker. In certain embodiments, the tumor antigen, tumor associated antigen or an antigenic fragment thereof provided herein, and the immunomodulatory peptide, polypeptide or protein provided herein are separated from each other via a self-cleaving peptide. A non-limiting example of a peptide linker is GSG. Non-limiting examples of a self-cleaving peptide are Porcine teschovirus-1 2A peptide, Thoseaasignavirus 2A peptide, or Foot-and-mouth disease virus 2A peptide.

In certain embodiments, the tumor antigen, tumor associated antigen or an antigenic fragment thereof provided herein, and the immunomodulatory peptide, polypeptide or protein provided herein are expressed on the same arenavirus particle. In certain embodiments, the tumor antigen, tumor associated antigen or an antigenic fragment thereof provided herein, and the immunomodulatory peptide, polypeptide or protein provided herein are expressed on different areanavirus particles. In certain embodiments, the tumor antigen, tumor associated antigen or an antigenic fragment thereof provided herein, and the immunomodulatory peptide, polypeptide or protein provided herein are expressed on different viruses of the same strain. In certain embodiments, the tumor antigen, tumor associated antigen or an antigenic fragment thereof provided herein, and the immunomodulatory peptide, polypeptide or protein provided herein are expressed on different viruses of different strains.

In certain embodiments, an arenavirus particle generated to encode one or more tumor antigens, tumor associated antigens or antigenic fragments thereof comprises one or more nucleotide sequences encoding tumor antigens, tumor associated antigens or antigenic fragments thereof provided herein. In specific embodiments the tumor antigens, tumor associated antigens or antigenic fragments thereof provided herein are separated by various one or more linkers, spacers, or cleavage sites as described herein.

5.5 Generation of an Arenavirus Particle and a Tri-Segmented Arenavirus Particle Generally, arenavirus particles can be recombinantly produced by standard reverse genetic techniques as described for LCMV (see Flatz et al., 2006, Proc Natl Acad Sci USA 103:4663-4668; Sanchez et al., 2006, Virology 350:370; Ortiz-Riano et al., 2013, J Gen Virol. 94:1175-88, which are incorporated by reference herein). To generate the arenavirus particles provided herein, these techniques can be applied as described below. The genome of the viruses can be modified as described herein.

5.5.1 Non-Natural Position Open Reading Frame

The generation of an arenavirus particle comprising a genomic segment that has been engineered to carry a viral ORF in a position other than the wild-type position of the ORF and a nucleotide sequence encoding a tumor antigen, tumor associated antigen or antigenic fragment thereof can be recombinantly produced by any reverse genetic techniques known to one skilled in the art.

(i) Infectious and Replication Competent Arenavirus Particle

In certain embodiments, the method of generating the arenavirus particle comprises (i) transfecting into a host cell the cDNA of the first arenavirus genomic segment; (ii) transfecting into a host cell the cDNA of the second arenavirus genomic segment; (iii) transfecting into a host cell plasmids expressing the arenavirus' minimal trans-acting factors NP and L; (iv) maintaining the host cell under conditions suitable for virus formation; and (v) harvesting the arenavirus particle. In certain more specific embodiments, the cDNA is comprised in a plasmid.

Once generated from cDNA, arenavirus particles (e.g., infectious and replication competent) can be propagated. In certain embodiments, the arenavirus particle can be propagated in any host cell that allows the virus to grow to titers that permit the uses of the virus as described herein. In one embodiment, the host cell allows the arenavirus particle to grow to titers comparable to those determined for the corresponding wild-type.

In certain embodiments, the arenavirus particle may be propagated in host cells. Specific examples of host cells that can be used include BHK-21, HEK 293, VERO or other. In a specific embodiment, the arenavirus particle may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

Plasmids that can be used for the generation of the arenavirus particle can include: i) a plasmid encoding the S genomic segment e.g., pol-I S, ii) a plasmid encoding the L genomic segment e.g., pol-I L. In certain embodiments, the plasmid encoding an arenavirus polymerase that direct intracellular synthesis of the viral L and S segments can be incorporated into the transfection mixture. For example, a plasmid encoding the L protein and/or a plasmid encoding NP (pC-L and pC-NP, respectively) can be present. The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In certain embodiments, the arenavirus genomic segments are under the control of a promoter. Typically, RNA polymerase I-driven expression cassettes, RNA polymerase II-driven cassettes or T7 bacteriophage RNA polymerase driven cassettes can be used. In certain embodiments, the plasmid(s) encoding the arenavirus genomic segments can be the same, i.e., the genome sequence and transacting factors can be transcribed by a promoter from one plasmid. Specific examples of promoters include an RNA polymerase I promoter, an RNA polymerase II promoter, an RNA polymerase III promoter, a T7 promoter, an SP6 promoter or a T3 promoter.

In addition, the plasmid(s) can feature a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Transfection of a host cell with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

For recovering the arenavirus particle described herein, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

The present application furthermore relates to expression of a heterologous ORF, wherein a plasmid encoding the genomic segment is modified to incorporated a heterologous ORF. The heterologous ORF can be incorporated into the plasmid using restriction enzymes.

(ii) Infectious, Replication-Defective Arenavirus Particle

Infectious, replication-defective arenavirus particles can be rescued as described above. However, once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the ORFs in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a cell line such as BHK-21, HEK 293, VERO or other with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids can be of two types: i) two plasmids, referred to as TF-plasmids for expressing intracellularly in C-cells the minimal transacting factors of the arenavirus, is derived from e.g., NP and L proteins of LCMV in the present example; and ii) plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e., the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. Alternatively, the transfected cells and supernatant may be passaged to a larger vessel (e.g., a T75 tissue culture flask) on day 3-5 after transfection, and culture supernatant is harvested up to five days after passage.

The invention furthermore relates to expression of a antigen in a cell culture wherein the cell culture is infected with an infectious, replication-deficient arenavirus expressing an antigen. When used for expression of a antigen in cultured cells, the following two procedures can be used:

i) The cell type of interest is infected with the arenavirus vector preparation described herein at a multiplicity of infection (MOI) of one or more, e.g., two, three or four, resulting in production of the antigen in all cells already shortly after infection.

ii) Alternatively, a lower MOI can be used and individual cell clones can be selected for their level of virally driven antigen expression. Subsequently individual clones can be expanded infinitely owing to the non-cytolytic nature of arenavirus vectors. Irrespective of the approach, the antigen can subsequently be collected (and purified) either from the culture supernatant or from the cells themselves, depending on the properties of the antigen produced. However, the invention is not limited to these two strategies, and other ways of driving expression of antigen using infectious, replication-deficient arenaviruses as vectors may be considered.

5.5.2 Generation of a Tri-Segmented Arenavirus Particle

A tri-segmented arenavirus particle comprising a nucleotide sequence encoding a tumor antigen, tumor associated antigen or antigenic fragment thereof can be recombinantly produced by reverse genetic techniques known in the art, for example as described by Emonet et al., 2008, PNAS, 106 (9):3473-3478; Popkin et al., 2011, J. Virol., 85 (15):7928-7932, which are incorporated by reference herein. The generation of the tri-segmented arenavirus particle provided herein can be modified as described in Section 5.2.

(i) Infectious and Replication Competent Tri-Segmented Arenavirus Particle

In certain embodiments, the method of generating the tri-segmented arenavirus particle comprises (i) transfecting into a host cell the cDNAs of the one L segment and two S segments or two L segments and one S segment; (ii) transfecting into a host cell plasmids expressing the arenavirus' minimal trans-acting factors NP and L; (iii) maintaining the host cell under conditions suitable for virus formation; and (iv) harvesting the arenavirus particle.

Once generated from cDNA, the tri-segmented arenavirus particle (i.e., infectious and replication competent) can be propagated. In certain embodiments tri-segmented arenavirus particle can be propagated in any host cell that allows the virus to grow to titers that permit the uses of the virus as described herein. In one embodiment, the host cell allows the tri-segmented arenavirus particle to grow to titers comparable to those determined for the corresponding wild-type.

In certain embodiments, the tri-segmented arenavirus particle may be propagated in host cells. Specific examples of host cells that can be used include BHK-21, HEK 293, VERO or other. In a specific embodiment, the tri-segmented arenavirus particle may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

In specific embodiments, the host cells are kept in culture and are transfected with one or more plasmid(s). The plasmid(s) express the viral gene(s) to be generated under control of one or more expression cassettes suitable for expression in mammalian cells, e.g., consisting of a polymerase I promoter and terminator.

Plasmids that can be used for generating the tri-segmented arenavirus comprising one L segment and two S segments can include: i) two plasmids each encoding the S genome segment e.g., pol-I S, ii) a plasmid encoding the L genome segment e.g., pol-I L. Plasmids needed for the tri-segmented arenavirus comprising two L segments and one S segments are: i) two plasmids each encoding the L genome segment e.g., pol-L, ii) a plasmid encoding the S genome segment e.g., pol-I S.

In certain embodiments, plasmids encoding an arenavirus polymerase that direct intracellular synthesis of the viral L and S segments can be incorporated into the transfection mixture. For example, a plasmid encoding the L protein and a plasmid encoding NP (pC-L and pC-NP, respectively). The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In addition, the plasmid(s) features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Transfection of BHK-21 cells with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

Typically, RNA polymerase I-driven expression cassettes, RNA polymerase II-driven cassettes or T7 bacteriophage RNA polymerase driven cassettes can be used, the latter preferentially with a 3'-terminal ribozyme for processing of the primary transcript to yield the correct end. In certain embodiments, the plasmids encoding the arenavirus genomic segments can be the same, i.e., the genome sequence and transacting factors can be transcribed by T7, polI and polII promoters from one plasmid.

For recovering the arenavirus the tri-segmented arenavirus vector, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

In certain embodiments, expression of a nucleotide sequence encoding a tumor antigen, tumor associated antigen or antigenic fragment thereof is provided, wherein a plasmid encoding the genomic segment is modified to incorporated a nucleotide sequence encoding a tumor antigen, tumor associated antigen or antigenic fragment thereof. The nucleotide sequence encoding a tumor antigen, tumor associated antigen or antigenic fragment thereof can be incorporated into the plasmid using restriction enzymes.

(ii) Infectious, Replication-Defective Tri-Segmented Arenavirus Particle

Infectious, replication-defective tri-segmented arenavirus particles can be rescued as described above. However, once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the ORFs in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK 293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids of two types can be used: i) two plasmids, referred to as TF-plasmids for expressing intracellularly in C-cells the minimal transacting factors of the arenavirus, is derived from e.g., NP and L proteins of LCMV in the present example; and ii) plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e., the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. Alternatively, the transfected cells and supernatant may be passaged to a larger vessel (e.g., a T75 tissue culture flask) on day 3-5 after transfection, and culture supernatant is harvested up to five days after passage.

The invention furthermore relates to expression of an antigen in a cell culture wherein the cell culture is infected with an infectious, replication-deficient tri-segmented arenavirus expressing a antigen. When used for expression of a CMV antigen in cultured cells, the following two procedures can be used:

i) The cell type of interest is infected with the arenavirus vector preparation described herein at a multiplicity of infection (MOI) of one or more, e.g., two, three or four, resulting in production of the tumor antigen, tumor associated antigen, or antigenic fragment thereof in all cells already shortly after infection.

ii) Alternatively, a lower MOI can be used and individual cell clones can be selected for their level of virally driven expression of a tumor antigen, tumor associated antigen or antigenic fragment thereof. Subsequently individual clones can be expanded infinitely owing to the non-cytolytic nature of arenavirus vectors. Irrespective of the approach, the tumor antigen, tumor associated antigen or antigenic fragment thereof can subsequently be collected (and purified) either from the culture supernatant or from the cells themselves, depending on the properties of the tumor antigen, tumor associated antigen or antigenic fragment produced. However, the invention is not limited to these two strategies, and other ways of driving expression of tumor antigen, tumor associated antigen or antigenic fragment thereof using infectious, replication-deficient arenaviruses as vectors may be considered.

5.6 Generation of Infectious, Replication-Deficient Arenavirus Expressing a Tumor Antigen, Tumor Associated Antigen or Antigenic Fragment Thereof Generally, arenavirus particles can be recombinantly produced by standard reverse genetic techniques as described for LCMV (L. Flatz, A. Bergthaler, J. C. de la Torre, and D. D. Pinschewer, Proc Natl Acad Sci USA 103:4663-4668, 2006; A. B. Sanchez and J. C. de la Torre, Virology 350:370, 2006; E. Ortiz-Riano, B. Y. Cheng, J. C. de la Torre, L. Martinez-Sobrido. J Gen Virol. 94:1175-88, 2013). To generate infectious, replication-deficient arenaviruses for use with the present invention these techniques can be used, however, the genome of the rescued virus is modified as described herein. These modifications can be: i) one or more, e.g., two, three or four, of the four arenavirus ORFs (glycoprotein (GP); nucleoprotein (NP); the matrix protein Z; the RNA-dependent RNA polymerase L) are removed or functionally inactivated to prevent formation of infectious particles in normal cells albeit still allowing gene expression in arenavirus vector-infected host cells; and ii) nucleotides encoding for a tumor antigen, tumor associated antigen, or antigenic fragment thereof can be introduced. Infectious, replication-deficient viruses as described herein can be produced as described in International Patent Application Publication No. WO 2009/083210 (application number PCT/

EP2008/010994) and International Patent Application Publication No. WO 2014/140301 (application number PCT/EP2014/055144), each of which is incorporated by reference herein in its entirety.

Once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the viral genes in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK 293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids that can be used can be of two types: i) Two plasmids, referred to as TF-plasmids for expressing intracellularly in C-cells the minimal transacting factors of the arenavirus, is derived from e.g., NP and L proteins of LCMV in the present example; and ii) Plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e. the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e. the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells.

The invention furthermore relates to expression of a tumor antigen, tumor associated antigen, or antigenic fragment thereof in a cell culture wherein the cell culture is infected with a bi-segmented infectious, replication-deficient arenavirus expressing a tumor antigen, tumor associated antigen, or antigenic fragment thereof. When used for expression of a tumor antigen, tumor associated antigen, or antigenic fragment thereof in cultured cells, the following two procedures can be used:

i) The cell type of interest is infected with the arenavirus vector preparation described herein at a multiplicity of infection (MOI) of one or more, e.g., two, three or four, resulting in production of the tumor antigen, tumor associated antigen, or antigenic fragment thereof in all cells already shortly after infection.

ii) Alternatively, a lower MOI can be used and individual cell clones can be selected for their level of virally driven expression of a tumor antigen, tumor associated antigen, or antigenic fragment thereof. Subsequently individual clones can be expanded infinitely owing to the non-cytolytic nature of arenavirus vectors. Irrespective of the approach, the tumor antigen, tumor associated antigen, or antigenic fragment thereof can subsequently be collected (and purified) either from the culture supernatant or from the cells themselves, depending on the properties of the tumor antigen, tumor associated antigen, or antigenic fragment thereof produced. However, the invention is not limited to these two strategies, and other ways of driving expression of a tumor antigen, tumor associated antigen, or antigenic fragment thereof using infectious, replication-deficient arenaviruses as vectors may be considered.

Alternatively, a rescue system consisting of three plasmids can be used: (1) the first plasmid expresses the protein NP by transcription via Polymerase II and subsequent translation in transfected cells; (2) the second plasmid gives rise to the (negative-stranded) L-Segment of the LCMV genome by transcription via Polymerase I as well as the L protein by transcription via Polymerase II from the same template in the opposite direction of the Polymerase I promoter; (3) the third plasmid gives rise to the S-segment of the LCMV genome (encoding the antigen coding sequence instead of the LCMV glycoprotein) via transcription by Polymerase I. 3 µg of each plasmid is used for electroporation of C-cells, followed by seeding of cells in 6-well plates and incubation at 37° C. After incubation, cells and supernatant from transfections are combined with freshly seeded C-cells, and vectors are harvested and cleared from cells & debris at a defined timepoint post infection. Once the vector has been generated, a nucleic acid encoding a tumor antigen, tumor associated antigen, or antigenic fragment thereof can be inserted into a plasmid from which a genomic segment of an infectious replication-deficient vector is transcribed by any technique known to the skilled artisan.

Owing to the removal or functional inactivation of one or more of the viral genes in arenavirus vectors (here deletion of the glycoprotein, GP, will be taken as an example) arenavirus vectors can be generated and expanded in cells that provide the deleted or functionally inactivated viral gene(s) (e.g., the GP) in trans. The resulting virus itself is infectious but is unable to produce further infectious progeny particles in non-complementing cells due to the lack of the deleted or functionally inactivated viral gene(s) (e.g., the GP). The complementing cell can provide the missing functionality either by stable transfection, transient transfection, or by infection with a helper virus that expresses the missing functionality.

In certain embodiments, the complementing cell provides the viral gene that has been deleted or functionally inactivated from the arenavirus vector genome. In a specific embodiment, the complementing cell provides the viral gene from a viral strain that is the same as the viral strain that was used to generate the genome of the arenavirus vector. In another embodiment, the complementing cell provides the viral gene from a viral strain that is different from the viral strain that was used to generate the genome of the arenavirus vector. For example, the viral gene provided in the complementing cell is obtained from the MP strain of LCMV. In another example, the viral gene provided in the complementing cell is obtained from the Clone 13 strain of LCMV. In another example, the viral gene provided in the complementing cell is obtained from the WE strain of LCMV.

In a specific embodiment, the complementing cell provides the GP of the MP strain of LCMV and the arenavirus vector comprises an ORF of a tumor antigen, tumor associated antigen, or antigenic fragment thereof as described herein in place of the ORF encoding the GP protein. In an even more specific embodiment, the complementing cell provides the GP of the MP strain of LCMV and the arenavirus vector is obtained from LCMV Clone 13 and comprises an ORF of a tumor antigen, tumor associated antigen, or antigenic fragment thereof as described herein in place of the ORF encoding the GP protein.

In a specific embodiment, the complementing cell provides the GP of the Clone 13 strain of LCMV and the arenavirus vector comprises an ORF of a tumor antigen, tumor associated antigen, or antigenic fragment thereof as described herein in place of the ORF encoding the GP protein. In an even more specific embodiment, the complementing cell provides the GP of the Clone 13 strain of LCMV and the arenavirus vector is obtained from LCMV MP strain and comprises an ORF of a tumor antigen, tumor associated antigen, or antigenic fragment thereof as described herein in place of the ORF encoding the GP protein.

In a specific embodiment, the complementing cell provides the GP of the WE strain of LCMV and the arenavirus vector comprises an ORF of a tumor antigen, tumor associated antigen, or antigenic fragment thereof as described herein in place of the ORF encoding the GP protein. In an even more specific embodiment, the complementing cell provides the GP of the WE strain of LCMV and the arenavirus vector is obtained from LCMV Clone 13 and comprises an ORF of a tumor antigen, tumor associated antigen, or antigenic fragment thereof as described herein in place of the ORF encoding the GP protein.

In a specific embodiment, the complementing cell provides the GP of the WE strain of LCMV and the arenavirus vector comprises an ORF of a tumor antigen, tumor associated antigen, or antigenic fragment thereof as described herein in place of the ORF encoding the GP protein. In an even more specific embodiment, the complementing cell provides the GP of the WE strain of LCMV and the arenavirus vector is obtained from LCMV MP strain and comprises an ORF of a tumor antigen, tumor associated antigen, or antigenic fragment thereof as described herein in place of the ORF encoding the GP protein.

5.7 Nucleic Acids, Vector Systems and Cell Lines

In certain embodiments, provided herein are cDNAs comprising or consisting of the arenavirus genomic segment or the tri-segmented arenavirus particle as described herein.

5.7.1 Non-Natural Position Open Reading Frame

In one embodiment, provided herein are nucleic acids that encode an arenavirus genomic segment as described in Section 5.1. In more specific embodiments, provided herein is a DNA nucleotide sequence or a set of DNA nucleotide sequences as set forth in Table 1. Host cells that comprise such nucleic acids are also provided Section 5.1.

In specific embodiments, provided herein is a cDNA of the arenavirus genomic segment engineered to carry an ORF in a position other than the wild-type position of the ORF and a nucleotide sequence encoding a tumor antigen, tumor associated antigen or antigenic fragment thereof, wherein the arenavirus genomic segment encodes a heterologous ORF as described in Section 5.1

In one embodiment, provided herein is a DNA expression vector system that encodes the arenavirus genomic segment engineered to carry an ORF in a position other than the wild-type position of the ORF and a nucleotide sequence encoding a tumor antigen, tumor associated antigen or antigenic fragment thereof. Specifically, provided herein is a DNA expression vector system wherein one or more vectors encodes two arenavirus genomic segments, namely, an L segment and an S segment, of an arenavirus particle described herein. Such a vector system can encode a nucleotide sequence encoding a tumor antigen, tumor associated antigen or antigenic fragment thereof.

In another embodiment, provided herein is a cDNA of the arenavirus S segment that has been engineered to carry an ORF in a position other than the wild-type position and a nucleotide sequence encoding a tumor antigen, tumor associated antigen or antigenic fragment thereof that is part of or incorporated into a DNA expression system. In other embodiments, provided herein is a cDNA of the arenavirus L segment that has been engineered to carry an ORF in a position other than the wild-type position and a nucleotide sequence encoding a tumor antigen, tumor associated antigen or antigenic fragment thereof that is part of or incorporated into a DNA expression system. In certain embodiments, is a cDNA of the arenavirus genomic segment that has been engineered to carry (i) an ORF in a position other than the wild-type position of the ORF; and (ii) and ORF encoding GP, NP, Z protein, or L protein has been removed and replaced with a nucleotide sequence encoding a tumor antigen, tumor associated antigen or antigenic fragment thereof.

In certain embodiments, the cDNA provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the cDNA is derived from LCMV Clone 13. In other specific embodiments, the cDNA is derived from LCMV MP strain.

In certain embodiments, the vector generated to encode an arenavirus particle or a tri-segmented arenavirus particle as described herein may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, an arenavirus particle or a tri-segmented arenavirus particle as described herein may be based on LCMV Clone 13. In other embodiments, the vector generated to encode an arenavirus particle or a tri-segmented arenavirus particle as described herein LCMV MP strain.

In another embodiment, provided herein is a cell, wherein the cell comprises a cDNA or a vector system described above in this section. Cell lines derived from such cells, cultures comprising such cells, methods of culturing such cells infected are also provided herein. In certain embodiments, provided herein is a cell, wherein the cell comprises a cDNA of the arenavirus genomic segment that has been engineered to carry an ORF in a position other than the wild-type position of the ORF and a nucleotide sequence encoding a tumor antigen, tumor associated antigen or antigenic fragment thereof. In some embodiments, the cell comprises the S segment and/or the L segment.

5.7.2 Tri-Segmented Arenavirus Particle

In one embodiment, provided herein are nucleic acids that encode a tri-segmented arenavirus particle as described in Section 5.2. In more specific embodiments, provided herein is a DNA nucleotide sequence or a set of DNA nucleotide sequences, for example, as set forth in Table 2 or Table 3. Host cells that comprise such nucleic acids are also provided Section 5.2.

In specific embodiments, provided herein is a cDNA consisting of a cDNA of the tri-segmented arenavirus particle that has been engineered to carry an ORF in a position other than the wild-type position of the ORF. In other embodiments, is a cDNA of the tri-segmented arenavirus particle that has been engineered to (i) carry an arenavirus ORF in a position other than the wild-type position of the ORF; and (ii) wherein the tri-segmented arenavirus particle encodes a heterologous ORF as described in Section 5.2.

In one embodiment, provided herein is a DNA expression vector system that together encode the tri-segmented arenavirus particle comprising a nucleotide sequence encoding a tumor antigen, tumor associated antigen or antigenic fragment thereof as described herein. Specifically, provided herein is a DNA expression vector system wherein one or more vectors encode three arenavirus genomic segments, namely, one L segment and two S segments or two L segments and one S segment of a tri-segmented arenavirus particle described herein. Such a vector system can encode a tumor antigen, tumor associated antigen or antigenic fragment thereof.

In another embodiment, provided herein is a cDNA of the arenavirus S segment(s) that has been engineered to carry an ORF in a position other than the wild-type position and a nucleotide sequence encoding a tumor antigen, tumor associated antigen or antigenic fragment thereof that is part of or incorporated into a DNA expression system. In other embodiments, a cDNA of the arenavirus L segment(s) that has been engineered to carry an ORF in a position other than the wild-type position and a nucleotide sequence encoding a tumor antigen, tumor associated antigen or antigenic fragment thereof that is part of or incorporated into a DNA expression system. In certain embodiments, is a cDNA of the tri-segmented arenavirus particle that has been engineered to carry (i) an ORF in a position other than the wild-type position of the ORF; and (ii) an ORF encoding GP, NP, Z protein, or L protein has been removed and replaced with a nucleotide sequence encoding a tumor antigen, tumor associated antigen or antigenic fragment thereof.

In certain embodiments, the cDNA provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the cDNA is derived from LCMV Clone 13. In other specific embodiments, the cDNA is derived from LCMV MP strain.

In certain embodiments, the vector generated to encode an arenavirus particle or a tri-segmented arenavirus particle as described herein may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, an arenavirus particle or a tri-segmented arenavirus particle as described herein may be based on LCMV Clone 13. In other embodiments, the vector generated to encode an arenavirus particle or a tri-segmented arenavirus particle as described herein LCMV MP strain.

In another embodiment, provided herein is a cell, wherein the cell comprises a cDNA or a vector system described above in this section. Cell lines derived from such cells, cultures comprising such cells, methods of culturing such cells infected are also provided herein. In certain embodiments, provided herein is a cell, wherein the cell comprises a cDNA of the tri-segmented arenavirus particle. In some embodiments, the cell comprises the S segment and/or the L segment.

5.7.3 Replication-Deficient Arenavirus

In one embodiment, described herein is a nucleic acid sequence which is the cDNA of the large genomic segment (L segment) of a bi-segmented infectious, replication-deficient arenavirus described herein, in which one ORF of the genomic segment is deleted or functionally inactivated, and the genomic segment comprises a nucleotide sequence encoding a tumor antigen, tumor associated antigen, or antigenic fragment thereof.

In one embodiment, described herein is a nucleic acid sequence that encodes the short genomic segment (S segment) of a bi-segmented infectious, replication-deficient arenavirus described herein, in which one ORF of the genomic segment is deleted or functionally inactivated and wherein the short genomic segment comprises a nucleotide sequence encoding a tumor antigen, tumor associated antigen, or antigenic fragment thereof. In another embodiment, described herein is a nucleic acid sequence that encodes the short genomic segment (S segment) of a bi-segmented infectious, replication-deficient arenavirus described herein, in which the ORF of the glycoprotein gene is deleted or functionally inactivated and wherein the short genomic segment comprises a nucleotide sequence encoding a tumor antigen, tumor associated antigen, or antigenic fragment thereof. In certain, more specific embodiments, the tumor antigen, tumor associated antigen, or antigenic fragment thereof is an antigen described in Section 5.4.

In certain embodiments, the nucleic acid sequences provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the nucleic acid is derived from LCMV Clone 13. In other specific embodiments, the nucleic acid is derived from LCMV MP strain.

In a more specific embodiment, provided herein is a nucleic acid that comprises an arenavirus genomic segment; and (ii) a nucleotide sequence encoding a tumor antigen, tumor associated antigen, or antigenic fragment thereof.

In one embodiment, described herein is a vector system comprising one or more vectors that together comprise the genome of a bi-segmented infectious, replication-deficient arenavirus particle described herein. Specifically, provided herein is a vector system wherein the one or more vectors comprise two arenavirus genomic segments, namely an L segment and an S segment, of a bi-segmented infectious, replication-deficient arenavirus described herein. Such a vector system can comprise (on one or more separate DNA molecules):

An arenavirus S genomic segment that is modified such that an arenavirus particle carrying this modified S genomic segment cannot produce infectious progeny virus particles and an arenavirus L genomic segment that comprises a nucleotide sequence encoding (in sense or antisense) a tumor antigen, tumor associated antigen, or antigenic fragment thereof;

An arenavirus L genomic segment that is modified such that an arenavirus particle carrying this modified L genomic segment cannot produce infectious progeny virus particles and an arenavirus S genomic segment that comprises a nucleotide sequence encoding (in sense or antisense) a tumor antigen, tumor associated antigen, or antigenic fragment thereof;

An arenavirus S genomic segment that is modified such that an arenavirus particle carrying this modified S genomic segment cannot produce infectious progeny virus particles and wherein the arenavirus S genomic segment comprises a nucleotide sequence encoding (in sense or antisense) a tumor antigen, tumor associated antigen, or antigenic fragment thereof and comprising a wild type arenavirus L genomic segment; or An arenavirus L genomic segment that is modified such that an arenavirus particle carrying this modified L genomic segment cannot produce infectious progeny virus particles and wherein the arenavirus L genomic segment comprises a nucleotide sequence encoding (in sense or antisense) a tumor antigen, tumor associated antigen, or antigenic fragment thereof and comprising a wild type arenavirus S genomic segment.

In certain embodiments, described herein is a nucleic acid sequence comprising an arenavirus (e.g., LCMV) genomic segment in which the ORF encoding the GP of the S genomic segment is substituted with a nucleotide sequence encoding a tumor antigen, tumor associated antigen, or antigenic fragment thereof, which is selected from the group consisting of oncogenic viral antigens, cancer-testis antigens, oncofetal antigens, tissue differentiation antigens, mutant protein antigens, neoantigens, Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX10, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pml-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or -SSX2 fusion protein, TGF-betaRII, Triose-phosphate isomerase, ormdm-2, LMP2, HPV E6/E7, EGFRvIII (epidermal growth factor variant III), Idiotype, GD2, ganglioside G2), Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, GD3, Fucosyl GM1, Mesothelin, PSCA, sLe(a), cyp1B1, PLAC1, GM3, BORIS, Tn, GLoboH, NY-BR-1, SART3, STn, Carbonic Anhydrase IX, OY-TES1, Sperm protein 17, LCK, high molecular weight melanoma-associated antigen (HMW-MAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysis, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, Carbohydrate/ganglioside GM2 (oncofetal antigen-immunogenic-1 OFA-I-1), GM3, CA 15-3 (CA 27.29\BCAA), CA 195, CA 242, CA 50, CAM 43, CEA, EBNA, EF2, Epstein-Barr virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-

PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, prostein, TARP (T cell receptor gamma alternate reading frame protein), Trp-p8, integrin αvβ3 (CD61), galactin, or Ral-B, CD123, CLL-1, CD38, CS-1, CD138, and ROR1.

In certain embodiments, described herein is a nucleic acid sequence comprising an arenavirus (e.g., LCMV) genomic segment in which the ORF encoding the GP of the S genomic segment is substituted with a nucleotide sequence encoding one or more a tumor antigen, tumor associated antigen, or antigenic fragment thereof (e.g., one or more of those listed in the above paragraph).

In another embodiment, provided herein is a cell wherein the cell comprises a nucleic acid or a vector system described above in this section. Cell lines derived from such cells, cultures comprising such cells, and methods of culturing such cells infected with nucleic acids or vector systems are also provided herein. In certain embodiments, provided herein is a cell wherein the cell comprises a nucleic acid comprising the large genomic segment (L segment) of a bi-segmented infectious, replication-deficient arenavirus described herein, in which one ORF of the genomic segment is deleted or functionally inactivated, and the genomic segment comprises a nucleotide sequence encoding a tumor antigen, tumor associated antigen, or antigenic fragment thereof.

In other embodiments, provided herein is a cell wherein the cell comprises a nucleic acid sequence that comprises the short genomic segment (S segment) of a bi-segmented infectious, replication-deficient arenavirus described herein, in which one ORF of the genomic segment is deleted or functionally inactivated and wherein the short genomic segment comprises a nucleotide sequence encoding a tumor antigen, tumor associated antigen, or antigenic fragment thereof.

In another embodiment, provided herein is a cell wherein the cell comprises two nucleic acids or vector systems described herein. Cell lines derived from such cells, cultures comprising such cells, and methods of culturing such cells infected with nucleic acids or vector systems are also provided herein.

5.8 Methods of Use

Vaccines have been successful for preventing and/or treating infectious diseases, such as those for polio virus and measles. However, therapeutic immunization in the setting of established, chronic disease, including cancer has been less successful. The ability to generate an arenavirus particle that is used in combination with an immune checkpoint inhibitor represents a new novel vaccine strategy.

In certain embodiments, provided herein are methods of treating a neoplastic disease in a subject. Such methods can include administering to a subject in need thereof an arenavirus particle provided herein and an immune checkpoint inhibitor provided herein. In certain embodiments, the arenavirus particle used in the methods is an infectious, replication-deficient arenavirus particle provided herein. In certain embodiments, the arenavirus particle used in the methods is a tri-segmented arenavirus particle provided herein, including an infectious, replication-deficient tri-segmented arenavirus particle or a replication-competent tri-segmented arenavirus particle. Thus, in certain embodiments, the arenavirus particle, including a tri-segmented arenavirus particle, used in the methods is replication-deficient, wherein the arenavirus particle is engineered to contain a genome comprising: (1) a nucleotide sequence encoding a tumor antigen, tumor associated antigen or an antigenic fragment thereof; and (2) the ability to amplify and express its genetic information in infected cells but unable to produce further infectious progeny particles in non-complementing cells. Moreover, in certain embodiments, a tri-segmented arenavirus particle used in the methods is replication-competent, wherein the tri-segmented arenafirus particle is engineered to contain a genome comprising: (1) a nucleotide sequence encoding a tumor antigen, tumor associated antigen or an antigenic fragment thereof; (2) the ability to amplify and express its genetic information in infected cells; and (3) the ability to produce further infectious progeny particles in normal, not genetically engineered cells. In certain embodiments, the arenavirus particle used in the methods is a bi-segmented infectious, replication-deficient arenavirus particle. Thus, in certain embodiments, the infectious, replication-deficient arenavirus particle used in the methods is engineered to contain a genome comprising: (1) a nucleotide sequence encoding a tumor antigen, tumor associated antigen or an antigenic fragment thereof; and (2) the ability to amplify and express its genetic information in infected cells but unable to produce further infectious progeny particles in non-complementing cells. In certain embodiments, the immune checkpoint inhibitor inhibits, decreases or interferes with the activity of a negative checkpoint regulator.

In one embodiment, provided herein are methods of treating a neoplastic disease in a subject comprising administering to the subject one or more arenavirus particles expressing a tumor antigen, tumor associated antigen or an antigenic fragment thereof as provided herein or a composition thereof, and an immune checkpoint inhibitor provided herein. In a specific embodiment, a method for treating a neoplastic disease described herein comprises administering to a subject in need thereof a therapeutically effective amount of one or more arenavirus particles expressing a tumor antigen, tumor associated antigen or an antigenic fragment thereof provided herein or a composition thereof, and an immune checkpoint inhibitor provided herein. The subject can be a mammal, such as but not limited to a human, a mouse, a rat, a guinea pig, a domesticated animal, such as, but not limited to, a cow, a horse, a sheep, a pig, a goat, a cat, a dog, a hamster, a donkey. In a specific embodiment, the subject is a human.

In another embodiment, provided herein are methods for inducing an immune response against a neoplastic cell or tissue, such as a cancer cell or tumor, in a subject comprising administering to the subject an arenavirus particle expressing a tumor antigen, tumor associated antigen or an antigenic fragment thereof provided herein, or a composition thereof, and an immune checkpoint inhibitor provided herein.

In another embodiment, the subjects to whom an arenavirus particle expressing a tumor antigen, tumor associated antigen or an antigenic fragment thereof provided herein, or a composition thereof, and an immune checkpoint inhibitor provided herein is administered have, are susceptible to, or are at risk for a neoplastic disease.

In another embodiment, the subjects to whom an arenavirus particle expressing a tumor antigen, tumor associated antigen or an antigenic fragment thereof provided herein, or a composition thereof, and an immune checkpoint inhibitor provided herein is administered have, are susceptible to, or are at risk for development of a neoplastic disease, such as cancer, or exhibit a pre-cancerous tissue lesion. In another specific embodiment, the subjects to whom arenavirus particle expressing a tumor antigen, tumor associated antigen or an antigenic fragment thereof provided herein, or a composition thereof, and an immune checkpoint inhibitor provided herein is administered are diagnosed with a neoplastic disease, such as cancer, or exhibit a pre-cancerous tissue lesion.

In another embodiment, the subjects to whom an arenavirus particle expressing a tumor antigen, tumor associated antigen or an antigenic fragment thereof provided herein, or a composition thereof, and an immune checkpoint inhibitor provided herein is administered are suffering from, are susceptible to, or are at risk for, a neoplastic disease selected from, but not limited to, acute lymphoblastic leukemia; acute lymphoblastic lymphoma; acute lymphocytic leukaemia; acute myelogenous leukemia; acute myeloid leukemia (adult/childhood); adrenocortical carcinoma; AIDS-related cancers; AIDS-related lymphoma; anal cancer; appendix cancer; astrocytomas; atypical teratoid/rhabdoid tumor; basal-cell carcinoma; bile duct cancer, extrahepatic (cholangiocarcinoma); bladder cancer; bone osteosarcoma/malignant fibrous histiocytoma; brain cancer (adult/childhood); brain tumor, cerebellar astrocytoma (adult/childhood); brain tumor, cerebral astrocytoma/malignant glioma brain tumor; brain tumor, ependymoma; brain tumor, medulloblastoma; brain tumor, supratentorial primitive neuroectodermal tumors; brain tumor, visual pathway and hypothalamic glioma; brainstem glioma; breast cancer; bronchial adenomas/carcinoids; bronchial tumor; Burkitt lymphoma; cancer of childhood; carcinoid gastrointestinal tumor; carcinoid tumor; carcinoma of adult, unknown primary site; carcinoma of unknown primary; central nervous system embryonal tumor; central nervous system lymphoma, primary; cervical cancer; childhood adrenocortical carcinoma; childhood cancers; childhood cerebral astrocytoma; chordoma, childhood; chronic lymphocytic leukemia; chronic myelogenous leukemia; chronic myeloid leukemia; chronic myeloproliferative disorders; colon cancer; colorectal cancer; craniopharyngioma; cutaneous T-cell lymphoma; desmoplastic small round cell tumor; emphysema; endometrial cancer; ependymoblastoma; ependymoma; esophageal cancer; ewing's sarcoma in the Ewing family of tumors; extracranial germ cell tumor; extragonadal germ cell tumor; extrahepatic bile duct cancer; gallbladder cancer; gastric (stomach) cancer; gastric carcinoid; gastrointestinal carcinoid tumor; gastrointestinal stromal tumor; germ cell tumor: extracranial, extragonadal, or ovarian gestational trophoblastic tumor; gestational trophoblastic tumor, unknown primary site; glioma; glioma of the brain stem; glioma, childhood visual pathway and hypothalamic; hairy cell leukemia; head and neck cancer; heart cancer; hepatocellular (liver) cancer; hodgkin lymphoma; hypopharyngeal cancer; hypothalamic and visual pathway glioma; intraocular melanoma; islet cell carcinoma (endocrine pancreas); Kaposi Sarcoma; kidney cancer (renal cell cancer); langerhans cell histiocytosis; laryngeal cancer; lip and oral cavity cancer; liposarcoma; liver cancer (primary); lung cancer, non-small cell; lung cancer, small cell; lymphoma, primary central nervous system; macroglobulinemia, Waldenström; male breast cancer; malignant fibrous histiocytoma of bone/osteosarcoma; medulloblastoma; medulloepithelioma; melanoma; melanoma, intraocular (eye); merkel cell cancer; merkel cell skin carcinoma; mesothelioma; mesothelioma, adult malignant; metastatic squamous neck cancer with occult primary; mouth cancer; multiple endocrine neoplasia syndrome; multiple myeloma/plasma cell neoplasm; mycosis fungoides, myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma, non-small cell lung cancer; non-hodgkin lymophoma; oligodendroglioma; oral cancer; oral cavity cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; papillomatosis; paranasal sinus and nasal cavity cancer; parathyroid cancer; penile cancer; pharyngeal cancer; pheochromocytoma; pineal astrocytoma; pineal germinoma; pineal parenchymal tumors of intermediate differentiation; pineoblastoma and supratentorial primitive neuroectodermal tumors; pituary tumor; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; respiratory tract carcinoma involving the NUT gene on chromosome 15; retinoblastoma; rhabdomyosarcoma, childhood; salivary gland cancer; sarcoma, Ewing family of tumors; Sézary syndrome; skin cancer (melanoma); skin cancer (non-melanoma); small cell lung cancer; small intestine cancer soft tissue sarcoma; soft tissue sarcoma; spinal cord tumor; squamous cell carcinoma; squamous neck cancer with occult primary, metastatic; stomach (gastric) cancer; supratentorial primitive neuroectodermal tumor; T-cell lymphoma, cutaneous (Mycosis Fungoides and Sézary syndrome); testicular cancer; throat cancer; thymoma; thymoma and thymic carcinoma; thyroid cancer; thyroid cancer, childhood; transitional cell cancer of the renal pelvis and ureter; urethral cancer; uterine cancer, endometrial; uterine sarcoma; vaginal cancer; vulvar cancer; and Wilms Tumor.

In another embodiment, an arenavirus particle expressing a tumor antigen, tumor associated antigen or an antigenic fragment thereof provided herein, or a composition thereof, and an immune checkpoint inhibitor provided herein is administered to a subject of any age group suffering from, are susceptible to, or are at risk for a neoplastic disease. In a specific embodiment, an arenavirus particle expressing a tumor antigen, tumor associated antigen or an antigenic fragment thereof provided herein, or a composition thereof, and an immune checkpoint inhibitor provided herein is administered to a subject with a compromised immune system, a pregnant subject, a subject undergoing an organ or bone marrow transplant, a subject taking immunosuppressive drugs, a subject undergoing hemodialysis, a subject who has cancer, or a subject who is suffering from, are susceptible to, or are at risk for a neoplastic disease. In a more specific embodiment, an arenavirus particle expressing a tumor antigen, tumor associated antigen or an antigenic fragment thereof provided herein, or a composition thereof, and an immune checkpoint inhibitor provided herein is administered to a subject who is a child of 0, 1, 2, 3, 4, 5, 6, 7, 8, 9, 10, 11, 12, 13, 14, 15, 16, or 17 years of age suffering from, are susceptible to, or are at risk for a neoplastic disease. In yet another specific embodiment, an arenavirus particle expressing a tumor antigen, tumor associated antigen or an antigenic fragment thereof provided herein, or a composition thereof, and an immune checkpoint inhibitor provided herein is administered to a subject who is an infant suffering from, is susceptible to, or is at risk for a neoplastic disease. In yet another specific embodiment, an arenavirus particle expressing a tumor antigen, tumor associated antigen or an antigenic fragment thereof provided herein, or a composition thereof, and an immune checkpoint inhibitor provided herein is administered to a subject who is an infant of 0, 1, 2, 3, 4, 5, 6, 7, 8, 9, 10, 11, or 12 months of age suffering from, is susceptible to, or is at risk for a neoplastic disease. In yet another specific embodiment, an arenavirus particle expressing a tumor antigen, tumor associated antigen or an antigenic fragment thereof provided herein, or a composition thereof, and an immune checkpoint inhibitor provided herein is administered to an elderly subject who is suffering from, is susceptible to, or is at risk for a neoplastic disease. In a more specific embodiment, an arenavirus particle expressing a tumor antigen, tumor associated antigen or an antigenic fragment thereof provided herein, or a composition thereof, and an immune checkpoint inhibitor provided herein is administered to a subject who is a senior subject of 65, 66, 67, 68, 69, 70, 71, 72, 73, 74, 75, 76, 77, 78, 79, 80, 81, 82, 83, 84, 85, 86, 87, 88, 89, or 90 years of age.

In another embodiment, an arenavirus particle expressing a tumor antigen, tumor associated antigen or an antigenic fragment thereof provided herein, or a composition thereof, and an immune checkpoint inhibitor provided herein is administered to subjects with a heightened risk of cancer metastasis. In a specific embodiment, an arenavirus particle expressing a tumor antigen, tumor associated antigen or an antigenic fragment thereof provided herein, or a composition thereof, and an immune checkpoint inhibitor provided herein is administered to subjects in the neonatal period with a neonatal and therefore immature immune system.

In another embodiment, an arenavirus particle expressing a tumor antigen, tumor associated antigen or an antigenic fragment thereof provided herein, or a composition thereof, and an immune checkpoint inhibitor provided herein is administered to a subject having grade 0 (i.e., in situ neoplasm), grade 1, grade 2, grade 3 or grade 4 cancer or a subcategory thereof, such as grade 3A, 3B, or 3C, or an equivalent thereof.

In another embodiment, an arenavirus particle expressing a tumor antigen, tumor associated antigen or an antigenic fragment thereof provided herein, or a composition thereof, and an immune checkpoint inhibitor provided herein is administered to a subject having cancer at a Tumor, Node, Metastasis (TNM) stage of any combination selected from Tumor T1, T2, T3, and T4, and Node N0, N1, N2, or N3, and Metastasis M0 and M1.

Successful treatment of a cancer patient can be assessed as prolongation of expected survival, induction of an antitumor immune response, or improvement of a particular characteristic of a cancer. Examples of characteristics of a cancer that might be improved include tumor size (e.g., T0, T is, or T1-4), state of metastasis (e.g., M0, M1), number of observable tumors, node involvement (e.g., N0, N1-4, Nx), grade (i.e., grades 1, 2, 3, or 4), stage (e.g., 0, I, II, III, or IV), presence or concentration of certain markers on the cells or in bodily fluids (e.g., AFP, B2M, beta-HCG, BTA, CA 15-3, CA 27.29, CA 125, CA 72.4, CA 19-9, calcitonin, CEA, chromgrainin A, EGFR, hormone receptors, HER2, HCG, immunoglobulins, NSE, NMP22, PSA, PAP, PSMA, S-100, TA-90, and thyroglobulin), and/or associated pathologies (e.g., ascites or edema) or symptoms (e.g., cachexia, fever, anorexia, or pain). The improvement, if measurable by percent, can be at least 5, 10, 15, 20, 25, 30, 40, 50, 60, 70, 80, or 90% (e.g., survival, or volume or linear dimensions of a tumor).

In another embodiment, an arenavirus particle expressing a tumor antigen, tumor associated antigen or an antigenic fragment thereof provided herein, or a composition thereof, and an immune checkpoint inhibitor provided herein is administered to a subject having a dormant cancer (e.g., the subject is in remission). Thus, provided herein is a method for preventing reactivation of a cancer.

In another embodiment, an arenavirus particle expressing a tumor antigen, tumor associated antigen or an antigenic fragment thereof provided herein, or a composition thereof, and an immune checkpoint inhibitor provided herein is administered to a subject having a recurrent a cancer.

In another embodiment, an arenavirus particle expressing a tumor antigen, tumor associated antigen or an antigenic fragment thereof provided herein, or a composition thereof, and an immune checkpoint inhibitor provided herein is administered to a subject with a genetic predisposition for a cancer. In another embodiment, an arenavirus particle expressing a tumor antigen, tumor associated antigen or an antigenic fragment thereof provided herein, or a composition thereof, and an immune checkpoint inhibitor provided herein is administered to a subject with risk factors. Exemplary risk factors include, aging, tobacco, sun exposure, radiation exposure, chemical exposure, family history, alcohol, poor diet, lack of physical activity, or being overweight.

In another embodiment, an arenavirus particle expressing a tumor antigen, tumor associated antigen or an antigenic fragment thereof provided herein, or a composition thereof, and an immune checkpoint inhibitor provided herein is administered to subjects who suffer from one or more types of cancers. In other embodiments, any type of neoplastic disease, such as cancer, that is susceptible to treatment with the compositions described herein might be targeted.

In another embodiment, administering an arenavirus particle expressing a tumor antigen, tumor associated antigen or an antigenic fragment thereof provided or a composition thereof to subjects confer cell-mediated immunity (CMI) against a neoplastic cell or tumor, such as a cancer cell or tumor. Without being bound by theory, in another embodiment, an arenavirus particle expressing a tumor antigen, tumor associated antigen or an antigenic fragment thereof provided or a composition thereof infects and expresses antigens of interest in antigen presenting cells (APC) of the host (e.g., macrophages) for direct presentation of antigens on Major Histocompatibility Complex (MHC) class I and II. In another embodiment, administering an arenavirus particle expressing a tumor antigen, tumor associated antigen or an antigenic fragment thereof provided herein, or a composition thereof, to subjects induces plurifunctional IFN-γ and TNF-α co-producing cancer-specific CD4+ and CD8+ T cell responses (IFN-γ is produced by CD4+ and CD8+ T cells and TNF-α is produced by CD4+ T cells) of high magnitude to treat a neoplastic disease.

In another embodiment, administering an arenavirus particle expressing a tumor antigen, tumor associated antigen or an antigenic fragment thereof provided herein, or a composition thereof, and an immune checkpoint inhibitor provided herein increases or improves one or more clinical outcome for cancer treatment. Non-limiting examples of such outcomes are overall survival, progression-free survival, time to progression, time to treatment failure, event-free survival, time to next treatment, overall response rate and duration of response. The increase or improvement in one or more of the clinical outcomes can be by at least about 10%, at least about 20%, at least about 25%, at least about 30%, at least about 35%, at least about 40%, at least about 50%, at least about 60%, at least about 70%, at least about 80%, at least about 90%, or more, compared to a patient or group of patients having the same neoplastic disease in the absence of such treatment.

Changes in cell-mediated immunity (CMI) response function against a neoplastic cell or tumor, including a cancer cell or tumor, induced by administering an arenavirus particle expressing a tumor antigen, tumor associated antigen or an antigenic fragment thereof provided, or a composition thereof, in subjects can be measured by any assay known to the skilled artisan including, but not limited to flow cytometry (see, e.g., Perfetto S. P. et al., Nat Rev Immun. 2004; 4(8):648-55), lymphocyte proliferation assays (see, e.g., Bonilla F. A. et al., Ann Allergy Asthma Immunol. 2008; 101:101-4; and Hicks M. J. et al., Am J Clin Pathol. 1983; 80:159-63), assays to measure lymphocyte activation including determining changes in surface marker expression following activation of measurement of cytokines of T lymphocytes (see, e.g., Caruso A. et al., Cytometry. 1997; 27:71-6), ELISPOT assays (see, e.g., Czerkinsky C. C. et al., J Immunol Methods. 1983; 65:109-121; and Hutchings P. R. Et al., J Immunol Methods. 1989; 120:1-8), or Natural killer cell cytotoxicity assays (see, e.g., Bonilla F. A. et al., Ann Allergy Asthma Immunol. 2005 May; 94(5 Suppl 1):S1-63).

Immune checkpoint inhibitors that can be used with the methods and compositions described herein can target any negative checkpoint regulator. In certain embodiments, such a negative checkpoint regulator is a protein involved in T-Cell activation. In certain, more specific embodiments, such a negative checkpoint regulator is Cytotoxic T-lymphocyte antigen-4 (CTLA-4), CD80, CD86, Programmed cell death 1 (PD-1), Programmed cell death ligand 1 (PD-L1), Programmed cell death ligand 2 (PD-L2), Lymphocyte activation gene-3 (LAG-3; also known as CD223), Galectin-3, B and T lymphocyte attenuator (BTLA), T-cell membrane protein 3 (TIM3), Galectin-9 (GAL9), B7-H1, B7-H3, B7-H4, T-Cell immunoreceptor with Ig and ITIM domains (TIGIT/Vstm3/WUCAM/VSIG9), V-domain Ig suppressor of T-Cell activation (VISTA), Glucocorticoid-induced tumor necrosis factor receptor-related (GITR) protein, Herpes Virus Entry Mediator (HVEM), OX40, CD27, CD28, CD137. CGEN-15001T, CGEN-15022, CGEN-15027, CGEN-15049, CGEN-15052, or CGEN-15092. An overview such checkpoint regulators and drugs that target them is set forth in Table 4.

TABLE 4

| Target for Immunotherapy | Mode of Action | Commercial Name | FDA Approval | Indication (human) | Preclinical Evaluation |
|---|---|---|---|---|---|
| PD1/ PD1-L(1,2) (programmed cell death protein-1) | Antibodies that bind to PD1 (Block receptor) | Nivolumab (Opdivo-Bristol Myers Squibb) | Yes | Metastatic Melanoma, Non-Small cell lung cancer | Yes. PD1 Ab alone and in combination with CTLA4 have been systematically evaluated in 7 different mouse models. (Barnes et al, AACR Annual Meeting Poster # 3362 (2015)) P815-B7-H1-modified (Mastocytoma) have also been evaluated. (See Hirano et al., Cancer Res, 65(3), 1089-96 (2005)) |
| | | Pembrolizumab (Keytruda, MK-3475 Merck) | Yes | Metastatic Melanoma (Clinical trials for lung cancer, lymphoma, mesothelioma) | |
| | | Pidilizumab (CT-011, Cure Tech) | No | Clinical Trials - multiple cancers | |
| | Antibodies bind PD-L1 (inhibit receptor binding) | BMS936559 (Bristol Myers-Squibb) | No | Melanoma, Non-Small cell lung cancer, Ovarian Cancer | |
| | | MPDL328OA (Roche) | No | Phase I: HIV NSCLC and melanoma (locally advanced or metatstatic tumor) | |
| CTLA4 (cytotoxic T lymphocyte-associated antigen 4) | By binding to CTLA4, the compounds enhance T-cell activation and block B7-1 and B7-2 T-cell co-stimulatory pathways | Ipilimumab (MDX010, Yervoy; Bristol Myers-Squibb) | Yes | Melanoma | Yes. See Simpson et al. J. Exp. Med. 2013: 210(9): 1695-710 variable abilities were allocated to different Ab clones. |
| | | Tremelimumab (CP-675, 206, Pfizer) | No | Clinical trials - Multiple Cancers | |
| TIM-3 (T-Cell immunoglobulin and mucin-containing protein 3) | Anti-TIM-3 IgGs inhibit binding of TIM-3 to its receptor and/or Ligand (perhaps galectin-9) | n. a. | No | n. a. | Yes. (See Sakuishi et al., J Exp. Med., 207(10), 2187-94 (2010)) CT26, 4T1 and B16 were tested in their respective background. |
| LAG-3/ Galectin-3 (lymphocyte-activated gene-3) | Anti-LAG-3 antibodies/depletion of galectin-3 | n. a. | No | n. a. | Yes. NT2.5 (neu-expressing tumor cell line) reported in Kouo et al. Cancer Immunol Res. 3(4): 412-23 (2015). B16 and MC38 reported in Woo et al. Cancer Res 72(4)_917-27 (.2012). |
| TIGIT (T-Cell immunoreceptor with Ig and ITIM domains) | Antibodies against TIGIT inhibit binding to PVR (receptor) disturbing the inhibitory signaling. | Under development (Genentech) | No | n. a. | Yes. (See Johnston et al., Cancer Cell. 26(6): 923-37 (2014)). |

TABLE 4-continued

| Target for Immunotherapy | Mode of Action | Commercial Name | FDA Approval | Indication (human) | Preclinical Evaluation |
|---|---|---|---|---|---|
| | Further CD226 can bind to PVR instead and deploy its T-Cell activating function/ Might be also involved in NK cell inhibition | | | | |
| BTLA (B and T lymphocyte attenuator) VISTA (V-domain Ig suppressor of T-Cell activation) | | | | | |

In certain embodiments, an arenavirus particle expressing a tumor antigen, tumor associated antigen or an antigenic fragment thereof provided herein, or a composition thereof, and an immune checkpoint inhibitor provided herein is preferably administered in multiple injections (e.g., at least 2, 3, 4, 5, 6, 7, 8, 9, 10, 12, 14, 16, 18, 20, 25, 30, 40, 45, or 50 injections) or by continuous infusion (e.g., using a pump) at multiple sites (e.g., at least 2, 3, 4, 5, 6, 7, 8, 9, 10, 12, or 14 sites). In certain embodiments, the arenavirus particle expressing a tumor antigen, tumor associated antigen or an antigenic fragment thereof provided herein, or a composition thereof, is administered in two or more separate injections over a 6-month period, a 12-month period, a 24-month period, or a 48-month period. In certain embodiments, the arenavirus particle expressing a tumor antigen, tumor associated antigen or an antigenic fragment thereof provided herein, or a composition thereof, is administered with a first dose at an elected date, a second dose at least 2 months after the first dose, and a third does 6 months after the first dose.

In one example, cutaneous injections are performed at multiple body sites to reduce extent of local skin reactions. On a given vaccination day, the patient receives the assigned total dose administered from one syringe in 3 to 5 separate intradermal injections of the dose (e.g., at least 0.4 ml, 0.2 ml, or 0.1 ml) each in an extremity spaced at least about 5 cm (e.g., at least 4.5, 5, 6, 7, 8, 9, or cm) at needle entry from the nearest neighboring injection. On subsequent vaccination days, the injection sites are rotated to different limbs in a clockwise or counter-clockwise manner.

In certain embodiments, the methods further comprise co-administration of the arenavirus particle provided herein and an immune checkpoint inhibitor. In certain embodiments, the co-administration is simultaneous. In another embodiment, the arenavirus particle is administered prior to administration of the immune checkpoint inhibitor. In other embodiments, the arenavirus particle is administered after administration of the immune checkpoint inhibitor. In certain embodiments, the interval between administration of the arenavirus particle and the immune checkpoint inhibitor is about 1 hour, about 2 hours, about 3 hours, about 4 hours, about 5 hours, about 6 hours, about 7 hours, about 8 hours, about 9 hours, about 10 hours, about 11 hours, or about 12 hours. In certain embodiments, the interval between administration of the arenavirus particle and the immune checkpoint inhibitor is about 1 day, about 2 days, about 2 days, about 3 days, about 4 days, about 5 days, about 6 days, about 1 week, about 8 days, about 9 days, about 10 days, about 11 days, about 12 days, about 13 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks. In certain embodiments, the interval between administration of the arenavirus particle and the immune checkpoint inhibitor is about 1 month, about 2 months, about 3 months, about 4 months, about 5 months, or about 6 months. In some embodiments, the method further includes administering at least one additional therapy.

In certain embodiments, provided herein are methods of treating a neoplastic disease in a subject comprising administering to the subject one or more arenavirus particles provided herein and an indoleamine-2,3 dioxygenase ("IDO") inhibitor. The method of treating a neoplastic disease in a subject can include administering to the subject one or more arenavirus particles expressing a tumour antigen, tumor associated antigen or an antigenic fragment thereof as provided herein, or a composition thereof, and an IDO inhibitor. In certain embodiments, provided herein are methods for inducing an immune response against a neoplastic cell or tissue, such as a cancer cell or tumor, in a subject comprising administration to the subject an arenavirus particle expressing a tumour antigen, tumor associated antigen or an antigenic fragment thereof as provided herein, or a composition thereof, and an IDO inhibitor. In certain embodiments, the methods comprise co-administration of an arenavirus particle provided herein and an IDO inhibitor. In certain embodiments, the methods comprise co-administration of the arenavirus particle provided herein, an immune checkpoint inhibitor provided herein and an IDO inhibitor.

In another embodiment, two arenavirus particles are administered in a treatment regime at molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In certain embodiments, provided herein is a method of treating neoplastic disease wherein a first arenavirus particle is administered first as a "prime," and a second arenavirus particle is administered as a "boost." The first and the second arenavirus particles can express the same or different tumor antigens, tumor associated antigens or antigenic fragments thereof. Alternatively, or additionally, some certain embodiments, the "prime" and "boost" administration are performed with an arenavirus particle derived from different species. In certain specific embodiments, the "prime" administration is performed with an arenavirus particle derived from LCMV, and the "boost" is performed with an arenavirus particle derived from Junin virus. In certain specific embodiments, the "prime" administration is performed with an arenavirus particle derived from Junin virus, and the "boost" is performed with an arenavirus particle derived from LCMV.

In certain embodiments, administering a first arenavirus particle expressing a tumor antigen, tumor associated antigen or antigenic fragment thereof, followed by administering a second arenavirus particle expressing a tumor antigen, tumor associated antigen or antigenic fragment thereof results in a greater antigen specific CD8+ T cell response than administering a single arenavirus particle expressing a tumor antigen, tumor associated antigen or antigenic fragment thereof. In certain embodiments, the antigen specific CD8+ T cell count increases by 50%, 100%, 150% or 200% after the second administration compared to the first administration. In certain embodiments, administering a third arenavirus particle expressing a tumor antigen, tumor associated antigen or antigenic fragment thereof results in a greater antigen specific CD8+ T cell response than administering two consecutive arenavirus particles expressing a tumor antigen, tumor associated antigen or antigenic fragment thereof. In certain embodiments, the antigen specific CD8+ T cell count increases by about 50%, about 100%, about 150%, about 200% or about 250% after the third administration compared to the first administration.

In certain embodiments, provided herein are methods for treating a neoplastic disease comprising administering two or more arenavirus particles, wherein the two or more arenavirus particles are homologous, and wherein the time interval between each administration is about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In certain embodiments, administering a first arenavirus particle expressing a tumor antigen, tumor associated antigen or antigenic fragment thereof and a second, heterologous, arenavirus particle expressing a tumor antigen, tumor associated antigen or antigenic fragment thereof elicits a greater CD8+ T cell response than administering a first arenavirus particle expressing a tumor antigen, tumor associated antigen or antigenic fragment thereof and a second, homologous, arenavirus particle expressing a tumor antigen, tumor associated antigen or antigenic fragment thereof.

5.9 Compositions, Administration, and Dosage

Also provided herein are vaccines, immunogenic compositions (e.g., vaccine formulations), and pharmaceutical compositions comprising an arenavirus particle provided herein, and, in certain embodiments, an immune checkpoint inhibitor provided herein. Such vaccines, immunogenic compositions and pharmaceutical compositions can be formulated according to standard procedures in the art.

In another embodiment, provided herein are compositions comprising an infectious, replication-deficient arenavirus particle described herein, and, in certain embodiments, an immune checkpoint inhibitor provided herein. Such compositions can be used in methods of treating a neoplastic disease. In another specific embodiment, the immunogenic compositions provided herein can be used to induce an immune response in a host to whom the composition is administered. The immunogenic compositions described herein can be used as vaccines and can accordingly be formulated as pharmaceutical compositions. In a specific embodiment, the immunogenic compositions described herein are used in the treatment of a neoplastic disease a subject (e.g., human subject). In other embodiments, the vaccine, immunogenic composition or pharmaceutical composition are suitable for veterinary and/or human administration.

In certain embodiments, provided herein are immunogenic compositions comprising an arenavirus particle (or a combination of different arenavirus particles) as described herein. In certain embodiments, such an immunogenic composition further comprises a pharmaceutically acceptable excipient. In certain embodiments, such an immunogenic composition further comprises an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to an infectious, replication-deficient arenavirus particle, but when the compound is administered alone does not generate an immune response to the infectious, replication-deficient arenavirus particle. In some embodiments, the adjuvant generates an immune response to the infectious, replication-deficient arenavirus particle and does not produce an allergy or other adverse reaction. Adjuvants can enhance an immune response by several mechanisms including, e.g., lymphocyte recruitment, stimulation of B and/or T cells, and stimulation of macrophages. When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)).

The compositions comprise the infectious, replication-deficient arenavirus particles described herein alone or together with a pharmaceutically acceptable carrier and/or an immune checkpoint inhibitor. Suspensions or dispersions of genetically engineered arenavirus particles, especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. In certain embodiments, such dispersions or suspensions may comprise viscosity-regulating agents. The suspensions or dispersions are kept at temperatures around 2-8° C., or preferentially for longer storage may be frozen and then thawed shortly before use. For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In certain embodiments, the compositions described herein additionally comprise a preservative, e.g., the mercury derivative thimerosal. In a specific embodiment, the pharmaceutical compositions described herein comprise 0.001% to 0.01% thimerosal. In other embodiments, the pharmaceutical compositions described herein do not comprise a preservative.

The pharmaceutical compositions comprise from about $10^3$ to about $10^{11}$ focus forming units of the genetically engineered arenavirus particles. Unit dose forms for parenteral administration are, for example, ampoules or vials, e.g., vials containing from about $10^3$ to $10^{10}$ focus forming units or $10^5$ to $10^{15}$ physical particles of genetically engineered arenavirus particles.

In another embodiment, a vaccine or immunogenic composition provided herein is administered to a subject by, including but not limited to, oral, intradermal, intramuscular, intraperitoneal, intravenous, topical, subcutaneous, percutaneous, intranasal and inhalation routes, and via scarification (scratching through the top layers of skin, e.g., using a bifurcated needle). Specifically, subcutaneous, intramuscular or intravenous routes can be used.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and a suitable powder base such as lactose or starch.

The dosage of the active ingredient depends upon the type of vaccination and upon the subject, and their age, weight, individual condition, the individual pharmacokinetic data, and the mode of administration.

In certain embodiments, the compositions can be administered to the patient in a single dosage comprising a therapeutically effective amount of the arenavirus particle and/or a therapeutically effective amount of an immune checkpoint inhibitor. In some embodiments, the arenavirus particle can be administered to the patient in a single dose comprising an arenavirus particle and an immune checkpoint inhibitor, each in a therapeutically effective amount.

In certain embodiments, the composition is administered to the patient as a single dose followed by a second dose three to six weeks later. In accordance with these embodiments, the booster inoculations may be administered to the subjects at six to twelve month intervals following the second inoculation. In certain embodiments, the booster inoculations may utilize a different arenavirus particle or composition thereof. In some embodiments, the administration of the same composition as described herein may be repeated and separated by at least 1 day, 2 days, 3 days, 4 days, 5 days, 10 days, 15 days, 30 days, 45 days, 2 months, 75 days, 3 months, or at least 6 months.

In certain embodiments, the vaccine, immunogenic composition, or pharmaceutical composition comprising an arenavirus particle can be used as a live vaccination. Exemplary doses for a live arenavirus particle may vary from 10-100, or more, PFU of live virus per dose. In some embodiments, suitable dosages of an arenavirus particle or the tri-segmented arenavirus particle are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed. In another embodiment, a live arenavirus is formulated such that a 0.2-mL dose contains $10^{6.5}$-$10^{7.5}$ fluorescent focal units of live arenavirus particle. In another embodiment, an inactivated vaccine is formulated such that it contains about 15 μg to about 100 μg, about μg to about 75 μg, about 15 μg to about 50 μg, or about 15 μg to about 30 μg of an arenavirus Also provided are processes and uses of an arenavirus particle and an immune checkpoint inhibitor for the manufacture of vaccines in the form of pharmaceutical preparations, which comprise the arenavirus particle and the immune checkpoint inhibitor as an active ingredient. Still further provided is a combination of an arenavirus particle provided herein and an immune checkpoint inhibitor provided herein for use in the treatment of a neoplastic disease described herein. In certain embodiments, the combination is in the same pharmaceutical composition. In certain embodiments, the combination is not in the same pharmaceutical composition, such as when the arenavirus particle and the immune checkpoint inhibitor are to be separately administered. The pharmaceutical compositions of the present application are prepared in a manner known per se, for example by means of conventional mixing and/or dispersing processes.

In certain embodiments, the methods and compositions provided herein are used in combination with personalized medicine. Personalized medicine seeks to benefit patients by using information from a patient's unique genetic and/or epigenetic profile to predict a patient's response to different therapies and identify which therapies are more likely to be effective. Techniques that can be used in combination with the methods and compositions provided herein to obtain a patient's unique genetic and/or epigenetic profile include, but are not limited to, genome sequencing, RNA sequencing, gene expression analysis and identification of a tumor antigen (e.g., neoantigen), tumor associated antigen or an antigenic fragment thereof. In certain embodiments, the selection of an arenavirus tumor antigen or tumor associated antigen for use in the methods and compositions provided herein is performed based on the genetic profile of the patient. In certain embodiments, the selection of an arenavirus tumor antigen or tumor associated antigen for use in the methods and compositions provided herein is performed based on the genetic profile of a tumor or tumor cell.

Also provided herein are kits that can be used to perform the methods described herein. In certain embodiments, the kit provided herein can include one or more containers. These containers can hold for storage the compositions (e.g., pharmaceutical, immunogenic or vaccine composition) provided herein. Also included in the kit are instructions for use. These instructions describe, in sufficient detail, a treatment protocol for using the compositions contained therein. For example, the instructions can include dosing and administration instructions as provided herein for the methods of treating a neoplastic disease.

In certain embodiments, a kit provided herein includes containers that each contains the active ingredients for performing the methods described herein. Thus, in certain embodiments, the kit provided herein includes two or more containers and instructions for use, wherein one of the containers comprises an infectious, replication-deficient arenavirus particle provided herein and another container that comprises an immune checkpoint inhibitor provided herein.

5.10 Assays 5.10.1 Arenavirus Detection Assays

The skilled artesian could detect an arenavirus genomic segment or tri-segmented arenavirus particle, as described herein using techniques known in the art. For example, RT-PCR can be used with primers that are specific to an arenavirus to detect and quantify an arenavirus genomic segment that has been engineered to carry an ORF in a position other than the wild-type position of the ORF or a tri-segmented arenavirus particle. Western blot, ELISA, radioimmunoassay, immuneprecipitation, immunecytochemistry, or immunocytochemistry in conjunction with FACS can be used to quantify the gene products of the arenavirus genomic segment or tri-segmented arenavirus particle.

5.10.2 Assay to Measure Infectivity

Any assay known to the skilled artisan can be used for measuring the infectivity of an arenavirus vector preparation. For example, determination of the virus/vector titer can be done by a "focus forming unit assay" (FFU assay). In brief, complementing cells, e.g., MC57 or HEK293 cells optionally expressing LCMV GP protein, are plated and inoculated with different dilutions of a virus/vector sample. After an incubation period, to allow cells to form a monolayer and virus to attach to cells, the monolayer is covered with Methylcellulose. When the plates are further incubated, the original infected cells release viral progeny. Due to the Methylcellulose overlay the spread of the new viruses is restricted to neighboring cells. Consequently, each infectious particle produces a circular zone of infected cells called a Focus. Such Foci can be made visible and by that countable using antibodies against LCMV-NP or another protein expressed by the arenavirus particle or the tri-segmented arenavirus particle and a HRP-based color reaction. The titer of a virus/vector can be calculated in focus-forming units per milliliter (FFU/mL).

5.10.3 Growth of an Arenavirus Particle

Growth of an arenavirus particle described herein can be assessed by any method known in the art or described herein (e.g., cell culture). Viral growth may be determined by inoculating serial dilutions of an arenavirus particle described herein into cell cultures (e.g., Vero cells or BHK-21 cells). After incubation of the virus for a specified time, the virus is isolated using standard methods.

5.10.4 Serum ELISA

Determination of the humoral immune response upon vaccination of animals (e.g., mice, guinea pigs) can be done by antigen-specific serum ELISA's (enzyme-linked immunosorbent assays). In brief, plates are coated with antigen (e.g., recombinant protein), blocked to avoid unspecific binding of antibodies and incubated with serial dilutions of sera. After incubation, bound serum-antibodies can be detected, e.g., using an enzyme-coupled anti-species (e.g., mouse, guinea pig)-specific antibody (detecting total IgG or IgG subclasses) and subsequent color reaction. Antibody titers can be determined as, e.g., endpoint geometric mean titer.

Immunocapture ELISA (IC-ELISA) may also be performed (see Shanmugham et al., 2010, Clin. Vaccine Immunol. 17(8):1252-1260), wherein the capture agents are cross-linked to beads.

5.10.5 Assay to Measure the Neutralizing Activity of Induced Antibodies

Determination of the neutralizing antibodies in sera is performed with the following cell assay using ARPE-19 cells from ATCC and a GFP-tagged virus. In addition supplemental serum (e.g., guinea pig serum) as a source of exogenous complement is used. The assay is started with seeding of $6.5 \times 10^3$ cells/well (50 µl/well) in a 384 well plate one or two days before using for neutralization. The neutralization is done in 96-well sterile tissue culture plates without cells for 1 h at 37° C. After the neutralization incubation step the mixture is added to the cells and incubated for additional 4 days for GFP-detection with a plate reader. A positive neutralizing human sera is used as assay positive control on each plate to check the reliability of all results. Titers (EC50) are determined using a 4 parameter logistic curve fitting. As additional testing the wells are checked with a fluorescence microscope.

5.10.6 Plaque Reduction Assay

In brief, plaque reduction (neutralization) assays for LCMV can be performed by use of a replication-competent or -deficient LCMV that is tagged with green fluorescent protein, 5% rabbit serum may be used as a source of exogenous complement, and plaques can be enumerated by fluorescence microscopy. Neutralization titers may be defined as the highest dilution of serum that results in a 50%, 75%, 90% or 95% reduction in plaques, compared with that in control (pre-immune) serum samples.

qPCR LCMV RNA genomes are isolated using QIAamp Viral RNA mini Kit (QIAGEN), according to the protocol provided by the manufacturer. LCMV RNA genome equivalents are detected by quantitative PCR carried out on an StepOnePlus Real Time PCR System (Applied Biosystems) with SuperScript® III Platinum® One-Step qRT-PCR Kit (Invitrogen) and primers and probes (FAM reporter and NFQ-MGB Quencher) specific for part of the LCMV NP coding region or another genomic stretch of the arenavirus particle or the tri-segmented arenavirus particle. The temperature profile of the reaction may be: 30 min at 60° C., 2 min at 95° C., followed by 45 cycles of 15 s at 95° C., 30 s at 56° C. RNA can be quantified by comparison of the sample results to a standard curve prepared from a log 10 dilution series of a spectrophotometrically quantified, in vitro-transcribed RNA fragment, corresponding to a fragment of the LCMV NP coding sequence or another genomic stretch of the arenavirus particle or the tri-segmented arenavirus particle containing the primer and probe binding sites.

5.10.7 Neutralization Assay in Guinea Pig Lung Fibroblast (GPL) Cells

In brief, serial dilutions of test and control (pre-vaccination) sera were prepared in GPL complete media with supplemental rabbit serum (1%) as a source of exogenous complement. The dilution series spanned 1:40 through 1:5120. Serum dilutions were incubated with eGFP tagged virus (100-200 pfu per well) for 30 min at 37° C., and then transferred to 12-well plates containing confluent GPL cells. Samples were processed in triplicate. After 2 hours incubation at 37° C. the cells were washed with PBS, re-fed with GPL complete media and incubated at 37° C./5% $CO_2$ for 5 days. Plaques were visualized by fluorescence microscopy, counted, and compared to control wells. That serum dilution resulting in a 50% reduction in plaque number compared to controls was designated as the neutralizing titer.

5.10.8 Western Blotting

Infected cells grown in tissue culture flasks or in suspension are lysed at indicated timepoints post infection using RIPA buffer (Thermo Scientific) or used directly without cell-lysis. Samples are heated to 99° C. for 10 minutes with reducing agent and NuPage LDS Sample buffer (NOVEX) and chilled to room temperature before loading on 4-12% SDS-gels for electrophoresis. Proteins are blotted onto membranes using Invitrogens iBlot Gel transfer Device and visualized by Ponceau staining. Finally, the preparations are probed with a primary antibodies directed against proteins of interest and alkaline phosphatase conjugated secondary antibodies followed by staining with 1-Step NBT/BCIP solution (INVITROGEN).

5.10.9 MHC-Peptide Multimer Staining Assay for Detection of Antigen-Specific CD8+ T-Cell Proliferation Any assay known to the skilled artisan can be used to test antigen-specific CD8+ T-cell responses. For example, the MHC-peptide tetramer staining assay can be used (see, e.g., Altman J. D. et al., Science. 1996; 274:94-96; and Murali-Krishna K. et al., Immunity. 1998; 8:177-187). Briefly, the assay comprises the following steps, a tetramer assay is used to detect the presence of antigen specific T-cells. In order for a T-cell to detect the peptide to which it is specific, it must both recognize the peptide and the tetramer of MHC molecules custom made for a defined antigen specificity and MHC haplotype of T-cells (typically fluorescently labeled). The tetramer is then detected by flow cytometry via the fluorescent label.

5.10.10 ELISPOT Assay for Detection of Antigen-Specific CD4+ T-Cell Proliferation.

Any assay known to the skilled artisan can be used to test antigen-specific CD4+ T-cell responses. For example, the ELISPOT assay can be used (see, e.g., Czerkinsky C. C. et al., J Immunol Methods. 1983; 65:109-121; and Hutchings P. R. et al., J Immunol Methods. 1989; 120:1-8). Briefly, the assay comprises the following steps: An immunospot plate is coated with an anti-cytokine antibody. Cells are incubated in the immunospot plate. Cells secrete cytokines and are then washed off. Plates are then coated with a second biotyinlated-anticytokine antibody and visualized with an avidin-HRP system.

5.10.11 Intracellular Cytokine Assay for Detection of Functionality of CD8+ and CD4+ T-Cell Responses.

Any assay known to the skilled artisan can be used to test the functionality of CD8+ and CD4+ T cell responses. For example, the intracellular cytokine assay combined with flow cytometry can be used (see, e.g., Suni M. A. et al., J Immunol Methods. 1998; 212:89-98; Nomura L. E. et al., Cytometry. 2000; 40:60-68; and Ghanekar S. A. et al., Clinical and Diagnostic Laboratory Immunology. 2001; 8:628-63). Briefly, the assay comprises the following steps: activation of cells via specific peptides or protein, an inhibition of protein transport (e.g., brefeldin A) is added to retain the cytokines within the cell. After a defined period of incubation, typically 5 hours, a washing steps follows, and antibodies to other cellular markers can be added to the cells. Cells are then fixed and permeabilized. The flurochrome-conjugated anti-cytokine antibodies are added and the cells can be analyzed by flow cytometry.

5.10.12 Assay for Confirming Replication-Deficiency of Viral Vectors

Any assay known to the skilled artisan that determines concentration of infectious and replication-competent virus particles can also be used as a to measure replication-deficient viral particles in a sample. For example, FFU assays with non-complementing cells can be used for this purpose.

Furthermore, plaque-based assays are the standard method used to determine virus concentration in terms of plaque forming units (PFU) in a virus sample. Specifically, a confluent monolayer of non-complementing host cells is infected with the virus at varying dilutions and covered with a semi-solid medium, such as agar to prevent the virus infection from spreading indiscriminately. A viral plaque is formed when a virus successfully infects and replicates itself in a cell within the fixed cell monolayer, and spreads to surrounding cells (see, e.g., Kaufmann, S. H.; Kabelitz, D. (2002). Methods in Microbiology Vol. 32: Immunology of Infection. Academic Press. ISBN 0-12-521532-0). Plaque formation can take 2-14 days, depending on the virus being analyzed. Plaques are generally counted manually and the results, in combination with the dilution factor used to prepare the plate, are used to calculate the number of plaque forming units per sample unit volume (PFU/mL). The PFU/mL result represents the number of infective replication-competent particles within the sample. When C-cells are used, the same assay can be used to titrate replication-deficient arenavirus particles or tri-segmented arenavirus particles.

5.10.13 Assay for Expression of Viral Antigen

Any assay known to the skilled artisan can be used for measuring expression of viral antigens. For example, FFU assays can be performed. For detection, mono- or polyclonal antibody preparation(s) against the respective viral antigens are used (transgene-specific FFU).

5.10.14 Animal Models

To investigate recombination and infectivity of an arenavirus particle described herein in vivo animal models can be used. In certain embodiments, the animal models that can be used to investigate recombination and infectivity of a tri-segmented arenavirus particle include mouse, guinea pig, rabbit, and monkeys. In a preferred embodiment, the animal models that can be used to investigate recombination and infectivity of an arenavirus include mouse. In a more specific embodiment, the mice can be used to investigate recombination and infectivity of an arenavirus particle are triple-deficient for type I interferon receptor, type II interferon receptor and recombination activating gene 1 (RAG1).

In certain embodiments, the animal models can be used to determine arenavirus infectivity and transgene stability. In some embodiments, viral RNA can be isolated from the serum of the animal model. Techniques are readily known by those skilled in the art. The viral RNA can be reverse transcribed and the cDNA carrying the arenavirus ORFs can be PCR-amplified with gene-specific primers. Flow cytometry can also be used to investigate arenavirus infectivity and transgene stability.

The safety, tolerance and immunogenic effectiveness of vaccines comprising of a bi-segmented infectious, replication-deficient arenavirus expressing a tumor antigen, tumor associate antigen or antigenic fragment thereof described herein or a composition thereof can be tested in animals models. In certain embodiments, the animal models that can be used to test the safety, tolerance and immunogenic effectiveness of the vaccines and compositions thereof used herein include mouse, guinea pig, rat, monkey, and chimpanzee. In a preferred embodiment, the animal models that can be used to test the safety, tolerance and immunogenic effectiveness of the vaccines and compositions thereof used herein include mouse.

5.10.15 Immune Checkpoint Inhibitor Assays

A number of assays have been devised to assess properties of proposed checkpoint inhibitors, for example as described in Lechner et al., J. Immunother. 36(9), 477-89 (2013). Tumor models that can be used to test the methods and compositions described herein include Colon26 (CT26), MC38 (mouse colon adenocarcinoma), B16F10 (B16), Lewis Lung (LLC), Madison109 (Mad 109), EMT-6 (murine breast cancer), 4T1 (4T1) (murine breast cancer), and (RENCA) (murine renal cancer).

In certain embodiments, in these model systems, "transplantable tumors" can be generated by subcutaneous (e.g., CT26, 4T1, MAD109, RENCA, LLC, or B16) or intracerebral (e.g., GL261, ONC26M4) inoculation of tumor cell lines into rodents, for example in adult female mice. Tumors can be developed over pre-determined time intervals, for example several days. These tumors are grown in syngeneic, immunocompetent rodent, e.g., mouse, strains. For example CT26, 4T1, MAD109, and RENCA can be grown in BALB/c mice, LLC, B16, and GL261 can be grown in C57BL/6 mice, and ONC26M4 can be grown in FVBN mice. "Spontaneous tumors" can be generated by intracerebral injection of DNA plasmids encoding a number (e.g., one, two, three or more) of oncogenes and encoding one or more reporter, e.g., firefly luciferase reporter, into neonatal C57BL/6 or FVBN mice to transform endogenous brain cells. Growth of gliomas can be monitored by techniques known in the art, e.g., bioluminescence imaging. Growth of subcutaneous tumors can be monitored by techniques known in the art, e.g., caliper measurements in three dimensions at specified time intervals.

6. EQUIVALENTS

The viruses, nucleic acids, methods, host cells, and compositions disclosed herein are not to be limited in scope by the specific embodiments described herein. Indeed, various modifications of the viruses, nucleic acids, methods, host cells, and compositions in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

Various publications, patents and patent applications are cited herein, the disclosures of which are incorporated by reference in their entireties.

7. EXAMPLES

The examples in this section are offered by way of illustration, and not by way of limitation.

7.1 Treatment with Tri-Segmented Arenavirus Vector and Immune Checkpoint Inhibitor in a Colon Adenocarcinoma Tumor Model This example demonstrates that treatment with an arenavirus vector encoding an exemplary tumor specific antigen (ovalbumin (OVA)) and an immune checkpoint inhibitor (anti-PD1 antibody) resulted in a synergistic effect on tumor growth and percent survival.

To determine the effects of treatment with a tri-segmented replication-competent LCMV vector encoding ovalbumin (OVA) (r3LCMV-OVA) and anti-PD1 checkpoint inhibitor (anti-PD1 antibody), a subcutaneous MC38-OVA mouse model was used. On day 0, MC38-OVA$^{dim}$ colon carcinomas tumor cells ($5\times10^5$) were implanted subcutaneously into the flank of C57BL/6 mice. When the tumors became palpable (at day 7), mice were either left untreated (group 1), treated with 12.5 mg/kg anti-PD1 antibody (clone RMP1-14, BioXCell) (administered intraperitoneally) on days 13, 17, 20 and 24 (group 2), injected intravenously with $10^5$ PFU r3LCMV-OVA on day 7 (group 3), or treated with a combination of r3LCMV-OVA and anti-PD1 antibody using the same treatment regimen (group 4). Five mice were left untreated, whereas all other groups included six mice per group. Tumor growth over time as well as animal survival was monitored.

Figure 3A:
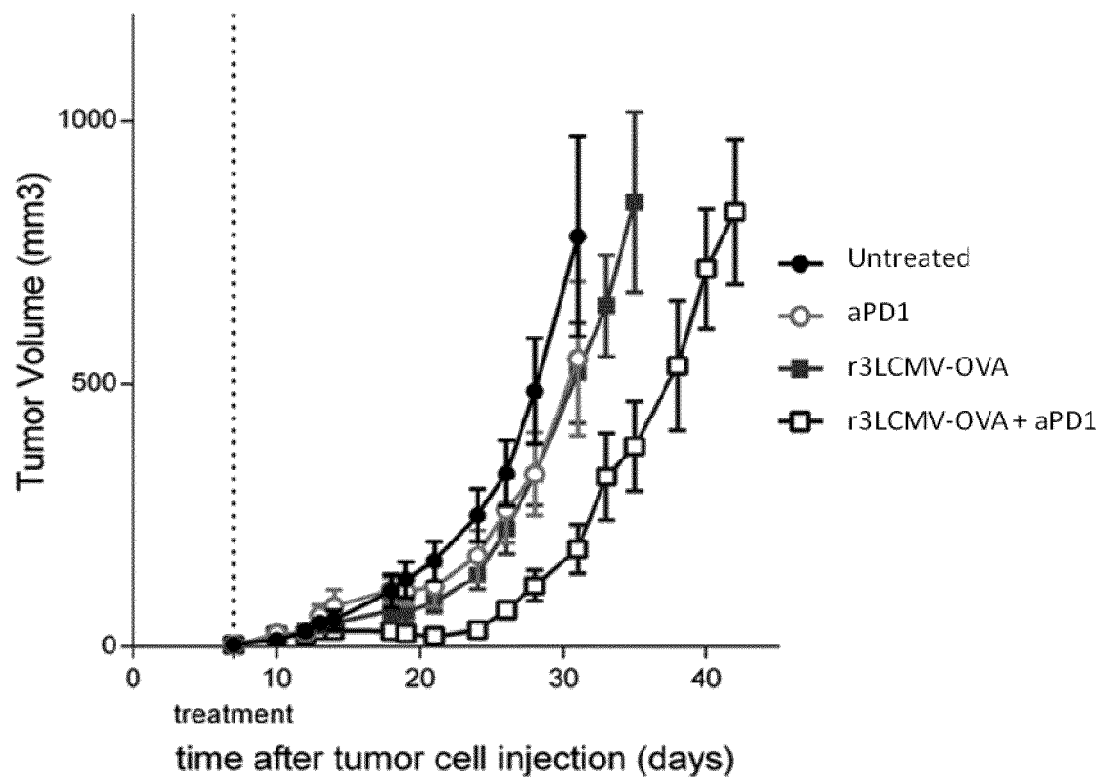
Figure 3B:
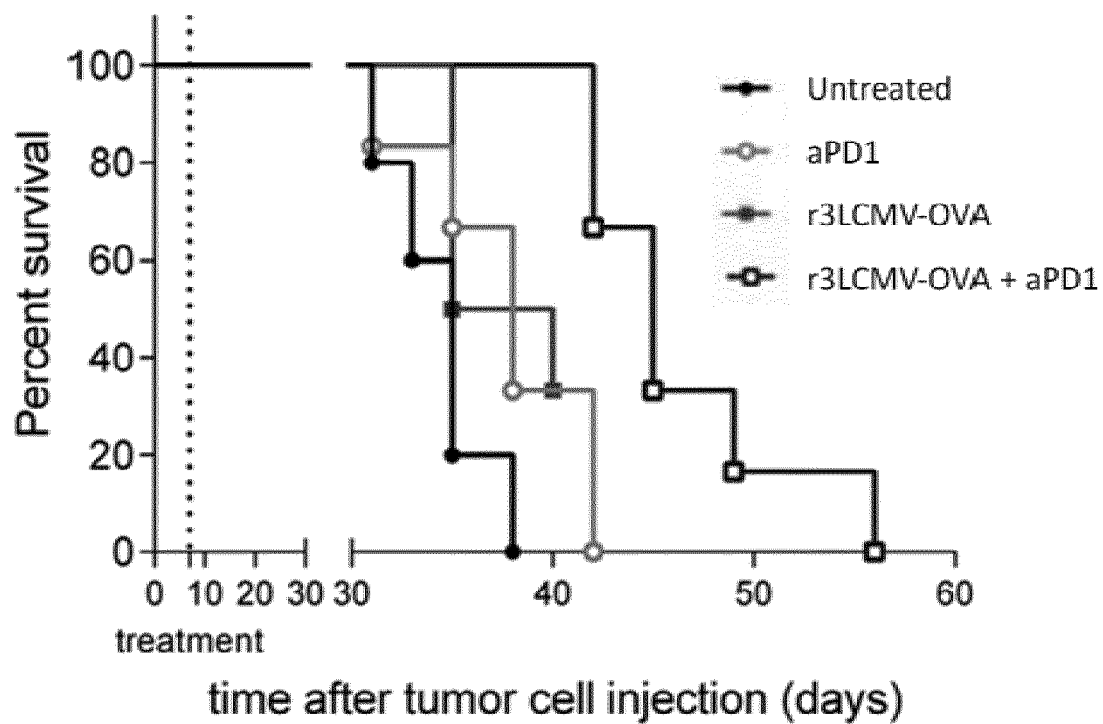

The above experiment showed that established tumors from OVA-expressing MC38 colon adenocarcinoma cells showed limited response to either anti-PD1 antibody or r3LCMV-OVA treatment alone, whereas a combination of anti-PD1 antibody and r3LCMV-OVA immunotherapy resulted in a synergy effect that lead to a significant reduction in tumor growth (FIG. 3A) as well as increased percent survival (FIG. 3B).

7.2. Treatment with Tri-Segmented or Bi-Segmented Arenavirus Vectors Encoding a Tumor Neoantigen and Immune Checkpoint Inhibitor in a Colon Adenocarcinoma Tumor Model This example demonstrates that treatment with an arenavirus vector encoding a neoantigen (MC-38 Adpgk$^{mut}$) and an immune checkpoint inhibitor (anti-PD1 antibody) resulted in a synergistic effect on induction of antigen specific CD8+ T cells, tumor growth and percent survival.

To determine the immunogenicity and effects of treatment with replication competent and replication-deficient arenavirus-based vectors encoding a tumor neoantigen (e.g., MC-38 Adpgk$^{mut}$ (R204M mutation in ADP-dependent glucokinase (Adpgk)); Yadav et al., 2014, Nature 515:572-576), mice implanted with MC-38 tumor cells were evaluated after treatment with Adpgk$^{mut}$-encoding tri-segmented replication competent (r3LCMV-Adpgk$^{mut}$) or replication-deficient bi-segmented (r2LCMV-Adpgk$^{mut}$) arenavirus vectors and PD1 checkpoint inhibition (anti-PD1 antibody).

On day −7 of the experiment MC-38 tumor cells (1×106) were implanted subcutaneously into the flank of C57BL/6 mice. Seven days later, on day 0 of the experiment, mice were immunized once by intravenous injection of $5.5\times10^5$ PFU of r2LCMV-Adpgk$^{mut}$ (groups 1 and 2) or $5.5\times10^4$ PFU of r3LCMV-Adpgk$^{mut}$ corresponding to a total of $5.5\times10^5$ viral particles (groups 3 and 4) or buffer (groups 5 and 6). Animals in groups 1, 3 and 5 were additionally treated by intraperitoneal injection of 6.8 mg/kg anti-PD1 antibody clone RMP1-14 on days 0, 3, 6 and 9. The induction of Adpgk$^{mut}$-specific CD8$^+$ T-cells was subsequently analyzed with MC-38 Adpgk$^{mut}$ specific pentamers (F4B-E-H-2Db-ASMTNMELM, ProImmune) in peripheral blood samples on days 7 and 14 after vaccination.

Figure 4A:
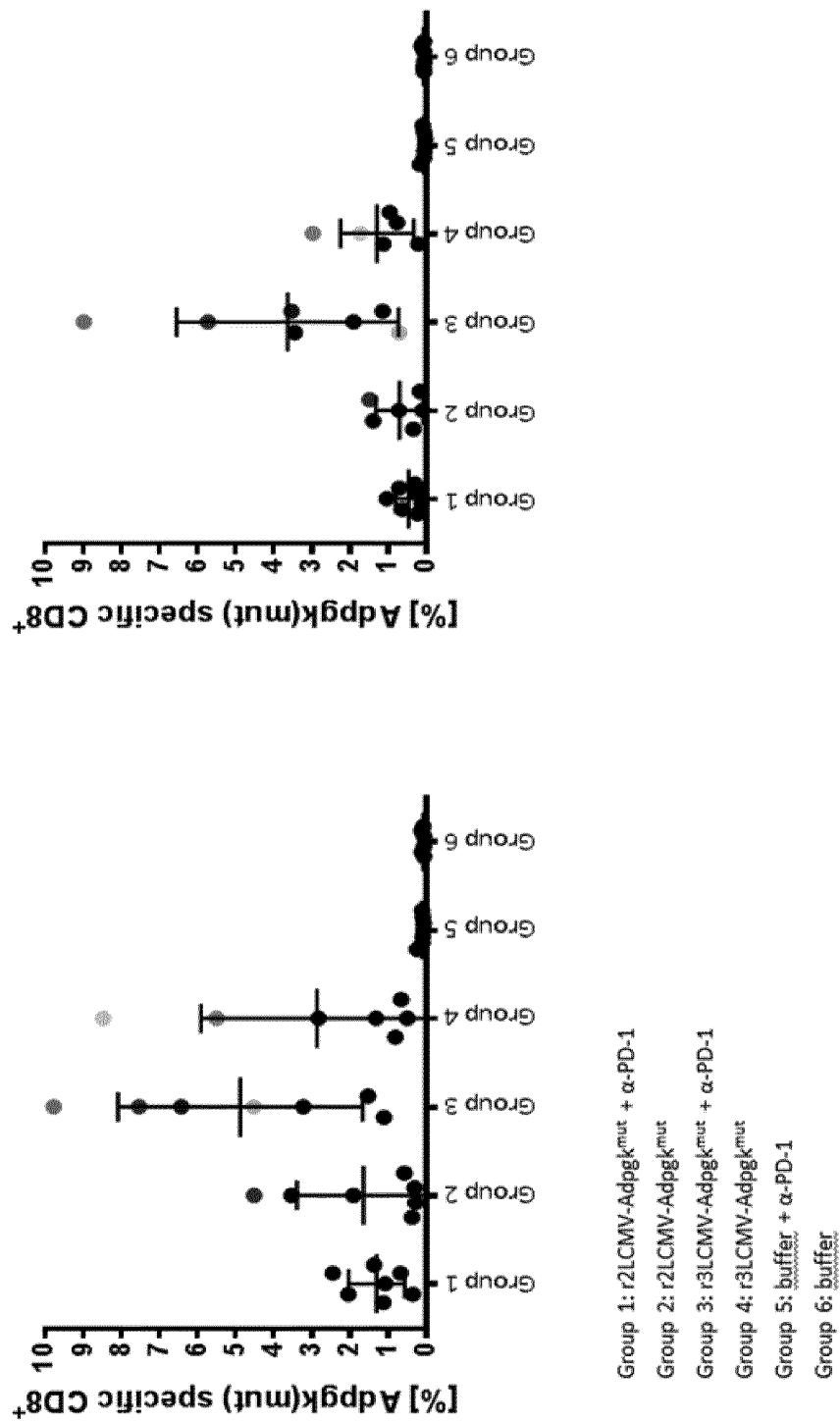
Figure 4B:
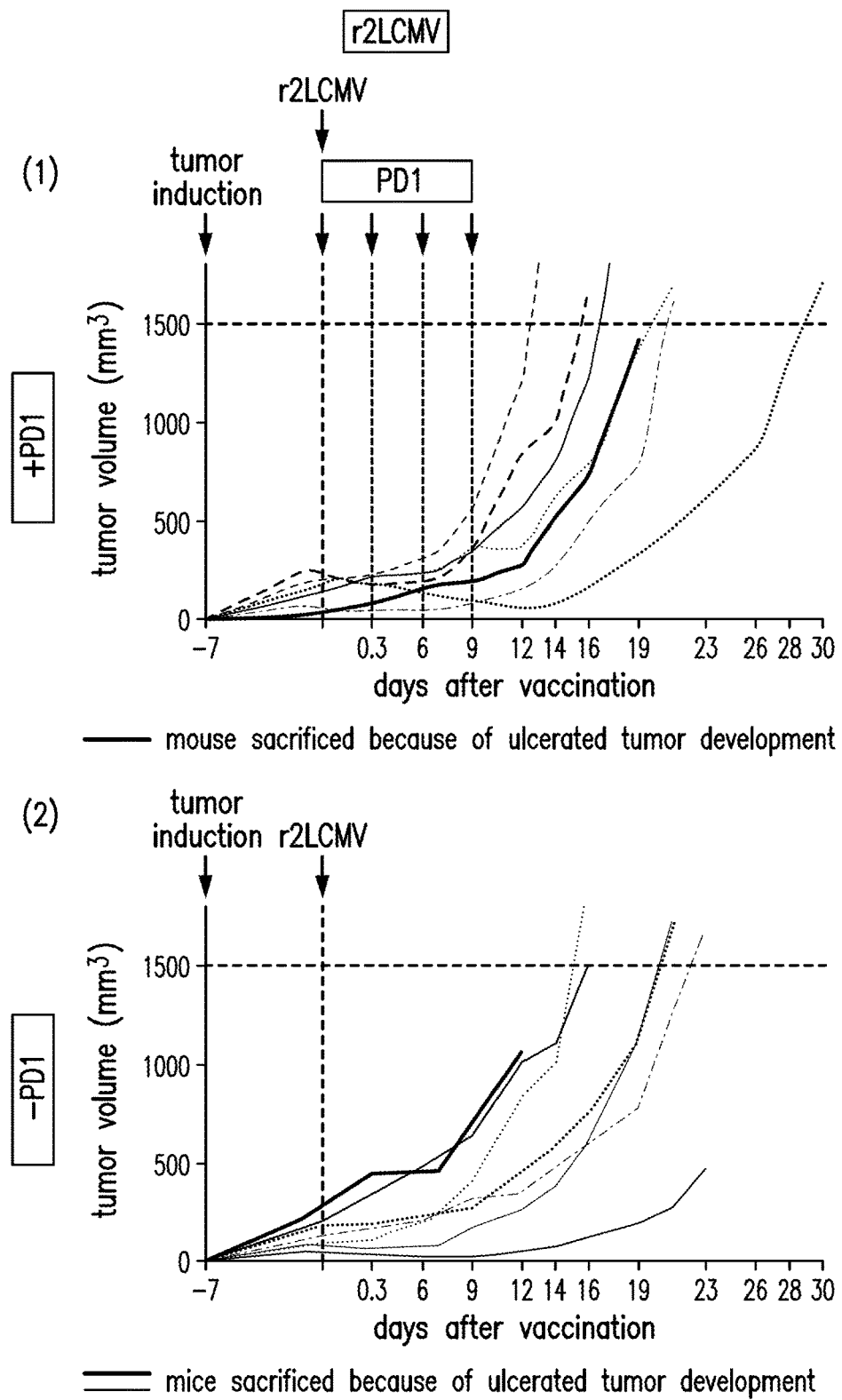
Figure 4B:
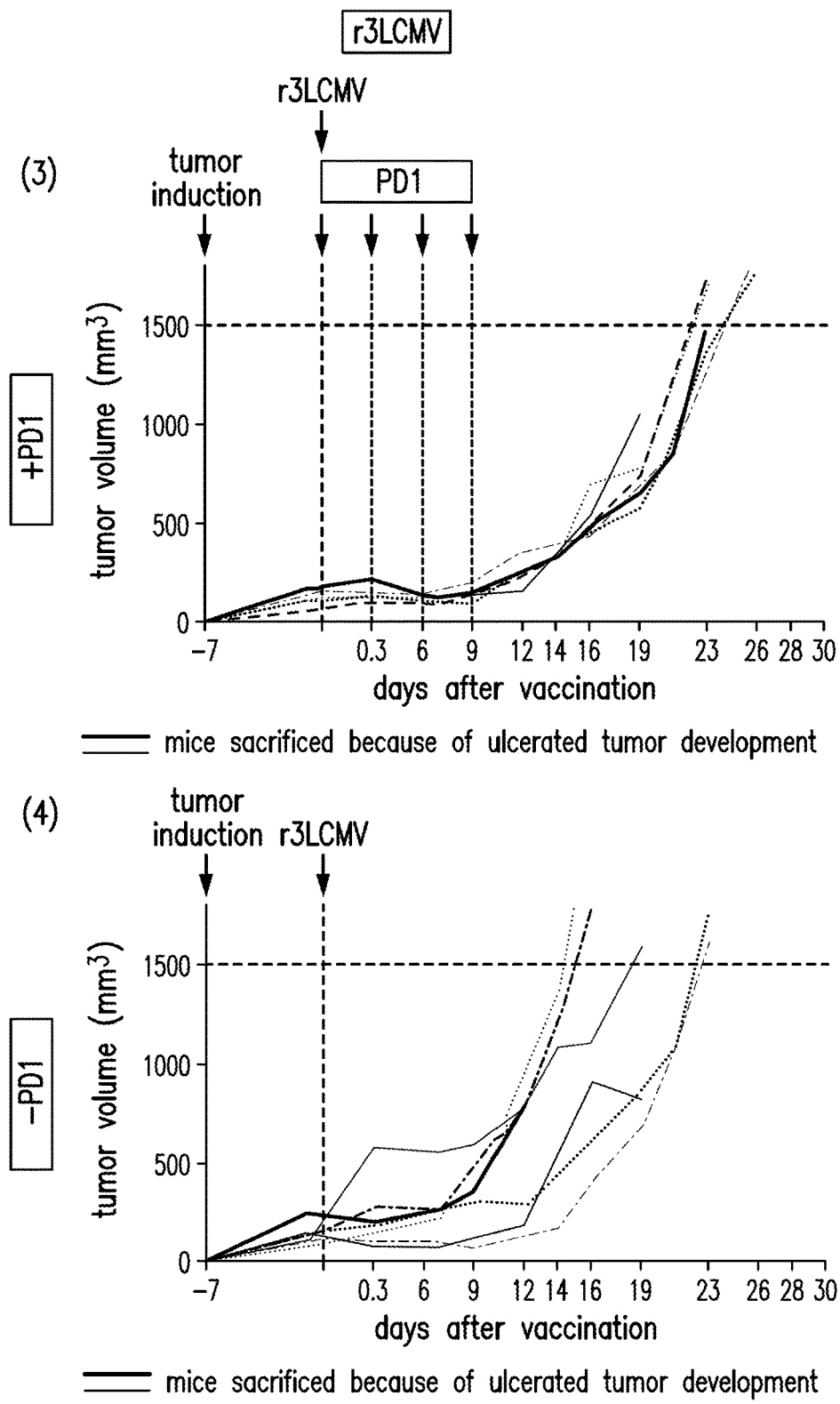
Figure 4B:
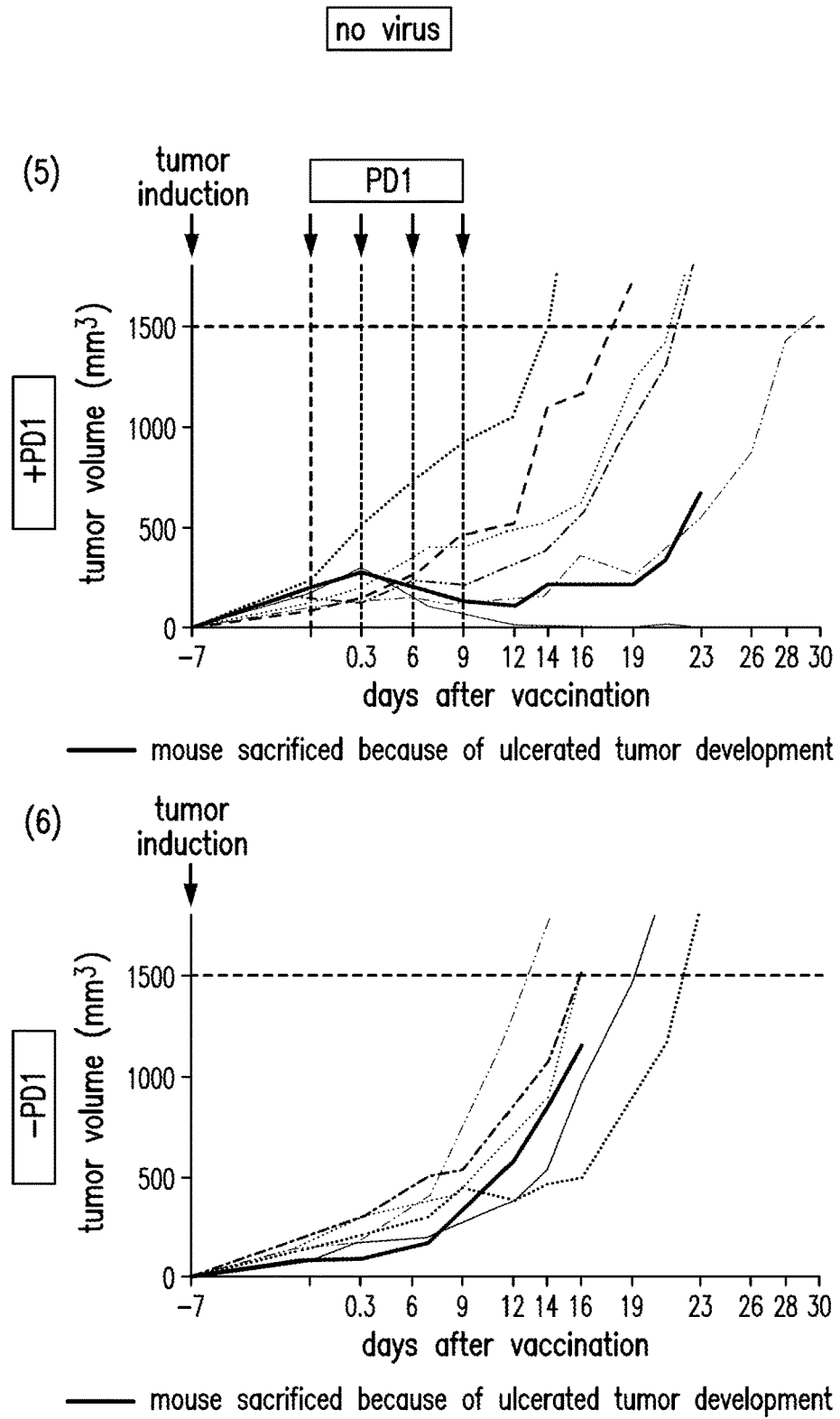
Figure 4C:
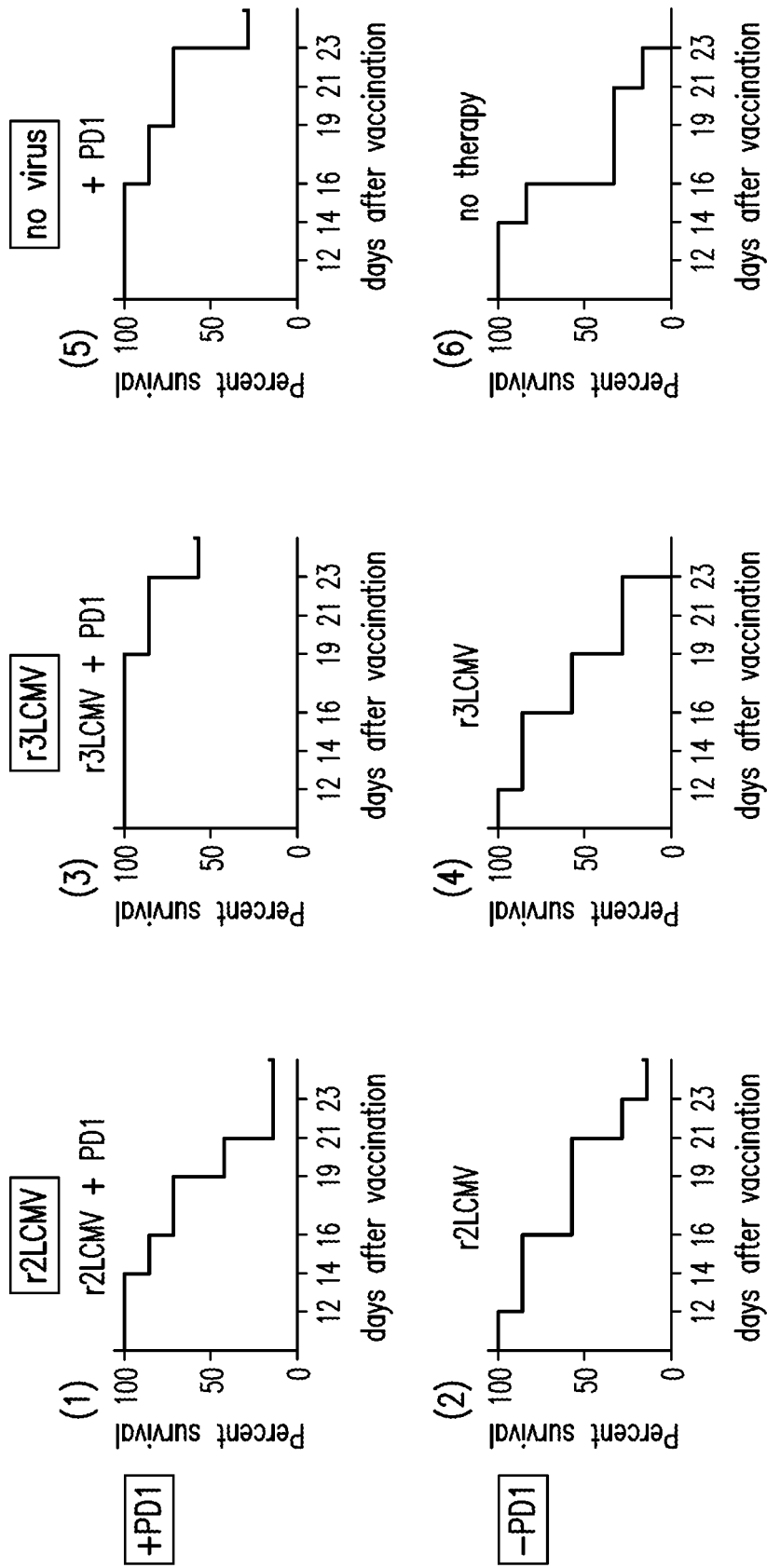

The above experiments showed that neoantigen-specific CD8$^+$ T-cell responses of considerable magnitude were induced in some animals treated with Adpgk$^{mut}$-expressing LCMV vectors (groups 1-4) (FIG. 4A). Significantly higher CD8$^+$ T-cell frequencies were, however, observed in animals treated with the tri-segmented replicating vector (groups 3 and 4) compared to the bi-segmented replication-deficient vector (groups 1 and 2) (FIG. 4A). Highest neoantigen-specific CD8+ T-cell responses were induced in mice treated with a Adpgk$^{mut}$-expressing replication competent LCMV vector and anti-PD1 antibody (group 3), pointing to a synergistic effect of the combination treatment on the immunogenicity of neoantigens (FIG. 4A). The highest level of tumor control and best survival rates were observed in animals treated with a combination of r3LCMV-Adpgk$^{mut}$ and anti-PD1 antibody (FIGS. 4B and 4C).

7.3. Treatment with Tri-Segmented or Bi-Segmented Arenavirus Vectors and Immune Checkpoint Inhibitor in a Melanoma Model This example demonstrates that treatment with a mixture of tri-segmented arenavirus vectors encoding melanoma antigens (glycoprotein 100 ("GP100"), tyrosinase-related protein 1 ("TRP1") and tyrosinase-related protein 2 ("TRP2")) with and without an immune checkpoint inhibitor (anti-PD1 antibody) resulted in reduced tumor size and increased animal survival (percent survival and overall days survived).

To determine the effects of treatment with replication competent and replication-deficient arenavirus-based vectors encoding melanoma antigens and PD1 checkpoint inhibition, a mouse B16F10 melanoma model was used.

Figure 5A:
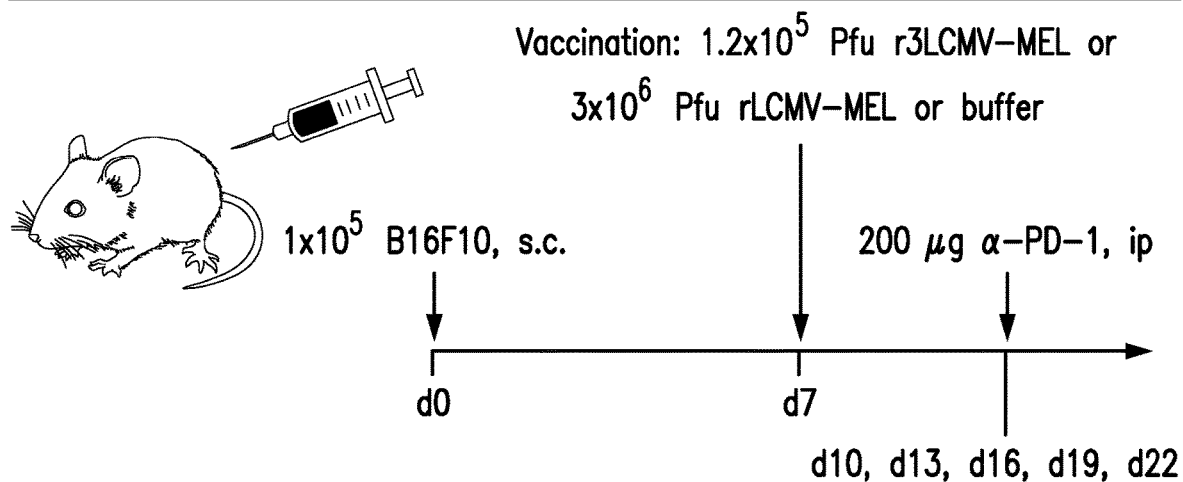

On day 0 of the experiment B16F10 melanoma cells ($1 \times 10^5$) were implanted subcutaneously into the flank of C57BL/6 mice (FIG. 5A). On day 7 of the experiment mice were injected intravenously with $1.2 \times 10^5$ RCV PFU (in total) of a mix of replication-competent tri-segmented arenavirus vectors ($4 \times 10^4$ PFU of each r3LCMV-GP100, r3LCMV-Trp1 and r3LCMV-Trp2) on day 7 (groups 1 and 4), with $1.2 \times 10^6$ PFU (in total) of a mix of replication-deficient bi-segmented arenavirus vectors ($4 \times 10^5$ PFU of each rLCMV-GP100, rLCMV-Trp1 and rLCMV-Trp2) on day 7 (groups 2 and 5), or with buffer only (groups 3 and 6). On days 10, 13, 16, 19 and 22 of the experiment mice in groups 1, 2 and 3 were additionally treated with 200 µg anti-PD1 antibody (clone 29F. 1A12, BioXCell), administered intraperitoneally. Tumor growth over time as well as percent of animal survival and days of survival were monitored. There were five mice per group.

Figure 5B:
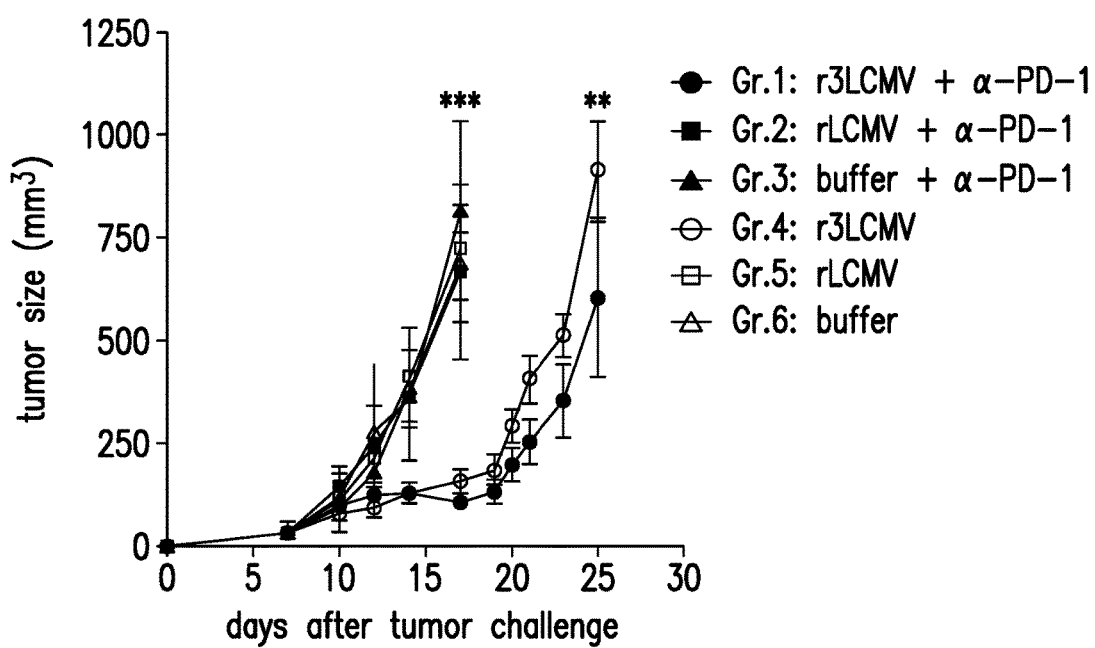
Figure 5C:
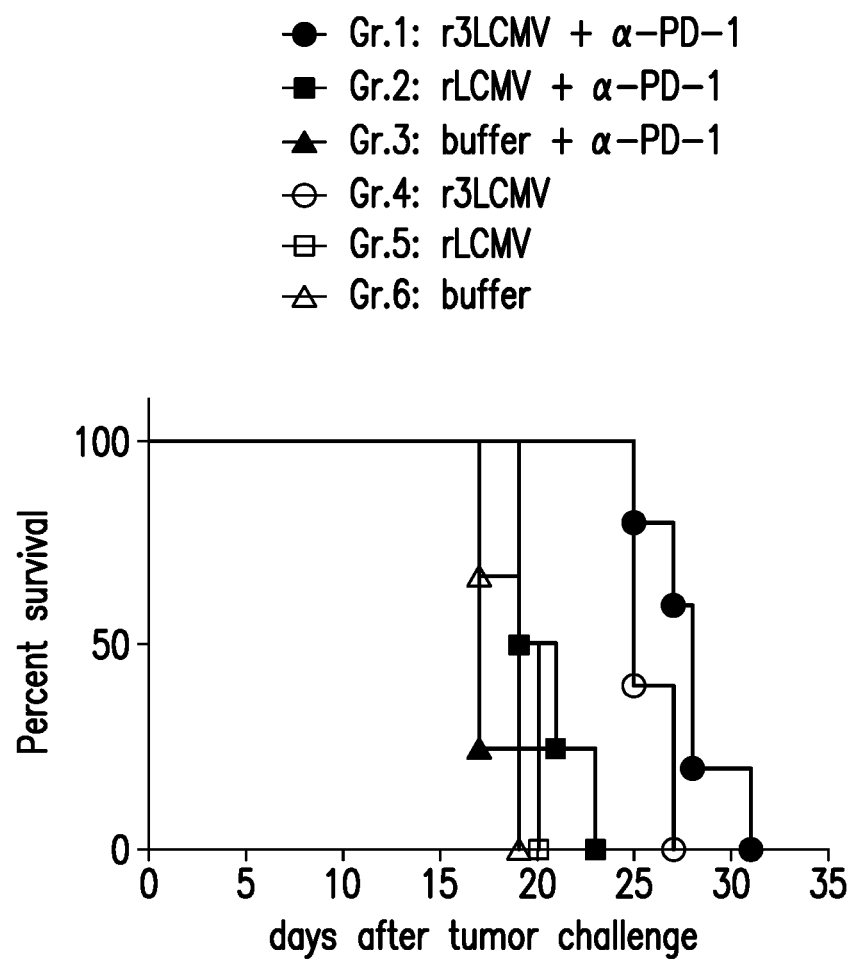
Figure 5D:
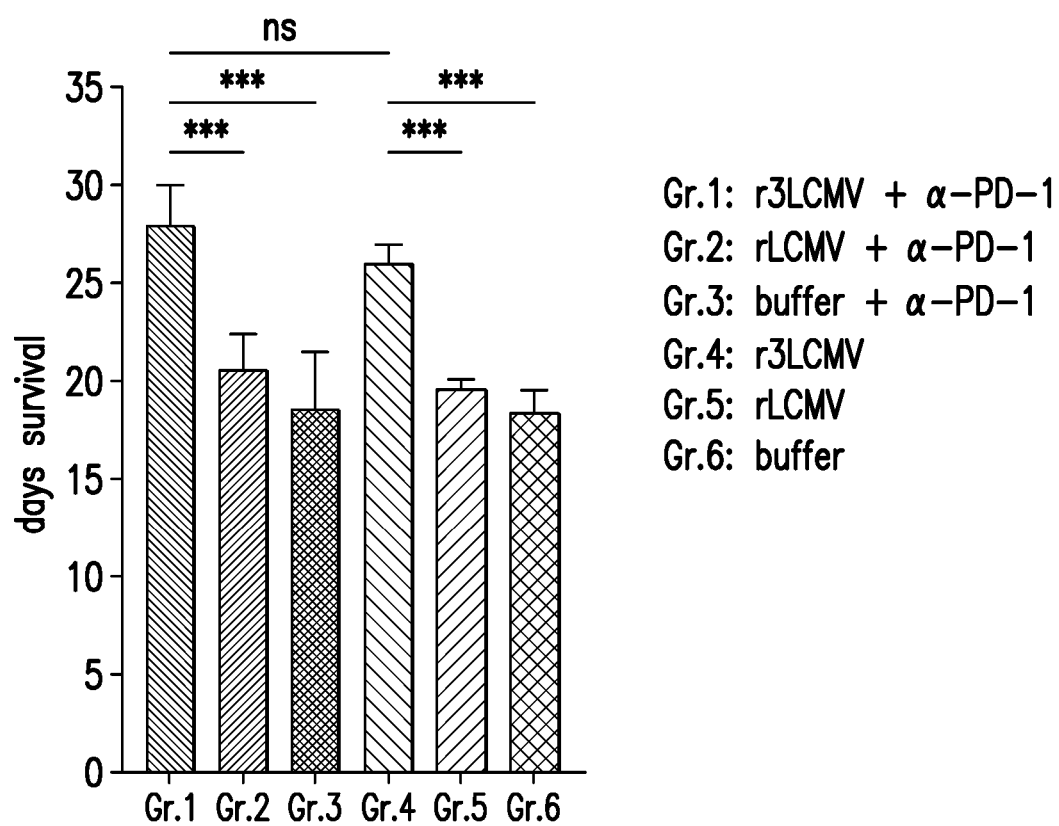

The above experiments showed that established melanoma tumors responded to a single treatment with a mix of tri-segmented replication-competent LCMV vectors expressing melanoma antigens GP100, Trp1 and Trp2 (group 4), as shown by reduced tumor volumes (FIG. 5B) and increased survival rates compared to control animals (group 6) (FIGS. 5C and 5D). In contrast, there was no response to treatment with a mix of bi-segmented replication-deficient LCMV vectors expressing the same melanoma antigens, independent of the presence or absence of checkpoint inhibition (groups 2 and 5) (FIGS. 5B-5D). Anti-PD1 blockade alone also had no effect on tumor growth or survival of the animals (group 3) (FIGS. 5B-5D). However, in mice treated with tri-segmented replication-competent melanoma antigen-expressing LCMV vectors in combination with anti-PD1 antibodies (group 1) an increase in survival rates that correlated with a decrease in tumor volumes was observed, compared to animals treated with a mix of tri-segmented replication-competent LCMV vectors alone, pointing to a synergistic effect of these treatment modalities (FIGS. 5B-5D).

8. SEQUENCES

The sequences in Table 5 are illustrative amino acid sequences and nucleotide sequences that can be used with the methods and compositions described herein. In some instances a DNA sequence is used to describe the RNA sequence of a viral genomic segment. The RNA sequence can be readily deduced from the DNA sequence.

TABLE 5

| SEQ ID NO. | Description | Sequence |
|---|---|---|
| 1 | Lymphocytic choriomeningitis virus clone 13 segment L, complete sequence (GenBank: DQ361066.1) (The genomic segment is RNA, the sequence in SEQ ID NO: 1 is shown for DNA; however, exchanging all thymidines ("T") in SEQ ID NO: 1 for uridines ("U") provides the RNA sequence.) | GCGCACCGGGGATCCTAGGCGTTTAGTTGCGCTGTTTGGTTGCACA ACTTTCTTCGTGAGGCTGTCAGAAGTGGACCTGGCTGATAGCGATG GGTCAAGGCAAGTCCAGAGAGGAGAAAGGCACCAATAGTACAAACA GGGCCGAAATCCTACCAGATACCACCTATCTTGGCCCTTTAAGCTG CAAATCTTGCTGGCAGAAATTTGACAGCTTGGTAAGATGCCATGAC CACTACCTTTGCAGGCACTGTTTAAACCTTCTGCTGTCAGTATCCG ACAGGTGTCCTCTTTGTAAATATCCATTACCAACCAGATTGAAGAT ATCAACAGCCCCAAGCTCTCCACCTCCCTACGAAGAGTAACACCGT CCGGCCCCGGCCCCGACAAACAGCCCAGCACAAGGGAACCGCACGT CaCCCAACGCACACAGACACAGCACCCAACACAGAACACGCACACA CACACACACACACACCCACACGCACGCGCCCCCACCACCGGGGGGC GCCCCCCCCGGGGGGCGGCCCCCCGGGAGCCCGGGCGGAGCCCCA CGGAGATGCCCATCAGTCGATGTCCTCGGCCACCGACCCGCCcAGC CAATCGTCGCAGGACCTCCCCTTGAGTCTAAACCTGCCCCCCACTg TTTCATACATCAAAGTGCTCCTAGATTTGCTAAAACAAAGTCTGCA ATCCTTAAAGGCGAACCAGTCTGGCAAAAGCGACAGTGGAATCAGC AGAATAGATCTGTCTATACATAGTTCCTGGAGGATTACACTTATCT CTGAACCCAACAAATGTTCACCAGTTCTGAATCGATGCAGGAAGAG GTTCCCAAGGACATCACTAATCTTTTCATAGCCCTCAAGTCCTGCT AGAAAGACTTTCATGTCCTTGGTCTCCAGCTTCACAATGATATTTT GGACAAGGTTTCTTCCTTCAAAAAGGGCACCCATCTTTACAGTCAG TGGCACAGGCTCCCACTCAGGTCCAACTCTCTCAAAGTCAATAGAT CTAATCCCATCCAGTATTCTTTTGGAGCCCAACAACTCAAGCTCAA GAGAATCACCAAGTATCAAGGGATCTTCCATGTAATCCTCAAACTC TTCAGATCTGATATCAAAGACACCATCGTTCACCTTGAAGACAGAG TCTGTCCTCAGTAAGTGGAGGCATTCATCCAACATTCTTCTATCTA TCTCACCCTTAAAGAGGTGAGAGCATGATAAAAGTTCAGCCACACC TGGATTCTGTAATTGGCACCTAACCAAGAATATCAATGAAAATTTC CTTAAACAGTCAGTATTATTCTGATTGTGCGTAAAGTCCACTGAAA TTGAAAACTCCAATACCCCTTTTGTGTAGTTGAGCATGTAGTCCCA |

TABLE 5-continued

| SEQ ID NO. | Description | Sequence |
|---|---|---|
| | | CAGATCCTTTAAGGATTTAAATGCCTTTGGGTTTGTCAGGCCCTGC
CTAATCAACATGGCAGCATTACACACAACATCTCCCATTCGGTAAG
AGAACCACCCAAAACCAAACTGCAAATCATTCCTAAACATAGGCCT
CTCCACATTTTTGTTCACCACCTTTGAGACAAATGATTGAAAGGGG
CCCAGTGCCTCAGCACCATCTTCAGATGGCATCATTTCTTTATGAG
GGAACCATGAAAAATTGCCTAATGTCCTGGTTGTTGCAACAAATTC
TCGAACAAATGATTCAAAATACACCTGTTTTAAGAAGTTCTTGCAG
ACATCCCTCGTGCTAACAACAAATTCATCAACCAGACTGGAGTCAG
ATCGCTGATGAGAATTGGCAAGGTCAGAAAACAGAACAGTGTAATG
TTCATCCCTTTTCCACTTAACAACATGAGAAATGAGTGACAAGGAT
TCTGAGTTAATATCAATTAAAACACAGAGGTCAAGGAATTTAATTC
TGGGACTCCACCTCATGTTTTTTGAGCTCATGTCAGACATAAATGG
AAGAAGCTGATCCTCAAAGATCTTGGGATATAGCCGCCTCACAGAT
TGAATCACTTGGTTCAAATTCACTTTGTCCTCCAGTAGCCTTGAGC
TCTCAGGCTTTCTTGCTACATAATCACATGGGTTTAAGTGCTTAAG
AGTTAGGTTCTCACTGTTATTCTTCCCTTTGGTCGGTTCTGCTAGG
ACCCAAACACCCAACTCAAAAGAGTTGCTCAATGAAATACAAATGT
AGTCCCAAAGAAGAGGCCTTAAAAGGCATATATGATCACGGTGGGC
TTCTGGATGAGACTGTTTGTCACAAATGTACAGCGTTATACCATCC
CGATTGCAAACTCTTGTCACATGATCATCTGTGGTTAGATCCTCAA
GCAGCTTTTTGATATACAGATTTTCCCTATTTTTGTTTCTCACACA
CCTGCTTCCTAGAGTTTTGCAAAGGCCTATAAAGCCAGATGAGATA
CAACTCTGGAAAGCTGACTTGTTGATTGCTTCTGACAGCAGCTTCT
GTGCACCCCTTGTGAATTTACTACAAAGTTTGTTCTGGAGTGTCTT
GATCAATGATGGGATTCTTTCCTCTTGGAAAGTCATCACTGATGGA
TAAACCACCTTTTGTCTTAAAACCATCCTTAATGGGAACATTTCAT
TCAAATTCAACCAGTTAACATCTGCTAACTGATTCAGATCTTCTTC
AAGACCGAGGAGGTCTCCCAATTGAAGAATGGCCTCCtTTTTATCT
CTGTTAAATAGGTCTAAGAAAAATTCTTCATTAAATTCACCATTTT
TGAGCTTATGATGCAGTTTCCTTACAAGCTTTCTTACAACCTTTGT
TTCATTAGGACACAGTTCCTCAATGAGTCTTTGTATTCTGTAACCT
CTAGAACCATCCAGCCAATCTTTCACATCAGTGTTGGTATTCAGTA
GAAATGGATCCAAAGGGAAATTGGCATACTTTAGGAGGTCCAGTGT
TCTCCTTTGGATACTATTAACTAGGGAGACTGGGACGCCATTTGCG
ATGGCTTGATCTGCAATTGTATCTATTGTTTCACAAAGTTGATGTG
GCTCTTTACACTTGACATTGTGTAGCGCTGCAGATACAAACTTTGT
GAGAAGAGGGACTTCCTCCCCCCATACATAGAATCTAGATTTAAAT
TCTGCAGCGAACCTCCCAGCCACACTTTTTGGGCTGATAAATTTGT
TTAACAAGCCGCTCAGATGAGATTGGAATTCCAACAGGACAAGGAC
TTCCTCCGGATCACTTACAACCAGGTCACTCAGCCTCCTATCAAAT
AAAGTGATCTGATCATCACTTGATGTGTAAGCCTCTGGTCTTTCGC
CAAAGATAACACCAATGCAGTAGTTGATGAACCTCTCGCTAAGCAA
ACCATAGAAGTCAGAAGCATTATGCAAGATTCCCTGCCCCATATCA
ATAAGGCTGGATATATGGGATGGCACTATCCCCATTTCAAAATATT
GTCTGAAAATTCTCTCAGTAACAGTTGTTTCTGAACCCCTGAGAAG
TTTTAGCTTCGACTTGACATATGATTTCATCATTGCATTCACAACA
GGAAAGGGGACCTCGACAAGCTTATGCATGTGCCAAGTTAACAAAG
TGCTAACATGATCTTTCCCGGAACGCACATACTGGTCATCACCTAG
TTTGAGATTTTGTAGAAACATTAAGAACAAAAATGGGCACATCATT
GGTCCCCATTTGCTGTGATCCATACTATAGTTTAAGAACCCTTCCC
GCACATTGATAGTCATTGACAAGATTGCATTTTCAAATTCCTTATC
ATTGTTTAAACAGGAGCCTGAAAAGAAACTTGAAAAAGACTCAAAA
TAATCTTCTATTAACCTTGTGAACATTTTTGTCCTCAAATCTCCAA
TATAGAGTTCTCTATTTCCCCCAACCTGCTCTTTATAAGATAGTGC
AAATTTCAGCCTTCCAGAGTCAGGACCTACTGAGGTGTATGATGTT
GGTGATTCTTCTGAGTAGAAGCACAGATTTTTCAAAGCAGCACTCA
TACATTgTGTCAACGACAGAGCTTTACTAAGGGACTCAGAATTACT
TTCCCTCTCACTGATTCTCACGTCTTCTTCCAGTTTGTCCCAGTCA
AATTTGAAATTCAAGCCTTGCCTTTGCATATGCCTGTATTTCCCTG
AGTACGCATTTGCATTCATTTGCAACAGAATCATCTTCATGCAAGA
AAACCAATCATTCTCAGAAAAGAACTTTCTACAAAGGTTTTTTGCC
ATCTCATCGAGGCCACACTGATCTTTAATGACTGAGGTGAAATACA
AAGGTGACAGCTCTGTGGAACCCTCAACAGCCTCACAGATAAATTT
CATGTCATCATTGGTTAGACATGATGGGTCAAAGTCTTCTACTAAA
TGGAAAGATATTTCTGACAAGATAACTTTTCTTAAGTGAGCCATCT
TCCCTGTTAGAATAAGCTGTAAATGATGTAGTCCTTTTGTATTTGT
AAGTTTTTCTCCATCTCCTTTGTCATTGGCCCTCCTACCTCTTCTG
TACCGTGCTATTGTGGTGTTGACCTTTTCTTCGAGACTTTTGAAGA
AGCTTGTCTCTTCTTCTCCATCAAAACATATTTCTGCCAGGTTGTC
TTCCGATCTCCCTGTCTCTTCTCCCTTGGAACCGATGACCAATCTA
GAGACTAACTTGGAAACTTTATATTCATAGTCTGAGTGGCTCAACT
TATACTTTTGTTTTCTTACGAAACTCTCCGTAATTTGACTCACAGC
ACTAACAAGCAATTTGTTAAAGTCATATTCCAGAAGTCGTTCTCCA
TTTAGATGCTTATTAACCACCACACTTTTGTTACTAGCAAGATCTA
ATGCTGTCGCACATCCAGAGTTAGTCATGGGATCTAGGCTGTTTAG
CTTCTTCTCTCCTTTGAAAATTAAAGTGCCGTTGTTAAATGAAGAC
ACCATTAGGCTAAAGGCTTCCAGATTAACACCTGGAGTTGTATGCT |

TABLE 5-continued

| SEQ ID NO. | Description | Sequence |
|---|---|---|
| | | GACAGTCAATTTCTTTACTAGTGAATCTCTTCATTTGCTCATAGAA |
| | | CACACATTCTTCCTCAGGAGTGATTGCTTCCTTGGGGTTGACAAAA |
| | | AAACCAAATTGACTTTTGGGCTCAAAGAACTTTTCAAAACATTTTA |
| | | TCTGATCTGTTAGCCTGTCAGGGGTCTCCTTTGTGATCAAATGACA |
| | | CAGGTATGACACATTCAACATAAATTTAAATTTTGCACTCAACAAC |
| | | ACCTTCTCACCAGTACCAAAAATAGTTTTTATTAGGAATCTAAGCA |
| | | GCTTATACACCACCTTCTCAGCAGGTGTGATCAGATCCTCCCTCAA |
| | | CTTATCCATTAATGATGTAGATGAAAAATCTGACACTATTGCCATC |
| | | ACCAAATATCTGACACTCTGTACCTGCTTTTGATTTCTCTTTGTTG |
| | | GGTTGGTGAGCATTAGCAACAATAGGGTCCTCAGTGCAACCTCAAT |
| | | GTCGGTGAGACAGTCTTTCAAATCAGGACATGATCTAATCCATGAA |
| | | ATCATGATGTCTATCATATTGTATAAGACCTCATCTGAAAAAATTG |
| | | GTAAAAGAACCTTTTAGGATCTGCATAGAAGGAAATTAAATGACC |
| | | ATCCGGGCCTTGTATGGAGTAGCACCTTGAAGATTCTCCAGTCTTC |
| | | TGGTATAATAGGTGGTATTCTTCAGAGTCCAGTTTTATTACTTGGC |
| | | AAAACACTTCTTTGCATTCTACCACTTGATATCTCACAGACCCTAT |
| | | TTGATTTTGCCTTAGTCTAGCAACTGAGCTAGTTTTCATACTGTTT |
| | | GTTAAGGCCAGACAAACAGATGATAATCTTCTCAGGCTCTGTATGT |
| | | TCTTCAGCTGCTCTGTGCTGGGTTGGAAATTGTAATCTTCAAACTT |
| | | CGTATAATACATTATCGGGTGAGCTCCAATTTTCATAAAGTTCTCA |
| | | AATTCAGTGAATGGTATGTGGCATTCTTGCTCAAGGTGTTCAGACA |
| | | GTCCGTAATGCTCGAAACTCAGTCCCACCACTAACAGGCATTTTTG |
| | | AATTTTTGCAATGAACTCACTAATAGAtGCCCTAAACAATTCCTCA |
| | | AAAGACACCTTTCTAAACACCTTTGACTTTTTTCTATTCCTCAAAA |
| | | GTCTAATGAACTCCTCTTTAGTGCTGTGAAAGCTTACCAGCCTATC |
| | | ATTCACACTACTATAGCAACAACCCACCCAGTGTTTATCATTTTTT |
| | | AACCCTTTGAATTTCGACTGTTTTATCAATGAGGAAAGACACAAAA |
| | | CATCCAGATTTAACAACTGTCTCCTTCTAGTATTCAACAGTTTCAA |
| | | ACTCTTGACTTTGTTTAACATAGAGAGGAGCCTCTCATATTCAGTG |
| | | CTAGTCTCACTTCCCCTTTCGTGCCCATGGGTCTCTGCAGTTATGA |
| | | ATCTCATCAAAGGACAGGATTCGACTGCCTCCCTGCTTAATGTTAA |
| | | GATATCATCACTATCAGCAAGGTTTTCATAGAGCTCAGAGAATTCC |
| | | TTGATCAAGCCTTCAGGGTTTACTTTCTGAAAGTTTCTCTTTAATT |
| | | TCCCACTTTCTAAATCTCTTCTAAACCTGCTGAAAAGAGAGTTTAT |
| | | TCCAAAAACCACATCATCACAGCTCATGTTGGGGTTGATGCCTTCG |
| | | TGGCACATCCTCATAATTTCATCATTGTGAGTTGACCTCGCATCTT |
| | | TCAGAATTTTCATAGAGTCCATACCGGAGCGCTTGTCGATAGTAGT |
| | | CTTCAGGGACTCACAGAGTCTAAAATATTCAGACTCTTCAAAGACT |
| | | TTCTCATTTTGGTTAGAATACTCCAAAAGTTTGAATAAAAGGTCTC |
| | | TAAATTTGAAGTTTGCCCACTCTGGCATAAAACTATTATCATAATC |
| | | ACAACGACCATCTACTATTGGAACTAATGTGACACCCGCAACAGCA |
| | | AGGTCTTCCCTGATGCATGCCAATTTGTTAGTGTCCTCTATAAATT |
| | | TCTTCTCAAAACTGGCTGGaGtGCTCCTAACAAAACACTCAAGAAG |
| | | AATGAGAGAATTGTCTATCAGCTTGTAACCATCAGGAATGATAAGT |
| | | GGTAGTCCTGGGCATACAATTCCAGACTCCACCAAAATTGTTTCCA |
| | | CAGACTTATCGTCGTGGTTGTGTGTGCAGCCACTCTTGTCTGCACT |
| | | GTCTATTTCAATGCAGCGTGACAGCAACTTGAGTCCCTCAATCAGA |
| | | ACCATTCTGGGTTCCCTTTGTCCCAGAAAGTTGAGTTTCTGCCTTG |
| | | ACAACCTCTCATCCTGTTCTATATAGTTTAAACATAACTCTCTCAA |
| | | TTCTGAGATGATTTCATCCATTGCGCATCAAAAAGCCTAGGATCCT |
| | | CGGTGCG |
| 2 | Lymphocytic choriomeningitis virus segment S, complete sequence (The genomic segment is RNA, the sequence in SEQ ID NO: 2 is shown for DNA; however, exchanging all thymidines ("T") in SEQ ID NO: 2 for uridines ("U") provides the RNA sequence.) | CGCACCGGGGATCCTAGGCTTTTTGGATTGCGCTTTCCTC TAGATCAACTGGGTGTCAGGCCCTATCCTACAGAAGGATG GGTCAGATTGTGACAATGTTTGAGGCTCTGCCTCACATCA TCGATGAGGTGATCAACATTGTCATTATTGTGCTTATCGT GATCACGGGTATCAAGGCTGTCTACAATTTTGCCACCTGT GGGATATTCGCATTGATCAGTTTCCTACTTCTGGCTGGCA GGTCCTGTGGCATGTACGGTCTTAAGGGACCCGACATTTA CAAAGGAGTTTACCAATTTAAGTCAGTGGAGTTTGATATG TCACATCTGAACCTGACCATGCCCAACGCATGTTCAGCCA ACAACTCCCACCATTACATCAGTATGGGGACTTCTGGACT AGAATTGACCTTCACCAATGATTCCATCATCAGTCACAAC TTTTGCAATCTGACCTCTGCCTTCAACAAAAAGACCTTTG ACCACACACTCATGAGTATAGTTTCGAGCCTACACCTCAG TATCAGAGGGAACTCCAACTATAAGGCAGTATCCTGCGAC TTCAACAATGGCATAACCATCCAATACAACTTGACATTCT CAGATCGACAAAGTGCTCAGAGCCAGTGTAGAACCTTCAG AGGTAGAGTCCTAGATATGTTTAGAACTGCCTTCGGGGGG AAATACATGAGGAGTGGCTGGGGCTGGACAGGCTCAGATG GCAAGACCACCTGGTGTAGCCAGACGAGTTACCAATACCT GATTATACAAAATAGAACCTGGGAAAACCACTGCACATAT GCAGGTCCTTTTGGGATGTCCAGGATTCTCCTTTCCCAAG AGAAGACTAAGTTCTTCACTAGGAGACTAGCGGGCACATT CACCTGGACTTTGTCAGACTCTTCAGGGGTGGAGAATCCA GGTGGTTATTGCCTGACCAAATGGATGATTCTTGCTGCAG AGCTTAAGTGTTTCGGGAACACAGCAGTTGCGAAATGCAA |

TABLE 5-continued

| SEQ ID NO. | Description | Sequence |
|---|---|---|
| | | TGTAAATCATGATGCCGAATTCTGTGACATGCTGCGACTA |
| | | ATTGACTACAACAAGGCTGCTTTGAGTAAGTTCAAAGAGG |
| | | ACGTAGAATCTGCCTTGCACTTATTCAAAACAACAGTGAA |
| | | TTCTTTGATTTCAGATCAACTACTGATGAGGAACCACTTG |
| | | AGAGATCTGATGGGGGTGCCATATTGCAATTACTCAAAGT |
| | | TTTGGTACCTAGAACATGCAAAGACCGGCGAAACTAGTGT |
| | | CCCCAAGTGCTGGCTTGTCACCAATGGTTCTTACTTAAAT |
| | | GAGACCCACTTCAGTGATCAAATCGAACAGGAAGCCGATA |
| | | ACATGATTACAGAGATGTTGAGGAAGGATTACATAAAGAG |
| | | GCAGGGGAGTACCCCCCTAGCATTGATGGACCTTCTGATG |
| | | TTTTCCACATCTGCATATCTAGTCAGCATCTTCCTGCACC |
| | | TTGTCAAAATACCAACACACAGGCACATAAAAGGTGGCTC |
| | | ATGTCCAAAGCCACACCGATTAACCAACAAAGGAATTTGT |
| | | AGTTGTGGTGCATTTAAGGTGCCTGGTGTAAAAACCGTCT |
| | | GGAAAAGACGCTGAAGAACAGCGCCTCCCTGACTCTCCAC |
| | | CTCGAAAGAGGTGGAGAGTCAGGGAGGCCCAGAGGGTCTT |
| | | AGAGTGTCACAACATTTGGGCCTCTAAAAATTAGGTCATG |
| | | TGGCAGAATGTTGTGAACAGTTTTCAGATCTGGGAGCCTT |
| | | GCTTTGGAGGCGCTTTCAAAAATGATGCAGTCCATGAGTG |
| | | CACAGTGCGGGGTGATCTCTTTCTTCTTTTTGTCCCTTAC |
| | | TATTCCAGTATGCATCTTACACAACCAGCCATATTTGTCC |
| | | CACACTTTGTCTTCATACTCCCTCGAAGCTTCCCTGGTCA |
| | | TTTCAACATCGATAAGCTTAATGTCCTTCCTATTCTGTGA |
| | | GTCCAGAAGCTTTCTGATGTCATCGGAGCCTTGACAGCTT |
| | | AGAACCATCCCCTGCGGAAGAGCACCTATAACTGACGAGG |
| | | TCAACCCGGGTTGCGCATTGAAGAGGTCGGCAAGATCCAT |
| | | GCCGTGTGAGTACTTGGAATCTTGCTTGAATTGTTTTTGA |
| | | TCAACGGGTTCCCTGTAAAAGTGTATGAACTGCCCGTTCT |
| | | GTGGTTGGAAAATTGCTATTTCCACTGGATCATTAAATCT |
| | | ACCCTCAATGTCAATCCATGTAGGAGCGTTGGGGTCAATT |
| | | CCTCCCATGAGGTCTTTTAAAAGCATTGTCTGGCTGTAGC |
| | | TTAAGCCCACCTGAGGTGGACCTGCTGCTCCAGGCGCTGG |
| | | CCTGGGTGAATTGACTGCAGGTTTCTCGCTTGTGAGATCA |
| | | ATTGTTGTGTTTTCCCATGCTCTCCCCACAATCGATGTTC |
| | | TACAAGCTATGTATGGCCATCCTTCACCTGAAAGGCAAAC |
| | | TTTATAGAGGATGTTTTCATAAGGGTTCCTGTCCCCAACT |
| | | TGGTCTGAAACAAACATGTTGAGTTTTCTCTTGGCCCCGA |
| | | GAACTGCCTTCAAGAGGTCCTCGCTGTTGCTTGGCTTGAT |
| | | CAAAATTGACTCTAACATGTTACCCCCATCCAACAGGGCT |
| | | GCCCCTGCCTTCACGGCAGCACCAAGACTAAAGTTATAGC |
| | | CAGAAATGTTGATGCTGGACTGCTGTTCAGTGATGACCCC |
| | | CAGAACTGGGTGCTTGTCTTTCAGCCTTTCAAGATCATTA |
| | | AGATTTGGATACTTGACTGTGTAAAGCAAGCCAAGGTCTG |
| | | TGAGCGCTTGTACAACGTCATTGAGCGGAGTCTGTGACTG |
| | | TTTGGCCATACAAGCCATAGTTAGACTTGGCATTGTGCCA |
| | | AATTGATTGTTCAAAAGTGATGAGTCTTTCACATCCCAAA |
| | | CTCTTACCACACCACTTGCACCCTGCTGAGGCTTTCTCAT |
| | | CCCAACTATCTGTAGGATCTGAGATCTTTGGTCTAGTTGC |
| | | TGTGTTGTTAAGTTCCCCATATATACCCCTGAAGCCTGGG |
| | | GCCTTTCAGACCTCATGATCTTGGCCTTCAGCTTCTCAAG |
| | | GTCAGCCGCAAGAGACATCAGTTCTTCTGCACTGAGCCTC |
| | | CCCACTTTCAAAACATTCTTCTTTGATGTTGACTTTAAAT |
| | | CCACAAGAGAATGTACAGTCTGGTTGAGACTTCTGAGTCT |
| | | CTGTAGGTCTTTGTCATCTCTCTTTTCCTTCCTCATGATC |
| | | CTCTGAACATTGCTGACCTCAGAGAAGTCCAACCCATTCA |
| | | GAAGGTTGGTTGCATCCTTAATGACAGCAGCCTTCACATC |
| | | TGATGTGAAGCTCTGCAATTCTCTTCTCAATGCTTGCGTC |
| | | CATTGGAAGCTCTTAACTTCCTTAGACAAGGACATCTTGT |
| | | TGCTCAATGGTTTCTCAAGACAAATGCGCAATCAAATGCC |
| | | TAGGATCCACTGTGCG |
| 3 | Lymphocytic choriomeningitis virus clone 13 segment S, complete sequence (GenBank: DQ361065.2) (The genomic segment is RNA, the sequence in SEQ ID NO: 3 is shown for DNA; however, exchanging all | GCGCACCGGGGATCCTAGGCTTTTTGGATTGCGCTTTCCT CTAGATCAACTGGGTGTCAGGCCCTATCCTACAGAAGGAT GGGTCAGATTGTGACAATGTTTGAGGCTCTGCCTCACATC ATCGATGAGGTGATCAACATTGTCATTATTGTGCTTATCG TGATCACGGGTATCAAGGCTGTCTACAATTTTGCCACCTG TGGGATATTCGCATTGATCAGTTTCCTACTTCTGGCTGGC AGGTCCTGTGGCATGTACGGTCTTAAGGGACCCGACATTT ACAAAGGAGTTTACCAATTTAAGTCAGTGGAGTTTGATAT GTCACATCTGAACCTGACCATGCCCAACGCATGTTCAGCC AACAACTCCCACCATTACATCAGTATGGGACTTCTGGAC TAGAATTGACCTTCACCAATGATTCCATCATCAGTCACAA CTTTTGCAATCTGACCTCTGCCTTCAACAAAAAGACCTTT |

TABLE 5-continued

| SEQ ID NO. | Description | Sequence |
|---|---|---|
| | thymidines ("T") in SEQ ID NO: 3 for uridines ("U") provides the RNA sequence.) | GACCACACACTCATGAGTATAGTTTCGAGCCTACACCTCA<br>GTATCAGAGGGAACTCCAACTATAAGGCAGTATCCTGCGA<br>CTTCAACAATGGCATAACCATCCAATACAACTTGACATTC<br>TCAGATGCACAAAGTGCTCAGAGCCAGTGTAGAACCTTCA<br>GAGGTAGAGTCCTAGATATGTTTAGAACTGCCTTCGGGGG<br>GAAATACATGAGGAGTGGCTGGGGCTGGACAGGCTCAGAT<br>GGCAAGACCACCTGGTGTAGCCAGACGAGTTACCAATACC<br>TGATTATACAAAATAGAACCTGGGAAAACCACTGCACATA<br>TGCAGGTCCTTTTGGGATGTCCAGGATTCTCCTTTCCCAA<br>GAGAAGACTAAGTTCCTCACTAGGAGACTAGCGGGCACAT<br>TCACCTGGACTTTGTCAGACTCTTCAGGGGTGGAGAATCC<br>AGGTGGTTATTGCCTGACCAAATGGATGATTCTTGCTGCA<br>GAGCTTAAGTGTTTCGGGAACACAGCAGTTGCGAAATGCA<br>ATGTAAATCATGATGAAGAATTCTGTGACATGCTGCGACT<br>AATTGACTACAACAAGGCTGCTTTGAGTAAGTTCAAAGAG<br>GACGTAGAATCTGCCTTGCACTTATTCAAACAACAGTGA<br>ATTCTTTGATTTCAGATCAACTACTGATGAGGAACCACTT<br>GAGAGATCTGATGGGGGTGCCATATTGCAATTACTCAAAG<br>TTTTGGTACCTAGAACATGCAAAGACCGGCGAAACTAGTG<br>TCCCCAAGTGCTGGCTTGTCACCAATGGTTCTTACTTAAA<br>TGAGACCCACTTCAGTGACCAAATCGAACAGGAAGCCGAT<br>AACATGATTACAGAGATGTTGAGGAAGGATTACATAAAGA<br>GGCAGGGGAGTACCCCCCTAGCATTGATGGACCTTCTGAT<br>GTTTTCCACATCTGCATATCTAGTCAGCATCTTCCTGCAC<br>CTTGTCAAAATACCAACACACAGGCACATAAAAGGTGGCT<br>CATGTCCAAAGCCACACCGATTAACCAACAAAGGAATTTG<br>TAGTTGTGGTGCATTTAAGGTGCCTGGTGTAAAAACCGTC<br>TGGAAAAGACGCTGAAGAACAGCGCCTCCCTGACTCTCCA<br>CCTCGAAAGAGGTGGAGAGTCAGGGAGGCCCAGAGGGTCT<br>TAGAGTGTCACAACATTTGGGCCTCTAAAAATTAGGTCAT<br>GTGGCAGAATGTTGTGAACAGTTTTCAGATCTGGGAGCCT<br>TGCTTTGGAGGCGCTTTCAAAAATGATGCAGTCCATGAGT<br>GCACAGTGCGGGGTGATCTCTTTCTTCTTTTTGTCCCTTA<br>CTATTCCAGTATGCATCTTACACAACCAGCCATATTTGTC<br>CCACACTTTGTCTTCATACTCCCTCGAAGCTTCCCTGGTC<br>ATTTCAACATCGATAAGCTTAATGTCCTTCCTATTCTGTG<br>AGTCCAGAAGCTTTCTGATGTCATCGGAGCCTTGACAGCT<br>TAGAACCATCCCCTGCGGAAGAGCACCTATAACTGACGAG<br>GTCAACCCGGGTTGCGCATTGAAGAGGTCGGCAAGATCCA<br>TGCCGTGTGAGTACTTGGAATCTTGCTTGAATTGTTTTTG<br>ATCAACGGGTTCCCTGTAAAAGTGTATGAACTGCCCGTTC<br>TGTGGTTGGAAAATTGCTATTTCCACTGGATCATTAAATC<br>TACCCTCAATGTCAATCCATGTAGGAGCGTTGGGGTCAAT<br>TCCTCCCATGAGGTCTTTTAAAAGCATTGTCTGGCTGTAG<br>CTTAAGCCCACCTGAGGTGGACCTGCTGCTCCAGGCGCTG<br>GCCTGGGTGAATTGACTGCAGGTTTCTCGCTTGTGAGATC<br>AATTGTTGTGTTTTCCCATGCTCTCCCCACAATCGATGTT<br>CTACAAGCTATGTATGGCCATCCTTCACCTGAAAGGCAAA<br>CTTTATAGAGGATGTTTTCATAAGGGTTCCTGTCCCCAAC<br>TTGGTCTGAAACAAACATGTTGAGTTTTCTCTTGGCCCCG<br>AGAACTGCCTTCAAGAGGTCCTCGCTGTTGCTTGGCTTGA<br>TCAAAATTGACTCTAACATGTTACCCCCATCCAACAGGGC<br>TGCCCCTGCCTTCACGGCAGCACCAAGACTAAAGTTATAG<br>CCAGAAATGTTGATGCTGGACTGCTGTTCAGTGATGACCC<br>CCAGAACTGGGTGCTTGTCTTTCAGCCTTTCAAGATCATT<br>AAGATTTGGATACTTGACTGTGTAAAGCAAGCCAAGGTCT<br>GTGAGCGCTTGTACAACGTCATTGAGCGGAGTCTGTGACT<br>GTTTGGCCATACAAGCCATAGTTAGACTTGGCATTGTGCC<br>AAATTGATTGTTCAAAAGTGATGAGTCTTTCACATCCCAA<br>ACTCTTACCACACCACTTGCACCCTGCTGAGGCTTTCTCA<br>TCCCAACTATCTGTAGGATCTGAGATCTTTGGTCTAGTTG<br>CTGTGTTGTTAAGTTCCCATATATACCCCTGAAGCCTGG<br>GGCCTTTCAGACCTCATGATCTTGGCCTTCAGCTTCTCAA<br>GGTCAGCCGCAAGAGACATCAGTTCTTCTGCACTGAGCCT<br>CCCCACTTTCAAAACATTCTTCTTTGATGTTGACTTTAAA<br>TCCACAAGAGAATGTACAGTCTGGTTGAGACTTCTGAGTC<br>TCTGTAGGTCTTTGTCATCTCTCTTTTCCTTCCTCATGAT<br>CCTCTGAACATTGCTGACCTCAGAGAAGTCCAACCCATTC<br>AGAAGGTTGGTTGCATCCTTAATGACAGCAGCCTTCACAT<br>CTGATGTGAAGCTCTGCAATTCTCTTCTCAATGCTTGCGT<br>CCATTGGAAGCTCTTAACTTCCTTAGACAAGGACATCTTG<br>TTGCTCAATGGTTTCTCAAGACAAATGCGCAATCAAATGC<br>CTAGGATCCACTGTGCG |
| 4 | Lymphocytic choriomeningitis strain MP segment | GCGCACCGGGGATCCTAGGCATTTTTGTTGCGCATTTTGT<br>TGTGTTATTTGTTGCACAGCCCTTCATCGTGGGACCTTCA<br>CAAACAAACCAAACCACCAGCCATGGGCCAAGGCAAGTCC |

TABLE 5-continued

| SEQ ID NO. | Description | Sequence |
|---|---|---|
| | L, complete sequence (The genomic segment is RNA, the sequence in SEQ ID NO: 4 is shown for DNA; however, exchanging all thymidines ("T") in SEQ ID NO: 4 for uridines ("U") provides the RNA sequence.) | AAAGAGGGAAGGGATGCCAGCAATACGAGCAGAGCTGAAA<br>TTCTGCCAGACACCACCTATCTCGGACCTCTGAACTGCAA<br>GTCATGCTGGCAGAGATTTGACAGTTTAGTCAGATGCCAT<br>GACCACTATCTCTGCAGACACTGCCTGAACCTCCTGCTGT<br>CAGTCTCCGACAGGTGCCCTCTCTGCAAACATCCATTGCC<br>AACCAAACTGAAAATATCCACGGCCCCAAGCTCTCCACCC<br>CCTTACGAGGAGTGACGCCCCGAGCCCCAACACCGACACA<br>AGGAGGCCACCAACACAACGCCCAACACGGAACACACACA<br>CACACACCCACACACACATCCACACACACGCGCCCCCACA<br>ACGGGGGCGCCCCCCCGGGGGTGGCCCCCCGGGTGCTCGG<br>GCGGAGCCCCACGGAGAGGCCAATTAGTCGATCTCCTCGA<br>CCACCGACTTGGTCAGCCAGTCATCACAGGACTTGCCCTT<br>AAGTCTGTACTTGCCCACAACTGTTTCATACATCACCGTG<br>TTCTTTGACTTACTGAAACATAGCCTACAGTCTTTGAAAG<br>TGAACCAGTCAGGCACAAGTGACAGCGGTACCAGTAGAAT<br>GGATCTATCTATACACAACTCTTGGAGAATTGTGCTAATT<br>TCCGACCCCTGTAGATGCTCACCAGTTCTGAATCGATGTA<br>GAAGAAGGCTCCCAAGGACGTCATCAAAATTTCCATAACC<br>CTCGAGCTCTGCCAAGAAAACTCTCATATCCTTGGTCTCC<br>AGTTTCACAACGATGTTCTGAACAAGGCTTCTTCCCTCAA<br>AAAGAGCACCCATTCTCACAGTCAAGGGCACAGGCTCCCA<br>TTCAGGCCCAATCCTCTCAAAATCAAGGGATCTGATCCCG<br>TCCAGTATTTTCCTTGAGCCTATCAGCTCAAGCTCAAGAG<br>AGTCACCGAGTATCAGGGGGTCCTCCATATAGTCCTCAAA<br>CTCTTCAGACCTAATGTCAAAAACACCATCGTTCACCTTG<br>AAGATAGAGTCTGATCTCAACAGGTGGAGGCATTCGTCCA<br>AGAACCTTCTGTCCACCTCACCTTTAAAGAGGTGAGAGCA<br>TGATAGGAACTCAGCTACACCTGGACCTTGTAACTGGCAC<br>TTCACTAAAAGATCAATGAAAACTTCCTCAAACAATCAG<br>TGTTATTCTGGTTGTGAGTGAAATCTACTGTAATTGAGAA<br>CTCTAGCACTCCCTCTGTATTATTTATCATGTAATCCCAC<br>AAGTTTCTCAAAGACTTGAATGCCTTTGGATTTGTCAAGC<br>CTTGTTTGATTAGCATGGCAGCATTGCACACAATATCTCC<br>CAATCGGTAAGAGAACCATCCAAATCCAAATTGCAAGTCA<br>TTCCTAAACATGGGCCTCTCCATATTTTTGTTCACTACTT<br>TTAAGATGAATGATTGGAAAGGCCCCAATGCTTCAGCGCC<br>ATCTTCAGATGGCATCATGTCTTTATGAGGGAACCATGAA<br>AAACTTCCTAGAGTTCTGCTTGTTGCTACAAATTCTCGTA<br>CAAATGACTCAAAATACACTTGTTTTAAAAAGTTTTTGCA<br>GACATCCCTTGTACTAACGACAAATTCATCAACAAGGCTT<br>GAGTCAGAGCGCTGATGGAATTTACAAGATCAGAAAATA<br>GAACAGTGTAGTGTTCGTCCCTCTTCCACTTAACTACATG<br>AGAAATGAGCGATAAAGATTCTGAATTGATATCGATCAAT<br>ACGCAAAGGTCAAGGAATTTGATTCTGGGACTCCATCTCA<br>TGTTTTTTGAGCTCATATCAGACATGAAGGGAAGCAGCTG<br>ATCTTCATAGATTTTAGGGTACAATCGCCTCACAGATTGG<br>ATTACATGGTTTAAACTTATCTTGTCCTCCAGTAGCCTTG<br>AACTCTCAGGCTTCCTTGCTACATAATCACATGGGTTCAA<br>GTGCTTGAGGCTTGAGCTTCCCTCATTCTTCCCTTTCACA<br>GGTTCAGCTAAGACCCAAACACCCAACTCAAAGGAATTAC<br>TCAGTGAGATGCAAATATAGTCCCAAAGGAGGGGCCTCAA<br>GAGACTGATGTGGTCGCAGTGAGCTTCTGGATGACTTTGC<br>CTGTCACAAATGTACAACATTATGCCATCATGTCTGTGGA<br>TTGCTGTCACATGCGCATCCATAGCTAGATCCTCAAGCAC<br>TTTTCTAATGTATAGATTGTCCCTATTTTTATTTCTCACA<br>CATCTACTTCCCAAAGTTTTGCAAAGACCTATAAAGCCTG<br>ATGAGATGCAACTTTGAAAGGCTGACTTATTGATTGCTTC<br>TGACAGCAACTTCTGTGCACCTCTTGTGAACTTACTGCAG<br>AGCTTGTTCTGGAGTGTCTTGATTAATGATGGGATTCTTT<br>CCTCTTGGAAAGTCATTACTGATGGATAAACCACTTTCTG<br>CCTCAAGACCATTCTTAATGGGAACAACTCATTCAAATTC<br>AGCCAATTTATGTTTGCCAATTGACTTAGATCCTCTTCGA<br>GGCCAAGGATGTTTCCCAACTGAAGAATGGCTTCCTTTTT<br>ATCCCTATTGAAGAGGTCTAAGAAGAATTCTTCATTGAAC<br>TCACCATTCTTGAGCTTATGATGTAGTCTCCTTACAAGCC<br>TTCTCATGACCTTCGTTTCACTAGGACACAATTCTTCAAT<br>AAGCCTTTGGATTCTGTAACCTCTAGAGCCATCCAACCAA<br>TCCTTGACATCAGTATTAGTGTTAAGCAAAAATGGGTCCA<br>AGGGAAAGTTGGCATATTTTAAGAGGTCTAATGTTCTCTT<br>CTGGATGCAGTTTACCAATGAAACTGGAACACCATTTGCA<br>ACAGCTTGATCGGCAATTGTATCTATTGTTTCACAGAGTT<br>GGTGTGGCTCTTTACACTTAACGTTGTGTAATGCTGCTGA<br>CACAAATTTTGTTAAAAGTGGGACCTCTTCCCCCCACACA<br>TAAAATCTGGATTTAAATTCTGCAGCAAATCGCCCCACCA<br>CACTTTTCGGACTGATGAACTTGTTAAGCAAGCCACTCAA<br>ATGAGAATGAAATTCCAGCAATACAAGGACTTCCTCAGGG<br>TCACTATCAACCAGTTCACTCAATCTCCTATCAAATAAGG |

TABLE 5-continued

| SEQ ID NO. Description | Sequence |
|---|---|
| | TGATCTGATCATCACTTGATGTGTAAGATTCTGGTCTCTC |
| | ACCAAAAATGACACCGATACAATAATTAATGAATCTCTCA |
| | CTGATTAAGCCGTAAAAGTCAGAGGCATTATGTAAGATTC |
| | CCTGTCCCATGTCAATGAGACTGCTTATATGGGAAGGCAC |
| | TATTCCTAATTCAAAATATTCTCGAAAGATTCTTTCAGTC |
| | ACAGTTGTCTCTGAACCCCTAAGAAGTTTCAGCTTTGATT |
| | TGATATATGATTTCATCATTGCATTCACAACAGGAAAAGG |
| | GACCTCAACAAGTTTGTGCATGTGCCAAGTTAATAAGGTG |
| | CTGATATGATCCTTTCCGGAACGCACATACTGGTCATCAC |
| | CCAGTTTGAGATTTTGAAGGAGCATTAAAAACAAAAATGG |
| | GCACATCATTGGCCCCCATTTGCTATGATCCATACTGTAG |
| | TTCAACAACCCCTCTCGCACATTGATGGTCATTGATAGAA |
| | TTGCATTTTCAAATTCTTTGTCATTGTTTAAGCATGAACC |
| | TGAGAAGAAGCTAGAAAAAGACTCAAAATAATCCTCTATC |
| | AATCTTGTAAACATTTTTGTTCTCAAATCCCCAATATAAA |
| | GTTCTCTGTTTCCTCCAACCTGCTCTTTGTATGATAACGC |
| | AAACTTCAACCTTCCGGAATCAGGACCAACTGAAGTGTAT |
| | GACGTTGGTGACTCCTCTGAGTAAAAACATAAATTCTTTA |
| | AAGCAGCACTCATGCATTTTGTCAATGATAGAGCCTTACT |
| | TAGAGACTCAGAATTACTTTCCCTTTCACTAATTCTAACA |
| | TCTTCTTCTAGTTTGTCCCAGTCAAACTTGAAATTCAGAC |
| | CTTGTCTTTGCATGTGCCTGTATTTCCCTGAGTATGCATT |
| | TGCATTCATTTGCAGTAGAATCATTTTCATACACGAAAAC |
| | CAATCACCCTCTGAAAAAAACTTCCTGCAGAGGTTTTTTG |
| | CCATTTCATCCAGACCACATTGTTCTTTGACAGCTGAAGT |
| | GAAATACAATGGTGACAGTTCTGTAGAAGTTTCAATAGCC |
| | TCACAGATAAATTTCATGTCATCATTGGTGAGACAAGATG |
| | GGTCAAAATCTTCCACAAGATGAAAAGAAATTTCTGATAA |
| | GATGACCTTCCTTAAATATGCCATTTTACCTGACAATATA |
| | GTCTGAAGGTGATGCAATCCTTTTGTATTTTCAAACCCCA |
| | CCTCATTTTCCCCTTCATTGGTCTTCTTGCTTCTTTCATA |
| | CCGCTTTATTGTGGAGTTGACCTTATCTTCTAAATTCTTG |
| | AAGAAACTTGTCTCTTCTTCCCCATCAAAGCATATGTCTG |
| | CTGAGTCACCTTCTAGTTTCCCAGCTTCTGTTTCTTTAGA |
| | GCCGATAACCAATCTAGAGACCAACTTTGAAACCTTGTAC |
| | TCGTAATCTGAGTGGTTCAATTTGTACTTCTGCTTTCTCA |
| | TGAAGCTCTCTGTGATCTGACTCACAGCACTAACAAGCAA |
| | TTTGTTAAAATCATACTCTAGGAGCCGTTCCCCATTTAAA |
| | TGTTTGTTAACAACCACACTTTTGTTGCTGGCAAGGTCTA |
| | ATGCTGTTGCACACCCAGAGTTAGTCATGGGATCCAAGCT |
| | ATTGAGCCTCTTCTCCCCTTTGAAAATCAAAGTGCCATTG |
| | TTGAATGAGGACACCATCATGCTAAAGGCCTCCAGATTGA |
| | CACCTGGGGTTGTGCGCTGACAGTCAACTTCTTTCCCAGT |
| | GAACTTCTTCATTTGGTCATAAAAAACACACTCTTCCTCA |
| | GGGGTGATTGACTCTTTAGGGTTAACAAAGAAGCCAAACT |
| | CACTTTTAGGCTCAAAGAATTTCTCAAAGCATTTAATTTG |
| | ATCTGTCAGCCTATCAGGGGTTTCCTTTGTGATTAAATGA |
| | CACAGGTATGACACATTCAACATGAACTTGAACTTTGCGC |
| | TCAACAGTACCTTTTCACCAGTCCCAAAAACAGTTTTGAT |
| | CAAAAATCTGAGCAATTTGTACACTACTTTCTCAGCAGGT |
| | GTGATCAAATCCTCCTTCAACTTGTCCATCAATGATGTGG |
| | ATGAGAAGTCTGAGACAATGGCCATCACTAAATACCTAAT |
| | GTTTTGAACCTGTTTTTGATTCCTCTTTGTTGGGTTGGTG |
| | AGCATGAGTAATAATAGGGTTCTCAATGCAATCTCAACAT |
| | CATCAATGCTGTCCTTCAAGTCAGGACATGATCTGATCCA |
| | TGAGATCATGGTGTCAATCATGTTGTGCAACACTTCATCT |
| | GAGAAGATTGGTAAAAAGAACCTTTTTGGGTCTGCATAAA |
| | AAGAGATTAGATGGCCATTGGGACCTTGTATAGAATAACA |
| | CCTTGAGGATTCTCCAGTCTTTTGATACAGCAGGTGATAT |
| | TCCTCAGAGTCCAATTTTATCACTTGGCAAAATACCTCTT |
| | TACATTCCACCACTTGATACCTTACAGAGCCCAATTGGTT |
| | TTGTCTTAATCTAGCAACTGAACTTGTTTTCATACTGTTT |
| | GTCAAAGCTAGACAGACAGATGACAATCTTTTCAAACTAT |
| | GCATGTTCCTTAATTGTTCCGTATTAGGCTGGAAATCATA |
| | ATCTTCAAACTTTGTATAATACATTATAGGATGAGTTCCG |
| | GACCTCATGAAATTCTCAAACTCAATAAATGGTATGTGGC |
| | ACTCATGCTCAAGATGTTCAGACAGACCATAGTGCCCAAA |
| | ACTAAGTCCCACCACTGACAAGCACCTTTGAACTTTTAAA |
| | ATGAACTCATTTATGGATGTTCTAAACAAATCCTCAAGAG |
| | ATACCTTTCTATACGCCTTTGACTTTCTCCTGTTCCTTAG |
| | AAGTCTGATGAACTCTTCCTTGGTGCTATGAAAGCTCACC |
| | AACCTATCATTCACACTCCCATAGCAACAACCAACCCAGT |
| | GCTTATCATTTTTTGACCCTTTGAGTTTAGACTGTTTGAT |
| | CAACGAAGAGAGACACAAGACATCCAAATTCAGTAACTGT |
| | CTCCTTCTGGTGTTCAATAATTTTAAACTTTTAACTTTGT |
| | TCAACATAGAGAGGAGCCTCTCATACTCAGTGCTAGTCTC |
| | ACTTCCTCTCTCATAACCATGGGTATCTGCTGTGATAAAT |

TABLE 5-continued

| SEQ ID NO. | Description | Sequence |
|---|---|---|
| | | CTCATCAAAGGACAGGATTCAACTGCCTCCTTGCTTAGTG<br>CTGAAATGTCATCACTGTCAGCAAGAGTCTCATAAAGCTC<br>AGAGAATTCCTTAATTAAATTTCCGGGGTTGATTTTCTGA<br>AAACTCCTCTTGAGCTTCCCAGTTTCCAAGTCTCTTCTAA<br>ACCTGCTGTAAAGGGAGTTTATGCCAAGAACCACATCATC<br>GCAGTTCATGTTTGGGTTGACACCATCATGGCACATTTTC<br>ATAATTTCATCATTGTGAAATGATCTTGCATCTTTCAAGA<br>TTTTCATAGAGTCTATACCGGAACGCTTATCAACAGTGGT<br>CTTGAGAGATTCGCAAAGTCTGAAGTACTCAGATTCCTCA<br>AAGACTTTCTCATCTTGGCTAGAATACTCTAAAAGTTTAA<br>ACAGAAGGTCTCTGAACTTGAAATTCACCCACTCTGGCAT<br>AAAGCTGTTATCATAATCACACCGACCATCCACTATTGGG<br>ACCAATGTGATACCCGCAATGGCAAGGTCTTCTTTGATAC<br>AGGCTAGTTTATTGGTGTCCTCTATAAATTTCTTCTCAAA<br>ACTAGCTGGTGTGCTTCTAACGAAGCACTCAAGAAGAATG<br>AGGGAATTGTCAATCAGTTTATAACCATCAGGAATGATCA<br>AAGGCAGTCCCGGGCACACAATCCCAGACTCTATTAGAAT<br>TGCCTCAACAGATTTATCATCATGGTTGTGTATGCAGCCG<br>CTCTTGTCAGCACTGTCTATCTCTATACAACGCGACAAAA<br>GTTTGAGTCCCTCTATCAATACCATTCTGGGTTCTCTTTG<br>CCCTAAAAAGTTGAGCTTCTGCCTTGACAACCTCTCATCT<br>TGTTCTATGTGGTTTAAGCACAACTCTCTCAACTCCGAAA<br>TAGCCTCATCCATTGCGCATCAAAAAGCCTAGGATCCTCG<br>GTGCG |
| 5 | Lymphocytic choriomeningitis strain MP segment S, complete sequence (The genomic segment is RNA, the sequence in SEQ ID NO: 5 is shown for DNA; however, exchanging all thymidines ("T") in SEQ ID NO: 5 for uridines ("U") provides the RNA sequence.) | CGCACCGGGGATCCTAGGCTTTTTGGATTGCGCTTTCCTC<br>AGCTCCGTCTTGTGGGAGAATGGGTCAAATTGTGACGATG<br>TTTGAGGCTCTGCCTCACATCATTGATGAGGTCATTAACA<br>TTGTCATTATCGTGCTTATTATCATCACGAGCATCAAAGC<br>TGTGTACAATTTCGCCACCTGCGGGATACTTGCATTGATC<br>AGCTTTCTTTTTCTGGCTGGCAGGTCCTGTGGAATGTATG<br>GTCTTGATGGGCCTGACATTTACAAAGGGGTTTACCGATT<br>CAAGTCAGTGGAGTTTGACATGTCTTACCTTAACCTGACG<br>ATGCCCAATGCATGTTCGGCAAACAACTCCCATCATTATA<br>TAAGTATGGGGACTTCTGGATTGGAGTTAACCTTCACAAA<br>TGACTCCATCATCACCCACAACTTTTGTAATCTGACTTCC<br>GCCCTCAACAAGAGGACTTTTGACCACACACTTATGAGTA<br>TAGTCTCAAGTCTGCACCTCAGCATTAGAGGGGTCCCCAG<br>CTACAAAGCAGTGTCCTGTGATTTTAACAATGGCATCACT<br>ATTCAATACAACCTGTCATTTTCTAATGCACAGAGCGCTC<br>TGAGTCAATGTAAGACCTTCAGGGGGAGAGTCCTGGATAT<br>GTTCAGAACTGCTTTTGGAGGAAAGTACATGAGGAGTGGC<br>TGGGGCTGGACAGGTTCAGATGGCAAGACTACTTGGTGCA<br>GCCAGACAAACTACCAATATCTGATTATACAAAACAGGAC<br>TTGGGAAAACCACTGCAGGTACGCAGGCCCTTTCGGAATG<br>TCTAGAATTCTCTTCGCTCAAGAAAAGACAAGGTTTCTAA<br>CTAGAAGGCTTGCAGGCACATTCACTTGGACTTTATCAGA<br>CTCATCAGGAGTGGAGAATCCAGGTGGTTACTGCTTGACC<br>AAGTGGATGATCCTCGCTGCAGAGCTCAAGTGTTTTGGGA<br>ACACAGCTGTTGCAAAGTGCAATGTAAATCATGATGAAGA<br>GTTCTGTGATATGCTACGACTGATTGATTACAACAAGGCT<br>GCTTTGAGTAAATTCAAAGAAGATGTAGAATCCGCTCTAC<br>ATCTGTTCAAGACAACAGTGAATTCTTTGATTTCTGATCA<br>GCTTTTGATGAGAAATCACCTAAGAGACTTGATGGGAGTG<br>CCATACTGCAATTACTCGAAATTCTGGTATCTAGAGCATG<br>CAAAGACTGGTGAGACTAGTGTCCCCAAGTGCTGGCTTGT<br>CAGCAATGGTTCTTATTTGAATGAAACCCATTTCAGCGAC<br>CAAATTGAGCAGGAAGCAGATAATATGATCACAGAAATGC<br>TGAGAAAGGACTACATAAAAAGGCAAGGGAGTACCCCTCT<br>AGCCTTGATGGATCTATTGATGTTTTCTACATCAGCATAT<br>TTGATCAGCATCTTTCTGCATCTTGTGAGGATACCAACAC<br>ACAGACACATAAAGGGCGGCTCATGCCCAAAACCACATCG<br>GTTAACCAGCAAGGGAATCTGTAGTTGTGGTGCATTTAAA<br>GTACCAGGTGTGGAAACCACCTGGAAAAGACGCTGAACAG<br>CAGCGCCTCCCTGACTCACCACCTCGAAAGAGGTGGTGAG<br>TCAGGGAGGCCCAGAGGGTCTTAGAGTGTTACGACATTTG<br>GACCTCTGAAGATTAGGTCATGTGGTAGGATATTGTGGAC<br>AGTTTTCAGGTCGGGGAGCCTTGCCTTGGAGGCGCTTTCA<br>AAGATGATACAGTCCATGAGTGCACAGTGTGGGGTGACCT<br>CTTTCTTTTTCTTGTCCCTCACTATTCCAGTGTGCATCTT<br>GCATAGCCAGCCATATTTGTCCCAGACTTTGTCCTCATAT<br>TCTCTTGAAGCTTCTTTAGTCATCTCAACATCGATGAGCT<br>TAATGTCTCTTCTGTTTTGTGAATCTAGGAGTTTCCTGAT<br>GTCATCAGATCCCTGACAACTTAGGACCATTCCCTGTGGA<br>AGAGCACCTATTACTGAAGATGTCAGCCCAGGTTGTGCAT<br>TGAAGAGGTCAGCAAGGTCCATGCCATGTGAGTATTTGGA<br>GTCCTGCTTGAATTGTTTTTGATCAGTGGGTTCTCTATAG |

TABLE 5-continued

| SEQ ID NO. | Description | Sequence |
|---|---|---|
| | | AAATGTATGTACTGCCCATTCTGTGGCTGAAATATTGCTA<br>TTTCTACCGGGTCATTAAATCTGCCCTCAATGTCAATCCA<br>TGTAGGAGCGTTAGGGTCAATACCTCCCATGAGGTCCTTC<br>AGCAACATTGTTTGGCTGTAGCTTAAGCCCACCTGAGGTG<br>GGCCCGCTGCCCCAGGCGCTGGTTTGGGTGAGTTGGCCAT<br>AGGCCTCTCATTTGTCAGATCAATTGTTGTGTTCTCCCAT<br>GCTCTCCCTACAACTGATGTTCTACAAGCTATGTATGGCC<br>ACCCCTCCCCTGAAAGACAGACTTTGTAGAGGATGTTCTC<br>GTAAGGATTCCTGTCTCCAACCTGATCAGAAACAAACATG<br>TTGAGTTTCTTCTTGGCCCCAAGAACTGCTTTCAGGAGAT<br>CCTCACTGTTGCTTGGCTTAATTAAGATGGATTCCAACAT<br>GTTACCCCCATCTAACAAGGCTGCCCCTGCTTTCACAGCA<br>GCACCGAGACTGAAATTGTAGCCAGATATGTTGATGCTAG<br>ACTGCTGCTCAGTGATGACTCCCAAGACTGGGTGCTTGTC<br>TTTCAGCCTTTCAAGGTCACTTAGGTTCGGGTACTTGACT<br>GTGTAAAGCAGCCCAAGGTCTGTGAGTGCTTGCACAACGT<br>CATTGAGTGAGGTTTGTGATTGTTTGGCCATACAAGCCAT<br>TGTTAAGCTTGGCATTGTGCCGAATTGATTGTTCAGAAGT<br>GATGAGTCCTTCACATCCCAGACCCTCACCACACCATTTG<br>CACTCTGCTGAGGTCTCCTCATTCCAACCATTTGCAGAAT<br>CTGAGATCTTTGGTCAAGCTGTTGTGCTGTTAAGTTCCCC<br>ATGTAGACTCCAGAAGTTAGAGGCCTTTCAGACCTCATGA<br>TTTTAGCCTTCAGTTTTTCAAGGTCAGCTGCAAGGGACAT<br>CAGTTCTTCTGCACTAAGCCTCCCTACTTTTAGAACATTC<br>TTTTTTGATGTTGACTTTAGGTCCACAAGGGAATACACAG<br>TTTGGTTGAGGCTTCTGAGTCTCTGTAAATCTTTGTCATC<br>CCTCTTCTCTTTCCTCATGATCCTCTGAACATTGCTCACC<br>TCAGAGAAGTCTAATCCATTCAGAAGGCTGGTGGCATCCT<br>TGATCACAGCAGCTTTCACATCTGATGTGAAGCCTTGAAG<br>CTCTCTCCTCAATGCCTGGGTCCATTGAAAGCTTTTAACT<br>TCTTTGGACAGAGACATTTTGTCACTCAGTGGATTTCCAA<br>GTCAAATGCGCAATCAAAATGCCTAGGATCCACTGTGCG |
| 6 | Amino acid sequence of the NP protein of the MP strain of LCMV | MSLSKEVKSFQWTQALRRELQGFTSDVKAAVIKDATSLLN<br>GLDFSEVSNVQRIMRKEKRDDKDLQRLRSLNQTVYSLVDL<br>KSTSKKNVLKVGRLSAEELMSLAADLEKLKAKIMRSERPL<br>TSGVYMGNLTAQQLDQRSQILQMVGMRRPQQSANGVVRVW<br>DVKDSSLLNNQFGTMPSLTMACMAKQSQTSLNDVVQALTD<br>LGLLYTVKYPNLSDLERLKDKHPVLGVITEQQSSINISGY<br>NFSLGAAVKAGAALLDGGNMLESILIKPSNSEDLLKAVLG<br>AKKKLNMFVSDQVGDRNPYENILYKVCLSGEGWPYIACRT<br>SVVGRAWENTTIDLTNERPMANSPKPAPGAAGPPQVGLSY<br>SQTMLLKDLMGGIDPNAPTWIDIEGRFNDPVEIAIFQPQN<br>GQYIHFYREPTDQKQFKQDSKYSHGMDLADLFNAQPGLTS<br>SVIGALPQGMVLSCQGSDDIRKLLDSQNRRDIKLIDVEMT<br>KEASREYEDKVWDKYGWLCKMHTGIVRDKKKKEVTPHCAL<br>MDCIIFESASKARLPDLKTVHNILPHDLIFRGPNVVTL |
| 7 | Amino acid sequence of the GP protein of the MP strain of LCMV | MGQIVTMFEALPHIIDEVINIVIIVLIIITSIKAVYNFAT<br>CGILALISFLFLAGRSCGMYGLDGPDIYKGVYRFKSVEFD<br>MSYLNLTMPNACSANNSHHYISMGTSGLELTFTNDSIITH<br>NFCNLTSALNKRTFDHTLMSIVSSLHLSIRGVPSYKAVSC<br>DFNNGITIQYNLSFSNAQSALSQCKTFRGRVLDMFRTAFG<br>GKYMRSGWGWTGSDGKTTWCSQTNYQYLIIQNRTWENHCR<br>YAGPFGMSRILFAQEKTRFLTRRLAGTFTWTLSDSSGVEN<br>PGGYCLTKWMILAAELKCFGNTAVAKCNVNHDEEFCDMLR<br>LIDYNKAALSKFKEDVESALHLFKTTVNSLISDQLLMRNH<br>LRDLMGVPYCNYSKFWYLEHAKTGETSVPKCWLVSNGSYL<br>NETHFSDQIEQEADNMITEMLRKDYIKRQGSTPLALMDLL<br>MFSTSAYLISIFLHLVRIPTHRHIKGGSCPKPHRLTSKGI<br>CSCGAFKVPGVETTWKRR |
| 8 | amino acid sequence of the L protein of the MP strain of LCMV | MDEAISELRELCLNHIEQDERLSRQKLNFLGQREPRMVLI<br>EGLKLLSRCIEIDSADKSGCIHNHDDKSVEAILIESGIVC<br>PGLPLIIPDGYKLIDNSLILLECFVRSTPASFEKKFIEDT<br>NKLACIKEDLAIAGITLVPIVDGRCDYDNSFMPEWVNFKF<br>RDLLFKLLEYSSQDEKVFEESEYFRLCESLKTTVDKRSGI<br>DSMKILKDARSFHNDEIMKMCHDGVNPNMNCDDVVLGINS<br>LYSRFRRDLETGKLKRSFQKINPGNLIKEFSELYETLADS<br>DDISALSKEAVESCPLMRFITADTHGYERGSETSTEYERL<br>LSMLNKVKSLKLLNTRRRQLLNLDVLCLSSLIKQSKLKGS<br>KNDKHWVGCCYGSVNDRLVSFHSTKEEFIRLLRNRRKSKA<br>YRKVSLEDLFRTSINEFILKVQRCLSVVGLSFGHYGLSEH<br>LEHECHIPPIEFENFMRSGTHPIMYYTKFEDYDFQPNTEQ<br>LRNMHSLKRLSSVCLALTNSMKTSSVARLRQNQLGSVRYQ<br>VVECKEVFCQVIKLDSEEYHLLYQKTGESSRCYSIQGPNG<br>HLISFYADPKRFFLPIFSDEVLHNMIDTMISWIRSCPDLK |

TABLE 5-continued

| SEQ ID NO. | Description | Sequence |
|---|---|---|
| | | DSIDDVEIALRTLLLLMLTNPTKRNQKQVQNIRYLVMAIV
SDFSSTSLMDKLKEDLITPAEKVVYKLLRFLIKTVFGTGE
KVLLSAKFKFMLNVSYLCHLITKETPDRLTDQIKCFEKFF
EPKSEFGFFVNPKESITPEEECVFYDQMKKFTGKEVDCQR
TTPGVNLEAFSMMVSSFNNGTLIFKGEKRLNSLDPMTNSG
CATALDLASNKSVVVNKHLNGERLLEYDFNKLLVSAVSQI
TESFMRKQKYKLNHSDYEYKVSKLVSRLVIGSKETEAGKL
EGDSADICFDGEEETSFFKNLEDKVNSTIKRYERSKKTNE
GENEVGFENTKGLHHLQTILSGKMAYLRKVILSEISFHLV
EDFDPSCLTNDDMKFICEAIETSTELSPLYFTSAVKEQCG
LDEMAKNLCRKFFSEGDWFSCMKMILLQMNANAYSGKYRH
MQRQGLNFKFDWDKLEEDVRISERESNSESLSKALSLTKC
MSAALKNLCFYSEESPTSYTSVGPDSGRLKFALSYKEQVG
GNRELYIGDLRTKMFTRLIEDYFESFSSFFSGSCLNNDKE
FENAILSMTINVREGLLNYSMDHSKWGPMMCPFLFLMLLQ
NLKLGDDQYVRSGKDHISTLLTWHMHKLVEVPFPVVNAMM
KSYIKSKLKLLRGSETTVTERIFREYFELGIVPSHISSLI
DMGQGILHNASDFYGLISERFINYCIGVIFGERPESYTSS
DDQITLFDRRLSELVDSDPEEVLVLLEFHSHLSGLLNKFI
SPKSVVGRFAAEFKSRFYVWGEEVPLLTKFVSAALHNVKC
KEPHQLCETIDTIADQAVANGVPVSLVNCIQKRTLDLLKY
ANFPLDPFLLNTNTDVKDWLDGSRGYRIQRLIEELCPSET
KVMRRLVRRLHHKLKNGEFNEEFFLDLFNRDKKEAILQLG
NILGLEEDLSQLANINWLNLNELFPLRMVLRQKVVYPSVM
TFQEERIPSLIKTLQNKLCSKFTRGAQKLLSEAINKSAFQ
SCISSSGFIGLCKTLGSRCVRNKNRDNLYIRKVLEDLAMDA
HVTAIHRHDGIMLYICDRQSHPEAHCDHISLLRPLLWDYI
CISLSNSFELGVWVLAEPVKGKNEGSSSLKHLNPCDYVAR
KPESSRLLEDKISLNHVIQSVRRLYPKIYEDQLLPFMSDM
SSKNMRWSPRIKFLDLCVLIDINSESLSLISHVVKWKRDE
HYTVLFSDLVNSHQRSDSSLVDEFVVSTRDVCKNFLKQVY
FESFVREFVATSRTLGSFSWFPHKDMMPSEDGAEALGPFQ
SFILKVVNKNMERPMFRNDLQFGFGWFSYRLGDIVCNAAM
LIKQGLTNPKAFKSLRNLWDYMINNTEGVLEFSITVDFTH
NQNNTDCLRKFSLIFLVKCQLQGPGVAEFLSCSHLFKGEV
DRRFLDECLHLLRSDSIFKVNDGVFDIRSEEFEDYMEDPL
ILGDSLELELIGSRKILDGIRSLDFERIGPEWEPVPLTVR
MGALFEGRSLVQNIVVKLETKDMRVFLAELEGYGNFDDVL
GSLLLHRFRTGEHLQGSEISTILQELCIDRSILLVPLSLV
PDWFTFKDCRLCFSKSKNTVMYETVVGKYRLKGKSCDDWL
TKSVVEEID |
| 9 | Amino acid sequence of the Z protein of the MP strain of LCMV | MGQGKSKEGRDASNTSRAEILPDTTYLGPLNCKSCWQRFD
SLVRCHDHYLCRHCLNLLLSVSDRCPLCKHPLPTKLKIST
APSSPPPYEE |
| 10 | Junin virus Candid#1 L segment | GCGCACCGGGGATCCTAGGCGTAACTTCATCATTAAAATCTCAGAT
TCTGCTCTGAGTGTGACTTACTGCGAAGAGGCAGACAAATGGGCAA
CTGCAACGGGGCATCCAAGTCTAACCAGCCAGACTCCTCAAGAGCC
ACACAGCCAGCCGCAGAATTTAGGAGGGTAGCTCACAGCAGTCTAT
ATGGTAGATATAACTGTAAGTGCTGCTGGTTTGCTGATACCAATTT
GATAACCTGTAATGATCACTACCTTTGTTTAAGGTGCCATCAGGGT
ATGTTAAGGAATTCAGATCTCTGCAATATCTGCTGGAAGCCCCTGC
CCACCACAATCACAGTACCGGTGGAGCCAACAGCACCACCACCATA
GGCAGACTGCACAGGGTCAGACCCGACCCCCCGGGGGGCCCCCATG
GGGACCCCCCGTGGGGGAACCCCGGGGGTGATGCGCCATTAGTCAA
TGTCTTTGATCTCGACTTTGTGCTTCAGTGGCCTGCATGTCACCCC
TTTCAATCTGAACTGCCCTTGGGGATCTGATATCAGCAGGTCATTT
AAAGATCTGCTGAATGCCACCTTGAAATTTGAGAATTCCAACCAGT
CACCAAATTTATCAAGTGAACGGATCAACTGCTCTTTGTGTAGATC
ATAAACGAGGACAAAGTCCTCTTGCTGAAATAATATTGTTTGTGAT
GTTGTTTTAGATAAGGCCATAGTTGGCTTAATAAGGTTTCCACAC
TATCAATGTCCTCTAGTGCTCCAATTGCCTTGACTATGACATCCCC
AGACAACTCAACTCTATATGTTGACAACCTTTCATTACCTCTGTAA
AAGATACCCTCTTTCAAGACAAGAGGTTCTCCTGGGTTATCTGGCC
CAATGAGGTCATATGCATACTTGTTACTTAGTTCAGAATAAAAGTC
ACCAAAGTTGAACTTAACATGGCTCAGAATATTGTCATCATTTGTC
GCAGCGTAGCCTGCATCAATAAACAAGCCAGCTAGGTCAAAGCTCT
CATGGCCTGTGAACAATGGTAGGCTAGCGATAACCAGTGCACCATC
CAACAATGAGTGGCTTCCCTCAGACCCAGAAACACATTGACTCATT
GCATCCACATTCAGCTCTAATTCAGGGGTACCGACATCATCCACTC
CTAGTGAACTGACAATGGTGTAACTGTACACCATCTTTCTTCTAAG
TTTAAATTTTGTCGAACTCGTGTGTGTTCTACTTGAATGATCAAT
TTTAGTTTCACAGCTTCTTGGCAAGCAACATTGCGCAACACAGTGT
GCAGGTCCATCATGTCTTCCTGAGGCAACAAGGAGATGTTGTCAAC
AGAGACACCCTCAAGGAAAACCTTGATATTATCAAAGCTAGAAACT |

TABLE 5-continued

| SEQ ID NO. | Description | Sequence |
|---|---|---|
| | | ACATAACCCATTGCAATGTCTTCAACAAACATTGCTCTTGATACTT
TATTATTCCTAACTGACAAGGTAAAATCTGTGAGTTCAGCTAGATC
TACTTGACTGTCATCTTCTAGATCTAGAACTTCATTGAACCAAAAG
AAGGATTTGAGACACGATGTTGACATGACTAGTGGGTTTATCATCG
AAGATAAGACAACTTGCACCATGAAGTTCCTGCAAACTTGCTGTGG
GCTGATGCCAACTTCCCAATTTGTATACTCTGACTGTCTAACATGG
GCTGAAGCGCAATCACTCTGTTTCACAATATAAACATTATTATCTC
TTACTTTCAATAAGTGACTTATAATCCCTAAGTTTTCATTCATCAT
GTCTAGAGCCACACAGACATCTAGAAACTTGAGTCTTCCACTATCC
AAAGATCTGTTCACTTGAAGATCATTCATAAAGGGTGCCAAATGTT
CTTCAAATAGTTTGGGGTAATTTCTTCGTATAGAATGCAATACATG
GTTCATGCCTAATTGGTCTTCTATCTGTCGTACTGCTTTGGGTTTA
ACAGCCCAGAAGAAATTCTTATTACATAAGACCAGAGGGGCCTGTG
GACTCTTAATAGCAGAAAACACCCACTCCCCTAACTCACAGGCATT
TGTCAGCACCAAAGAGAAGTAATCCCACAAAATTGGTTTAGAAAAT
TGGTTAACTTCTTTAAGTGATTTTTGACAGTAAATAACTTTAGGCT
TTCTCTCACAAATTCCACAAAGACATGGCATTATTCGAGTAAATAT
GTCCTTTATATACAGAAATCCGCCTTTACCATCCCTAACACACTTA
CTCCCCATACTCTTACAAAACCCAATGAAGCCTGAGGCAACAGAAG
ACTGAAATGCAGATTTGTTGATTGACTCTGCCAAGATCTTCTTCAC
GCCTTTTGTGAAATTTCTTGACAGCCTGGACTGTATTGTCCTTATC
AATGTTGGCATCTCTTCTTTCTCTAACACTCTTCGACTTGTCATGA
GTTTGGTCCTCAAGACCAACCTCAAGTCCCCAAAGCTCGCTAAATT
GACCCATCTGTAGTCTAGAGTTTGTCTGATTTCATCTTCACTACAC
CCGGCATATTGCAGGAATCCGGATAAAGCCTCATCCCCTCCCCTGC
TTATCAAGTTGATAAGGTTTTCCTCAAAGATTTTGCCTCTCTTAAT
GTCATTGAACACTTTCCTCGCGCAGTTCCTTATAAACATTGTCTCC
TTATCATCAGAAAAAATAGCTTCAATTTTCCTCTGTAGACGGTACC
CTCTAGACCCATCAACCCAGTCTTTGACATCTTGTTCTTCAATAGC
TCCAAACGGAGTCTCTCTGTATCCAGAGTATCTAATCAATTGGTTG
ACTCTAATGGAAATCTTTGACACTATATGAGTGCTAACCCCATTAG
CAATACATTGATCACAAATTGTGTCTATGGTCTCTGACAGTTGTGT
TGGAGTTTTACACTTAACGTTGTGTAGAGCAGCAGACACAAACTTG
GTGAGTAAAGGAGTCTCTTCACCCATGACAAAAAATCTTGACTTAA
ACTCAGCAACAAAAGTTCCTATCACACTCTTTGGGCTGATAAACTT
GTTTAATTTAGAAGATAAGAATTCATGGAAGCACACCATTTCCAGC
AGTTCTGTCCTGTCTTGAAACTTTTCATCACTAAGGCAAGGAATTT
TTATAAGGCTAACCTGGTCATCGCTGGAGGTATAAGTGACAGGTAT
CACATCATACAATAAGTCAAGTGCATAACACAGAAATTGTTCAGTA
ATTAGCCCATATAAATCTGATGTGTTGTGCAAGATTCCCTGGCCCA
TGTCCAAGACAGACATTATATGGCTGGGGACCTGGTCCCTTGACTG
CAGATACTGGTGAAAAACTCTTCACCAACACTAGTACAGTCACAA
CCCATTAAACCTAAAGATCTCTTCAATTTCCCTACACAGTAGGCTT
CTGCAACATTAATTGGAACTTCAACGACCTTATGAAGATGCCATTT
GAGAATGTTCATTACTGGTTCAAGATTCACCTTTGTTCTATCTCTG
GGATTCTTCAATTCTAATGTGTACAAAAAAGAAAGGAAAAGTGCTG
GGCTCATAGTTGGTCCCCATTTGGAGTGGTCATATGAACAGGACAA
GTCACCATTGTTAACAGCCATTTTCATATCACAGATTGCACGTTCG
AATTCCTTTTCTGAATTCAAGCATGTGTATTTCATTGAACTACCCA
CAGCTTCTGAGAAGTCTTCAACTAACCTGGTCATCAGCTTAGTGTT
GAGGTCTCCCACATACAGTTCTCTATTTGAGCCAACCTGCTCCTTA
TAACTTAGTCCAAATTTCAAGTTCCCTGTATTTGAGCTGATGCTTG
TGAACTCTGTAGGAGAGTCGTCTGAATAGAAACATAAATTCCGTAG
GGCTGCATTTGTAAAATAACTTTTGTCTAGCTTATCAGCAATGGCT
TCAGAATTGCTTTCCCTGGTACTAAGCCGAACCTCATCCTTTAGTC
TCAGAACTTCACTGGAAAAGCCCAATCTAGATCTACTTCTATGCTC
ATAACTACCCAATTTCTGATCATAATGTCCTTGAATTAAAAGATAC
TTGAAGCATTCAAAGAATTCATCTTCTTGGTAGGCTATTGTTGTCA
AATTTTTTAATAACAAACCCAAAGGGCAGATGTCCTGCGGTGCTTC
AAGAAAATAAGTCAATTTAAATGGAGATAGATAAACAGCATCACAT
AACTCTTTATACACATCAGACCTGAGCACATCTGGATCAAAATCCT
TCACCTCATGCATTGACACCTCTGCTTTAATCTCTCAACACTCC
AAAAGGGGCCCACAATGACTCAAGAGACTCTCGCTCATCAACAGAT
GGATTTTTTGATTTCAACTTGGTGATCTCAACTTTTGTCCCCTCAC
TATTAGCCATCTTGGCTAGTGTCATTTGTACGTCATTTCTAATACC
CTCAAAGGCCCTTACTTGATCCTCTGTTAAACTCTCATACATCACT
GATAATTCTTCTTGATTGGTTCTGGTTCTTGAACCGGTGCTCACAA
GACCTGTTAGATTTTTTAATATTAAGTAGTCCATGGAATCAGGATC
AAGATTATACCTGCCTTTTGTTTTAAACCTCTCAGCCATAGTAGAA
ACGCATGTTGAAACAAGTTTCTCCTTATCATAAACAGAAAGAATAT
TTCCAAGTTCGTCGAGCTTGGGGATTACCACACTTTTATTGCTTGA
CAGATCCAGAGCTGTGCTAGTGATGTTAGGCCTGTAGGGATTGCTT
TTCAGTTCACCTGTAACTTTAAGTCTTCCTCTATTGAAGAGAGAAA
TGCAGAAGGACAAAATCTCTTTACACACTCCTGGAATTTGAGTATC
TGAGGAAGTCTTAGCCTCTTTGGAAAAGAATCTGTCCAATCCTCTT
ATCATGGTGTCCTCTTGTTCCAGTGTTAGACTCCCACTTAGAGGGG
GGTTTACAACAACACAATCAAACTTGACTTTGGGCTCAATAAACTT |

TABLE 5-continued

| SEQ ID NO. | Description | Sequence |
|---|---|---|
| | | CTCAAAACACTTTATTTGATCTGTCAGGCGATCAGGTGTCTCTTTG
GTTACCAAGTGACACAGATAACTAACATTTAATAGATATTTAAACC
TTCTTGCAAAGTAAAGATCTGCATCTTCCCCTTCACCCAAAATTGT
CTGGAAAAGTTCCACAGCCATCCTCTGAATCAGCACCTCTGATCCA
GACATGCAGTCGACCCTTAACTTTGACATCAAATCCACATGATGGA
TTTGATTTGCATATGCCATCAAGAAATATCTTAGACCTTGTAAAAA
TGTCTGGTTCCTTTTGGAAGGGGAACAGAGTACAGCTAACACTAAC
AATCTTAATATTGGCCTTGTCATTGTCATGAGTTCGTGGCTAAAAT
CCAACCAGCTGGTCATTTCCTCACACATTTCAATTAACACATCCTC
CGAAAATATAGGCAGGAAAAATCTCTTTGGATCACAGTAAAAAGAG
CCTTGTTCTTCCAATACCCCATTGATGGATAGATAGATAGAATAGC
ACCTTGACTTCTCACCTGTTTTTTGGTAAAACAAGAGACCAAATGT
ATTCTTTGTCAGATGAAATCTTTGTACATAACACTCTCTTAGTCTA
ACATTCCCAAAATATCTAGAATACTCTCTTTCATTGATTAACAATC
GGGAGGAAAATGATGTCTTCATCGAGTTGACCAATGCAAGGGAAAT
GGAGGACAAAATCCTAATAATTTCTTCTGCTCACCTTCCACTAAG
CTGCTGAATGGCTGATGTCTACAGATTTTCTCAAATTCCTTGTTAA
TAGTATATCTCATCACTGGTCTGTCAGAAACAAGTGCCTGAGCTAA
AATCATCAAGCTATCCATATCAGGGTGTTTTATTAGTTTTTCCAGC
TGTGACCAGAGATCTTGATGAGAGTTCTTCAATGTTCTGGAACACG
CTTGAACCCACTTGGGGCTGGTCATCAATTTCTTCCTTATTAGTTT
AATCGCCTCCAGAATATCTAGAAGTCTGTCATTGACTAACATTAAC
ATTTGTCCAACAACTATTCCCGCATTTCTTAACCTTACAATTGCAT
CATCATGCGTTTTGAAAAGATCACAAAGTAAATTGAGTAAAACTAA
GTCCAGAAACAGTAAAGTGTTTCTCCTGGTGTTGAAAACTTTTAGA
CCTTTCACTTTGTTACACACGGAAAGGGCTTGAAGATAACACCTCT
CTACAGCATCAATAGATATAGAATTCTCATCTGACTGGCTTTCCAT
GTTGACTTCATCTATTGGATGCAATGCGATAGAGTAGACTACATCC
ATCAACTTGTTTGCACAAAAAGGGCAGCTGGGCACATCACTGTCTT
TGTGGCTTCCTAATAAGATCAAGTCATTTATAAGCTTAGACTTTTG
TGAAAATTTGAATTTCCCCAACTGCTTGTCAAAAATCTCCTTCTTA
AACCAAAACCTTAACTTTATGAGTTCTTCTCTTATGACAGATTCTC
TAATGTCTCCTCTAACCCCAACAAAGAGGGATTCATTTAACCTCTC
ATCATAACCCAAAGAATTCTTTTTCAAGCATTCGATGTTTTCTAAT
CCCAAGCTCTGGTTTTTTGTGTTGGACAAACTATGGATCAATCGCT
GGTATTCTTGTTCTTCAATATTAATCTCTTGCATAAATTTTGATTT
CTTTAGGATGTCGATCAGCAACCACCGAACTCTTTCAACAACCCAA
TCAGCAAGGAATCTATTGCTGTAGCTAGATCTGCCATCAACCACAG
GAACCAACGTAATCCCTGCCCTTAGTAGGTCGGACTTTAGGTTTAA
GAGCTTTGACATGTCACTCTTCCATTTTCTCTCAAACTCATCAGGA
TTGACCCTAACAAAGGTTTCCAATAGGATGAGTGTTTTCCCTGTGA
GTTTGAAGCCATCCGGAATGACTTTTGGAAGGGTGGGACATAGTAT
GCCATAGTCAGACAGGATCACATCAACAAACTTCTGATCTGAATTG
ATCTGACAGGCGTGTGCCTCACAGGACTCAAGCTCTACTAAACTTG
ACAGAAGTTTGAACCCTTCCAACAACAGAGAGCTGGGGTGATGTTG
AGATAAAAAGATGTCCCTTTGGTATGCTAGCTCCTGTCTTTCTGGA
AAATGCTTTCTAATAAGGCTTTTTATTTCATTTACTGATTCCTCCA
TGCTCAAGTGCCGCCTAGGATCCTCGGTGCG |
| 11 | Junin virus Candid#1 S segment | GCGCACCGGGGATCCTAGGCGATTTTGGTTACGCTATAATTGTAAC
TGTTTTCTGTTTGGACAACATCAAAAACATCCATTGCACAATGGGG
CAGTTCATTAGCTTCATGCAAGAAATACCAACCTTTTTGCAGGAGG
CTCTGAACATTGCTCTTGTTGCAGTCAGTCTCATTGCCATCATTAA
GGGTATAGTGAACTTGTACAAAAGTGGTTTATTCCAATTCTTTGTA
TTCCTAGCGCTTGCAGGAAGATCCTGCACAGAAGAAGCTTTCAAAA
TCGGACTGCACACTGAGTTCCAGACTGTGTCCTTCTCAATGGTGGG
TCTCTTTTCCAACAATCCACATGACCTACCTTTGTTGTGTACCTTA
AACAAGAGCCATCTTTACATTAAGGGGGCAATGCTTCATTTCAGA
TCAGCTTTGATGATATTGCAGTATTGTTGCCACAGTATGATGTTAT
AATACAACATCCAGCAGATATGAGCTGGTGTTCCAAAAGTGATGAT
CAAATTTGGTTGTCTCAGTGGTTCATGAATGCTGTGGGACATGATT
GGCATCTAGACCCACCATTTCTGTGTAGGAACCGTGCAAAGACAGA
AGGCTTCATCTTTCAAGTCAACACCTCCAAGACTGGTGTCAATGGA
AATTATGCTAAGAAGTTTAAGACTGGCATGCATCATTTATATAGAG
AATATCCTGACCCTTGCTTGAATGGCAAACTGTGCTTAATGAAGGC
ACAACCTACCAGTTGGCCTCTCCAATGTCCACTCGACCACGTTAAC
ACATTACACTTCCTTACAAGAGGTAAAAACATTCAACTTCCAAGGA
GGTCCTTGAAAGCATTCTTCTCCTGGTCTTTGACAGACTCATCCGG
CAAGGATACCCCTGGAGGCTATTGTCTAGAAGAGTGGATGCTCGTA
GCAGCCAAAATGAAGTGTTTTGGCAATACTGCTGTAGCAAAATGCA
ATTTGAATCATGACTCTGAATTCTGTGACATGTTGAGGCTCTTTGA
TTACAACAAAAATGCTATCAAAACCCTAAATGATGAAACTAAGAAA
CAAGTAAATCTGATGGGGCAGACAATCAATGCCCTGATATCTGACA
ATTTATTGATGAAAACAAAATTAGGGAACTGATGAGTGTCCCTTA
CTGCAATTACACAAAATTTTGGTATGTCAACCACACACTTTCAGGA
CAACACTCATTACCAAGGTGCTGGTTAATAAAAAACAACAGCTATT
TGAACATCTCTGACTTCCGTAATGACTGGATATTAGAAAGTGACTT |

TABLE 5-continued

| SEQ ID NO. | Description | Sequence |
|---|---|---|
| | | CTTAATTTCTGAAATGCTAAGCAAAGAGTATTCGGACAGGCAGGGT<br>AAAACTCCTTTGACTTTAGTTGACATCTGTATTTGGAGCACAGTAT<br>TCTTCACAGCGTCACTCTTCCTTCACTTGGTGGGTATACCCTCCCA<br>CAGACACATCAGGGGCGAAGCATGCCCTTTGCCACACAGGTTGAAC<br>AGCTTGGGTGGTTGCAGATGTGGTAAGTACCCCAATCTAAAGAAAC<br>CAACAGTTTGGCGTAGAGGACACTAAGACCTCCTGAGGGTCCCCAC<br>CAGCCCGGGCACTGCCCGGGCTGGTGTGGCCCCCCAGTCCGCGGCC<br>TGGCCGCGGACTGGGGAGGCACTGCTTACAGTGCATAGGCTGCCTT<br>CGGGAGGAACAGCAAGCTCGGTGGTAATAGAGGTGTAGGTTCCTCC<br>TCATAGAGCTTCCCATCTAGCACTGACTGAAACATTATGCAGTCTA<br>GCAGAGCACAGTGTGGTTCACTGGAGGCCAACTTGAAGGGAGTATC<br>CTTTTCCCTCTTTTTCTTATTGACAACCACTCCATTGTGATATTTG<br>CATAAGTGACCATATTTCTCCCAGACCTGTTGATCAAACTGCCTGG<br>CTTGTTCAGATGTGAGCTTAACATCAACCAGTTTAAGATCTCTTCT<br>TCCATGGAGGTCAAACAACTTCCTGATGTCATCGGATCCTTGAGTA<br>GTCACAACCATGTCTGGAGGCAGCAAGCCGATCACGTAACTAAGAA<br>CTCCTGGCATTGCATCTTCTATGTCCTTCATTAAGATGCCGTGAGA<br>GTGTCTGCTACCATTTTTAAACCCTTTCTCATCATGTGGTTTTCTG<br>AAGCAGTGAATGTACTGCTTACCTGCAGGTTGGAATAATGCCATCT<br>CAACAGGGTCAGTGGCTGGTCCTTCAATGTCGAGCCAAAGGGTGTT<br>GGTGGGGTCGAGTTTCCCCACTGCCTCTCTGATGACAGCTTCTTGT<br>ATCTCTGTCAAGTTAGCCAATCTCAAATTCTGACCGTTTTTTTCCG<br>GCTGTCTAGGACCAGCAACTGGTTTCCTTGTCAGATCAATACTTGT<br>GTTGTCCCATGACCTGCCTGTGATTTGTGATCTAGAACCAATATAA<br>GGCCAACCATCGCCAGAAAGACAAAGTTTGTACAAAAGGTTTTCAT<br>AAGGATTTCTATTGCCTGGTTTCTCATCAATAAACATGCCTTCTCT<br>TCGTTTAACCTGAATGGTTGATTTTATGAGGGAAGAGAAGTTTTCT<br>GGGGTGACTCTGATTGTTTCCAACATGTTTCCACCATCAAGAATAG<br>ATGCTCCAGCCTTTACTGCAGCTGAAAGACTGAAGTTGTAACCAGA<br>AATATTGATGGAGCTTTCATCTTTAGTCACAATCTGAAGGCAGTCA<br>TGTTCCTGAGTCAGTCTGTCAAGGTCACTTAAGTTTGGATACTTCA<br>CAGTGTATAGAAGCCCAAGTGAGGTTAAAGCTTGTATGACACTGTT<br>CATTGTCTCACCTCCTTGAACAGTCATGCATGCAATTGTCAATGCA<br>GGAACAGAGCCAAACTGATTGTTTAGCTTTGAAGGGTCTTTAACAT<br>CCCATATCCTCACCACACCATTTCCCCCAGTCCCTTGCTGTTGAAA<br>TCCCAGTGTTCTCAATATCTCTGATCTTTTAGCAAGTTGTGACTGG<br>GACAAGTTACCCATGTAAACCCCTGAGAGCCTGTCTCTGCTCTTC<br>TTATCTTGTTTTTTAATTTCTCAAGGTCAGACGCCAACTCCATCAG<br>TTCATCCCTCCCCAGATCTCCCACCTTGAAAACTGTGTTTCGTTGA<br>ACACTCCTCATGGACATGAGTCTGTCAACCTCTTTATTCAGGTCCC<br>TCAACTTGTTGAGGTCTTCTTCCCCCTTTTTAGTCTTTCTGAGTGC<br>CCGCTGCACCTGTGCCACTTGGTTGAAGTCGATGCTGTCAGCAATT<br>AGCTTGGCGTCCTTCAAAACATCTGACTTGACAGTCTGAGTGAATT<br>GGCTCAAACCTCTCCTTAAGGACTGAGTCCATCTAAAGCTTGGAAC<br>CTCCTTGGAGTGTGCCATGCCAGAAGTTCTGGTGATTTTGATCTAG<br>AATAGAGTTGCTCAGTGAAAGTGTTAGACACTATGCCTAGGATCCA<br>CTGTGCG |
| 12 | Amino acid sequence of the NP protein of the Clone 13 strain of LCMV (GenBank Accession No. ABC96002.1; GI:86440166) | MSLSKEVKSFQWTQALRRELQSFTSDVKAAVIKDATNLLNGLDFSE<br>VSNVQRIMRKEKRDDKDLQRLRSLNQTVHSLVDLKSTSKKNVLKVG<br>RLSAEELMSLAADLEKLKAKIMRSERPQASGVYMGNLTTQQLDQRS<br>QILQIVGMRKPQQGASGVVRVWDVKDSSLLNNQFGTMPSLTMACMA<br>KQSQTPLNDVVQALTDLGLLYTVKYPNLNDLERLKDKHPVLGVITE<br>QQSSINISGYNFSLGAAVKAGAALLDGGNMLESILIKPSNSEDLLK<br>AVLGAKRKLNMFVSDQVGDRNPYENILYKVCLSGEGWPYIACRTSI<br>VGRAWENTTIDLTSEKPAVNSPRPAPGAAGPPQVGLSYSQTMLLKD<br>LMGGIDPNAPTWIDIEGRFNDPVEIAIFQPQNGQPIHFYREPVDQK<br>QFKQDSKYSHGMDLADLFNAQPGLTSSVIGALPQGMVLSCQGSDDI<br>RKLLLDSQNRKDIKLIDVEMTREASREYEDKVWDKYGWLCKMHTGIV<br>RDKKKKEITPHCALMDCIIFESASKARLPDLKTVHNILPHDLIFRG<br>PNVVTL |
| 13 | Amino acid sequence of the GP protein of the Clone 13 strain of LCMV (GenBank Accession No. ABC96001.2; GI:116563462) | MGQIVTMFEALPHIIDEVINIVIIVLIVITGIKAVYNFATCGIFAL<br>ISFLLLAGRSCGMYGLKGPDIYKGVYQFKSVEFDMSHLNLTMPNAC<br>SANNNSHHYISMGTSGLELTFTNDSIISHNFCNLTSAFNKKTFDHTL<br>MSIVSSLHLSIRGNSNYKAVSCDFNNGITIQYNLTFSDAQSAQSQC<br>RTFBRGRVLDMFRTAFGGKYMRSGWGWTGSDGKTTWCSQTSYQYLII<br>QNRTWENHCTYAGPFGMSRILLSQEKTKFLTRRLAGTFTWTLSDSS<br>GVENPGGYCLTKWMILAAELKCFGNTAVAKCNVNHDEEFCDMLRLI<br>DYNKAALSKFKEDVESALHLFKTTVNSLISDQLLMRNHLRDLMGVP<br>YCNYSKFWYLEHAKTGETSVPKCWLVTNGSYLNETHFSDQIEQEAD<br>NMITEMLRKDYIKRQGSTPLALMDLLMFSTSAYLVSIFLHLVKIPT<br>HRHIKGGSCPKPHRLTNKGICSCGAFKVPGVKTVWKRR |
| 14 | amino acid sequence of the L protein of the Clone 13 strain | MDEIISELRELCLNYIEQDERLSRQKLNFLGQREPRMVLIEGLKLL<br>SRCIEIDSADKSGCTHNHDDKSVETILVESGIVCPGLPLIIPDGYK<br>LIDNSLILLECFVRSTPASFEKKFIEDTNKLACIREDLAVAGVTLV |

TABLE 5-continued

| SEQ ID NO. | Description | Sequence |
|---|---|---|
| | of LCMV (GenBank Accession No. ABC96004.1; GI:86440169) | PIVDGRCDYDNSFMPEWANFKFRDLLFKLLEYSNQNEKVFEESEYF RLCESLKTTIDKRSGMDSMKILKDARSTHNDEIMRMCHEGINPNMS CDDVVFGINSLFSRFRRDLESGKLKRNFQKVNPEGLIKEFSELYEN LADSDDILTLSREAVESCPLMRFITAETHGHERGSETSTEYERLLS MLNKVKSLKLLNTRRQLLNLDVLCLSSLIKQSKFKGLKNDKHWVG CCYSSVNDRLVSFHSTKEEFIRLLRNRKKSKVFRKVSFEELFRASI SEFIAKIQKCLLVVGLSFEHYGLSEHLEQECHIPPFTEFENFMKIGA HPIMYYTKFEDYNFQPSTEQLKNIQSLRRLSSVCLALTNSMKTSSV ARLRQNQIGSVRYQVVECKEVFCQVIKLDSEEYHLLYQKTGESSRC YSIQGPDGHLISFYADPKRFFLPIFSDEVLYNMIDIMISWIRSCPD LKDCLTDIEVALRTLLLLMLTNPTKRNQKQVQSVRYLVMAIVSDFS STSLMDKLREDLITPAEKVVYKLLRFLIKTIFGTGEKVLLSAKFKF MLNVSYLCHLITKETPDRLTDQIKCFEKFFEPKSQFGFFVNPKEAI TPEEECVFYEQMKRFTSKEIDCQHTTPGVNLEAFSLMVSSFNNGTL IFKGEKKLNSLDPMTNSGCATALDLASNKSVVVNKHLNGERLLEYD FNKLLVSAVSQITESFVRKQKYKLSHSDYEYKVSKLVSRLVIGSKG EETGRSEDNLAEICFDGEEETSFFKSLEEKVNTTIARYRRGRRAND KGDGEKLTNTKGLHHLQLILTGKMAHLRKVILSEISFHLVEDFDPS CLTNDDMKFICEAVEGSTELSPLYFTSVIKDQCGLDEMAKNLCRKF FSENDWFSCMKMILLQMNANAYSGKYRHMQRQGLNFKFDWDKLEED VRISERESNSESLSKALSLTQCMSAALKNLCFYSEESPTSYTSVGP DSGRLKFALSYKEQVGGNRELYIGDLRTKMFTRLIEDYFESFSSFF SGSCLNNDKEFENAILSMTINVREGFLNYSMDHSKWGPMMCPFLFL MFLQNLKLGDDQYVRSGKDHVSTLLTWHMHKLVEVPFPVVNAMMKS YVKSKLKLLRGSETTVTERIFRQYFEMGIVPSHISSLIDMGQGILH NASDFYGLLSERFINYCIGVIFGERPEAYTSSDDQITLFDRRLSDL VVSDPEEVLVLLEFQSHLSGLLNKFISPKSVAGRFAAEFKSRFYVW GEEVPLLTKFVSAALHNVKCKEPHQLCETIDTIADQAIANGVPVSL VNSIQRRTLDLLKYANFPLDPFLLNTNTDVKDWLDGSRGYRIQRLI EELCPNETKVVRKLVRKLHHKLKNGEFNEEFFLDLFNRDKKEAILQ LGDLLGLEEDLNQLADVNWLNLNEMFPLRMVLRQKVVYPSVMTFQE ERIPSLIKTLQNKLCSKFTRGAQKLLSEAINKSAFQSCISSGFIGL CKTLGSRCVRNKNRENLYIKKLLEDLTTDDHVTRVCNRDGITLYIC DKQSHPEAHRDHICLLRPLLWDYICISLSNSFELGVWVLAEPTKGK NNSENLTLKHLNPCDYVARKPESSRLLEDKVNLNQVIQSVRRLYPK IFEDQLLPFMSDMSSKNMRWSPRIKFLDLCVLIDINSESLSLISHV VKWKRDEHYTVLFSDLANSHQRSDSSLVDEFVVSTRDVCKNFLKQV YFESFVREFVATTRTLGNFSWFPHKEMMPSEDGAEALGPFQSFVSK VVNKNVERPMFRNDLQFGFGWFSYRMGDVVCNAAMLIRQGLTNPKA FKSLKDLWDYMLNYTKGVLEFSISVDFTHNQNNTDCLRKFSLIFLV RCQLQNPGVAELLSCSHLFKGEIDRRMLDECLHLLRTDSVFKVNDG VFDIRSEEFEDYMEDPLILGDSLELELLGSKRILDGIRSIDFERVG PEWEPVPLTVKMGALFEGRNLVQNIIVKLETKDMKVFLAGLEGYEK ISDVLGNLFLHRFRTGEHLLGSEISVILQELCIDRSILLIPLSLLP DWFAFKDCRLCFSKSRSTLMYETVGGRFRLKGRSCDDWLGGSVAED ID |
| 15 | Amino acid sequence of the Z protein of the Clone 13 strain of LCMV (GenBank Accession No. ABC96003.1; GI:86440168) | MGQGKSREEKGTNSTNRAEILPDTTYLGPLSCKSCWQKFDSLVRCH DHYLCRHCLNLLLSVSDRCPLCKYPLPTRLKISTAPSSPPPYEE |
| 16 | Amino acid sequence of the GP protein of the WE strain of LCMV | MGQIVTMFEALPHIIDEVINIVIIVLIIITSIKAVYNFATCGILAL VSFLFLAGRSCGMYGLNGPDIYKGVYQFKSVEFDMSHLNLTMPNAC SANNSHHYISMGSSGLELTFTNDSILNHNFCNLTSAFNKKTFDHTL MSIVSSLHLSIRGNSNHKAISQCDFNNGITIQYNLSFSDPQSAISQC RTFRGRVLDMFRTAFGGKYMRSGWGWAGSDGKTTWCSQTSYQYLII QNRTWENHCRYAGPFGMSRILFAQEKTKFLTRRLAGTFTWTLSDSS GVENPGGYCLTKWMILAAELKCFGNTAVAKCNVNHDEEFCDMLRLI DYNKAALSKFKQDVESALHVFKTTVNSLISDQLLMRNHLRDLMGVP YCNYSKFWYLEHAKTGETSVPKCWLVTNGSYLNETHFSDQIEQEAD NMITEMLRKDYIKRQGSTPLALMDLLMFSTSAYLISIFLHLVKIPT HRHIKGGSCPKPHRLTNKGICSCGAFKVPGVKTIWKRR |
| 17 | WE specific primer | 5'AATCGTCTCTAAGGATGGGTCAGATTGTGACAATG-3' |
| 18 | WE specific fusion-primer carrying an overhang complementary to the WET-specific primer | 5'AATCGTCTCTAAGGATGGGTCAGATTGTGACAATG-3' |

TABLE 5-continued

| SEQ ID NO. | Description | Sequence |
|---|---|---|
| 19 | WE specific primer | 5'CTCGGTGATCATGTTATCTGCTTCTTGTTCGATTTGA-3' |
| 20 | WE specific fusion-primer complementary to the WE-sequence | 5'AATCGTCTCTTTCTTTATCTCCTCTTCCAGATGG-3' |
| 21 | Primer specific for LCMV NP | 5'-GGCTCCCAGATCTGAAAACTGTT-3' |
| 22 | NP- and GP-specific primers; NP-specific: same as in RT reaction, GP-specific: 5' | 5'-GCTGGCTTGTCACTAATGGCTC-3' |

What is claimed is:

1. A method for treating a neoplastic disease in a subject comprising, administering to a subject in need thereof an arenavirus particle and an immune checkpoint inhibitor, wherein said arenavirus particle is engineered to contain an arenavirus genomic segment comprising:
   a nucleotide sequence encoding a tumor antigen, tumor associated antigen or an antigenic fragment thereof; and
   (ii) at least one arenavirus open reading frame ("ORF") in a position other than the wild-type position of said ORF, wherein said ORF encodes the glycoprotein ("GP"), the nucleoprotein ("NP"), the matrix protein Z ("Z protein") or the RNA dependent RNA polymerase L ("L protein") of said arenavirus particle, and
   wherein said immune checkpoint inhibitor inhibits, decreases or interferes with the activity of Programmed cell death 1 (PD-1) or Programmed cell death ligand 1 (PD-L1), and
   wherein the tumor antigen or tumor associated antigen is HPV E6 and/or E7 or an antigenic fragment thereof.

2. The method of claim 1, wherein said tumor antigen or tumor associated antigen is HPV E6 and E7 or an antigenic fragment thereof.

3. The method of claim 1, wherein said subject is suffering from, is susceptible to, or is at risk for a neoplastic disease selected from the group consisting of anal cancer; carcinoma of adult, unknown primary site; carcinoma of unknown primary; cervical cancer; head and neck cancer; hypopharyngeal cancer; laryngeal cancer; metastatic squamous neck cancer with occult primary nasal cavity and paranasal sinus cancer; nasopharyngeal carcinoma; oral cancer; oral cavity cancer; oropharyngeal cancer; paranasal sinus and nasal cavity cancer; penile cancer; pharyngeal cancer; rectal cancer; squamous cell carcinoma; squamous neck cancer with occult primary, metastatic vaginal cancer; and vulvar cancer.

4. The method of claim 1, wherein said arenavirus particle and said immune checkpoint inhibitor are co-administered simultaneously.

5. The method of claim 1, wherein said arenavirus particle is administered:
   prior to administration of said immune checkpoint inhibitor; or
   (ii) after administration of said immune checkpoint inhibitor.

6. The method of claim 5, wherein the interval between administration of said arenavirus particle and said immune checkpoint inhibitor is about 1 hour, about 2 hours, about 3 hours, about 4 hours, about 5 hours, about 6 hours, about 7 hours, about 8 hours, about 9 hours, about 10 hours, about 11 hours, about 12 hours, about 1 day, about 2 days, about 3 days, about 4 days, about 5 days, about 6 days, about 1 week, about 8 days, about 9 days, about 10 days, about 11 days, about 12 days, about 13 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 1 month, about 2 months, about 3 months, about 4 months, about 5 months, about 6 months, or more.

7. The method of claim 1, wherein said arenavirus particle and said immune checkpoint inhibitor are administered in a therapeutically effective amount.

8. The method of claim 1, wherein said method comprises administering to said subject said arenavirus particle, and administering to said subject, after a period of time, a second arenavirus particle.

9. The method of claim 8, wherein said arenavirus particle and said second particle are derived from different arenavirus species.

10. The method of claim 1, wherein said arenavirus genomic segment is selected from the group consisting of:
    an S segment, wherein the ORF encoding the NP is under control of an arenavirus 5' untranslated region ("UTR");
    (ii) an S segment, wherein the ORF encoding the Z protein is under control of an arenavirus 5' UTR;
    (iii) an S segment, wherein the ORF encoding the L protein is under control of an arenavirus 5' UTR;
    (iv) an S segment, wherein the ORF encoding the GP is under control of an arenavirus 3' UTR;
    (v) an S segment, wherein the ORF encoding the L protein is under control of an arenavirus 3' UTR;
    (vi) an S segment, wherein the ORF encoding the Z protein is under control of an arenavirus 3' UTR;
    (vii) an L segment, wherein the ORF encoding the GP is under control of an arenavirus 5' UTR;
    (viii) an L segment, wherein the ORF encoding the NP is under control of an arenavirus 5' UTR;
    (ix) an L segment, wherein the ORF encoding the L protein is under control of an arenavirus 5' UTR;
    (x) an L segment, wherein the ORF encoding the GP is under control of an arenavirus 3' UTR;
    (xi) an L segment, wherein the ORF encoding the NP is under control of an arenavirus 3' UTR; and
    (xii) an L segment, wherein the ORF encoding the Z protein is under control of an arenavirus 3' UTR,
    wherein said arenavirus 3' UTR is the 3' UTR of the arenavirus S segment or the arenavirus L segment, and wherein said arenavirus 5' UTR is the 5' UTR of the arenavirus S segment or the arenavirus L segment.

11. The method of claim 1, wherein said arenavirus particle comprises a second arenavirus genomic segment so that said arenavirus particle comprises an S segment and an L segment.

12. The method of claim 11, wherein said arenavirus particle is attenuated, infectious, and replication-competent.

13. The method of claim 1, wherein the arenavirus particle is a tri-segmented arenavirus particle comprising one L segment and two S segments.

14. The method of claim 13, wherein propagation of said tri-segmented arenavirus particle does not result in a replication-competent bi-segmented viral particle after 70 days of persistent infection in mice lacking type I interferon receptor, type II interferon receptor and recombination activating gene 1 (RAG1) and having been infected with $10^4$ PFU of said tri-segmented arenavirus particle.

15. The method of claim 13, wherein inter-segmental recombination of two S segments, uniting two arenavirus ORFs on only one instead of two separate segments, abrogates viral promoter activity.

16. The method of claim 13, wherein the two S segments comprise: (i) one or two nucleotide sequences each encoding a tumor antigen, tumor associated antigen or an antigenic fragment thereof; or (ii) one or two duplicated arenavirus ORFs; or (iii) one nucleotide sequence encoding a tumor antigen, tumor associated antigen or an antigenic fragment thereof and one duplicated arenavirus ORF.

17. The method of claim 1, wherein said arenavirus particle is derived from lymphocytic choriomeningitis virus ("LCMV").

18. The method of claim 17, wherein said LCMV is MP strain, WE strain, Armstrong strain, or Armstrong Clone 13 strain.

19. The method of claim 1, wherein the growth or infectivity of said arenavirus particle is not affected by said nucleotide sequence encoding a tumor antigen, tumor associated antigen or an antigenic fragment thereof.

20. A pharmaceutical composition comprising an arenavirus particle, an immune checkpoint inhibitor and a pharmaceutically acceptable carrier, wherein said arenavirus particle is engineered to contain an arenavirus genomic segment comprising:

a nucleotide sequence encoding a tumor antigen, tumor associated antigen or an antigenic fragment thereof; and (ii) at least one arenavirus open reading frame ("ORF") in a position other than the wild-type position of said ORF, wherein said ORF encodes the glycoprotein ("GP"), the nucleoprotein ("NP"), the matrix protein Z ("Z protein") or the RNA dependent RNA polymerase L ("L protein") of said arenavirus particle, and wherein said immune checkpoint inhibitor inhibits, decreases or interferes with the activity of Programmed cell death 1 (PD-1) or Programmed cell death ligand 1 (PD-L1), and wherein the tumor antigen or tumor associated antigen is HPV E6 and/or E7 or an antigenic fragment thereof.

21. A kit comprising one or more containers and instructions for use, wherein said one or more containers comprise said pharmaceutical composition of claim 20.

22. A kit comprising two or more containers and instructions for use, wherein one of said containers comprises an arenavirus particle and another of said containers comprises an immune checkpoint inhibitor, wherein said arenavirus particle is engineered to contain an arenavirus genomic segment comprising:

a. a nucleotide sequence encoding a tumor antigen, tumor associated antigen or an antigenic fragment thereof; and b. at least one arenavirus open reading frame ("ORF") in a position other than the wild-type position of said ORF, wherein said ORF encodes the glycoprotein ("GP"), the nucleoprotein ("NP"), the matrix protein Z ("Z protein") or the RNA dependent RNA polymerase L ("L protein") of said arenavirus particle, and wherein said immune checkpoint inhibitor inhibits, decreases or interferes with the activity of Programmed cell death 1 (PD-1) or Programmed cell death ligand 1 (PD-L1), and wherein the tumor antigen or tumor associated antigen is HPV E6 and/or E7 or an antigenic fragment thereof.

23. The method of claim 1, wherein said immune checkpoint inhibitor inhibits, decreases or interferes with the activity of Programmed cell death ligand 1 (PD-L1).

24. The method of claim 1, wherein said immune checkpoint inhibitor is an antibody that binds to or inhibits activity of Programmed cell death 1 (PD1).

25. The method of claim 8, wherein said arenavirus particle and said second arenavirus particle comprise nucleotide sequences encoding different tumor antigens, tumor associated antigens or antigenic fragments thereof.

26. The method of claim 8 or claim 9, wherein said second arenavirus particle comprises a nucleotide sequence encoding a tumor antigen, tumor associated antigen or an antigenic fragment thereof, wherein the tumor antigen or tumor associated antigen is HPV E6 and/or E7 or an antigenic fragment thereof.

* * * * *